(12) United States Patent
Adams et al.

(10) Patent No.: US 8,802,864 B2
(45) Date of Patent: Aug. 12, 2014

(54) TRIAZOLONES AS FATTY ACID SYNTHASE INHIBITORS

(75) Inventors: Nicholas D. Adams, Collegeville, PA (US); Christopher Joseph Aquino, Research Triangle Park, NC (US); Amita M. Chaudhari, Collegeville, PA (US); Jonathan M. Ghergurovich, Collegeville, PA (US); Terence John Kiesow, Collegeville, PA (US); Cynthia A. Parrish, Collegeville, PA (US); Alexander Joseph Reif, Collegeville, PA (US); Kenneth Wiggall, Collegeville, PA (US)

(73) Assignee: GlaxoSmithKline LLC, Wilmington, DE (US)

(*) Notice: Subject to any disclaimer, the term of this patent is extended or adjusted under 35 U.S.C. 154(b) by 15 days.

(21) Appl. No.: 13/579,040

(22) PCT Filed: Feb. 22, 2011

(86) PCT No.: PCT/US2011/025661
§ 371 (c)(1),
(2), (4) Date: Aug. 15, 2012

(87) PCT Pub. No.: WO2011/103546
PCT Pub. Date: Aug. 25, 2011

(65) Prior Publication Data
US 2012/0316151 A1    Dec. 13, 2012

Related U.S. Application Data

(60) Provisional application No. 61/357,587, filed on Jun. 23, 2010, provisional application No. 61/306,709, filed on Feb. 22, 2010.

(51) Int. Cl.
*C07D 249/12* (2006.01)
*A61K 31/4196* (2006.01)

(52) U.S. Cl.
USPC ........................................ 548/264.6

(58) Field of Classification Search
USPC ....................... 548/264.6; 514/384
See application file for complete search history.

(56) References Cited

U.S. PATENT DOCUMENTS

| 5,728,834 A * | 3/1998 | Nacharaju et al. ............ 544/366 |
| 2009/0176307 A1 | 7/2009 | Morgan et al. |
| 2009/0291903 A1 | 11/2009 | Carruthers et al. |

FOREIGN PATENT DOCUMENTS

| WO | WO 2005/095362 A1 | 10/2005 |
| WO | WO 2005095362 | * 10/2005 |

OTHER PUBLICATIONS

Kridel, et al., "Fatty acid synthase inhibitors: new directions for oncology", Expert Opin. Investig. Drugs, vol. 16, No. 11, pp. 1817-1829 (2007).

* cited by examiner

*Primary Examiner* — Yong Chu
*Assistant Examiner* — Sonya Wright
(74) *Attorney, Agent, or Firm* — Wayne J. Dustman; Edward R. Gimmi

(57) ABSTRACT

This invention relates to the use of triazolone derivatives of Formula (I) for the modulation, notably the inhibition of the activity or function of fatty acid synthase (FAS). Suitably, the present invention relates to the use of triazolones in the treatment of cancer.

15 Claims, No Drawings

TRIAZOLONES AS FATTY ACID SYNTHASE INHIBITORS

This application is a §371 of International Application No. PCT/US2011/025661, filed 22 Feb. 2011, which claims the benefit of U.S. Provisional Application No. 61/357,587, filed 23 Jun. 2010, and 61/306,709, filed 22 Feb. 2010, which are incorporated herein in their entireties.

FIELD OF INVENTION

This invention relates to novel triazolones which are inhibitors of fatty acid synthase (FAS), to pharmaceutical compositions containing them, to processes for their preparation, and to their use in therapy for the treatment of cancers.

BACKGROUND

Fatty acids have an essential role in a variety of cellular processes including building blocks for membranes, anchors for targeting membrane proteins, precursors in the synthesis of lipid second messengers and as a medium to store energy, Menendez J S and Lupu R, *Fatty acid synthase and the lipogenic phenotype in cancer pathogenesis*, Nature Reviews Cancer, 7: 763-777 (2007). Fatty acids can either be obtained from the diet or can be synthesized de novo from carbohydrate precursors. The biosynthesis of the latter is catalyzed by the multi-functional homodimeric FAS. FAS synthesizes long chain fatty acids by using acetyl-CoA as a primer and Malonyl Co-A as a 2 carbon donor, and NADPH as reducing equivalents (Wakil S J, Lipids, *Structure and function of animal fatty acid synthase*, 39: 1045-1053 (2004), Asturias F J et al., *Structure and molecular organization of mammalian fatty acid synthase*, Nature Struct. Mol. Biol. 12:225-232 (2005), Maier T, et al., *Architecture of Mammalian Fatty Acid Synthase at 4.5 Å Resolution*, Science 311:1258-1262 (2006)).

De novo fatty acid synthesis is active during embryogenesis and in fetal lungs where fatty acids are used for the production of lung surfactant. In adults, most normal human tissues preferentially acquire fatty acids from the diet. Therefore the level of de novo lipogensis and expression of liopogenic enzymes is low (Weiss L, et al., *Fatty-acid biosynthesis in man, a pathway of minor importance. Purification, optimal assay conditions, and organ distribution of fatty-acid synthase. Biological Chemistry Hoppe-Seyler* 367(9):905-912 (1986)). In contrast, many tumors have high rates of de novo fatty acid synthesis (Medes G, et al., *Metabolism of Neoplastic Tissue. IV. A Study of Lipid Synthesis in Neoplastic Tissue Slices in Vitro*, Can Res, 13:27-29, (1953)). FAS has now been shown to be overexpressed in numerous cancer types including prostate, ovary, colon, endometrium lung, bladder, stomach and kidney (Kuhajda F P, *Fatty-acid synthase and human cancer: new perspectives on its role in tumor biology*, Nutrition; 16:202-208 (2000)). This differential expression and function of FAS in tumors and normal cells provide an approach for cancer therapy with the potential of a substantial therapeutic window.

Pharmacological and small interference RNA mediated inhibition of FAS has demonstrated a preferential inhibition of cancer cell proliferation. Additionally these inhibitors induce apoptosis in cancers cells in vitro and retard growth in human tumors in murine xenograft models in vivo (Menendez J S and Lupu R, Nature Reviews Cancer, 7: 763-777 (2007)). Based upon these findings, FAS is considered a major potential target of antineoplastic intervention.

SUMMARY OF THE INVENTION

This invention relates to compounds of the Formula (I), as shown below

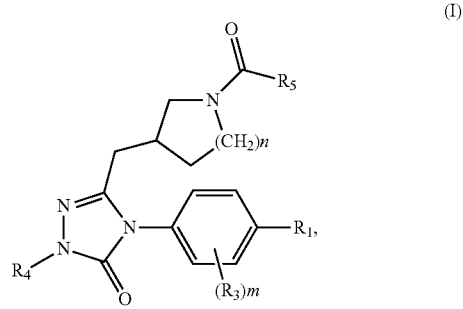

(I)

wherein, $R_1$ is a 6-membered aryl or heteroaryl ring which may be substituted or unsubstituted, in which adjacent substituents together may form an additional optionally substituted five or six membered ring which contains 0-3 hetero atoms and 0 to 2 double bonds;

each $R_3$ is independently selected from the group consisting of: halogen, C1-6alkyl, hydroxyl and alkoxy;

$R_4$ is H or C1-6alkyl;

$R_5$ is selected from the group consisting of: C1-6alkyl, C3-7cycloalkyl, —OC1-6alkyl, $C_{4-6}$heterocycloalkyl, amino and alkylamino;

m is 0-3, n is 0-1;

or pharmaceutically acceptable salts thereof.

This invention also relates to pharmaceutical compositions, which comprise compounds of Formula (I) and pharmaceutically acceptable carriers.

This invention also relates to methods of treating cancer which comprise administering an effective amount of a compound of Formula (I) to a human in need thereof.

This invention also relates to methods of treating cancer which comprise co-administering an compound of Formula (I) and a second compound to a human in need thereof.

DETAILED DESCRIPTION OF THE INVENTION

This invention relates to compounds of Formula (I), or pharmaceutically acceptable salts thereof.

This invention also relates to compounds of Formula (I)(A),

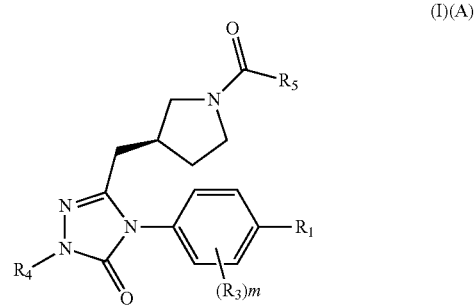

(I)(A)

wherein, $R_1$ is a 6-membered aryl or heteroaryl ring which may be substituted or unsubstituted, in which adjacent substituents together may form an additional optionally substituted five or six membered ring which contains 0-3 hetero atoms and 0 to 2 double bonds;
each $R_3$ is independently selected from the group consisting of: halogen, C1-6alkyl, hydroxyl and alkoxy;
$R_4$ is H or C1-6alkyl;
$R_5$ is selected from the group consisting of: C1-6alkyl, C3-7cycloalkyl, —OC1-6alkyl, $C_{4-6}$heterocycloalkyl, amino and alkylamino;
m is 0-3;
or pharmaceutically acceptable salts thereof.
This invention also relates to compounds of Formula (I)(B),

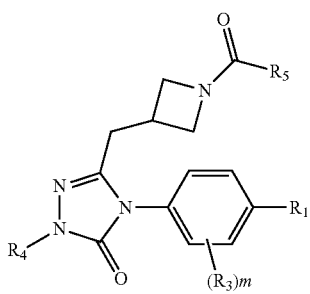

wherein R1, R3, R4, R5 and m are defined according to Formula (I).
In one embodiment, this invention also relates to compounds of Formula (I)(A) or (I)(B), wherein $R_1$ is a substituted or unsubstituted 6-membered aryl ring, in which adjacent substituents together may form an additional optionally substituted five or six membered ring which contains 0-3 hetero atoms and 0 to 2 double bonds; or pharmaceutically acceptable salts thereof.
In another embodiment, this invention also relates to compounds of Formula (I)(A) or (I)(B), wherein $R_1$ is a substituted or unsubstituted 6-membered heteroaryl ring, in which adjacent substituents together may form an additional optionally substituted five or six membered ring which contains 0-3 hetero atoms and 0 to 2 double bonds; or pharmaceutically acceptable salts thereof.
In another embodiment, this invention also relates to compounds of Formula (I)(A) or (I)(B), wherein $R_1$ is a substituted or unsubstituted pyridine or pyrimidine, in which adjacent substituents together may form an additional optionally substituted five or six membered ring which contains 0-3 hetero atoms and 0 to 2 double bonds; or pharmaceutically acceptable salts thereof.
In another embodiment, this invention also relates to compounds of Formula (I)(A) or (I)(B), wherein $R_1$ is a 6-membered aryl optionally substituted by one to three substituents selected from the group consisting of: halogen, C1-6alkyl, alkoxy, hydroxyl, amino, substituted amino, sulfamide, and cyano, or pharmaceutically acceptable salts thereof.
In another embodiment, this invention also relates to compounds of Formula (I)(A) or (I)(B), wherein $R_1$ is a 6-membered heteroaryl optionally substituted by one to three substituents selected from the group consisting of: halogen, C1-6alkyl, alkoxy, hydroxyl, amino, substituted amino, sulfamide, and cyano, or pharmaceutically acceptable salts thereof.
In another embodiment, this invention also relates to compounds of Formula (I)(A) or (I)(B), wherein $R_1$ is an optionally substituted bicyclic ring selected from the group consisting of: benzimidazole, indole, benzofuran, dihydrobenzofuran, dihydroindole, imidazopyridine, quinoline, azaindole, isoquinoline, isoquinolone, quinazoline, naphthalene, dihydroindene, indene, and indazole; or pharmaceutically acceptable salts thereof.
In another embodiment, this invention also relates to compounds of any of the above embodiments, wherein $R_3$ is fluoro, chloro, hydroxyl, methoxy, or methyl, m is 0-1, or pharmaceutically acceptable salts thereof.
In another embodiment, this invention also relates to compounds of any of the above embodiments, wherein $R_4$ is H, or pharmaceutically acceptable salts thereof.
In another embodiment, this invention also relates to compounds of any of the above embodiments, wherein $R_5$ is cyclopropyl, methyl, ethyl or isopropyl, or pharmaceutically acceptable salts thereof.
In another embodiment, this invention also relates to compounds of any of the above embodiments, wherein $R_5$ is cyclopropyl, or pharmaceutically acceptable salts thereof.
This invention also relates to the following compounds:
4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one,
5-{[(3S)-1-(cyclopropylcarbonyl)-3-pyrrolidinyl]methyl}-4-[4-(1H-indol-6-yl)phenyl]-2,4-dihydro-3H-1,2,4-triazol-3-one,
5-{[(3S)-1-(cyclopropylcarbonyl)-3-pyrrolidinyl]methyl}-4-[4'-(methyloxy)-4-biphenylyl]-2,4-dihydro-3H-1,2,4-triazol-3-one,
4'-(3-{[(3S)-1-(cyclopropylcarbonyl)-3-pyrrolidinyl]methyl}-5-oxo-1,5-dihydro-4H-1,2,4-triazol-4-yl)-4-biphenylcarbonitrile,
5-{[(3S)-1-(cyclopropylcarbonyl)-3-pyrrolidinyl]methyl}-4-(2',4'-dichloro-4-biphenylyl)-2,4-dihydro-3H-1,2,4-triazol-3-one,
5-{[(3S)-1-(cyclopropylcarbonyl)-3-pyrrolidinyl]methyl}-4-(4-imidazo[1,2-a]pyridin-7-ylphenyl)-2,4-dihydro-3H-1,2,4-triazol-3-one,
4-[4-(1-benzofuran-5-yl)phenyl]-5-{[(3S)-1-(cyclopropylcarbonyl)-3-pyrrolidinyl]methyl}-2-methyl-2,4-dihydro-3H-1,2,4-triazol-3-one,
(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetic acid,
4-[4-(1-benzofuran-5-yl)phenyl]-5-{[(3S)-1-(cyclopropylcarbonyl)-3-pyrrolidinyl]methyl}-2-(1-methylethyl)-2,4-dihydro-3H-1,2,4-triazol-3-one,
4-[4-(1-benzofuran-5-yl)phenyl]-5-{[(3S)-1-(cyclopropylcarbonyl)-3-pyrrolidinyl]methyl}-2-[2-(methyloxy)ethyl]-2,4-dihydro-3H-1,2,4-triazol-3-one, methyl (4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetate,
4-[4-(1-benzofuran-5-yl)phenyl]-5-{[(3S)-1-(cyclopropylcarbonyl)-3-pyrrolidinyl]methyl}-2-(2-hydroxyethyl)-2,4-dihydro-3H-1,2,4-triazol-3-one,
5-{[(3S)-1-(cyclopropylcarbonyl)-3-pyrrolidinyl]methyl}-4-[4-(1H-indol-4-yl)phenyl]-2,4-dihydro-3H-1,2,4-triazol-3-one,
4-[4-(1-benzofuran-6-yl)phenyl]-5-{[(3S)-1-(cyclopropylcarbonyl)-3-pyrrolidinyl]methyl}-2,4-dihydro-3H-1,2,4-triazol-3-one,
N'-[4'-(3-{[(3S)-1-(cyclopropylcarbonyl)-3-pyrrolidinyl]methyl}-5-oxo-1,5-dihydro-4H-1,2,4-triazol-4-yl)-3-biphenylyl]-N,N-dimethylsulfamide,
5-{[(3S)-1-(cyclopropylcarbonyl)-3-pyrrolidinyl]methyl}-4-[4-(3-methyl-1-benzofuran-5-yl)phenyl]-2,4-dihydro-3H-1,2,4-triazol-3-one, 5-{[(3S)-1-(cyclopropylcarbonyl)-3-pyrrolidinyl]methyl}-4-[4-(1H-indol-5-yl)phenyl]-2,4-dihydro-3H-1,2,4-triazol-3-one, 5-{[(3S)-1-(cyclopropylcarbonyl)-3-pyrrolidinyl]methyl}-4-[4-(2-methyl-1H-benzimidazol-5-yl)phenyl]-2,4-dihydro-3H-1,2,4-triazol-3-one, 5-{[(3S)-1-(cyclopropylcarbonyl)-3-pyrrolidinyl]methyl}-4-[4-(2,3-dihydro-1H-indol-5-yl)phenyl]-2,4-dihydro-3H-1,2,4-triazol-3-one, 5-{[(3S)-1-(cyclopropylcarbonyl)-3-pyrrolidinyl]methyl}-4-(4-imidazo[1,5-a]pyridin-5-ylphenyl)-2,4-dihydro-3H-1,2,4-triazol-3-one, 2-(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetamide, (4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetonitrile, 5-{[(3S)-1-(cyclopropylcarbonyl)-3-pyrrolidinyl]methyl}-4-[4-(1-methyl-1H-benzimidazol-5-yl)phenyl]-2,4-dihydro-3H-1,2,4-triazol-3-one, 5-{[(3S)-1-(cyclopropylcarbonyl)-3-pyrrolidinyl]methyl}-4-[4-(1-methyl-1H-indol-5-yl)phenyl]-2,4-dihydro-3H-1,2,4-triazol-3-one, 2-(2-aminoethyl)-4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(3-methyl-1H-indol-5-yl)phenyl]-2,4-dihydro-3H-1,2,4-triazol-3-one, 5-{[(3S)-1-(cyclopropylcarbonyl)-3-pyrrolidinyl]methyl}-4-[4-(2-methyl-1-benzofuran-5-yl)phenyl]-2,4-dihydro-3H-1,2,4-triazol-3-one, 5-{[(3S)-1-(cyclopropylcarbonyl)-3-pyrrolidinyl]methyl}-4-[4-(2-methyl-1H-indol-5-yl)phenyl]-2,4-dihydro-3H-1,2,4-triazol-3-one, 4-[4-(1-benzofuran-5-yl)phenyl]-5-{[(3S)-1-(cyclopropylcarbonyl)-3-pyrrolidinyl]methyl}-2-(2-hydroxy-2-methylpropyl)-2,4-dihydro-3H-1,2,4-triazol-3-one, 5-{[(3S)-1-(cyclopropylcarbonyl)-3-pyrrolidinyl]methyl}-4-[2-fluoro-4-(1H-indol-6-yl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(1H-indol-5-yl)phenyl]-2,4-dihydro-3H-1,2,4-triazol-3-one, 4-[4-(1-benzofuran-5-yl)-2-fluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(7-methyl-1-benzofuran-5-yl)phenyl]-2,4-dihydro-3H-1,2,4-triazol-3-one, 5-{[(3S)-1-(cyclopropylcarbonyl)-3-pyrrolidinyl]methyl}-4-(4'-fluoro-4-biphenylyl)-2,4-dihydro-3H-1,2,4-triazol-3-one, 5-{[(3S)-1-(cyclopropylcarbonyl)-3-pyrrolidinyl]methyl}-4-[4-(6-quinolinyl)phenyl]-2,4-dihydro-3H-1,2,4-triazol-3-one, 5-{[(3S)-1-(cyclopropylcarbonyl)-3-pyrrolidinyl]methyl}-4-[4-(1H-indazol-5-yl)phenyl]-2,4-dihydro-3H-1,2,4-triazol-3-one, 5-{[(3S)-1-(cyclopropylcarbonyl)-3-pyrrolidinyl]methyl}-4-[4-(2,3-dihydro-1-benzofuran-5-yl)phenyl]-2,4-dihydro-3H-1,2,4-triazol-3-one, 4-[4-(1,3-benzodioxol-5-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4'-(dimethylamino)-4-biphenylyl]-2,4-dihydro-3H-1,2,4-triazol-3-one, 4-[4-(1-benzofuran-5-yl)-2-methylphenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(1H-indol-5-yl)-2-methylphenyl]-2,4-dihydro-3H-1,2,4-triazol-3-one, 5-{[(3S)-1-(cyclopropylcarbonyl)-3-pyrrolidinyl]methyl}-4-[4-(1H-indol-6-yl)-2-methylphenyl]-2,4-dihydro-3H-1,2,4-triazol-3-one, 5-{[(3S)-1-(cyclopropylcarbonyl)-3-pyrrolidinyl]methyl}-4-(4'-fluoro-3-methyl-4-biphenylyl)-2,4-dihydro-3H-1,2,4-triazol-3-one, 4-[4-(1-benzofuran-5-yl)phenyl]-5-{[(3S)-1-propanoyl-3-pyrrolidinyl]methyl}-2,4-dihydro-3H-1,2,4-triazol-3-one, 4-[4-(1-benzofuran-5-yl)phenyl]-5-{[(3S)-1-(2-methylpropanoyl)-3-pyrrolidinyl]methyl}-2,4-dihydro-3H-1,2,4-triazol-3-one, 4-(4'-amino-4-biphenylyl)-5-{[(3S)-1-(cyclopropylcarbonyl)-3-pyrrolidinyl]methyl}-2,4-dihydro-3H-1,2,4-triazol-3-one, 4-[4-(6-amino-3-pyridinyl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-(3,3'-difluoro-4'-methyl-4-biphenylyl)-2,4-dihydro-3H-1,2,4-triazol-3-one, 4-(3'-chloro-3-fluoro-4'-methyl-4-biphenylyl)-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2,6-difluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2,6-difluoro-4-(7-quinolinyl)phenyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3',5'-difluoro-3-methyl-4-biphenylcarbonitrile, 5-{[(3S)-1-(cyclopropylcarbonyl)-3-pyrrolidinyl]methyl}-4-[2,6-difluoro-4-(1H-indol-6-yl)phenyl]-2,4-dihydro-3H-1,2,4-triazol-3-one, 5-{[(3S)-1-(cyclopropylcarbonyl)-3-pyrrolidinyl]methyl}-4-[3,5-difluoro-4'-(methyloxy)-4-biphenylyl]-2,4-dihydro-3H-1,2,4-triazol-3-one, 4-(4'-chloro-2',3,5-trifluoro-4-biphenylyl)-5-{[(3S)-1-(cyclopropylcarbonyl)-3-pyrrolidinyl]methyl}-2,4-dihydro-3H-1,2,4-triazol-3-one, 4-(4'-chloro-3,5-difluoro-4-biphenylyl)-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-3-(methyloxy)phenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2-(trifluoromethyl)phenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2-hydroxyphenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2,5-difluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2,5-difluoro-4-(7-quinolinyl)phenyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-2',5'-difluoro-3-methyl-4-biphenylcarbonitrile, 5-{[(3S)-1-(cyclopropylcarbonyl)-3-pyrrolidinyl]methyl}-4-[2,5-difluoro-4-(1H-indol-6-yl)phenyl]-2,4-dihydro-3H-1,2,4-triazol-3-one, 4-[4-(1-benzofuran-5-yl)-2,3-difluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2,3-difluoro-4-(7-quinolinyl)phenyl]-2,4-dihydro-3H-1,2,4-triazol-3-one, 5-{[1-(cyclopropylcarbonyl)-3-azetidinyl]methyl}-4-[4-(1H-indazol-6-yl)phenyl]-2,4-dihydro-3H-1,2,4-triazol-3-one, 5-{[1-(cyclopropylcarbonyl)-3-azetidinyl]methyl}-4-[4-(1H-indol-6-yl)phenyl]-2,4-dihydro-3H-1,2,4-triazol-3-one, 5-{[1-(cyclopropylcarbonyl)-3-azetidinyl]methyl}-4-[4-(6-quinolinyl)phenyl]-2,4-dihydro-3H-1,2,4-triazol-3-one, 5-{[1-(cyclopropylcarbonyl)-3-azetidinyl]methyl}-4-[4'-(methyloxy)-4-biphenylyl]-2,4-dihydro-3H-1,2,4-triazol-3-one, 5-{[1-(cyclopropylcarbonyl)-3-azetidinyl]methyl}-4-[4'-(dimethylamino)-4-biphenylyl]-2,4-dihydro-3H-1,2,4-triazol-3-one, 4-[4-(1-benzofuran-5-yl)phenyl]-5-{[1-(cyclopropylcarbonyl)-3-azetidinyl]methyl}-2,4-dihydro-3H-1,2,4-triazol-3-one, 5-{[1-(cyclopropylcarbonyl)-3-azetidinyl]methyl}-4-[2-fluoro-4-(1H-indol-6-yl)phenyl]-2,4-dihydro-3H-1,2,4-triazol-3-one, 4'-(3-{[1-(cyclopropylcarbonyl)-3-azetidinyl]methyl}-5-oxo-1,5-dihydro-4H-1,2,4-triazol-4-yl)-3'-fluoro-4-biphenylcarbonitrile, 5-{[(3S)-1-(cyclopropylcarbonyl)-3-pyrrolidinyl]methyl}-4-[3'-(phenylcarbonyl)-4-biphenylyl]-2,4-dihydro-3H-1,2,4-triazol-3-one, 5-{[(3S)-1-(cyclopropylcarbonyl)-3-pyrrolidinyl]methyl}-4-[3-fluoro-3'-(phenylcarbonyl)-4-biphenylyl]-2,4-dihydro-3H-1,2,4-triazol-3-one, 4-[2-chloro-4-(1H-indol-5-yl)phenyl]-5-{[(3S)-1-(cyclopropylcarbonyl)-3-pyrrolidinyl]methyl}-2,4-dihydro-3H-1,2,4-triazol-3-one, 4-[2-chloro-4-(1H-indazol-5-yl)phenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2-chlorophenyl]-5-{[(3S)-1-(cyclopropylcarbonyl)-3-pyrrolidinyl]methyl}-2,4-dihydro-3H-1,2,4-triazol-3-one, 4-[2-chloro-4-(1H-indol-6-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4'-fluoro-3-(methyloxy)-4-biphenylyl]-2,4-dihydro-3H-1,2,4-triazol-3-one, 5-{[(3S)-1-(cyclopropylcarbonyl)-3-pyrrolidinyl]methyl}-4-[4-(1H-indol-5-yl)-2-(methyloxy)phenyl]-2,4-dihydro-3H-1,2,4-triazol-3-one, 4-[4-(1-benzofuran-5-yl)-2-(methyloxy)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(1H-indol-6-yl)-2-(methyloxy)phenyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3'-(methyloxy)-4-biphenylcarbonitrile, 5-{[(3S)-1-(cyclopropylcarbonyl)-3-pyrrolidinyl]methyl}-4-[4-(7-fluoro-1-benzofuran-5-yl)phenyl]-2,4-dihydro-3H-1,2,4-triazol-3-one, 4-[4-(2,1,3-benzoxadiazol-5-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2-fluoro-4-(1H-indazol-5-yl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(6-quinolinyl)phenyl]-2,4-dihydro-3H-1,2,4-triazol-3-one, 5-[4-(3-{[(3S)-1-(cyclopropylcarbonyl)-3-pyrrolidinyl]methyl}-5-oxo-1,5-dihydro-4H-1,2,4-triazol-4-yl)phenyl]-1,3-dihydro-2H-indol-2-one, 5-{[(3S)-1-(cyclopropylcarbonyl)-3-pyrrolidinyl]methyl}-4-[4-(1H-indazol-6-yl)phenyl]-2,4-dihydro-3H-1,2,4-triazol-3-one, 7-[4-(3-{[(3S)-1-(cyclopropylcarbonyl)-3-pyrrolidinyl]methyl}-5-oxo-1,5-dihydro-4H-1,2,4-triazol-4-yl)phenyl]-1(2H)-isoquinolinone, 5-{[(3S)-1-(cyclopropylcarbonyl)-3-pyrrolidinyl]methyl}-4-[4-(2,3-dihydro-1-benzofuran-5-yl)-2-fluorophenyl]-2,4-dihydro-3H-1,2,4-triazol-3-one, 5-{[(3S)-1-(cyclopropylcarbonyl)-3-pyrrolidinyl]methyl}-4-[4-(2,3-dihydro-1H-indol-5-yl)-2-fluorophenyl]-2,4-dihydro-3H-1,2,4-triazol-3-one, 4-[4-(1,3-benzothiazol-5-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-{4'-[(dimethylamino)methyl]-4-biphenylyl}-2,4-dihydro-3H-1,2,4-triazol-3-one, 5-{[(3S)-1-(cyclopropylcarbonyl)-3-pyrrolidinyl]methyl}-4-(3'-fluoro-4-biphenylyl)-2,4-dihydro-3H-1,2,4-triazol-3-one, 5-{[(3S)-1-(cyclopropylcarbonyl)-3-pyrrolidinyl]methyl}-4-[3'-(methyloxy)-4-biphenylyl]-2,4-dihydro-3H-1,2,4-triazol-3-one, 5-{[(3S)-1-(cyclopropylcarbonyl)-3-pyrrolidinyl]methyl}-4-[3'-(dimethylamino)-4-biphenylyl]-2,4-dihydro-3H-1,2,4-triazol-3-one, 5-{[(3S)-1-(cyclopropylcarbonyl)-3-pyrrolidinyl]methyl}-4-[4'-(hydroxymethyl)-4-biphenylyl]-2,4-dihydro-3H-1,2,4-triazol-3-one, 5-{[(3S)-1-(cyclopropylcarbonyl)-3-pyrrolidinyl]methyl}-4-[3'-(hydroxymethyl)-4-biphenylyl]-2,4-dihydro-3H-1,2,4-triazol-3-one, 4-[4-(1,3-benzoxazol-5-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4'-(1H-pyrazol-1-yl)-4-biphenylyl]-2,4-dihydro-3H-1,2,4-triazol-3-one, 5-{[(3S)-1-(cyclopropylcarbonyl)-3-pyrrolidinyl]methyl}-4-[3'-(1H-pyrazol-5-yl)-4-biphenylyl]-2,4-dihydro-3H-1,2,4-triazol-3-one, 4-[4-(1,3-benzothiazol-5-yl)-2-fluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(2-naphthalenyl)phenyl]-2,4-dihydro-3H-1,2,4-triazol-3-one, 5-{[(3S)-1-(cyclopropylcarbonyl)-3-pyrrolidinyl]methyl}-4-[3'-(1H-pyrazol-1-yl)-4-biphenylyl]-2,4-dihydro-3H-1,2,4-triazol-3-one, 5-{[(3S)-1-(cyclopropylcarbonyl)-3-pyrrolidinyl]methyl}-4-[4'-(1H-pyrazol-5-yl)-4-biphenylyl]-2,4-dihydro-3H-1,2,4-triazol-3-one, 4-[4-(1,3-benzothiazol-6-yl)phenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-{3'-[(dimethylamino)methyl]-4-biphenylyl}-2,4-dihydro-3H-1,2,4-triazol-3-one, 5-{[(3S)-1-(cyclopropylcarbonyl)-3-pyrrolidinyl]methyl}-4-(3,4'-difluoro-4-biphenylyl)-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarbonitrile, 5-{[(3S)-1-(cyclopropylcarbonyl)-3-pyrrolidinyl]methyl}-4-[4'-(dimethylamino)-3-fluoro-4-biphenylyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3,3'-difluoro-4-biphenylcarbonitrile, 5-{[(3S)-1-(cyclopropylcarbonyl)-3-pyrrolidinyl]methyl}-4-[3-fluoro-4'-(1H-pyrazol-1-yl)-4-biphenylyl]-2,4-dihydro-3H-1,2,4-triazol-3-one, 5-{[(3S)-1-(cyclopropylcarbonyl)-3-pyrrolidinyl]methyl}-4-[2-fluoro-4-(5-quinolinyl)phenyl]-2,4-dihydro-3H-1,2,4-triazol-3-one, 5-{[(3S)-1-(cyclopropylcarbonyl)-3-pyrrolidinyl]methyl}-4-[3-fluoro-4'-(methyloxy)-4-biphenylyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-methyl-4-biphenylcarbonitrile, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-(methyloxy)-4-biphenylcarbonitrile, 5-{[(3S)-1-(cyclopropylcarbonyl)-3-pyrrolidinyl]methyl}-4-[2-fluoro-4-(6-quinoxalinyl)phenyl]-2,4-dihydro-3H-1,2,4-triazol-3-one, 5-{[(3S)-1-(cyclopropylcarbonyl)-3-pyrrolidinyl]methyl}-4-[4-(1-methyl-1H-indol-6-yl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(6-quinazolinyl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(2-methyl-6-quinolinyl)phenyl]-2,4-dihydro-3H-1,2,4-triazol-3-one, 5-{[(3S)-1-(cyclopropylcarbonyl)-3-pyrrolidinyl]methyl}-4-[4-(1-naphthalenyl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(7-quinolinyl)phenyl]-2,4-dihydro-3H-1,2,4-triazol-3-one, 5-{[(3S)-1-(cyclopropylcarbonyl)-3-pyrrolidinyl]methyl}-4-(1,1':4',1"-terphenyl-4-yl)-2,4-dihydro-3H-1,2,4-triazol-3-one, 5-{[(3S)-1-(cyclopropylcarbonyl)-3-pyrrolidinyl]methyl}-4-[4-(3-quinolinyl)phenyl]-2,4-dihydro-3H-1,2,4-triazol-3-one, 5-{[(3S)-1-(cyclopropylcarbonyl)-3-pyrrolidinyl]methyl}-4-[3,3'-difluoro-4'-(1H-pyrazol-1-yl)-4-biphenylyl]-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-2,3'-difluoro-4-biphenylcarbonitrile, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-2-methyl-4-biphenylcarbonitrile, 3-chloro-4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarbonitrile, 5-{[(3S)-1-(cyclopropylcarbonyl)-3-pyrrolidinyl]methyl}-4-[4-(6-hydroxy-2-naphthalenyl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(6-isoquinolinyl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(7-isoquinolinyl)phenyl]-2,4-dihydro-3H-1,2,4-triazol-3-one, 5-{[(3S)-1-(cyclopropylcarbonyl)-3-pyrrolidinyl]methyl}-4-[4-(2,3-dihydro-1H-inden-5-yl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(2-methyl-7-quinolinyl)phenyl]-2,4-dihydro-3H-1,2,4-triazol-3-one, 5-{[(3S)-1-(cyclopropylcarbonyl)-3-pyrrolidinyl]methyl}-4-[4'-(dimethylamino)-3-fluoro-3'-methyl-4-biphenylyl]-2,4-dihydro-3H-1,2,4-triazol-3-one, 5-{[(3S)-1-(cyclopropylcarbonyl)-3-pyrrolidinyl]methyl}-4-[2-fluoro-4-(1-methyl-2,3-dihydro-1H-indol-5-yl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(3-quinolinyl)phenyl]-2,4-dihydro-3H-1,2,4-triazol-3-one, 5-{[(3S)-1-(cyclopropylcarbonyl)-3-pyrrolidinyl]methyl}-4-(3',4'-dichloro-3-fluoro-4-biphenylyl)-2,4-dihydro-3H-1,2,4-triazol-3-one, 5-{[(3S)-1-(cyclopropylcarbonyl)-3-pyrrolidinyl]methyl}-4-[4'-(dimethylamino)-3-fluoro-2'-methyl-4-biphenylyl]-2,4-dihydro-3H-1,2,4-triazol-3-one, 4-(4'-chloro-3,3'-difluoro-4-biphenylyl)-5-{[(3S)-1-(cyclopropylcarbonyl)-3-pyrrolidinyl]methyl}-2,4-dihydro-3H-1,2,4-triazol-3-one, 4-(4'-chloro-3-fluoro-3'-methyl-4-biphenylyl)-5-{[(3S)-1-(cyclopropylcarbonyl)-3-pyrrolidinyl]methyl}-2,4-dihydro-3H-1,2,4-triazol-3-one, 4-[4'-chloro-3-fluoro-3'-(methyloxy)-4-biphenylyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-(2',4'-dichloro-3-fluoro-4-biphenylyl)-2,4-dihydro-3H-1,2,4-triazol-3-one, 4-(4'-chloro-2',3-difluoro-4-biphenylyl)-5-{[(3S)-1-(cyclopropylcarbonyl)-3-pyrrolidinyl]methyl}-2,4-dihydro-3H-1,2,4-triazol-3-one, 4-(4'-chloro-3-fluoro-2'-methyl-4-biphenylyl)-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2-fluoro-4-(7-quinazolinyl)phenyl]-2,4-dihydro-3H-1,2,4-triazol-3-one, 4-(4'-chloro-3-fluoro-4-biphenylyl)-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[4-(2,3-dihydro-1H-inden-5-yl)-2-fluorophenyl]-2,4-dihydro-3H-1,2,4-triazol-3-one, 5-{[(3S)-1-(cyclopropylcarbonyl)-3-pyrrolidinyl]methyl}-4-[2-fluoro-4-(1-oxo-2,3-dihydro-1H-inden-5-yl)phenyl]-2,4-dihydro-3H-1,2,4-triazol-3-one, 5-{[(3S)-1-(cyclopropylcarbonyl)-3-pyrrolidinyl]methyl}-4-[4'-(4-morpholinyl)-4-biphenylyl]-2,4-dihydro-3H-1,2,4-triazol-3-one, 5-{[(3S)-1-(cyclopropylcarbonyl)-3-pyrrolidinyl]methyl}-4-[4'-(1H-pyrrol-1-yl)-4-biphenylyl]-2,4-dihydro-3H-1,2,4-triazol-3-one, 5-{[(3S)-1-(cyclopropylcarbonyl)-3-pyrrolidinyl]methyl}-4-[4'-(1-pyrrolidinyl)-4-biphenylyl]-2,4-dihydro-3H-1,2,4-triazol-3-one, 5-{[(3S)-1-(cyclopropylcarbonyl)-3-pyrrolidinyl]methyl}-4-[4-(7-quinolinyl)phenyl]-2,4-dihydro-3H-1,2,4-triazol-3-one, 5-{[(3S)-1-(cyclopropylcarbonyl)-3-pyrrolidinyl]methyl}-4-(2',3,4'-trifluoro-4-biphenylyl)-2,4-dihydro-3H-1,2,4-triazol-3-one, 5-{[(3S)-1-(cyclopropylcarbonyl)-3-pyrrolidinyl]methyl}-4-[2',3-difluoro-4'-(methyloxy)-4-biphenylyl]-2,4-dihydro-3H-1,2,4-triazol-3-one, 5-{[(3S)-1-(cyclopropylcarbonyl)-3-pyrrolidinyl]methyl}-4-[2-fluoro-4-(4-quinolinyl)phenyl]-2,4-dihydro-3H-1,2,4-triazol-3-one, N-[4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylyl]acetamide, 4-[4-(1-benzofuran-5-yl)phenyl]-5-{[(3R)-1-(cyclopropylcarbonyl)-3-pyrrolidinyl]methyl}-2,4-dihydro-3H-1,2,4-triazol-3-one, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarboxylic acid, 4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-biphenylcarboxylic acid, 5-{[1-(cyclopropylcarbonyl)-3-azetidinyl]methyl}-4-[4-(7-quinolinyl)phenyl]-2,4-dihydro-3H-1,2,4-triazol-3-one, 5-{[1-(cyclopropylcarbonyl)-3-azetidinyl]methyl}-4-[2-fluoro-4-(7-quinolinyl)phenyl]-2,4-dihydro-3H-1,2,4-triazol-3-one, 4-[2-fluoro-4-(7-quinolinyl)phenyl]-5-[(1-propanoyl-3-azetidinyl)methyl]-2,4-dihydro-3H-1,2,4-triazol-3-one, 5-[(1-propanoyl-3-azetidinyl)methyl]-4-[4-(7-quinolinyl)phenyl]-2,4-dihydro-3H-1,2,4-triazol-3-one, 3-({4-[2-fluoro-4-(7-quinolinyl)phenyl]-5-oxo-4,5-dihydro-1H-1,2,4-triazol-3-yl}methyl)-N,N-dimethyl-1-azetidinecarboxamide, 4-[2-fluoro-4-(7-quinolinyl)phenyl]-5-({1-[(1-methylcyclopropyl)carbonyl]-3-azetidinyl}methyl)-2,4-dihydro-3H-1,2,4-triazol-3-one, 4-[5-chloro-2-fluoro-4-(7-quinolinyl)phenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-5-chloro-2-fluorophenyl]-5-{[(3S)-1-(cyclopropylcarbonyl)-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[2-fluoro-5-methyl-4-(7-quinolinyl)phenyl]-2,4-dihydro-3H-1,2,4-triazol-3-one, 4-[4-(1-benzofuran-5-yl)-2-fluoro-5-methylphenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-2-chloro-6-fluorophenyl]-5-{[(3S)-1-(cyclopropylcarbonyl)-3-pyrrolidinyl]methyl}-2,4-dihydro-3H-1,2,4-triazol-3-one, 4-[4-(1-benzofuran-5-yl)-3-hydroxyphenyl]-5-{[(3S)-1-(cyclopropylcarbonyl)-3-pyrrolidinyl]methyl}-2,4-dihydro-3H-1,2,4-triazol-3-one, 6-[4-(3-{[(3S)-1-(cyclopropylcarbonyl)-3-pyrrolidinyl]methyl}-5-oxo-1,5-dihydro-4H-1,2,4-triazol-4-yl)-3-fluorophenyl]-4(1H)-quinazolinone, 7-[4-(3-{[(3S)-1-(cyclopropylcarbonyl)-3-pyrrolidinyl]methyl}-5-oxo-1,5-dihydro-4H-1,2,4-triazol-4-yl)-3-fluorophenyl]-4(1H)-quinazolinone, 4-(4'-acetyl-3-fluoro-4-biphenylyl)-5-{[(3S)-1-(cyclopropylcarbonyl)-3-pyrrolidinyl]methyl}-2,4-dihydro-3H-1,2,4-triazol-3-one, N-[4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-biphenylyl]acetamide, 5-{[(3S)-1-(cyclopropylcarbonyl)-3-pyrrolidinyl]methyl}-4-[3-fluoro-4'-(1-pyrrolidinyl)-4-biphenylyl]-2,4-dihydro-3H-1,2,4-triazol-3-one, 5-{[(3S)-1-(cyclopropylcarbonyl)-3-pyrrolidinyl]methyl}-4-[4'-(2-methyl-1,3-thiazol-4-yl)-4-biphenylyl]-2,4-dihydro-3H-1,2,4-triazol-3-one, 5-{[(3S)-1-(cyclopropylcarbonyl)-3-pyrrolidinyl]methyl}-4-[4'-(5-methyl-1,3,4-oxadiazol-2-yl)-4-biphenylyl]-2,4-dihydro-3H-1,2,4-triazol-3-one, 5-{[(3S)-1-(cyclopropylcarbonyl)-3-pyrrolidinyl]methyl}-4-[2-fluoro-4-(3-oxo-2,3-dihydro-1H-inden-5-yl)phenyl]-2,4-dihydro-3H-1,2,4-triazol-3-one, 5-{[(3S)-1-(cyclopropylcarbonyl)-3-pyrrolidinyl]methyl}-4-[4-(2,3-dihydro-1H-indol-6-yl)-2-fluorophenyl]-2,4-dihydro-3H-1,2,4-triazol-3-one, 5-{[(3S)-1-(cyclopropylcarbonyl)-3-pyrrolidinyl]methyl}-4-[3-fluoro-4'-(2-oxo-1-pyrrolidinyl)-4-biphenylyl]-2,4-dihydro-3H-1,2,4-triazol-3-one, 5-{[(3S)-1-(cyclopropylcarbonyl)-3-pyrrolidinyl]methyl}-4-[2-fluoro-4-(1,2,3,4-tetrahydro-7-quinolinyl)phenyl]-2,4-dihydro-3H-1,2,4-triazol-3-one, 5-{[(3S)-1-acetyl-3-pyrrolidinyl]methyl}-4-[4-(7-quinolinyl)phenyl]-2,4-dihydro-3H-1,2,4-triazol-3-one, 5-{[(3S)-1-propanoyl-3-pyrrolidinyl]methyl}-4-[4-(7-quinolinyl)phenyl]-2,4-dihydro-3H-1,2,4-triazol-3-one, (3S)—N,N-dimethyl-3-({5-oxo-4-[4-(7-quinolinyl)phenyl]-4,5-dihydro-1H-1,2,4-triazol-3-yl}methyl)-1-pyrrolidinecarboxamide, 5-{[(3S)-1-(2-methylpropanoyl)-3-pyrrolidinyl]methyl}-4-[4-(7-quinolinyl)phenyl]-2,4-dihydro-3H-1,2,4-triazol-3-one, 5-{[(3S)-1-(2,2-dimethylpropanoyl)-3-pyrrolidinyl]methyl}-4-[4-(7-quinolinyl)phenyl]-2,4-dihydro-3H-1,2,4-triazol-3-one, 5-({(3S)-1-[(1-methylcyclopropyl)carbonyl]-3-pyrrolidinyl}methyl)-4-[4-(7-quinolinyl)phenyl]-2,4-dihydro-3H-1,2,4-triazol-3-one, (3S)-3-({4-[3-fluoro-4'-(methyloxy)-4-biphenylyl]-5-oxo-4,5-dihydro-1H-1,2,4-triazol-3-yl}methyl)-N,N-dimethyl-1-pyrrolidinecarboxamide, 4-[3-fluoro-4'-(methyloxy)-4-biphenylyl]-5-{[(3S)-1-propanoyl-3-pyrrolidinyl]methyl}-2,4-dihydro-3H-1,2,4-triazol-3-one, 5-{[(3S)-1-(2,2-dimethylpropanoyl)-3-pyrrolidinyl]methyl}-4-[3-fluoro-4'-(methyloxy)-4-biphenylyl]-2,4-dihydro-3H-1,2,4-triazol-3-one, (3S)-3-({4-[2-fluoro-4-(7-quinolinyl)phenyl]-5-oxo-4,5-dihydro-1H-1,2,4-triazol-3-yl}methyl)-N,N-dimethyl-1-pyrrolidinecarboxamide, 4-[3-fluoro-4'-(methyloxy)-4-biphenylyl]-5-({(3S)-1-[(1-methylcyclopropyl)carbonyl]-3-pyrrolidinyl}methyl)-2,4-dihydro-3H-1,2,4-triazol-3-one, 4-[2-fluoro-4-(7-quinolinyl)phenyl]-5-{[(3S)-1-propanoyl-3-pyrrolidinyl]methyl}-2,4-dihydro-3H-1,2,4-triazol-3-one, 5-{[(3S)-1-(2,2-dimethylpropanoyl)-3-pyrrolidinyl]methyl}-4-[2-fluoro-4-(7-quinolinyl)phenyl]-2,4-dihydro-3H-1,2,4-triazol-3-one, 4-[2-fluoro-4-(7-quinolinyl)phenyl]-5-({(3S)-1-[(1-methylcyclopropyl)carbonyl]-3-pyrrolidinyl}methyl)-2,4-dihydro-3H-1,2,4-triazol-3-one, (3S)—N-ethyl-3-({4-[2-fluoro-4-(7-quinolinyl)phenyl]-5-oxo-4,5-dihydro-1H-1,2,4-triazol-3-yl}methyl)-1-pyrrolidinecarboxamide, 5-{[(3S)-1-(4-morpholinylcarbonyl)-3-pyrrolidinyl]methyl}-4-[4-(7-quinolinyl)phenyl]-2,4-dihydro-3H-1,2,4-triazol-3-one, 4-[3-fluoro-4'-(methyloxy)-4-biphenylyl]-5-{[(3S)-1-(2-methylpropanoyl)-3-pyrrolidinyl]methyl}-2,4-dihydro-3H-1,2,4-triazol-3-one, 4-[2-fluoro-4-(7-quinolinyl)phenyl]-5-{[(3S)-1-(2-methylpropanoyl)-3-pyrrolidinyl]methyl}-2,4-dihydro-3H-1,2,4-triazol-3-one, 4-[3-fluoro-3'-(methyloxy)-4-biphenylyl]-5-{[(3S)-1-propanoyl-3-pyrrolidinyl]methyl}-2,4-dihydro-3H-1,2,4-triazol-3-one, 5-{[(3S)-1-(cyclopropylcarbonyl)-3-pyrrolidinyl]methyl}-4-[3-fluoro-3'-(methyloxy)-4-biphenylyl]-2,4-dihydro-3H-1,2,4-triazol-3-one, 5-{[(3S)-1-(cyclopropylcarbonyl)-3-pyrrolidinyl]methyl}-4-(3-fluoro-3'-hydroxy-4-biphenylyl)-2,4-dihydro-3H-1,2,4-triazol-3-one, 5-{[(3S)-1-(cyclopropylcarbonyl)-3-pyrrolidinyl]methyl}-4-(3-fluoro-4'-hydroxy-4-biphenylyl)-2,4-dihydro-3H-1,2,4-triazol-3-one, 5-{[(3S)-1-(cyclopropylcarbonyl)-3-pyrrolidinyl]methyl}-4-[2-fluoro-4-(6-fluoro-2-naphthalenyl)phenyl]-2,4-dihydro-3H-1,2,4-triazol-3-one, 5-{[(3S)-1-(cyclopropylcarbonyl)-3-pyrrolidinyl]methyl}-4-[2-fluoro-4-(8-fluoro-2-naphthalenyl)phenyl]-2,4-dihydro-3H-1,2,4-triazol-3-one, and pharmaceutically acceptable salt thereof.

This invention also relates to compounds exemplified in the Experimental section. Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts. In general, the salts are formed from pharmaceutically acceptable inorganic and organic acids. More specific examples of suitable acid salts include maleic, hydrochloric, hydrobromic, sulphuric, phosphoric, nitric, perchloric, fumic, acetic, propionic, succinic, glycolic, formic, lactic, aleic, tartaric, citric, palmoic, malonic, hydroxymaleic, phenylacetic, glutamic, benzoic, salicylic, fumaric, toluenesulfonic, methansulfonic (mesylate), naphthalene-2-sulfonic, benzenesulfonic, hydroxynaphthoic, hydroiodic, malic, teroic, tannic, and the like.

Other representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrobromide, hydrochloride, hydroxynaphthoate, iodide, isethionate, lactate, lactobionate, laurate, malate, maleate, mandelate, mesylate, methylsulfate, mono-potassium maleate, mucate, napsylate, nitrate, oxalate, pamoate (embonate), palmitate, pantothenate, phosphate/diphosphate, polygalacturonate, salicylate, stearate, subacetate, succinate, sulfate, tannate, tartrate, teoclate, tosylate, triethiodide, and valerate salts.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compound or salt represented by Formula (I) as mixtures with isomers thereof in which one or more chiral centers are inverted. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compound represented by Formula (I), as well as any wholly or partially equilibrated mixtures thereof. The present invention also includes the individual isomers of the compound or salt represented by the Formula (I) as well as mixtures with isomers thereof in which one or more chiral centers are inverted. It is to be understood that the present invention includes all combinations and subsets of the particular groups defined hereinabove.

DEFINITIONS

Terms are used within their accepted meanings. The following definitions are meant to clarify, but not limit, the terms defined.

As used herein, the term "alkyl" (or "alkylene") refers to a straight or branched chain alkyl, preferably having from one to twelve carbon atoms, which may be unsubstituted or substituted, saturated or unsaturated with multiple degrees of substitution included within the present invention. Suitable substituents are selected from the group consisting of: halogen, amino, substituted amino, cyano, hydroxyl, alkoxy, alkylthio, alkylsulfonyl, amidosulfonyl, carboxylic acid, carboxylic ester, carboxamide, aminocarbonyl, and heterocyclyl. Examples of "alkyl" as used herein include methyl, ethyl, propyl, isopropyl, isobutyl, n-butyl, t-butyl, isopentyl, n-pentyl, and the like, as well as substituted versions thereof.

As used herein, the term "cycloalkyl" refers to an unsubstituted or substituted mono- or polycyclic non-aromatic saturated ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and the like, as well as unsubstituted and substituted versions thereof.

As used herein, the term "alkoxy" refers to the group —ORa, where Ra is C1-3alkyl or C3-7cycloalkyl as defined above.

As used herein, the term "substituted amino" is meant —NR'R" wherein each R' and R" is independently selected from a group including hydrogen, C1-6alkyl, acyl, C3-C7cycloalkyl, wherein at least one of R' and R" is not hydrogen. Examples of substituted amino includes, but are not limited to alkylamino, dialkylamino, acylamino, and cycloalkylamino.

As used herein, the term "heterocycle" or "heterocyclyl" or "heterocycloalkyl" refers to unsubstituted and substituted mono- or polycyclic non-aromatic ring system containing one or more heteroatoms. Preferred heteroatoms include N, O, and S, including N-oxides, sulfur oxides, and dioxides. Preferably the ring is three to eight-membered and is either fully saturated or has one or more degrees of unsaturation. Multiple degrees of substitution are included within the present definition. Examples of "heterocyclic" groups include, but are not limited to tetrahydrofuranyl, pyranyl, 1,4-dioxanyl, 1,3-dioxanyl, piperidinyl, pyrrolidinyl, morpholinyl, azetidinyl, piperazinyl, pyrrolidinonyl, piperazinonyl, pyrazolidinyl, and their various tautomers, as well as unsubstituted and substituted versions thereof.

As used herein, the term "aryl", unless otherwise defined, is meant aromatic, hydrocarbon, ring system. The ring system may be monocyclic or fused polycyclic (e.g., bicyclic, tricyclic, etc.), substituted or unsubstituted. In various embodiments, the monocyclic aryl ring is C5-C10, or C5-C7, or C5-C6, where these carbon numbers refer to the number of carbon atoms that form the ring system. A C6 ring system, i.e. a phenyl ring, is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group. Suitable substituents for aryl are described in the definition of "optionally substituted".

As used herein, the term "heteroaryl", unless otherwise defined, is meant an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiophene, furan, imidazole, indole, isothiazole, oxazole, pyrazine, pyrazole, pyridazine, pyridine, pyrimidine, pyrrole, quinoline, quinazoline, quinoxaline, thiazole, and thiophene. Suitable substituents for heteroaryl are described in the definition of "optionally substituted".

As used herein, the term "cyano" refers to the group —CN.

As used herein, the term "acetyl" refers to the group —C(O)Rb, where Rb is alkyl, cycloalkyl, or heterocyclyl, as each is defined herein.

As used herein, the term "optionally" means that the subsequently described event(s) may or may not occur, and includes both event(s) that occur and event(s) that do not occur.

As used herein, unless otherwise defined, the phrase "optionally substituted" or variations thereof denote an optional substitution, including multiple degrees of substitution, with one or more substituent group. The phrase should not be interpreted as duplicative of the substitutions herein described and depicted. Exemplary optional substituent groups include acyl, alkyl, alkylsulfonyl, alkoxy, alkoxycarbonyl, cyano, halogen, haloalkyl, hydroxyl, oxo, amide, sulfamide, urea, amino, substituted amino, acylamino, phenylcarbonyl, dialkylaminosulfonamide, morpholino, sulfonamide, thiourea, nitro, pyrrolidinyl, pyrazolyl, pyrrolyl, phenyl, and tetrazolyl, wherein pyrrolidinyl, pyrazolyl and tetrazolyl can be further substituted with one to three C1-3alkyl.

The invention further provides a pharmaceutical composition (also referred to as pharmaceutical formulation) comprising a compound of Formula (I) or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula (I) or salt thereof with at least one excipient.

Pharmaceutical Compositions

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

As used herein, the term "treatment" includes prophylaxis and refers to alleviating the specified condition, eliminating or reducing one or more symptoms of the condition, slowing or eliminating the progression of the condition, and preventing or delaying the reoccurrence of the condition in a previously afflicted or diagnosed patient or subject. Prophylaxis (or prevention or delay of disease onset) is typically accomplished by administering a drug in the same or similar manner as one would to a patient with the developed disease or condition.

The present invention provides a method of treatment in a mammal, especially a human, suffering from disease conditions targeted by the present compounds. Such treatment comprises the step of administering a therapeutically effective amount of a compound of Formula (I) or salt thereof to said mammal, particularly a human. Treatment can also comprise the step of administering a therapeutically effective amount of a pharmaceutical composition containing a compound of Formula (I) or salt thereof to said mammal, particularly a human.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

While it is possible that, for use in therapy, a therapeutically effective amount of a compound of Formula (I) or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula (I) or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 1000 mg/day, and preferably from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula (I) per se. Similar dosages should be appropriate for treatment (including prophylaxis) of the other conditions referred herein for treatment. In general, determination of appropriate dosing can be readily arrived at by one skilled in medicine or the pharmacy art.

Combinations

When a compound of Formula (I) is administered for the treatment of cancer, the term "co-administering" and derivatives thereof as used herein is meant either simultaneous administration or any manner of separate sequential administration of a FAS inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice f Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present FAS inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G$_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperi-dinopiperidino)carbonyloxy]-1H-pyrano[3',4',6,7]in-dolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quino-line-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

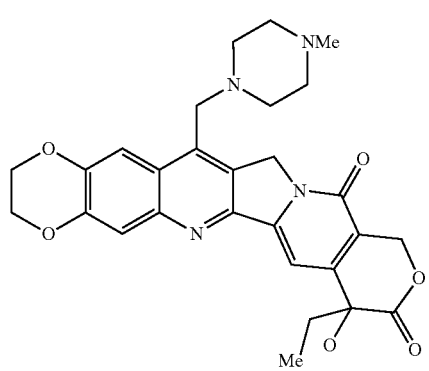

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Experimentals

Abbreviations: Boc, t-butyloxycarbonyl; DCC, N,N'-dicyclohexylcarbodiimide; DCM, dichloromethane; DIEA, diisopropylethylamine; DMAP, 4-N,N-dimethylaminopyridine; DMF, N,N-dimethylformamide; DMSO, dimethylsulfoxide; EDC, N-(3-dimethylaminopropyl)-N'-ethylcarbodiimide hydrochloride; EtOAc, ethyl acetate; EtOH, ethanol; HOAc, acetic acid; HOAt, 1-hydroxy-7-azabenzotriazole; HOBt, 1-hydroxybenzotriazole; MeOH, methanol; TEA, triethylamine;

Preparation

The derivatives described herein were prepared by the general methods described below:

Schemes/Experimentals

The pyrrolidine amide or carbamate intermediates can be prepared according to Scheme I from either racemic or optically-active starting material. The acid can be converted to the ester under standard conditions. The hydrazide can be formed from the ester using a protected pyrrolidine or after deprotection and formation of the pyrrolidine amide as shown.

Scheme I:

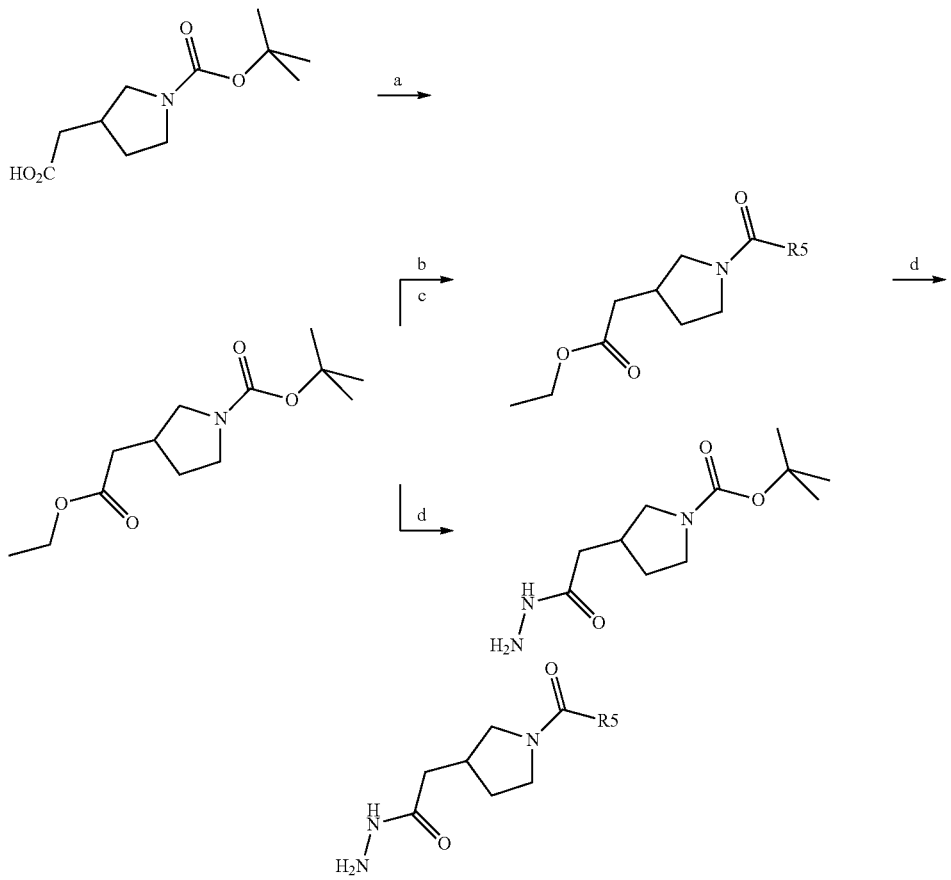

Conditions: a) EtOH, EDC, DMAP (cat.), Et$_2$O; b) HCl, dioxane; c) R5—C(O)Cl, DIPEA, CH$_2$Cl$_2$; d) H$_2$NNH$_2$·H$_2$O, EtOH, 80° C.

The hydrazide can be condensed with various isocyanates under standard conditions, as outlined in Scheme II. This intermediate can then be cyclized to a triazolone under refluxing aqueous potassium carbonate.

Scheme II:

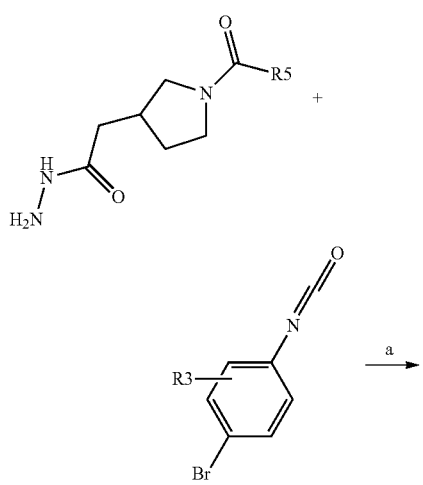

-continued

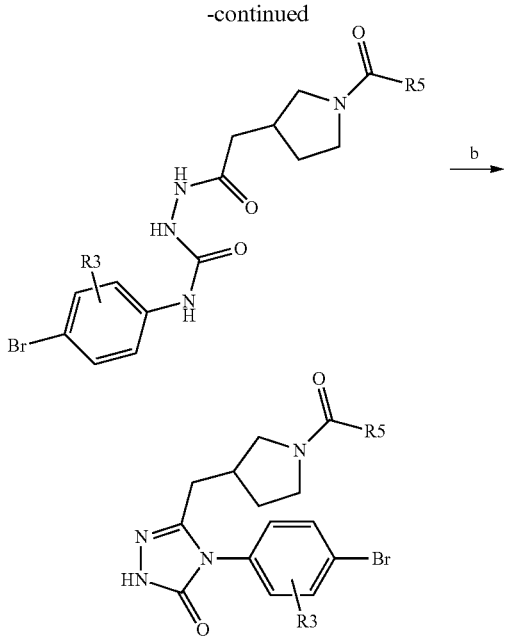

Conditions: a) CH$_2$Cl$_2$, 0° C. to rt; b) aq K$_2$CO$_3$, reflux.

The triazolone bromide can then be coupled with an aryl boronic acid/ester under Suzuki coupling conditions or can be first converted to the intermediate boronic ester to allow metal-mediated cross-coupling with aryl halides or sulfonates (Scheme III).

Scheme III:

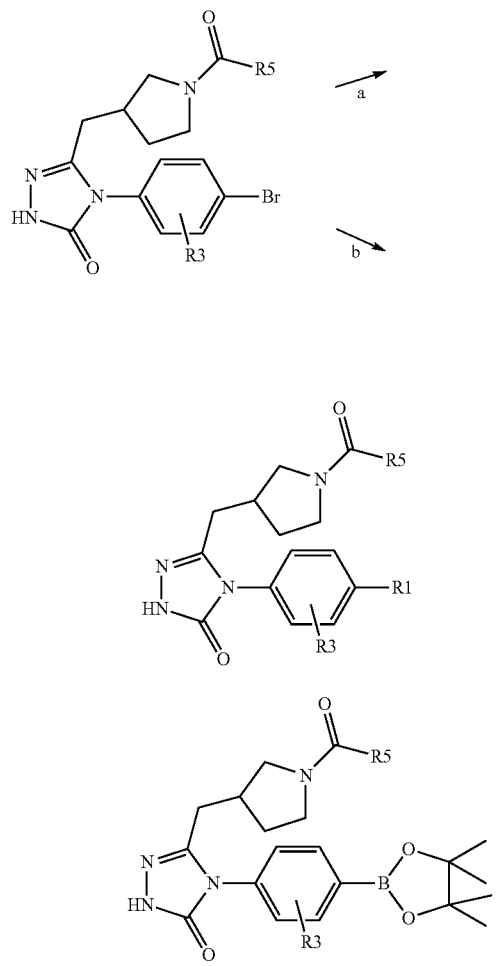

Substitution of the triazolone core can occur under basic alkylation conditions at the amide nitrogen, as shown in Scheme IV.

Scheme IV:

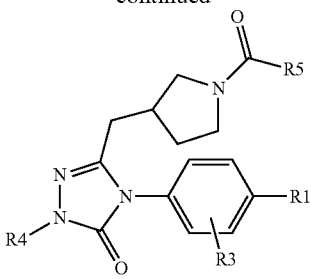

-continued

Conditions: a) R4-X, K$_2$CO$_3$, DMF, 80-180° C.

Functionalization at the R5 position can also proceed at a later stage following the route outlined in Scheme V. The protected hydrazide can be condensed with various isocyanates and then cyclized to form the triazolone core using similar conditions as in the above examples. Reprotection of the pyrrolidine, Suzuki cross-coupling with various aryl boronic acids/esters, and then deprotection of the pyrrolidine can then lead to a pyrrolidine intermediate which can be acylated under standard conditions to afford the fully functionalized compounds.

Scheme V:

-continued

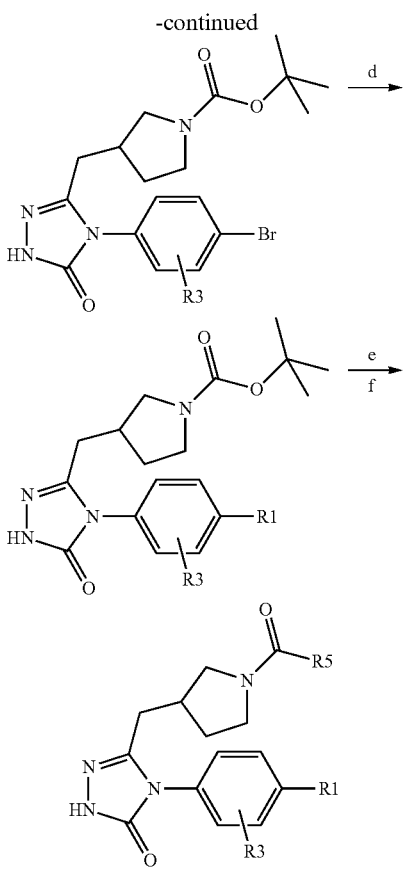

Conditions: a) CH₂Cl₂, rt; b) aq K₂CO₃, reflux; c) BOC₂O, aq NaOH; d) R1-B(OR)₂, PdCl₂dppf (cat.), sat'd aq NaHCO₃, dioxane, 100° C.; e) HCl, dioxane; f) R5-C(O)Cl, DIPEA, CH₂Cl₂.

Similarly, the azetidine amide or carbamate intermediates can be prepared as outlined in the above Schemes for the pyrrolidine intermediates starting from the azetidine acetic acid, as demonstrated in the examples below.

Example 1

4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one

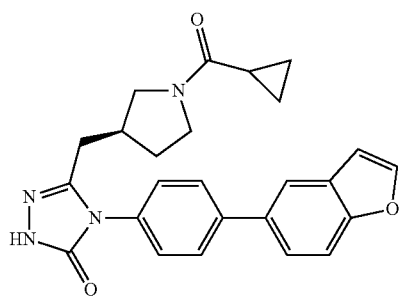

a) 1,1-dimethylethyl (3S)-3-[2-(ethyloxy)-2-oxoethyl]-1-pyrrolidinecarboxylate

In an oven-dried 2 L round bottom flask under nitrogen, ((3S)-1-{[(1,1-dimethylethyl)oxy]carbonyl}-3-pyrrolidinyl) acetic acid (60 g, 262 mmol) dissolved in diethyl ether (600 mL) was treated with 1-ethyl-3-(3-dimethylaminopropyl) carbodiimide hydrochloride (55.2 g, 288 mmol), 4-(dimethylamino)pyridine (3.20 g, 26.2 mmol), and ethanol (33.6 ml, 576 mmol) at room temperature and the mixture was stirred for 40 h. The reaction mixture began as a white suspension, but then became a pale yellow solution with gummy yellow material at the bottom of the flask after 1 h, which was difficult to stir. Another stir bar was added in order to get the mixture stirring; however, a vortex was not obtained so the reaction was stirred longer than overnight to ensure the reaction went to completion. The reaction mixture was diluted with ether (400 mL) and washed with 1M aqueous sodium hydrogen sulfate solution (800 mL) and saturated aqueous sodium bicarbonate solution (800 mL). The organic phase was isolated, dried over magnesium sulfate, and concentrated to dryness to give the title compound as a clear pale yellow liquid (64.1 g, 249 mmol, 95%). MS(ES)+ m/e 258.2 [M+H]⁺, 280.2 [M+Na]⁺.

b) ethyl[(3S)-1-(cyclopropylcarbonyl)-3-pyrrolidinyl]acetate

In a round bottom flask, a solution of 1,1-dimethylethyl (3S)-3-[2-(ethyloxy)-2-oxoethyl]-1-pyrrolidinecarboxylate (64.1 g, 249 mmol) in 4M HCl in dioxane (600 mL, 2400 mmol) was stirred at room temperature for 1 h. Analysis of an aliquot by LCMS confirmed complete removal of the BOC group from the starting material. The reaction was concentrated in vacuo to give a pale orange liquid. A solution of this intermediate as the HCl salt in dichloromethane (500 mL) was treated with N,N-diisopropylethylamine (87 mL, 498 mmol) and stirred for 5 min at room temperature. The yellow solution was cooled to 0° C. and was treated with cyclopropanecarbonyl chloride (24.9 mL, 274 mmol) by syringe. The resultant orange solution was allowed to warm to room temperature and stirred for 1 h. The reaction was diluted with water (400 mL), the layers were separated, and the aqueous layer was extracted with 200 mL dichloromethane. The organic layers were combined, dried over MgSO₄, concentrated in vacuo, and pumped under high vacuum to give the title compound as an orange liquid (249 mmol, quantitative). MS(ES)+ m/e 226.2 [M+H]⁺, 451.1 [2M+H]⁺.

c) 2-[(3S)-1-(cyclopropylcarbonyl)-3-pyrrolidinyl]acetohydrazide

In a round bottom flask equipped with reflux condenser, an orange solution of ethyl [(3S)-1-(cyclopropylcarbonyl)-3-pyrrolidinyl]acetate (56.1 g, 249 mmol) in ethanol (356 mL) was treated with hydrazine monohydrate (242 mL, 4.98 mol). The resultant yellow solution was stirred at 80° C. (reflux) for 15 h. The reaction was cooled to room temperature and concentrated in vacuo. Ethanol (100 mL) was added and the reaction was concentrated (2×) to give a pale yellow clear oil. The oil was dissolved in dichloromethane (white solution observed), dried over MgSO₄, concentrated in vacuo, and pumped under high vacuum overnight (16 h) to give the title compound as a clear pale yellow oil (249 mmol, quantitative). MS(ES)+ m/e 212.0 [M+H]⁺, 423.2 [2M+H]⁺.

d) N-(4-bromophenyl)-2-{[(3S)-1-(cyclopropylcarbonyl)-3-pyrrolidinyl]acetyl}hydrazinecarboxamide In a round bottom flask under nitrogen, a solution of 2-[(3S)-1-(cyclopropylcarbonyl)-3-pyrrolidinyl]acetohydrazide (52.6 g, 249 mmol) in dichloromethane (356 mL) was cooled to 0° C. and 4-bromophenylisocyanate (49.3 g, 249 mmol) was added. Once the isocyanate dissolved, the cooling bath was removed and the reaction was allowed to warm to room temperature and was stirred for 27 h. White precipitate formed quickly. The reaction was filtered to collect the white precipitate, washed with 50 mL cold dichloromethane, and air dried. The white solid was washed with additional cold dichloromethane (300 mL) and dried under vacuum suction overnight to provide the title compound (108.29 g, 63% pure, 167 mmol, 67% yield). MS(ES)+ m/e 409.2, 411.2 [M+H]+.

e) 4-(4-bromophenyl)-5-{[(3S)-1-(cyclopropylcarbonyl)-3-pyrrolidinyl]methyl}-2,4-dihydro-3H-1,2,4-triazol-3-one In a 10 L 3-necked round bottom flask equipped with reflux condenser, mechanical stirrer and a stopper, a mixture of crude N-(4-bromophenyl)-2-{[(3S)-1-(cyclopropylcarbonyl)-3-pyrrolidinyl]acetyl}hydrazinecarboxamide (108.29 g, 63% purity, 167 mmol) and potassium carbonate (115 g, 833 mmol) in water (6 L) was stirred at reflux (variac heating mantle ~130° C.) for 18 h. The variac heating was turned off and the flask was removed from the mantle and allowed to cool to ~70° C. White solid settled to the bottom of the flask during this time. The liquid layer was siphoned into 2 L Erlenmeyer flasks using gravity and tygon tubing initially filled with water. When no more liquid could be siphoned, the remaining slurry was filtered. The filtrate was added to an Erlenmeyer flask and all the contents of these flasks were concentrated in vacuo using a large Buchi rotovap. LCMS analysis of the filtered white solid showed that it contained desired product. The filtered solid was added to the solid obtained from rotovapping. Ethyl acetate (2 L) and water (500 mL) were added to the contents of the flask and the mixture was acidified to pH~5.5 using 6N aq HCl solution. The aqueous layer was extracted with ethyl acetate (5×500 mL). Then the aqueous layer was divided into 3 smaller portions and each was extracted with ethyl acetate (2×200 mL). The organic layers were combined, dried over magnesium sulfate and concentrated in vacuo to give a white solid. Trituration of the solid with dichloromethane (50 mL) followed by vacuum suction drying provided the title compound as a white solid (59.27 g, 74% pure, 112 mmol, 67% yield). MS(ES)+ m/e 391.1, 393.3 [M+H]+. The filtrate was concentrated in vacuo, dissolved in minimal dichloromethane and loaded directly onto a silica gel column. Purification by silica gel chromatography (Analogix IF280, 0-100% 10% MeOH in CH2Cl2/CH2Cl2 (effectively 0-10% MeOH/CH2Cl2), SF65-400 g, 60 min) provided another batch of the title compound as a white solid (9.5 g, 90% pure, 22 mmol, 13%). Impure product could be further purified by silica gel chromatography (Analogix IF280, 0-5% MeOH/CH2Cl2 over 30 min, then 5-10% MeOH/CH2Cl2 over 15 min) to afford clean desired product as a white solid. Purified material was used in subsequent reactions. MS(ES)+ m/e 391.1, 392.8 [M+H]+.

f) 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one In a microwave vial, a mixture of 4-(4-bromophenyl)-5-{[(3S)-1-(cyclopropylcarbonyl)-3-pyrrolidinyl]methyl}-2,4-dihydro-3H-1,2,4-triazol-3-one (322 mg, 0.77 mmol), 5-(4,4,5,5-tetramethyl-1,3,2-dioxaborolan-2-yl)-1-benzofuran (208 mg, 0.85 mmol), and 1,1'-bis(diphenylphosphino)ferrocene-palladium(II)dichloride dichloromethane complex (32 mg, 0.04 mmol) in 2M aq potassium carbonate solution (1.5 mL, 3 mmol) and 1,4-dioxane (3 mL) was stirred at 100° C. for 3 h. The reaction was cooled to room temperature. The layers were separated and an aliquot of the basic potassium carbonate aqueous layer was analyzed by LCMS and showed that desired product was present. The aqueous layer was acidified using 1N aq HCl solution to pH~6 by pH paper and was extracted with ethyl acetate (2×50 mL). The combined organic layers were dried over MgSO4 and concentrated in vacuo. Purification of the residue by silica gel chromatography (Analogix IF280, 0-10% MeOH/CH2Cl2, SF15-12 g, 20 min) followed by another purification (100% EtOAc for 10 min and then 0-8% MeOH/CH2Cl2 for 15 min) and finally subsequent purification by silica gel chromatography (Analogix IF280, SF15-4-g, Solvent A=EtOAc; Solvent B=10% MeOH/CH2Cl2; Gradient: 100% A for 10 min then ramped to 100% B over 20 min (i.e. 0-100% of B/A) provided the title product as a pale yellow solid (232 mg, 0.53 mmol, 69%). MS(ES)+ m/e 428.9 [M+H]+.

Example 2

5-{[(3S)-1-(cyclopropylcarbonyl)-3-pyrrolidinyl]methyl}-4-[4-(1H-indol-6-yl)phenyl]-2,4-dihydro-3H-1,2,4-triazol-3-one

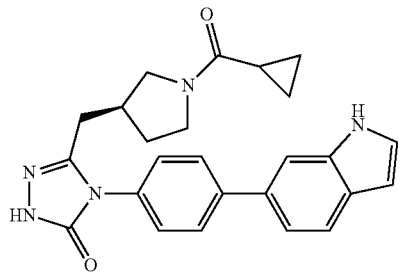

4-(4-Bromophenyl)-5-{[(3S)-1-(cyclopropylcarbonyl)-3-pyrrolidinyl]methyl}-2,4-dihydro-3H-1,2,4-triazol-3-one (0.100 g, 0.256 mmol), 1H-indol-6-ylboronic acid (0.082 g, 0.511 mmol), tetrakis(triphenylphosphine)palladium(0) (0.030 g, 0.026 mmol), and K3PO4 (0.217 g, 1.022 mmol) were combined in ethanol (4 mL) and water (4 mL), purged with N2, and irradiated in a microwave reactor for 1 h at 110° C. after which time LCMS indicated complete conversion. The reaction mixture was filtered through Celite, diluted with 100 mL EtOH and concentrated to dryness. The residue was partitioned between dichloromethane and water (a minimal amount of CH3OH was added to achieve complete solubility), and the organic phase was isolated, dried over MgSO4, filtered and concentrated to dryness. The residue was purified on 40 g silica gel eluted with 100% EtOAc to 10% CH3OH/CH2Cl2 to give 5-{[(3S)-1-(cyclopropylcarbonyl)-3-pyrrolidinyl]methyl}-4-[4-(1H-indol-6-yl)phenyl]-2,4-dihydro-3H-1,2,4-triazol-3-one (0.115 g, 0.269 mmol, quantitative yield) as a white foam. LC-MS (ES−) m/z 426.51 [M−1]. LC-MS (ES+) m/z 428.30 [M+H]. 1H NMR (400 MHz, DMSO-d6) δ ppm 11.72 (d, J=4.08 Hz, 1H), 11.23 (s, 1H), 7.82 (dd, J=8.49, 2.79 Hz, 2H), 7.69 (s, 1H), 7.64 (d, J=8.27 Hz, 1H), 7.48 (dd, J=8.43, 6.50 Hz, 2H), 7.41 (t, J=2.69 Hz, 1H), 7.36 (dd, J=8.27, 1.50 Hz, 1H), 6.47 (t, J=2.04 Hz, 1H), 3.61-3.86 (m, 1H), 3.47-3.60 (m, 1H), 2.87-3.43 (m, 2H), 2.34-2.66 (m, 3H), 1.91-2.13 (m, 1H), 1.44-1.74 (m, 2H), 0.61-0.73 (m, 4H).

Example 3

5-{[(3S)-1-(cyclopropylcarbonyl)-3-pyrrolidinyl]methyl}-4-[4'-(methyloxy)-4-biphenylyl]-2,4-dihydro-3H-1,2,4-triazol-3-one

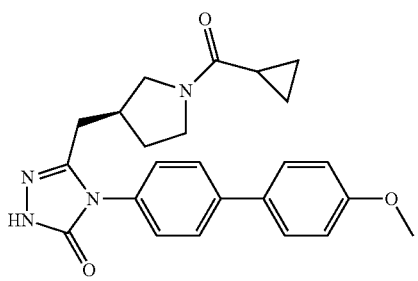 [SMILES: COc1ccc(-c2ccc(-n3c(C[C@@H]4CCN(C(=O)C5CC5)C4)n[nH]c3=O)cc2)cc1]

A vial was charged with a slurry of 4-(4-bromophenyl)-5-{[(3S)-1-(cyclopropylcarbonyl)-3-pyrrolidinyl]methyl}-2,4-dihydro-3H-1,2,4-triazol-3-one (100 mg, 0.256 mmol), [4-(methyloxy)phenyl]boronic acid (78 mg, 0.511 mmol), tetrakis(triphenylphosphine)palladium(0) (29.5 mg, 0.026 mmol) and tripotassium phosphate (217 mg, 1.022 mmol) in ethanol (4.0 mL) and water (4.00 mL) then purged with nitrogen and sealed with a standard teflon septa (crimped aluminum seal). The reaction was then heated in an aluminum block at 110° C. for 3 h. The resulting yellow slurry was diluted with ethanol then evaporated to dryness under reduced pressure. The residue was triturated from dichloromethane then the decanted solution was applied directly to a standard stock silica column (Analogix SF25-40 g) and eluted first with 100% ethyl acetate for 5 min and then with 7% methanol in dichloromethane. The combined desired fractions were evaporated to a colorless oil that was crystallized from hexanes/ethyl acetate to afford the title compound as a white solid (78 mg, 72.2%). MS(ES)+ m/e 419.2 [M+H]+.

Example 4

4'-(3-{[(3S)-1-(cyclopropylcarbonyl)-3-pyrrolidinyl]methyl}-5-oxo-1,5-dihydro-4H-1,2,4-triazol-4-yl)-4-biphenylcarbonitrile

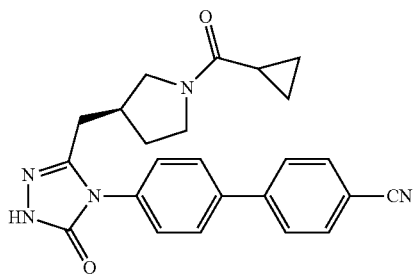 [SMILES: N#Cc1ccc(-c2ccc(-n3c(C[C@@H]4CCN(C(=O)C5CC5)C4)n[nH]c3=O)cc2)cc1]

A vial was charged with a slurry of 4-(4-bromophenyl)-5-{[(3S)-1-(cyclopropylcarbonyl)-3-pyrrolidinyl]methyl}-2,4-dihydro-3H-1,2,4-triazol-3-one (100 mg, 0.256 mmol), (4-cyanophenyl)boronic acid (75 mg, 0.511 mmol), tetrakis(triphenylphosphine)palladium(0) (29.5 mg, 0.026 mmol) and tripotassium phosphate (217 mg, 1.022 mmol) in ethanol (4.0 mL) and water (4.00 mL) then purged with nitrogen and sealed with a standard teflon septa (crimped aluminum seal). The reaction was then heated in an aluminum block at 110° C. for 2 h. The resulting yellow slurry was diluted with ethanol, treated with silica powder (2 g) then evaporated under reduced pressure. The dried powder was placed in a column adaptor (Analogix Dasi adapter) attached to a standard stock silica column (Analogix SF25-40 g) and eluted with ethyl acetate for 10 min and then with 7% methanol in dichloromethane. The combined desired fractions were evaporated to a colorless oil that was crystallized from hexanes/ethyl acetate to afford the title compound as a white solid (30 mg, 28.1%). MS(ES)+ m/e 414.2 [M+H]+.

Example 5

5-{[(3S)-1-(cyclopropylcarbonyl)-3-pyrrolidinyl]methyl}-4-(2',4'-dichloro-4-biphenylyl)-2,4-dihydro-3H-1,2,4-triazol-3-one

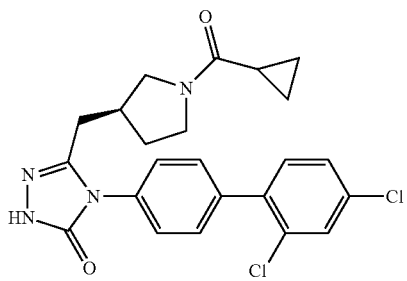 [SMILES: O=C(C1CC1)N1CC[C@@H](Cc2n[nH]c(=O)n2-c2ccc(-c3ccc(Cl)cc3Cl)cc2)C1]

A vial was charged with a slurry of 4-(4-bromophenyl)-5-{[(3S)-1-(cyclopropylcarbonyl)-3-pyrrolidinyl]methyl}-2,4-dihydro-3H-1,2,4-triazol-3-one (100 mg, 0.256 mmol), (2,4-dichlorophenyl)boronic acid (98 mg, 0.511 mmol), tetrakis(triphenylphosphine)palladium(0) (29.5 mg, 0.026 mmol) and tripotassium phosphate (217 mg, 1.022 mmol) in ethanol (4.0 mL) and water (4.00 mL) then purged with nitrogen and sealed with a standard teflon septa (crimped aluminum seal). The reaction was heated in an aluminum block at 110° C. for 2 h. The cooled reaction was diluted with ethanol then evaporated under reduced pressure to a yellow residue. The residue was triturated from methanol and the filtered methanol layer was purified by reverse phase HPLC (LUNA C-18: 30×50 mm column; 20-70% acetonitrile w/0.1% TFA/water w/0.1% TFA). The desired product fractions were combined and evaporated in vacuo to a residue that was recrystallized from hexanes/ethyl acetate to afford the title compound as a white solid (26 mg, 21.8%). MS(ES)+ m/e 457.0, 459.2 [M+H]+, chlorine pattern.

Example 6

5-{[(3S)-1-(cyclopropylcarbonyl)-3-pyrrolidinyl]methyl}-4-(4-imidazo[1,2-a]pyridin-7-ylphenyl)-2,4-dihydro-3H-1,2,4-triazol-3-one

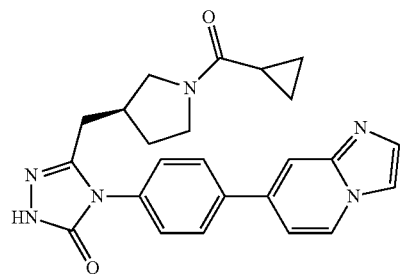 [SMILES: O=C(C1CC1)N1CC[C@@H](Cc2n[nH]c(=O)n2-c2ccc(-c3ccn4ccnc4c3)cc2)C1]

A vial was charged with a slurry of 4-(4-bromophenyl)-5-{[(3S)-1-(cyclopropylcarbonyl)-3-pyrrolidinyl]methyl}-2,4-dihydro-3H-1,2,4-triazol-3-one (100 mg, 0.256 mmol), imidazo[1,2-a]pyridin-7-ylboronic acid (83 mg, 0.511 mmol), tetrakis(triphenylphosphine)palladium(0) (29.5 mg, 0.026 mmol) and tripotassium phosphate (217 mg, 1.022 mmol) in absolute ethanol (5.0 mL) and water (5.00 mL) then purged with nitrogen and sealed with a standard teflon septa (crimped aluminum seal). The reaction was then heated in an aluminum block at 95° C. for 6 h. The resulting yellow solution was evaporated in vacuo to a residue that was triturated in DMSO, filtered through a nylon syringe adapter, then purified by reverse phase HPLC (LUNA C-18: 30×50 mm column; 10-40% acetonitrile w/0.1% TFA/water w/0.1% TFA). The desired product fractions were combined, treated with saturated aqueous sodium bicarbonate and evaporated to a residue that was slurried in 5% MeOH in dichloromethane and filtered through a short pad of silica (~2 g). The filtrate was evaporated in vacuo to afford the title compound as a tan solid (56 mg, 48.6%). MS(ES)+ m/e 429.0 [M+H]+.

Example 7

4-[4-(1-benzofuran-5-yl)phenyl]-5-{[(3S)-1-(cyclopropylcarbonyl)-3-pyrrolidinyl]methyl}-2-methyl-2,4-dihydro-3H-1,2,4-triazol-3-one

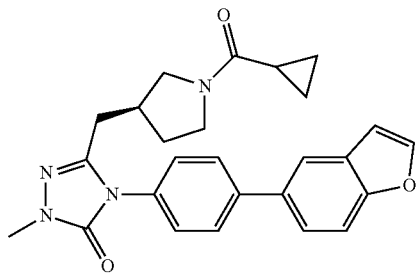 [SMILES: Cn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (85 mg, 0.198 mmol) in N,N-dimethylformamide (1 mL) in a 5 mL microwaveable vial was added potassium carbonate (55 m mg, 0.398 mmol, 2 eq) and methyl iodide (2M in t-butylmethyl ether, 0.100 mL, 1 eq). The reaction vial was capped, purged with nitrogen gas, and stirred for 16 h at 80° C. Analysis by LC/MS displayed the reaction had progress by 70%. An additional 0.050 mL of 2M solution of methyl iodide was added and the reaction mixture was stirred at 80° C. for 6 h. Analysis by LC/MS displayed the reaction had progress by 95%. The reaction mixture was cooled to room temperature and then poured into a mixture of dichloromethane and water. The organic layer was separated. The aqueous layer was washed with dichloromethane. The organic extracts were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 23-55% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (37 mg, 42%). MS(ES)+ m/e 443.2 [M+H]+.

Example 8

(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetic Acid

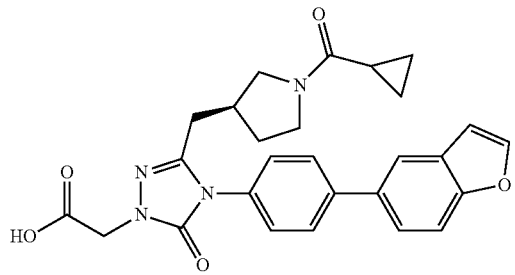 [SMILES: O=C(O)Cn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (50 mg, 0.117 mmol) in N,N-dimethylformamide (1 mL) in a 5 mL microwaveable vial was added potassium carbonate (80 mg, 0.58 mmol, 5 eq) and tert-butylchloroacetate (21 mg, 0.14 mmol, 1.2 eq). The vial was capped, purged with nitrogen gas, and stirred for 16 h at 80° C. Analysis by LC/MS displayed the reaction was complete. The reaction mixture was cooled to room temperature and then poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo to afford the crude intermediate ester (MS(ES)+ m/e 487.3 [M+H]+). In a 50 mL round bottom flask, the crude 1,1-dimethylethyl (4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetate was dissolved in 9 mL dichloromethane. Trifluoroacetic acid (1 mL, 12.98 mmol) was added to the solution, which was allowed to stir at room temperature for 16 h under a nitrogen bubbler. Analysis by LC/MS displayed the reaction complete. The reaction was concentrated to dryness and the residue was purified by reverse phase HPLC (LUNA C-18: 30×50 mm column; 10-75% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (32 mg, 56%). MS(ES)+ m/e 487.3 [M+H]+.

Example 9

4-[4-(1-benzofuran-5-yl)phenyl]-5-{[(3S)-1-(cyclopropylcarbonyl)-3-pyrrolidinyl]methyl}-2-(1-methylethyl)-2,4-dihydro-3H-1,2,4-triazol-3-one

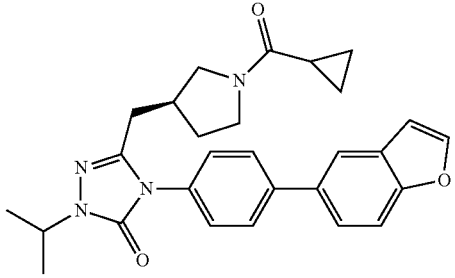 [SMILES: CC(C)n1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (60 mg, 0.14 mmol) in N,N-dimethylformamide (1 mL) in a 5 mL microwaveable vial was added potassium carbonate (60 mg, 0.434 mmol, 3.1 eq) and 2-iodopropane (34 mg, 0.200 mmol, 1.4 eq). The vial was capped and purged with nitrogen gas, and the reaction was stirred for 16 h at 80° C. Analysis by LC/MS displayed the reaction had progressed only 15%. To the reaction mixture was added another equivalent of 2-iodopropane and the solution was irradiated in the microwave at 160° C. for 30 min. Analysis by LC/MS displayed the reaction had progressed to 35% completion. The reaction mixture was subjected to several iterations of microwave conditions, increasing the reaction temperature and reaction time, until the final conditions of 180° C. for 3 h was reached. It was determined via analysis by LC/MS that the reaction had proceeded to 90% completion. The reaction mixture was poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 25-65% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (18 mg, 27%). MS(ES)+ m/e 471.3 [M+H]$^+$.

Example 10

4-[4-(1-benzofuran-5-yl)phenyl]-5-{[(3S)-1-(cyclopropylcarbonyl)-3-pyrrolidinyl]methyl}-2-[2-(methyloxy)ethyl]-2,4-dihydro-3H-1,2,4-triazol-3-one

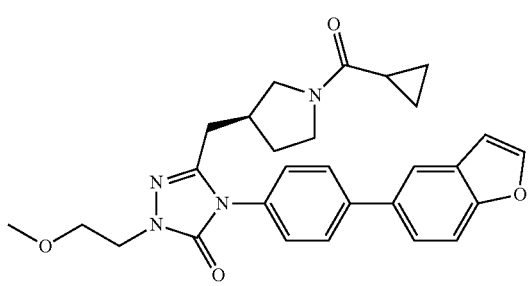 [SMILES: COCCn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (60 mg, 0.14 mmol) in N,N-dimethylformamide (1 mL) in a 5 mL microwaveable vial was added potassium carbonate (60 mg, 0.434 mmol, 3.1 eq) and 2-chloroethyl methyl ether (21 mg, 0.220 mmol, 1.5 eq). The vial was capped and purged with nitrogen gas, and the reaction mixture was stirred for 16 h at 80° C. Analysis by LC/MS displayed the reaction had progressed to 80% completion. The reaction mixture was cooled to room temperature and poured into a mixture of dichloromethane and water. The aqueous layer was separated. The aqueous layer was washed with dichloromethane. The organic extracts were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 25-65% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (24 mg, 33%). MS(ES)+ m/e 487.3 [M+H]$^+$.

Example 11 methyl (4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetate

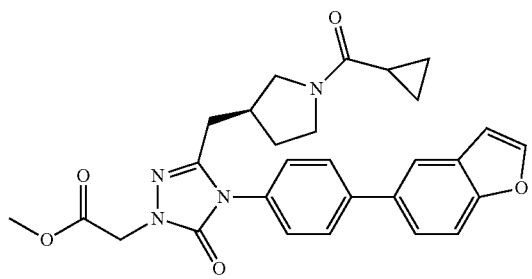 [SMILES: COC(=O)Cn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (55 mg, 0.128 mmol) in N,N-dimethylformamide (1 mL) in a 5 mL microwaveable vial was added potassium carbonate (60 mg, 0.434 mmol, 3.3 eq) and methyl chloroacetate (25 mg, 0.227 mmol, 1.7 eq). The vial was capped and purged with nitrogen gas, and the reaction mixture was stirred for 16 h at 80° C. Analysis by LC/MS displayed the reaction had gone to completion. The reaction mixture was cooled to room temperature and poured into a mixture of dichloromethane and water. The organic layer was separated. The aqueous layer was washed with dichloromethane. The organic extracts were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 20-55% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (37 mg, 57%). MS(ES)+ m/e 501.1 [M+H]$^+$.

Example 12

4-[4-(1-benzofuran-5-yl)phenyl]-5-{[(3S)-1-(cyclopropylcarbonyl)-3-pyrrolidinyl]methyl}-2-(2-hydroxyethyl)-2,4-dihydro-3H-1,2,4-triazol-3-one

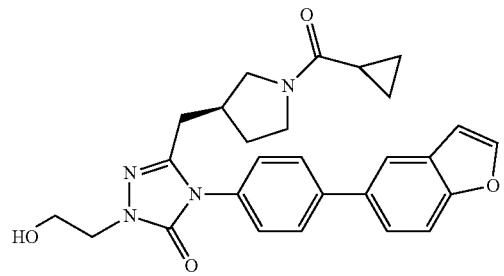 [SMILES: O=C(C1CC1)N1CC[C@@H](Cc2nn(CCO)c(=O)n2-c2ccc(-c3ccc4occc4c3)cc2)C1]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (55 mg, 0.128 mmol) in N,N-dimethylformamide (1 mL) in a 5 mL microwaveable vial was added potassium carbonate (60 mg, 0.434 mmol, 3.3 eq) and 2-chloroethanol (24 mg, 0.299 mmol, 2.3 eq). The vial was capped and purged with nitrogen gas, and the reaction mixture was stirred for 16 h at 80° C. Analysis by LC/MS displayed the reaction had gone to completion. The reaction mixture was cooled to room temperature and poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 20-55% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (41 mg, 67%). MS(ES)+ m/e 473.2 [M+H]+.

Example 13

5-{[(3S)-1-(cyclopropylcarbonyl)-3-pyrrolidinyl]methyl}-4-[4-(1H-indol-4-yl)phenyl]-2,4-dihydro-3H-1,2,4-triazol-3-one

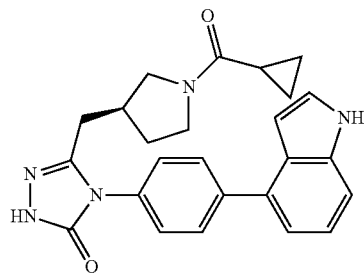 [SMILES: O=C(C1CC1)N1CC[C@@H](Cc2n[nH]c(=O)n2-c2ccc(-c3cccc4[nH]ccc34)cc2)C1]

a) A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in dioxane (2 mL) was treated with 1H-indol-4-ylboronic acid (0.386 mmol), dichloro[1,1'-bis(diphenylphosphino)ferrocene]palladium(II)-dichloromethane adduct (10.4 mg), and 2M aq potassium carbonate (0.511 mmol). The reaction mixture was purged with nitrogen, sealed, and stirred at 100° C. overnight. The reaction mixture was cooled to room temperature and was diluted with water (50 mL). The aqueous layer was acidified to pH ~4 using 1N aq HCl and was extracted with dichloromethane. The organic layer was dried over magnesium sulfate, filtered, and concentrated in vacuo. The brown residue was purified by reverse phase HPLC (LUNA C-18: 30×50 mm column; 20-40% acetonitrile w/0.1% TFA/water w/0.1% TFA). The combined product fractions were neutralized with the addition of saturated aq sodium bicarbonate, concentrated under reduced pressure, and extracted with dichloromethane. The combined organic layers were dried over magnesium sulfate, filtered, and concentrated in vacuo. Further purification of the resulting solid by flash chromatography (0-7% methanol/dichloromethane) gave the title compound as a white amorphous solid (55 mg, 48% yield). MS(ES)+ m/e 428.0 [M+H]+.

Example 14

4-[4-(1-benzofuran-6-yl)phenyl]-5-{[(3S)-1-(cyclopropylcarbonyl)-3-pyrrolidinyl]methyl}-2,4-dihydro-3H-1,2,4-triazol-3-one

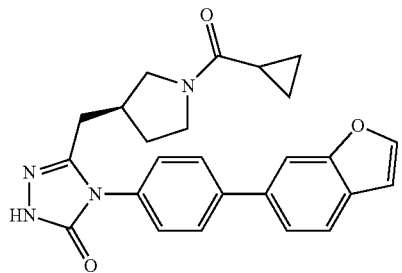 [SMILES: O=C(C1CC1)N1CC[C@@H](Cc2n[nH]c(=O)n2-c2ccc(-c3ccc4ccoc4c3)cc2)C1]

a) 5-{[(3S)-1-(cyclopropylcarbonyl)-3-pyrrolidinyl]methyl}-4-[4-(4,4,5,5-tetramethyl 1,3,2-dioxaborolan-2-yl)phenyl]-2,4-dihydro-3H-1,2,4-triazol-3-one A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in dioxane (2 mL) was treated with bis(pinocolato)diboron (0.268 mmol), dichloro[1,1'-bis(diphenylphosphino)ferrocene]palladium(II)-dichloromethane adduct (10.4 mg) and potassium acetate (0.639 mmol). The black reaction mixture was purged with nitrogen, sealed, and stirred at 100° C. for six h. The reaction mixture was then cooled to room temperature, diluted with ethyl acetate (20 mL), and was filtered through Celite. The filtrate was concentrated to dryness in vacuo to afford the crude title compound as a brown solid (quantitative). No further purification was carried out and the product was used as is. MS(ES)+ m/e 439.0 [M+H]+ (boronic ester partially hydrolyzes to free acid with MS(ES)+ m/e 357.0 [M+H]+ on LC/MS).

b) 4-[4-(1-benzofuran-6-yl)phenyl]-5-{[(3S)-1-(cyclopropylcarbonyl)-3-pyrrolidinyl]methyl}-2,4-dihydro-3H-1,2,4-triazol-3-one A solution of 5-{[(3S)-1-(cyclopropylcarbonyl)-3-pyrrolidinyl]methyl}-4-[4-(4,4,5,5-tetramethyl-1,3,2-dioxaborolan-2-yl)phenyl]-2,4-dihydro-3H-1,2,4-triazol-3-one (0.235 mmol) in dioxane (1.5 mL) was treated with 1-benzofuran-6-yl trifluoromethanesulfonate (0.230 mmol), dichloro[1,1'-bis(diphenylphosphino)ferrocene]palladium(II)-dichloromethane adduct (11.5 mg), and 2M aq potassium carbonate (0.705 mmol). The reaction mixture was purged with nitrogen, sealed, and stirred at 100° C. overnight. The reaction mixture was cooled to room temperature and was diluted with water (50 mL). The aqueous layer was acidified to pH ~4 using 1N aq HCl and was extracted with dichloromethane. The organic layer was dried over magnesium sulfate, filtered, and concentrated in vacuo. The crude residue was purified by flash chromatography (0-8% methanol/dichloromethane), followed by purification by reverse phase HPLC (LUNA C-18: 30×50 mm column; 20-45% acetonitrile w/0.1% TFA/ water w/0.1% TFA). The combined product fractions were neutralized with the addition of saturated aqueous sodium bicarbonate, concentrated under reduced pressure, and extracted with dichloromethane. The combined organic layers were dried over magnesium sulfate, filtered, and concentrated in vacuo to afford the title compound as an off-white amorphous solid (16 mg, 15% yield). MS(ES)+ m/e 428.9 [M+H]+.

Example 15

N'-[4'-(3-{[(3S)-1-(cyclopropylcarbonyl)-3-pyrrolidinyl]methyl}-5-oxo-1,5-dihydro-4H-1,2,4-triazol-4-yl)-3-biphenylyl]-N,N-dimethylsulfamide

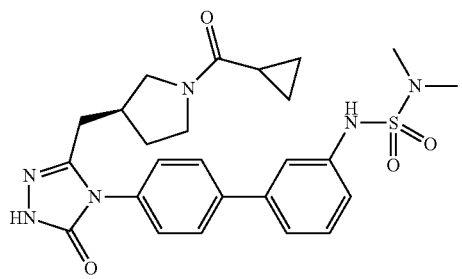 [SMILES: CN(C)S(=O)(=O)Nc1cccc(-c2ccc(-n3c(C[C@@H]4CCN(C(=O)C5CC5)C4)n[nH]c3=O)cc2)c1]

a) Following the procedure described in Example 13a with (3-{[(dimethylamino)sulfonyl]amino}phenyl)boronic acid (1.05 eq) provided the title compound as a white solid (37%). Reverse phase HPLC (LUNA C-18: 30×50 mm column; 5-25% acetonitrile w/0.1% TFA/water w/0.1% TFA) was utilized in purifying this compound. MS(ES)+ m/e 511.2 [M+H]+.

Example 16

5-{[(3S)-1-(cyclopropylcarbonyl)-3-pyrrolidinyl]methyl}-4-[4-(3-methyl-1-benzofuran-5-yl)phenyl]-2,4-dihydro-3H-1,2,4-triazol-3-one

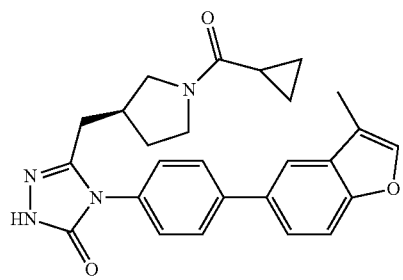 [SMILES: Cc1coc2ccc(-c3ccc(-n4c(C[C@@H]5CCN(C(=O)C6CC6)C5)n[nH]c4=O)cc3)cc12]

a) [(2-acetyl-4-bromophenyl)oxy]acetic Acid

A solution of 1-(5-bromo-2-hydroxyphenyl)ethanone (9.53 mmol) in water (70 mL) was treated with chloroacetic acid (11.64 mmol) and a solution of NaOH (21.25 mmol) in water (20 mL). The resulting yellow suspension was flushed with N₂ and stirred at reflux overnight. Analysis by LCMS indicated the consumption of starting material and desired product formation. The reaction was cooled to room temperature and then acidified to pH~3 with 1N aq HCl. The mixture was then cooled to 0° C. resulting in precipitate formation. A grey sticky solid was filtered and used without further purification. MS(ES)+ m/e 273/275 [M+H]+ (bromide isotope pattern).

b) 5-bromo-3-methyl-1-benzofuran

A solution of [(2-acetyl-4-bromophenyl)oxy]acetic acid (1.648 mmol) in acetic acid (2.075 mL) was treated with sodium acetate (9.89 mmol) and acetic anhydride (21.42 mmol). The reaction solution was heated with stirring to 140° C. for 3.5 h. Analysis by LCMS showed a major product that did not ionize, and consumption of starting material. The mixture was diluted with water and ethyl acetate and was washed with 1N aq NaOH until the aqueous phase was basic (pH~12). The mixture was extracted with ethyl acetate. The combined organic layers were washed with brine, dried over sodium sulfate, filtered, and concentrated to an oil in vacuo. No further purification was carried out. ¹H NMR (400 MHz, chloroform-d) δ ppm 7.67 (d, J=1.77 Hz, 1H) 7.38-7.45 (m, 2H) 7.32-7.38 (m, 1H) 2.24 (d, J=1.26 Hz, 3H).

c) 5-{[(3S)-1-(cyclopropylcarbonyl)-3-pyrrolidinyl]methyl}-4-[4-(3-methyl-1-benzofuran-5-yl)phenyl]-2,4-dihydro-3H-1,2,4-triazol-3-one Following the procedure described in Example 14b with 5-bromo-3-methyl-1-benzofuran provided the title compound as an off-white solid (33%). Reverse phase HPLC (LUNA C-18: 30×50 mm column; 15-45% acetonitrile w/0.1% TFA/water w/0.1% TFA) was utilized in purifying this compound. MS(ES)+ m/e 443.1 [M+H]+.

Example 17

5-{[(3S)-1-(cyclopropylcarbonyl)-3-pyrrolidinyl]methyl}-4-[4-(1H-indol-5-yl)phenyl]-2,4-dihydro-3H-1,2,4-triazol-3-one

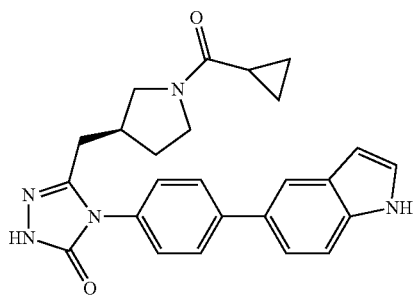 [SMILES: O=C(C1CC1)N1CC[C@@H](Cc2n[nH]c(=O)n2-c2ccc(-c3ccc4[nH]ccc4c3)cc2)C1]

a) Following the procedure described in Example 13a with 5-(4,4,5,5-tetramethyl-1,3,2-dioxaborolan-2-yl)-1H-indole (1.05 eq) provided the title compound as a pink solid (45%).

Reverse phase HPLC (LUNA C-18: 30×50 mm column; 15-35% acetonitrile w/0.1% TFA/water w/0.1% TFA) was utilized in purifying this compound. MS(ES)+ m/e 428.0 [M+H]+.

Example 18

5-{[(3S)-1-(cyclopropylcarbonyl)-3-pyrrolidinyl]methyl}-4-[4-(2-methyl-1H-benzimidazol-5-yl)phenyl]-2,4-dihydro-3H-1,2,4-triazol-3-one

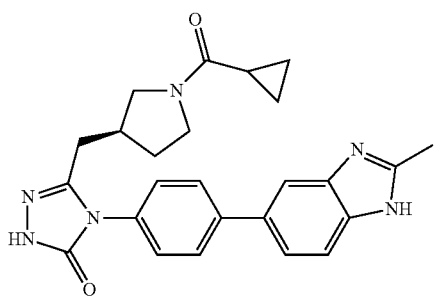

a) Following the procedure described in Example 14b with 5-bromo-2-methyl-1H-benzimidazole provided the title compound. However, the title compound was only slightly soluble in dichloromethane, so the completed reaction mixture was cooled to room temperature and diluted with water (50 mL). The aqueous layer was acidified to pH ~4 using 1N aq HCl and was concentrated to dryness in vacuo. The crude material was triturated with methanol, filtered and concentrated to dryness in vacuo. The crude brown residue was then purified by reverse phase HPLC (Gilson, Xbridge C-18: 19×100 mm column; 0-35% acetonitrile/water+0.1% NH₄OH) to afford the title compound as an off-white solid (19%). MS(ES)+ m/e 443.2 [M+H]+.

Example 19

5-{[(3S)-1-(cyclopropylcarbonyl)-3-pyrrolidinyl]methyl}-4-[4-(2,3-dihydro-1H-indol-5-yl)phenyl]-2,4-dihydro-3H-1,2,4-triazol-3-one

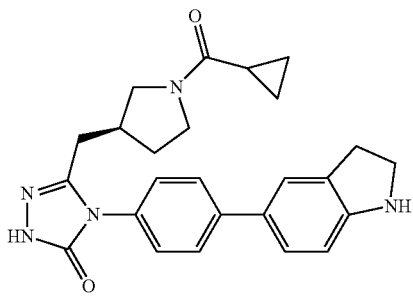 [SMILES: O=C(C1CC1)N1CC[C@@H](Cc2n[nH]c(=O)n2-c2ccc(-c3ccc4c(c3)CCN4)cc2)C1]

a) Following the procedure described in Example 14b with 5-bromo-2,3-dihydro-1H-indole provided the title compound as a white solid (18%). Silica gel chromatography (0-9% methanol/dichloromethane) and reverse phase HPLC (LUNA C-18: 30×50 mm column; 0-25% acetonitrile w/0.1% TFA/water w/0.1% TFA) were utilized in purifying this compound. MS(ES)+ m/e 430.1 [M+H]+.

Example 20

5-{[(3S)-1-(cyclopropylcarbonyl)-3-pyrrolidinyl]methyl}-4-(4-imidazo[1,5-a]pyridin-5-ylphenyl)-2,4-dihydro-3H-1,2,4-triazol-3-one

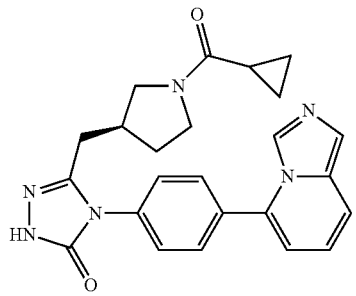 [SMILES: O=C(C1CC1)N1CC[C@@H](Cc2n[nH]c(=O)n2-c2ccc(-c3cccc4cncn34)cc2)C1]

a) Following the procedure described in Example 14b with 5-bromoimidazo[1,5-a]pyridine provided the title compound as an off-white solid (22%). Reverse phase HPLC (LUNA C-18: 30×50 mm column; 0-25% acetonitrile w/0.1% TFA/water w/0.1% TFA) was utilized in purifying this compound. MS(ES)+ m/e 429.0 [M+H]+.

Example 21

2-(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetamide

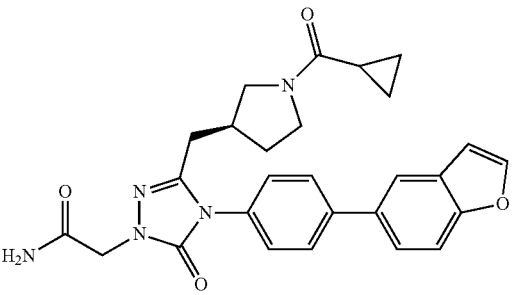 [SMILES: NC(=O)Cn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (50 mg, 0.117 mmol) in N,N-dimethylformamide (1 mL) in a 5 mL microwaveable vial was added potassium carbonate (50 mg, 0.362 mmol, 3.1 eq) and 2-chloroacetamide (16 mg, 0.175 mmol, 1.5 eq). The vial was capped and purged with nitrogen gas, and the reaction mixture was stirred for 16 h at 80° C. Analysis by LC/MS displayed the reaction had gone to completion. The reaction mixture was cooled to room temperature and poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 20-50% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (25 mg, 44%). MS(ES)+ m/e 486.2 [M+H]+.

Example 22

(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)acetonitrile

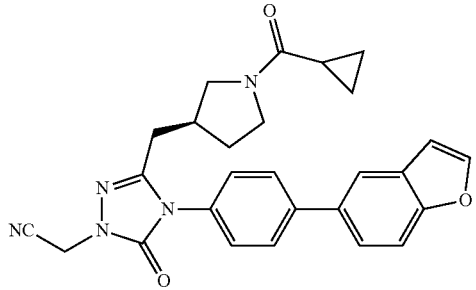 [SMILES: N#CCn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (55 mg, 0.128 mmol) in N,N-dimethylformamide (1 mL) in a 5 mL microwaveable vial was added potassium carbonate (70 mg, 0.51 mmol, 4 eq) and chloroacetonitrile (17 mg, 0.231 mmol, 1.8 eq). The vial was capped and purged with nitrogen gas, and the reaction mixture was stirred for 16 h at 80° C. Analysis by LC/MS displayed the reaction was complete. The reaction mixture was cooled to room temperature and poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 25-60% acetonitrile w/0.1% TFA/ water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (29 mg, 48%). MS(ES)+ m/e 468.2 [M+H]+.

Example 23

5-{[(3S)-1-(cyclopropylcarbonyl)-3-pyrrolidinyl]methyl}-4-[4-(1-methyl-1H-benzimidazol-5-yl)phenyl]-2,4-dihydro-3H-1,2,4-triazol-3-one

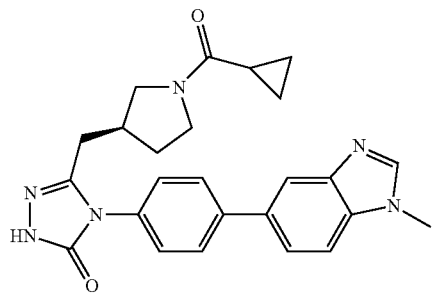 [SMILES: Cn1cnc2cc(-c3ccc(-n4c(C[C@@H]5CCN(C(=O)C6CC6)C5)n[nH]c4=O)cc3)ccc21]

a) Following the procedure described in Example 14b with 5-bromo-1-methyl-1H-benzimidazole provided the title compound as an off-white solid (6%). Reverse phase HPLC (Gilson, Xbridge C-18: 19×100 mm column; 0-35% acetonitrile/water+0.1% NH4OH) was utilized in purifying this compound. MS(ES)+ m/e 443.2 [M+H]+.

Example 24

5-{[(3S)-1-(cyclopropylcarbonyl)-3-pyrrolidinyl] methyl}-4-[4-(1-methyl-1H-indol-5-yl)phenyl]-2,4-dihydro-3H-1,2,4-triazol-3-one

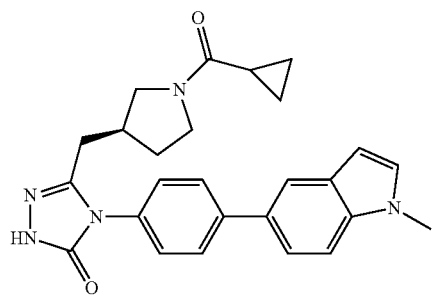 [SMILES: Cn1ccc2cc(-c3ccc(-n4c(C[C@@H]5CCN(C(=O)C6CC6)C5)n[nH]c4=O)cc3)ccc21]

a) 5-bromo-1-methyl-1H-indole

A solution of 5-bromo-1H-indole (1.530 mmol) in dimethyl sulfoxide (10 mL) was treated with NaOH (2.295 mmol) and stirred at room temperature for 30 min. The solution was then treated with methyl iodide (4.59 mmol) and was stirred for 3 days at room temperature. The solution was diluted with water (100 mL) and was extracted with ethyl acetate. The combined organic phases were washed with water, washed with brine, dried over magnesium sulfate, filtered, and concentrated in vacuo. The yellow oil was used without further purification. MS(ES)+ m/e 210/212 [M+H]+ (bromide isotope pattern).

b) 5-{[(3S)-1-(cyclopropylcarbonyl)-3-pyrrolidinyl] methyl}-4-[4-(1-methyl-1H-indol-5-yl)phenyl]-2,4-dihydro-3H-1,2,4-triazol-3-one Following the procedure described in Example 14b with 5-bromo-1-methyl-1H-indole provided the title compound as an off-white solid (28%). Reverse phase HPLC (LUNA C-18: 30×50 mm column; 0-10% acetonitrile w/0.1% TFA/water w/0.1% TFA) was utilized in purifying this compound. MS(ES)+ m/e 442.2 [M+H]+.

Example 25

2-(2-aminoethyl)-4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one

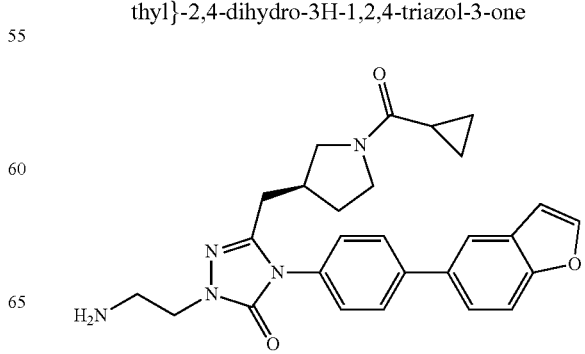

a) 2-[2-(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)ethyl]-1H-isoindole-1,3(2H)-dione To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (300 mg, 0.699 mmol) in N,N-dimethylformamide (3 mL) in a 5 mL microwaveable vial was added potassium carbonate (300 mg, 2.1 mmol, 3 eq) and N-(2-chloroethyl)phthalimide (300 mg, 1.43 mmol, 2 eq). The vial was capped and purged with nitrogen gas, and the reaction mixture was stirred for 16 h at 90° C. Analysis by LC/MS displayed the reaction had progressed to 20% completion. The reaction was irradiated in the microwave at 185° C. for 60 min. Analysis by LC/MS displayed the reaction was complete. The reaction mixture was poured into a mixture of dichloromethane and water. The organic layer was separated. The aqueous layer was washed with dichloromethane. The organic extracts were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 30-60% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the intermediate compound (142 mg, 33%). MS(ES)+ m/e 602.0 [M+H]+.

b) 2-(2-aminoethyl)-4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one To a 50 mL round bottom flask containing 2-[2-(4-[4-(1-benzofuran-5-yl)phenyl]-3-{[(3S)-1-(cyclopropylcarbonyl)-3-pyrrolidinyl]methyl}-5-oxo-4,5-dihydro-1H-1,2,4-triazol-1-yl)ethyl]-1H-isoindole-1,3(2H)-dione (130 mg, 0.216 mmol) was added hydrazine monohydrate (82 mg, 2.55 mmol, 11 eq). The flask was equipped with a condenser and the reaction was stirred at 60° C. for 1 h. Analysis by LC/MS displayed the phthalimide deprotection was complete. The reaction was cooled to room temperature and concentrated in vacuo. The residue was purified by reverse phase HPLC (LUNA C-18: 30×50 mm column; 10-45% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (65 mg, 63%). MS(ES)+ m/e 472.2 [M+H]+.

Example 26

5-{[(3S)-1-(cyclopropylcarbonyl)-3-pyrrolidinyl]methyl}-4-[4-(3-methyl-1H-indol-5-yl)phenyl]-2,4-dihydro-3H-1,2,4-triazol-3-one

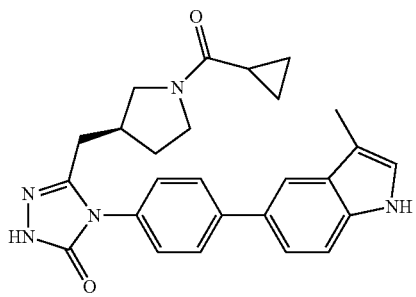 [SMILES: Cc1c[nH]c2ccc(-c3ccc(-n4c(C[C@@H]5CCN(C(=O)C6CC6)C5)n[nH]c4=O)cc3)cc12]

a) Following the procedure described in Example 14b with 5-bromo-3-methyl-1H-indole provided the title compound as an off-white solid (21%). Reverse phase HPLC (Gilson, Xbridge C-18:19×100 mm column; 20-50% acetonitrile/water+0.1% NH4OH) was utilized in purifying this compound. MS(ES)+ m/e 442.2 [M+H]+.

Example 27

5-{[(3S)-1-(cyclopropylcarbonyl)-3-pyrrolidinyl]methyl}-4-[4-(2-methyl-1-benzofuran-5-yl)phenyl]-2,4-dihydro-3H-1,2,4-triazol-3-one

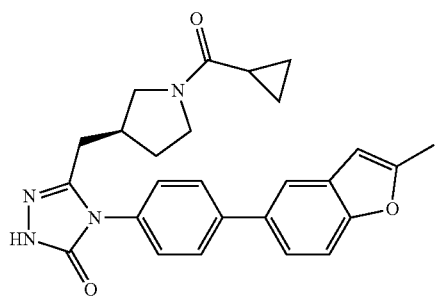 [SMILES: Cc1cc2cc(-c3ccc(-n4c(C[C@@H]5CCN(C(=O)C6CC6)C5)n[nH]c4=O)cc3)ccc2o1]

a) 2-[(4-bromo-2-formylphenyl)oxy]propanoic Acid

A solution of 5-bromo-2-hydroxybenzaldehyde (4.97 mmol) in acetonitrile (30 mL) was treated with potassium carbonate (14.92 mmol) and ethyl 2-bromopropanoate (5.97 mmol). The resulting mixture was stirred at room temperature overnight. Analysis by LCMS indicated the formation of the desired intermediate ester, and the reaction mixture was concentrated to dryness in vacuo. The crude material was dissolved in a 3:1 methanol:water mixture (20 mL) and was heated to 50° C. with stirring. The reaction was then cooled to room temperature and was acidified to pH~3 using 1N aq HCl. The methanol was removed in vacuo and the resulting aqueous suspension was diluted with water (100 mL). The solution was extracted with dichloromethane. The combined organic layers were washed with brine, dried over magnesium sulfate, filtered, and concentrated in vacuo. The resulting beige solid was used without further purification (1.38 grams, 80% yield). MS(ES)+ m/e 273/275 [M+H]+ (bromide isotope pattern).

b) 5-bromo-2-methyl-1-benzofuran

A solution of 2-[(4-bromo-2-formylphenyl)oxy]propanoic acid (5.08 mmol) in acetic anhydride (6 mL) was treated with sodium acetate (15.25 mmol). The resulting solution was heated to reflux and stirred overnight. The brown reaction solution was allowed to cool to room temperature, and was diluted with toluene (10 mL). The solution was then treated with 1N aq NaOH (10 mL) and was stirred at room temperature for 20 min. The solution was then further diluted with water (50 mL) and was extracted using ethyl acetate. The combined organic layers were dried over magnesium sulfate, filtered, and concentrated in vacuo. The resulting brown residue was purified by flash chromatography (hexanes), affording the title compound as a clear oil (660 mg, 62% yield). 1H NMR (400 MHz, DMSO-d6) δ ppm 7.73 (d, J=2.02 Hz, 1H) 7.47 (d, J=8.59 Hz, 1H) 7.35 (dd, J=8.72, 2.15 Hz, 1H) 6.58 (s, 1H) 2.45 (d, J=1.01 Hz, 3H).

c) 5-{[(3S)-1-(cyclopropylcarbonyl)-3-pyrrolidinyl]methyl}-4-[4-(2-methyl-1-benzofuran-5-yl)phenyl]-2,4-dihydro-3H-1,2,4-triazol-3-one Following the procedure described in Example 14b with 5-bromo-2-methyl-1-benzofuran provided the title compound as an off-white solid (14%). Reverse phase HPLC (Gilson, Xbridge C-18:19×100 mm column; 20-50% acetonitrile/water+0.1% NH₄OH) was utilized in purifying this compound. MS(ES)+ m/e 443.2 [M+H]⁺.

Example 28

5-{[(3S)-1-(cyclopropylcarbonyl)-3-pyrrolidinyl]methyl}-4-[4-(2-methyl-1H-indol-5-yl)phenyl]-2,4-dihydro-3H-1,2,4-triazol-3-one

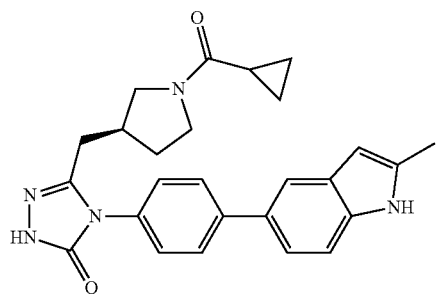 [SMILES: Cc1cc2cc(-c3ccc(-n4c(C[C@@H]5CCN(C(=O)C6CC6)C5)n[nH]c4=O)cc3)ccc2[nH]1]

a) Following the procedure described in Example 14b with 5-bromo-2-methyl-1H-indole provided the title compound as an off-white solid (25%). Reverse phase HPLC (Gilson, Xbridge C-18:19×100 mm column; 20-50% acetonitrile/water+0.1% NH₄OH) and flash chromatography (0-8% methanol/dichloromethane) were utilized in purifying this compound. MS(ES)+ m/e 442.2 [M+H]⁺.

Example 29

4-[4-(1-benzofuran-5-yl)phenyl]-5-{[(3S)-1-(cyclopropylcarbonyl)-3-pyrrolidinyl]methyl}-2-(2-hydroxy-2-methylpropyl)-2,4-dihydro-3H-1,2,4-triazol-3-one

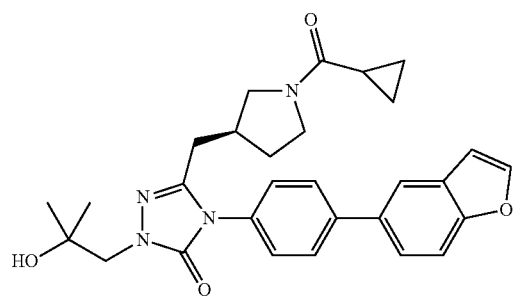 [SMILES: CC(C)(O)Cn1nc(C[C@@H]2CCN(C(=O)C3CC3)C2)n(-c2ccc(-c3ccc4occc4c3)cc2)c1=O]

a) To a solution of 4-[4-(1-benzofuran-5-yl)phenyl]-5-{[(3S)-1-(cyclopropylcarbonyl)-3-pyrrolidinyl]methyl}-2,4-dihydro-3H-1,2,4-triazol-3-one (100 mg, 0.233 mmol) in N,N-dimethylformamide (1 mL) in a 5 mL microwaveable vial was added potassium carbonate (100 mg, 0.724 mmol, 3.1 eq) and 1-chloro-2-methyl-2-propanol (50 mg, 0.461 mmol, 2 eq). The vial was capped and purged with nitrogen gas, and the reaction mixture was stirred for 16 h at 80° C. Analysis by LC/MS displayed no reaction. The solution was then irradiated in the microwave at 185° C. for 60 min. Analysis by LC/MS displayed the reaction was complete. The reaction mixture was poured into a mixture of dichloromethane and water. The organic layer was separated. The aqueous layer was washed with dichloromethane. The organic extractions were combined and washed 3× with a dilute brine solution. The organic layer was separated, dried over sodium sulfate, filtered, and concentrated in vacuo. The crude product was purified by reverse phase HPLC (LUNA C-18: 30×50 mm column; 25-55% acetonitrile w/0.1% TFA/water w/0.1% TFA). The product fractions were neutralized with the addition of saturated aq sodium bicarbonate, combined, and extracted with dichloromethane. The organic layer was dried over sodium sulfate, filtered, and concentrated in vacuo to afford the title compound (56 mg, 48%). MS(ES)+ m/e 501.1 [M+H]⁺.

Example 30

5-{[(3S)-1-(cyclopropylcarbonyl)-3-pyrrolidinyl]methyl}-4-[2-fluoro-4-(1H-indol-6-yl)phenyl]-2,4-dihydro-3H-1,2,4-triazol-3-one

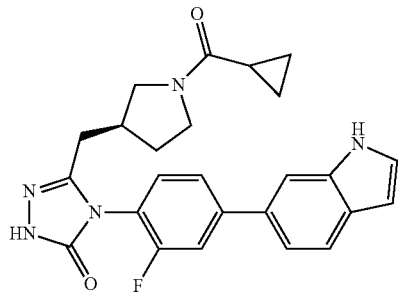

a) Following the procedure described in Example 32d with 1H-indol-6-ylboronic acid (1.0 eq) provided the title compound as an off-white solid (58%). Reverse phase HPLC (Gilson, Xbridge C-18:19×100 mm column; 25-50% acetonitrile/water+0.1% NH₄OH) was utilized in purifying this compound. MS(ES)+ m/e 446.2 [M+H]⁺.

Example 31

5-{[(3S)-1-(cyclopropylcarbonyl)-3-pyrrolidinyl]methyl}-4-[2-fluoro-4-(1H-indol-5-yl)phenyl]-2,4-dihydro-3H-1,2,4-triazol-3-one

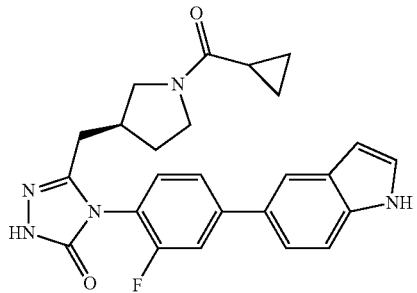 [SMILES: O=C(C1CC1)N1CC[C@@H](Cc2n[nH]c(=O)n2-c2ccc(-c3ccc4[nH]ccc4c3)cc2F)C1]

a) Following the procedure described in Example 32d with 5-(4,4,5,5-tetramethyl-1,3,2-dioxaborolan-2-yl)-1H-indole provided the title compound as an off-white solid (45%). Reverse phase HPLC (Gilson, Xbridge C-18:19×100 mm column; 25-50% acetonitrile/water+0.1% NH$_4$OH) was utilized in purifying this compound. MS(ES)+ m/e 446.3 [M+H]$^+$.

Example 32

4-[4-(1-benzofuran-5-yl)-2-fluorophenyl]-5-{[(3S)-1-(cyclopropylcarbonyl)-3-pyrrolidinyl]methyl}-2,4-dihydro-3H-1,2,4-triazol-3-one

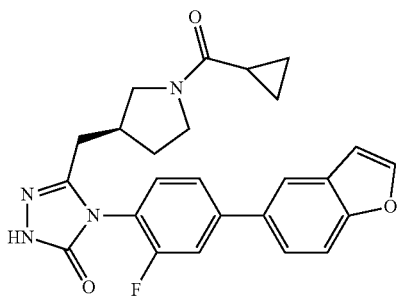 [SMILES: O=C(C1CC1)N1CC[C@@H](Cc2n[nH]c(=O)n2-c2ccc(-c3ccc4occc4c3)cc2F)C1]

a) 1,1-dimethylethyl (3S)-3-(2-hydrazino-2-oxoethyl)-1-pyrrolidinecarboxylate

A solution of ((3S)-1-{[(1,1-dimethylethyl)oxy]carbonyl}-3-pyrrolidinyl)acetic acid (5 g, 21.81 mmol) in diethyl ether (50 mL) was treated with N,N-dimethyl-4-pyridinamine (2.181 mmol), N-[3-(dimethylamino)propyl]-N'-ethylcarbodiimide(HCl) (23.99 mmol), and ethanol (48.0 mmol) and was stirred at room temperature overnight. Analysis by LCMS indicated that all starting material had converted to the desired methyl ester. The reaction contents were diluted with ether (100 mL) and washed with saturated aq NaHSO$_4$ solution, water, and brine. The organic phase was dried over magnesium sulfate, filtered and concentrated to dryness in vacuo. The resulting clear oil was dissolved in ethanol (25 mL), treated with hydrazine monohydrate (436 mmol), and was stirred overnight at 80° C. LCMS analysis indicated complete conversion of the intermediate. The reaction solution was concentrated to dryness in vacuo to afford the title compound as a clear oil (4.65 grams, 88% yield). No further purification was utilized. MS(ES)+ m/e 244.2 [M+H]$^+$.

b) 1,1-dimethylethyl (3S)-3-[2-(2-{[(4-bromo-2-fluorophenyl)amino]carbonyl}hydrazino)-2-oxoethyl]-1-pyrrolidinecarboxylate A solution of 1,1-dimethylethyl (3S)-3-(2-hydrazino-2-oxoethyl)-1-pyrrolidinecarboxylate (6.58 mmol) in dichloromethane (15 mL) was cooled to 0° C. and was treated drop-wise with 4-bromo-2-fluoro-1-isocyanatobenzene (6.58 mmol). The reaction was allowed to warm to room temperature, and after ~30 min a white solid had formed. The reaction contents were concentrated to dryness in vacuo. No further purification was carried out on the resulting white solid (3.01 grams, 100%). MS(ES)+ m/e 459/461 [M+H]$^+$ (bromide isotope pattern).

c) 4-(4-bromo-2-fluorophenyl)-5-{[(3S)-1-(cyclopropylcarbonyl)-3-pyrrolidinyl]methyl}-2,4-dihydro-3H-1,2,4-triazol-3-one A solution of 1,1-dimethylethyl (3S)-3-[2-(2-{[(4-bromo-2-fluorophenyl)amino]carbonyl}hydrazino)-2-oxoethyl]-1-pyrrolidinecarboxylate (3.59 mmol) in water (150 mL) was treated with potassium carbonate (17.96 mmol). The reaction was heated to reflux and was stirred overnight. A white solid had formed on the top of the aqueous solution. The reaction was allowed to cool to room temperature. Analysis by LCMS indicated complete consumption of the starting material and the mixture was concentrated to dryness in vacuo. The crude material was dissolved in dichloromethane (100 mL) and was treated with a solution of cyclopropanecarbonyl chloride (3.59 mmol) in dichloromethane (5 mL). After 30 min of stirring, LCMS analysis indicated that the intermediate amine had converted to a mixture of the desired product and a product that corresponded to bis-acylated product. The reaction solution was concentrated to dryness in vacuo and was dissolved in methanol (50 mL). The suspension was stirred at room temperature for 30 min. Analysis by LCMS indicated that the majority of the material now existed as a mixture of the desired product and the intermediate amine. Additional portions of cyclopropanecarbonyl chloride (3.59 mmol) were added to the reaction mixture twice (30 min apart). Analysis by LCMS indicated the complete conversion of the intermediate amine. The reaction mixture was diluted with water (100 mL) and acidified to pH~4 using 1N aq HCl. The methanol was removed in vacuo, and the resulting aqueous phase was extracted with ethyl acetate. The combined organic phases were washed with saturated aq sodium bicarbonate, washed with brine, dried over MgSO$_4$, filtered and concentrated in vacuo to dryness. The resulting solid was purified by flash chromatography (0-10% methanol/dichloromethane) to give the title compound as a white amorphous solid (850 mg, 58% yield). MS(ES)+ m/e 409/411 [M+H]$^+$ (bromide isotope pattern).

d) 4-[4-(1-benzofuran-5-yl)-2-fluorophenyl]-5-{[(3S)-1-(cyclopropylcarbonyl)-3-pyrrolidinyl]methyl}-2,4-dihydro-3H-1,2,4-triazol-3-one A solution of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol) in dioxane (1.5 mL) was treated with 5-(4,4,5,5-tetramethyl-1,3,2-dioxaborolan-2-yl)-1-benzofuran (0.269 mmol), dichloro[1,1'-bis(diphenylphosphino)ferrocene]palladium(II)-dichloromethane adduct (9.9 mg), and 2M aq potassium carbonate (0.733 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, filtered, and concentrated in vacuo. The brown residue was purified by reverse phase HPLC (Gilson, Xbridge C-18:19×100 mm column; 25-55% acetonitrile/water+0.1% NH$_4$OH). Product fractions were selected, combined and concentrated to dryness in vacuo to afford the title compound as a white amorphous solid (57 mg, 50% yield). MS(ES)+ m/e 447.2 [M+H]+.

Example 33

5-{[(3S)-1-(cyclopropylcarbonyl)-3-pyrrolidinyl] methyl}-4-[4-(7-methyl-1-benzofuran-5-yl)phenyl]-2,4-dihydro-3H-1,2,4-triazol-3-one

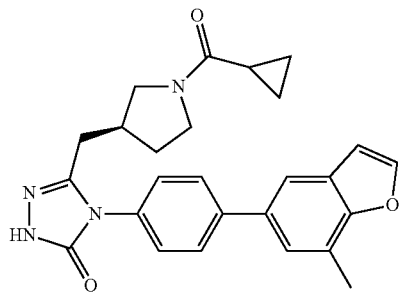 [SMILES: Cc1cc(-c2ccc(-n3c(C[C@@H]4CCN(C(=O)C5CC5)C4)n[nH]c3=O)cc2)cc2ccoc12]

a) [(4-chloro-2-formyl-6-methylphenyl)oxy]acetic Acid

A solution of 5-chloro-2-hydroxy-3-methylbenzaldehyde (5.86 mmol) in acetonitrile (30 mL) was treated with potassium carbonate (17.59 mmol). The reaction mixture was stirred for 30 min and was then treated with methyl bromoacetate (7.03 mmol). The resulting mixture was stirred at room temperature overnight. Analysis by LCMS indicated the formation of the desired intermediate ester, and the reaction mixture was concentrated to dryness in vacuo. The crude material was dissolved in a 3:1 methanol:water mixture (20 mL) and was heated to 50° C. with stirring. The reaction was then cooled to room temperature and was acidified to pH~3 using 1N aq HCl. The methanol was removed in vacuo and the resulting aqueous suspension was diluted with water (100 mL) and was extracted with dichloromethane. The combined organic layers were washed with brine, dried over magnesium sulfate, filtered, and concentrated in vacuo. The resulting beige solid was used without further purification (1.07 grams, 80% yield). MS(ES)+ m/e 229.1 [M+H]+.

b) 5-chloro-7-methyl-1-benzofuran

A solution of [(4-chloro-2-formyl-6-methylphenyl)oxy] acetic acid (4.69 mmol) in acetic anhydride (20 mL) was treated with sodium acetate (14.07 mmol). The resulting solution was heated to reflux and stirred for three days. The brown reaction solution was allowed to cool to room temperature, and was diluted with toluene (10 mL). The solution was then treated with 1N aq NaOH (10 mL) and was stirred at room temperature for 20 min. The solution was then further diluted with water (50 mL) and was extracted using ethyl acetate. The combined organic layers were dried over magnesium sulfate, filtered, and concentrated in vacuo. The resulting brown residue was purified by flash chromatography (hexanes) to provide the title compound as a clear oil (120 mg, 15% yield). 1H NMR (400 MHz, DMSO-$d_6$) δ ppm 8.07 (d, J=2.27 Hz, 1H) 7.55 (d, J=1.77 Hz, 1H) 7.20 (d, J=1.01 Hz, 1H) 6.94 (d, J=2.27 Hz, 1H) 2.47 (s, 3H).

c) 5-{[(3S)-1-(cyclopropylcarbonyl)-3-pyrrolidinyl] methyl}-4-[4-(7-methyl-1-benzofuran-5-yl)phenyl]-2,4-dihydro-3H-1,2,4-triazol-3-one Following the procedure described in Example 14b with 5-chloro-7-methyl-1-benzofuran (1.2 eq) and stirring for 3 days provided the title compound as an off-white solid (21%). Reverse phase HPLC (Gilson, Xbridge C-18:19×100 mm column; 20-50% acetonitrile/water+0.1% NH4OH) was utilized in purifying this compound. MS(ES)+ m/e 443.1 [M+H]+.

Example 34

5-{[(3S)-1-(cyclopropylcarbonyl)-3-pyrrolidinyl] methyl}-4-(4'-fluoro-4-biphenylyl)-2,4-dihydro-3H-1,2,4-triazol-3-one

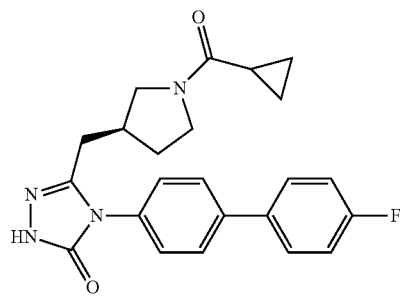 [SMILES: O=C(C1CC1)N1CC[C@@H](Cc2n[nH]c(=O)n2-c2ccc(-c3ccc(F)cc3)cc2)C1]

a) Following the procedure described in Example 13a with (4-fluorophenyl)boronic acid (1.1 eq) provided the title compound as a white solid (59%). Reverse phase HPLC (Gilson, Xbridge C-18: 19×100 mm column; 20-50% acetonitrile/water+0.1% NH4OH) was utilized in purifying this compound. MS(ES)+ m/e 407.2 [M+H]+.

Example 35

5-{[(3S)-1-(cyclopropylcarbonyl)-3-pyrrolidinyl] methyl}-4-[4-(6-quinolinyl)phenyl]-2,4-dihydro-3H-1,2,4-triazol-3-one

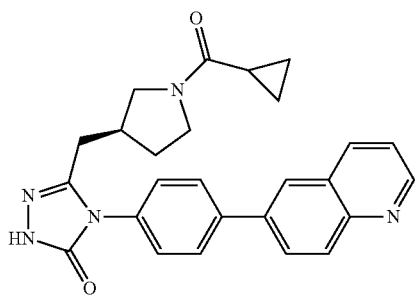 [SMILES: O=C(C1CC1)N1CC[C@@H](Cc2n[nH]c(=O)n2-c2ccc(-c3ccc4ncccc4c3)cc2)C1]

a) Following the procedure described in Example 13a with 6-(4,4,5,5-tetramethyl-1,3,2-dioxaborolan-2-yl)quinoline (1.0 eq) provided the title compound as a white solid (58%). Reverse phase HPLC (Gilson, Xbridge C-18: 19×100 mm column; 10-40% acetonitrile/water+0.1% NH$_4$OH) was utilized in purifying this compound. MS(ES)+ m/e 440.1 [M+H]$^+$.

Example 36

5-{[(3S)-1-(cyclopropylcarbonyl)-3-pyrrolidinyl]methyl}-4-[4-(1H-indazol-5-yl)phenyl]-2,4-dihydro-3H-1,2,4-triazol-3-one

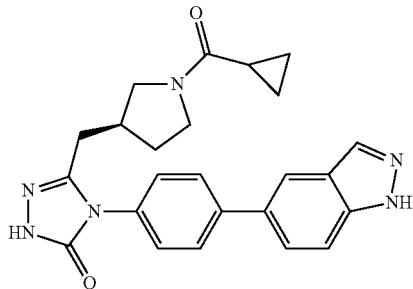 [SMILES: O=C(C1CC1)N1CC[C@@H](Cc2n[nH]c(=O)n2-c2ccc(-c3ccc4[nH]ncc4c3)cc2)C1]

a) Following the procedure described in Example 13a with 5-(4,4,5,5-tetramethyl-1,3,2-dioxaborolan-2-yl)-1H-indazole (1.0 eq) provided the title compound as an off-white amorphous solid (46%). Reverse phase HPLC (Gilson, Xbridge C-18: 19×100 mm column; 10-40% acetonitrile/water+0.1% NH$_4$OH) was utilized in purifying this compound. MS(ES)+ m/e 429.0 [M+H]$^+$.

Example 37

5-{[(3S)-1-(cyclopropylcarbonyl)-3-pyrrolidinyl]methyl}-4-[4-(2,3-dihydro-1-benzofuran-5-yl)phenyl]-2,4-dihydro-3H-1,2,4-triazol-3-one

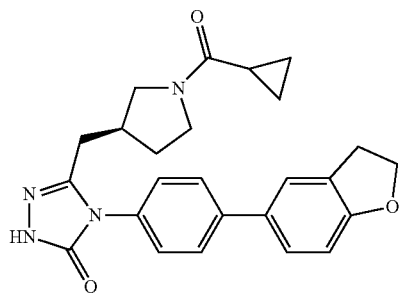

a) Following the procedure described in Example 13a with 2,3-dihydro-1-benzofuran-5-ylboronic acid (1.1 eq) provided the title compound as an off-white amorphous solid (54%). Reverse phase HPLC (Gilson, Xbridge C-18: 19×100 mm column; 20-50% acetonitrile/water+0.1% NH$_4$OH) was utilized in purifying this compound. MS(ES)+ m/e 431.1 [M+H]$^+$.

Example 38

4-[4-(1,3-benzodioxol-5-yl)phenyl]-5-{[(3S)-1-(cyclopropylcarbonyl)-3-pyrrolidinyl]methyl}-2,4-dihydro-3H-1,2,4-triazol-3-one

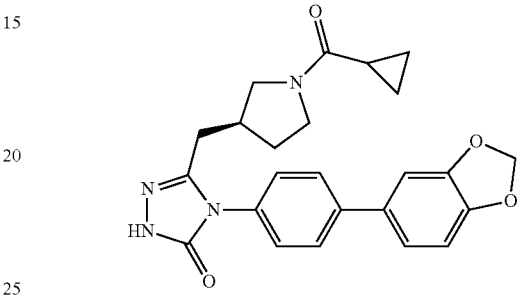

a) Following the procedure described in Example 13a with 1,3-benzodioxol-5-ylboronic acid, (1.1 eq) provided the title compound as an off-white amorphous solid (39%). Reverse phase HPLC (Gilson, Xbridge C-18: 19×100 mm column; 20-50% acetonitrile/water+0.1% NH$_4$OH) was utilized in purifying this compound. MS(ES)+ m/e 433.2 [M+H]$^+$.

Example 39

5-{[(3S)-1-(cyclopropylcarbonyl)-3-pyrrolidinyl]methyl}-4-[4'-(dimethylamino)-4-biphenylyl]-2,4-dihydro-3H-1,2,4-triazol-3-one

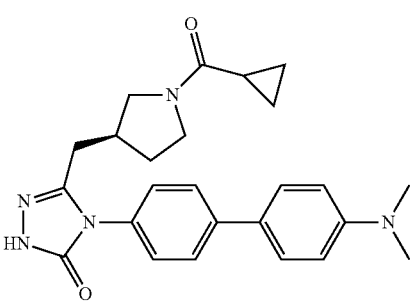 [SMILES: CN(C)c1ccc(-c2ccc(-n3c(C[C@@H]4CCN(C(=O)C5CC5)C4)n[nH]c3=O)cc2)cc1]

a) Following the procedure described in Example 13a with [4-(dimethylamino)phenyl]boronic acid (1.1 eq) provided the title compound as an off-white amorphous solid (63%).

Reverse phase HPLC (Gilson, Xbridge C-18: 19×100 mm column; 20-50% acetonitrile/water+0.1% NH$_4$OH) was utilized in purifying this compound. MS(ES)+ m/e 432.2 [M+H]$^+$.

Example 40

4-[4-(1-benzofuran-5-yl)-2-methylphenyl]-5-{[(3S)-1-(cyclopropylcarbonyl)-3-pyrrolidinyl]methyl}-2,4-dihydro-3H-1,2,4-triazol-3-one

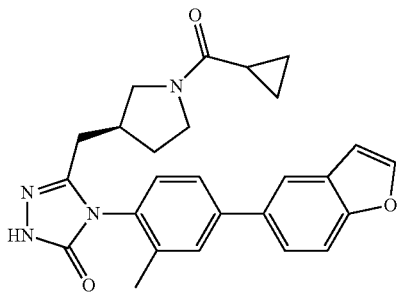 [SMILES: Cc1cc(-c2ccc3occc3c2)ccc1-n1c(C[C@@H]2CCN(C(=O)C3CC3)C2)n[nH]c1=O]

a) N-(4-Bromo-2-methylphenyl)-2-{[(3S)-1-(cyclopropylcarbonyl)-3-pyrrolidinyl]acetyl}hydrazinecarboxamide To a solution of 2-[(3S)-1-(cyclopropylcarbonyl)-3-pyrrolidinyl]acetohydrazide (800 mg, 3.79 mmol) in dry dichloromethane (5 mL) was added 4-bromo-1-isocyanato-2-methylbenzene (803 mg, 3.79 mmol). The reaction was allowed to progress for 1 h at room temperature (became a thick suspension that could not be stirred). The reaction mixture was diluted with dichloromethane (10 mL) and the precipitate was collected by filtration. A second crop was obtained by filtration and the two crops were combined, rinsed with minimal dichloromethane and dried to constant weight under high vacuum to provide the title product (1.54 g, 3.64 mmol, 96% yield) as a white solid. MS(ES)+ m/e 422.9 [M+H]$^+$. This material was 76% pure by LCMS (UV214) and was used as is in the next step.

b) 4-(4-Bromo-2-methylphenyl)-5-{[(3S)-1-(cyclopropylcarbonyl)-3-pyrrolidinyl]methyl}-2,4-dihydro-3H-1,2,4-triazol-3-one To a suspension of N-(4-bromo-2-methylphenyl)-2-{[(3S)-1-(cyclopropylcarbonyl)-3-pyrrolidinyl]acetyl}hydrazinecarboxamide (925 mg, 2.185 mmol) in water (45 mL) was added K$_2$CO$_3$ (1510 mg, 10.93 mmol). The reaction flask was equipped with a reflux condenser and heated to reflux (bath=130° C.) with stirring. After 5 h (LCMS indicated no starting material remained), the reaction mixture was cooled to room temperature and filtered to collect a small amount of white precipitate (this was determined to contain very little product so it was discarded). The aqueous filtrate was adjusted to pH~5.5 with 1N aq HCl and extracted with three 100 mL portions of ethyl acetate. The combined organics were dried over Na$_2$SO$_4$, filtered, concentrated under reduced pressure and dried to constant weight under high vacuum to provide 4-(4-bromo-2-methylphenyl)-5-{[(3S)-1-(cyclopropylcarbonyl)-3-pyrrolidinyl]methyl}-2,4-dihydro-3H-1,2,4-triazol-3-one (485 mg, 1.197 mmol, 54.8% yield) as a white solid. MS(ES)+ m/e 405.2, 407.4 [M+H]$^+$. The product was determined to be 90% pure by LCMS (UV214) and was carried on in the next step without further purification.

c) 4-[4-(1-Benzofuran-5-yl)-2-methylphenyl]-5-{[(3S)-1-(cyclopropylcarbonyl)-3-pyrrolidinyl]methyl}-2,4-dihydro-3H-1,2,4-triazol-3-one A microwaveable vial was charged with 4-(4-bromo-2-methylphenyl)-5-{[(3S)-1-(cyclopropylcarbonyl)-3-pyrrolidinyl]methyl}-2,4-dihydro-3H-1,2,4-triazol-3-one (100 mg, 0.247 mmol), 5-(4,4,5,5-tetramethyl-1,3,2-dioxaborolan-2-yl)-1-benzofuran (63.2 mg, 0.259 mmol), PdCl$_2$(dppf) (9.03 mg, 0.012 mmol), K$_2$CO$_3$ (85 mg, 0.617 mmol), 1,4-dioxane (3 mL) and water (1 mL). The reaction was purged with nitrogen, sealed and heated in a microwave reactor at 150° C. for 30 min (LCMS indicated complete conversion of starting material to desired product). The reaction mixture was concentrated under reduced pressure and the residue was dissolved in DMSO, filtered through a syringe filter and purified by reverse phase HPLC (Gilson, YMC-Pack ODS-A C18 5 µm 75×30 mm column, 10-90% MeCN/water+0.1% TFA, 3×1 mL injections). The appropriate fractions were concentrated to dryness and the residue was diluted with water (10 mL) and adjusted to pH 5 with conc. NH$_4$OH. The resulting precipitate was collected by filtration and dried to constant weight under vacuum to provide the title product (40 mg, 0.090 mmol, 36.6% yield) as a white solid. MS(ES)+ m/e 443.1 [M+H]$^+$.

Example 41

5-{[(3S)-1-(cyclopropylcarbonyl)-3-pyrrolidinyl]methyl}-4-[4-(1H-indol-5-yl)-2-methylphenyl]-2,4-dihydro-3H-1,2,4-triazol-3-one

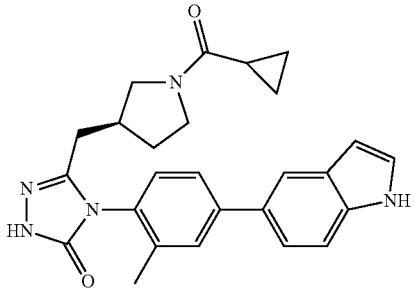 [SMILES: Cc1cc(-c2ccc3[nH]ccc3c2)ccc1-n1c(C[C@@H]2CCN(C(=O)C3CC3)C2)n[nH]c1=O]

a) A microwaveable vial was charged with 4-(4-bromo-2-methylphenyl)-5-{[(3S)-1-(cyclopropylcarbonyl)-3-pyrrolidinyl]methyl}-2,4-dihydro-3H-1,2,4-triazol-3-one (100 mg, 0.247 mmol), 5-(4,4,5,5-tetramethyl-1,3,2-dioxaborolan-2-yl)-1H-indole (60.0 mg, 0.247 mmol), PdCl$_2$(dppf) (9.03 mg, 0.012 mmol), K$_2$CO$_3$ (85 mg, 0.617 mmol), 1,4-dioxane (3 mL) and water (1 mL). The reaction was purged with nitrogen, sealed and heated in a microwave reactor at 150° C. for 30 min (LCMS indicated complete conversion of starting material to desired product). The reaction mixture was concentrated under reduced pressure and the residue was dissolved in DMSO, filtered through a syringe filter and purified by reverse phase HPLC (Gilson, YMC-Pack ODS-A C18 5 µm 75×30 mm column, 10-90% MeCN/water+0.1% TFA, 3×1 mL injections). The appropriate fractions were concentrated to remove a majority of the MeCN, leaving an aqueous suspension of product. The precipitate was collected by filtration, rinsed with minimal water and dried to constant weight under vacuum to provide the title product (58 mg, 0.131 mmol, 53.2% yield) as a white solid. MS(ES)+ m/e 442.2 [M+H]+. $^1$H NMR (400 MHz, DMSO-d$_6$) δ ppm 11.73 (d, J=4.04 Hz, 1H), 11.21 (br. s., 1H), 7.90 (s, 1H), 7.74 (br. s., 1H), 7.57-7.67 (m, 1H), 7.43-7.54 (m, 2H), 7.32-7.43 (m, 2H), 6.51 (d, J=2.27 Hz, 1H), 3.60-3.89 (m, 1H), 3.47-3.59 (m, 1H), 3.39-2.86 (m, 2H), 2.28-2.49 (m, 3H), 2.13-2.21 (m, 3H), 1.96 (d, J=9.35 Hz, 1H), 1.41-1.75 (m, 2H), 0.60-0.76 (m, 4H).

Example 42

5-{[(3S)-1-(cyclopropylcarbonyl)-3-pyrrolidinyl]methyl}-4-[4-(1H-indol-6-yl)-2-methylphenyl]-2,4-dihydro-3H-1,2,4-triazol-3-one

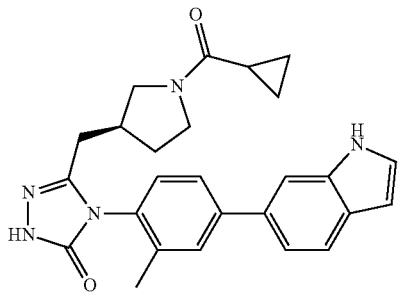 [SMILES: Cc1cc(-c2ccc3cc[nH]c3c2)ccc1-n1c(C[C@@H]2CCN(C(=O)C3CC3)C2)n[nH]c1=O]

a) A microwave vial was charged with 4-(4-bromo-2-methylphenyl)-5-{[(3S)-1-(cyclopropylcarbonyl)-3-pyrrolidinyl]methyl}-2,4-dihydro-3H-1,2,4-triazol-3-one (105 mg, 0.259 mmol), 1H-indol-6-ylboronic acid (41.7 mg, 0.259 mmol), PdCl$_2$(dppf) (9.48 mg, 0.013 mmol), K$_2$CO$_3$ (90 mg, 0.648 mmol), 1,4-dioxane (3 mL) and water (1 mL). The reaction was purged with nitrogen, sealed and heated in a microwave reactor at 150° C. for 30 min (LCMS indicated complete conversion of starting material to desired product). The reaction mixture was concentrated under reduced pressure and the residue was dissolved in DMSO, filtered through a syringe filter and purified by reverse phase HPLC (Gilson, YMC-Pack ODS-A C18 5 µm 75×30 mm column, 10-90% MeCN/water+0.1% TFA, 3×1 mL injections). The appropriate fractions were concentrated to remove a majority of the MeCN, leaving an aqueous suspension of product. The precipitate was collected by filtration, rinsed with minimal water and dried to constant weight under vacuum to provide the title product (56 mg, 0.127 mmol, 49.0% yield) as a white solid. MS(ES)+ m/e 442.3 [M+H]+. $^1$H NMR (400 MHz, DMSO-d$_6$) δ ppm 11.74 (d, J=3.79 Hz, 1H), 11.24 (s, 1H), 7.74 (br. s., 1H), 7.70 (s, 1H), 7.64 (d, J=8.34 Hz, 2H), 7.31-7.44 (m, 3H), 6.47 (d, J=2.27 Hz, 1H), 3.63-3.85 (m, 1H), 2.87-3.57 (m, 3H), 2.30-2.47 (m, 3H), 2.13-2.21 (m, 3H), 2.08 (s, 1H), 1.44-1.76 (m, 2H), 0.61-0.78 (m, 4H).

Example 43

5-{[(3S)-1-(cyclopropylcarbonyl)-3-pyrrolidinyl]methyl}-4-(4'-fluoro-3-methyl-4-biphenylyl)-2,4-dihydro-3H-1,2,4-triazol-3-one

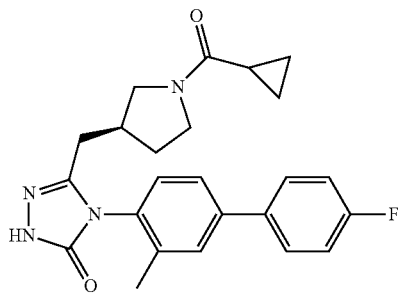 [SMILES: Cc1cc(-c2ccc(F)cc2)ccc1-n1c(C[C@@H]2CCN(C(=O)C3CC3)C2)n[nH]c1=O]

a) A microwave vial was charged with 4-(4-bromo-2-methylphenyl)-5-{[(3S)-1-(cyclopropylcarbonyl)-3-pyrrolidinyl]methyl}-2,4-dihydro-3H-1,2,4-triazol-3-one (60.0 mg, 0.148 mmol), (4-fluorophenyl)boronic acid (20.71 mg, 0.148 mmol), PdCl$_2$(dppf) (5.42 mg, 7.40 µmol), K$_2$CO$_3$ (51.2 mg, 0.370 mmol), 1,4-dioxane (3 mL) and water (1 mL). The reaction was purged with nitrogen, sealed and heated in a microwave reactor at 150° C. for 30 min. The reaction mixture was concentrated under reduced pressure and the residue was dissolved in DMSO, filtered through a syringe filter and purified by reverse phase HPLC (Gilson, YMC-Pack ODS-A C18 5 µm 75×30 mm column, 10-90% MeCN/water+0.1% TFA, 2×1 mL injections). The appropriate fractions were concentrated to remove a majority of the MeCN. The remaining aqueous mixture (product had oiled out) was extracted with two portions of dichloromethane. The combined dichloromethane layers were dried over Na$_2$SO$_4$, filtered, concentrated under reduced pressure and dried to constant weight under vacuum to provide the title product (36 mg, 0.086 mmol, 57.8% yield) as a yellow solid. MS(ES)+ m/e 421.1 [M+H]+. $^1$H NMR (400 MHz, DMSO-d$_6$) δ ppm 11.75 (d, J=4.04 Hz, 1H), 7.75-7.86 (m, 2H), 7.73 (br. s., 1H), 7.58-7.66 (m, 1H), 7.42 (td, J=8.34, 4.29 Hz, 1H), 7.33 (t, J=8.84 Hz, 2H), 3.59-3.88 (m, 1H), 3.46-3.59 (m, 1H), 2.82-3.38 (m, 2H), 2.28-2.49 (m, 3H), 2.12-2.20 (m, 3H), 1.87-2.07 (m, 1H), 1.39-1.76 (m, 2H), 0.59-0.76 (m, 4H).

Example 44

4-[4-(1-benzofuran-5-yl)phenyl]-5-{[(3S)-1-propanoyl-3-pyrrolidinyl]methyl}-2,4-dihydro-3H-1,2,4-triazol-3-one

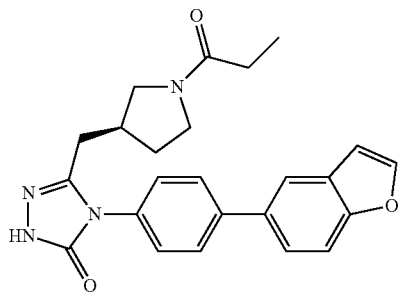 [SMILES: CCC(=O)N1CC[C@@H](Cc2n[nH]c(=O)n2-c2ccc(-c3ccc4occc4c3)cc2)C1]

a) 1,1-dimethylethyl (3S)-3-(2-hydrazino-2-oxoethyl)-1-pyrrolidinecarboxylate Following the procedure described in example 1c with 1,1-dimethylethyl (3S)-3-[2-(ethyloxy)-2-oxoethyl]-1-pyrrolidinecarboxylate provided the title compound as a thick clear oil (85%). MS(ES)+ m/e 244.4 [M+H]$^+$, 487.5 [2M+H]$^+$.

b) 1,1-dimethylethyl (3S)-3-[2-(2-{[(4-bromophenyl)amino]carbonyl}hydrazino)-2-oxoethyl]-1-pyrrolidinecarboxylate Following the procedure described in example 1d with 1,1-dimethylethyl (3S)-3-(2-hydrazino-2-oxoethyl)-1-pyrrolidinecarboxylate at room temperature for 1 h provided the title compound as a white solid (86%). Trituration in ethyl acetate/hexanes was utilized to purify this compound. MS(ES)+ m/e 441.1, 443.1 [M+H]$^+$.

c) 1,1-dimethylethyl (3S)-3-{[4-(4-bromophenyl)-5-oxo-4,5-dihydro-1H-1,2,4-triazol-3-yl]methyl}-1-pyrrolidinecarboxylate In a round bottom flask, a mixture of 1,1-dimethylethyl (3S)-3-[2-(2-{[(4-bromophenyl)amino]carbonyl}hydrazino)-2-oxoethyl]-1-pyrrolidinecarboxylate (9.49 g, 21.50 mmol) and potassium carbonate (14.86 g, 108 mmol) in water (430 mL) was heated to reflux (oil bath at 130° C.) and stirred for 69 h. The reaction mixture initially contained undissolved white solid, but after 4 h the white solid was almost fully dissolved to give a colorless solution. The reaction was cooled to room temperature. Analysis by LCMS showed complete conversion to the desired BOC-deprotected and cyclized intermediate. MS(ES)+ m/e 322.9, 325.0 [M+H]$^+$. The reaction was concentrated in vacuo and the solid was pumped under high vacuum overnight. The white solid was dissolved in 1M aq sodium hydroxide solution (43.0 mL, 43.0 mmol) and treated with di-tert-butyl dicarbonate (4.99 mL, 21.50 mmol) at room temperature. The reaction was stirred at room temperature over a long weekend. As the reaction had not gone to completion, additional di-tert-butyl dicarbonate (4.99 mL, 21.50 mmol) was added and the reaction was stirred for 3 h. The reaction mixture was then diluted with ethyl acetate (400 mL) and acidified to pH~6 by pH paper using 1N aq HCl solution. The aqueous layer was extracted with ethyl acetate (2×50 mL). The organic layers were combined, dried over MgSO$_4$ and concentrated in vacuo. Purification of the residue by silica gel chromatography (Analogix IF280, SF40-115g, 100% ethyl acetate for 5 min, then a gradient of 0-50% (10% methanol in dichloromethane)/ethyl acetate) provided the title product as a white foamy solid (5.86 g, 64.4%). MS(ES)+ m/e 422.9 [M+H]$^+$. Another batch of the product was obtained by combining and concentrating fractions containing the minor peak off the column and some trailing tubes from the major (product) peak. By LCMS, it appeared that the minor product was a bis-BOC compound. Methanol (20 mL), 10N aq sodium hydroxide solution and 3 pellets sodium hydroxide were added at room temperature and the yellow solution was stirred at room temperature for 6 days. The reaction mixture was concentrated to an aqueous slurry and diluted with ethyl acetate (200 mL). With the flask in an ice bath, the mixture was acidified to pH~5.5 by pH paper using 6N aq HCl solution. The aqueous layer was extracted with ethyl acetate (300 mL). The organic layers were combined, dried over MgSO$_4$ and concentrated in vacuo. Purification of the residue by silica gel chromatography (Analogix IF280, SF25-40 g, 100% ethyl acetate for 5 min, then a gradient of 0-50% (10% methanol in dichloromethane)/ethyl acetate) gave the second batch of the title compound as a white foamy solid (0.569 g, 6.3%). MS(ES)+ m/e 422.9, 424.8 [M+H]$^+$.

d) 1,1-dimethylethyl (3S)-3-({4-[4-(1-benzofuran-5-yl)phenyl]-5-oxo-4,5-dihydro-1H-1,2,4-triazol-3-yl}methyl)-1-pyrrolidinecarboxylate In a sealed pressure tube, a mixture of 1,1-dimethylethyl (3S)-3-{[4-(4-bromophenyl)-5-oxo-4,5-dihydro-1H-1,2,4-triazol-3-yl]methyl}-1-pyrrolidinecarboxylate (2.5 g, 5.91 mmol), 5-(4,4,5,5-tetramethyl-1,3,2-dioxaborolan-2-yl)-1-benzofuran (1.514 g, 6.20 mmol), 1,1'-bis(diphenylphosphino)ferrocene-palladium(II)dichloride dichloromethane complex (0.241 g, 0.295 mmol), and sodium bicarbonate (1.488 g, 17.72 mmol) in 1,4-dioxane (30 mL) and water (15 mL) was stirred at 100° C. for 24 h. The reaction was cooled to room temperature. The reaction was diluted with ethyl acetate (300 mL) and water (100 mL), and the layers were separated. The aqueous layer was acidified to pH~6 using a 1N aq HCl solution and then extracted with ethyl acetate (3×100 mL). The combined organic layers were dried over magnesium sulfate and concentrated in vacuo. Purification of the residue by silica gel chromatography (Analogix IF280, SF40-115g, Solvent A: ethyl acetate; Solvent B: 10% methanol/dichloromethane; Gradient: 100% A for 10 min, then 0-50% B/A over 20 min) provided the title compound as a tan solid (2.6 g, 96%). MS(ES)+ m/e 461.4 [M+H]$^+$.

e) 4-[4-(1-benzofuran-5-yl)phenyl]-5-[(3S)-pyrrolidin-3-ylmethyl]-2,4-dihydro-3H-1,2,4-triazol-3-one Hydrochloride In a round bottom flask under nitrogen, a yellow mixture of tert-butyl (3S)-3-({4-[4-(1-benzofuran-5-yl)phenyl]-5-oxo-4,5-dihydro-1H-1,2,4-triazol-3-yl}methyl)pyrrolidine-1-carboxylate (2.58 g, 5.60 mmol) in 4M HCl in dioxane (1.40 mL, 5.60 mmol) was stirred at room temperature for 30 min. The reaction mixture was concentrated in vacuo. Ethanol (300 mL) was added to the flask and the solvent was removed by concentration in vacuo to give the title compound as a cream coloured solid (2.14 g, 96%). MS(ES)+ m/e 361.1 [M+H]$^+$.

f) 4-[4-(1-benzofuran-5-yl)phenyl]-5-{[(3S)-1-propanoyl-3-pyrrolidinyl]methyl}-2,4-dihydro-3H-1,2,4-triazol-3-one Under nitrogen, a mixture of 4-[4-(1-benzofuran-5-yl)phenyl]-5-[(3S)-3-pyrrolidinylmethyl]-2,4-dihydro-3H-1,2,4-triazol-3-one hydrochloride (116 mg, 0.292 mmol) and N,N-diisopropylethylamine (0.15 mL, 0.88 mmol) in dichloromethane (1.3 mL) was stirred at room temperature for 2 min. The mixture was cooled to 0° C. and treated with propionyl chloride (0.026 mL, 0.292 mmol) dropwise by syringe. The mixture became a dark brown solution and the reaction was stirred at 0° C. for 90 min. The reaction was quenched with water (2 mL) and diluted with ethyl acetate (20 mL). The mixture was transferred to a separatory funnel, water (10 mL) was added and the layers were separated. The pH of the aqueous layer was tested by pH paper and found to be pH~5-6. The aqueous layer was extracted with ethyl acetate (10 mL). The organic layers were combined, dried over magnesium sulfate and concentrated in vacuo to give a tan foamy solid. Purification of the residue by silica gel chromatography (Analogix IF280, SF10-4 g, 0-10% MeOH/EtOAc, 30 min) provided the title product as an ivory solid (74 mg, 61%). MS(ES)+ m/e 417.2 [M+H]+.

Example 45

4-[4-(1-benzofuran-5-yl)phenyl]-5-{[(3S)-1-(2-methylpropanoyl)-3-pyrrolidinyl]methyl}-2,4-dihydro-3H-1,2,4-triazol-3-one

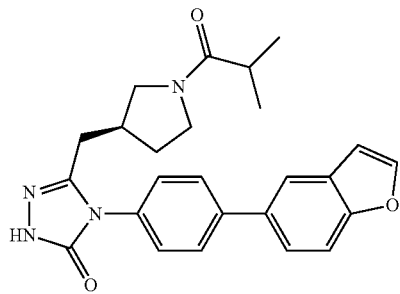 [SMILES: CC(C)C(=O)N1CC[C@@H](Cc2n[nH]c(=O)n2-c2ccc(-c3ccc4occc4c3)cc2)C1]

a) Following the procedure described in example 44f using isobutyryl chloride provided the title compound as an ivory solid (59%). MS(ES)+ m/e 431.3 [M+H]+.

Example 46

4-(4'-amino-4-biphenylyl)-5-{[(3S)-1-(cyclopropylcarbonyl)-3-pyrrolidinyl]methyl}-2,4-dihydro-3H-1,2,4-triazol-3-one

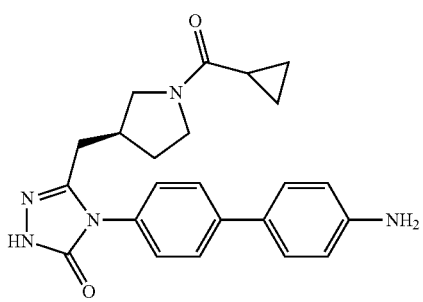

a) The procedure described in example 13a was followed using 4-(4,4,5,5-tetramethyl-1,3,2-dioxaborolan-2-yl)aniline and 1.00 mmol of 2M aq potassium carbonate. Once <10% starting material remained, the reaction mixture was poured into water (50 mL) and the pH was adjusted to 5 with addition of 1N aq HCl. The aqueous layer was extracted with ethyl acetate (3×50 mL) and the combined organic layers were dried over sodium sulfate, filtered, and concentrated in vacuo. Purification of the residue by flash chromatography (100% ethyl acetate followed by 0-10% methanol/ethyl acetate to elute) followed by precipitation of solid product in ethyl acetate, filtration, and concentration in vacuo provided the title compound as a tan solid (14%). MS(ES)+ m/e 404.3 [M+H]+.

Example 47

4-[4-(6-amino-3-pyridinyl)phenyl]-5-{[(3S)-1-(cyclopropylcarbonyl)-3-pyrrolidinyl]methyl}-2,4-dihydro-3H-1,2,4-triazol-3-one

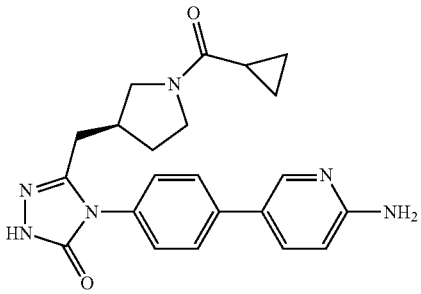 [SMILES: Nc1ccc(-c2ccc(-n3c(C[C@@H]4CCN(C(=O)C5CC5)C4)n[nH]c3=O)cc2)cc1]

a) Following the procedure described in example 46a using 5-(4,4,5,5-tetramethyl-1,3,2-dioxaborolan-2-yl)-2-pyridinamine afforded the title compound as a tan solid (10%). MS(ES)+ m/e 405.3 [M+H]+.

Example 48

5-{[(3S)-1-(cyclopropylcarbonyl)-3-pyrrolidinyl]methyl}-4-(3,3'-difluoro-4'-methyl-4-biphenylyl)-2,4-dihydro-3H-1,2,4-triazol-3-one

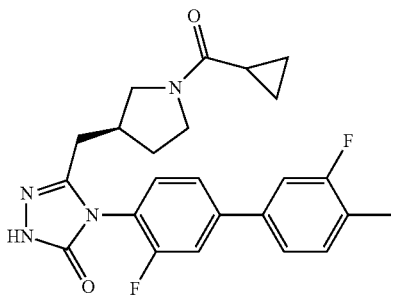 [SMILES: Cc1ccc(-c2ccc(-n3c(C[C@@H]4CCN(C(=O)C5CC5)C4)n[nH]c3=O)c(F)c2)cc1F]

a) A mixture of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol), (3-fluoro-4-methylphenyl)boronic acid (0.370 mmol), and dichloro[1,1'-bis(diphenylphosphino)ferrocene]palladium(II)-dichloromethane adduct (0.012 mmol) in dioxane (2.0 mL) and 2M aq potassium carbonate (0.5 mL) was irradiated in the microwave at 150° C. for 15 min. The reaction mixture was poured into water (50 mL) and the pH was adjusted to 5 with addition of 1N aq HCl. The aqueous layer was extracted with ethyl acetate (3×50 mL) and the combined organic layers were dried over sodium sulfate, filtered, and concentrated in vacuo. Purification of the residue by flash chromatography (100% ethyl acetate) and then reverse phase HPLC (30-65% acetonitrile/water with 0.1% NH$_4$OH) provided the title compound as a tan solid (58%). MS(ES)+ m/e 439.2 [M+H]$^+$.

Example 49

4-(3'-chloro-3-fluoro-4'-methyl-4-biphenylyl)-5-{[(3S)-1-(cyclopropylcarbonyl)-3-pyrrolidinyl]methyl}-2,4-dihydro-3H-1,2,4-triazol-3-one

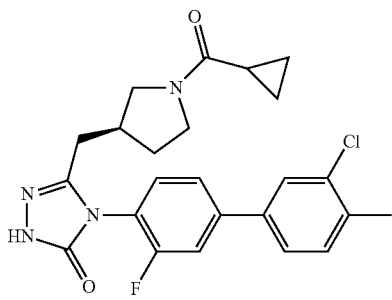 [SMILES: Cc1ccc(-c2ccc(-n3c(C[C@@H]4CCN(C(=O)C5CC5)C4)n[nH]c3=O)c(F)c2)cc1Cl]

a) Following the procedure described in example 48a using (3-chloro-4-methylphenyl)boronic acid afforded the title compound as a tan solid (44%). MS(ES)+ m/e 455.0 [M+H]$^+$.

Example 50

4-[4-(1-benzofuran-5-yl)-2,6-difluorophenyl]-5-{[(3S)-1-(cyclopropylcarbonyl)-3-pyrrolidinyl]methyl}-2,4-dihydro-3H-1,2,4-triazol-3-one

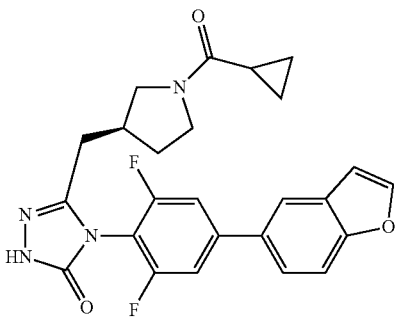 [SMILES: O=C(C1CC1)N1CC[C@@H](Cc2n[nH]c(=O)n2-c2c(F)cc(-c3ccc4occc4c3)cc2F)C1]

a) N-(4-bromo-2,6-difluorophenyl)-2-{[(3S)-1-(cyclopropylcarbonyl)-3-pyrrolidinyl]acetyl}hydrazinecarboxamide In a round-bottom flask, 5-bromo-1,3-difluoro-2-isocyanatobenzene (1550 mg, 6.62 mmol) was dissolved in dichloromethane (10 mL) under nitrogen and cooled to −78° C. In a separate vial, 2-[(3S)-1-(cyclopropylcarbonyl)-3-pyrrolidinyl]acetohydrazide (1357 mg, 6.42 mmol) was dissolved in 10 mL of dichloromethane and then added to the cooled solution. The resultant reaction mixture was allowed to warm to room temperature and stirred for 1 h. A precipitate began to form and analysis by LCMS indicated formation of the desired product. The precipitated product was collected under vacuum filtration and washed with dichloromethane to afford the title product as a white solid (2850 mg, 99%). MS(ES)+ m/e 445.2, 447.1 [M+H]$^+$.

b) 4-(4-bromo-2,6-difluorophenyl)-5-{[(3S)-1-(cyclopropylcarbonyl)-3-pyrrolidinyl]methyl}-2,4-dihydro-3H-1,2,4-triazol-3-one To a round bottom flask, N-(4-bromo-2,6-difluorophenyl)-2-{[(3S)-1-(cyclopropylcarbonyl)-3-pyrrolidinyl]acetyl}hydrazinecarboxamide (2860 mg, 6.42 mmol) and potassium carbonate (4000 mg, 28.9 mmol) were added and suspended in water (200 mL). The mixture was refluxed for 16 h at 115° C. Analysis by LCMS indicated consumption of starting material and formation of desired product and by-products related to the starting material. The solution was neutralized to pH=7 with 1N aq HCl and 150 mL of ethyl acetate was added. The aqueous phase was extracted with ethyl acetate (3×) and the combined organic layers were washed with brine, dried over sodium sulfate, and concentrated in vacuo. Purification of the residue by silica gel chromatography (0-20% isopropanol/ethyl acetate) provided the title product as a white solid (360 mg, 13%). MS(ES)+ m/e 426.9, 428.6 [M+H]$^+$.

c) 4-[4-(1-benzofuran-5-yl)-2,6-difluorophenyl]-5-{[(3S)-1-(cyclopropylcarbonyl)-3-pyrrolidinyl]methyl}-2,4-dihydro-3H-1,2,4-triazol-3-one To a microwave vial, 4-(4-bromo-2,6-difluorophenyl)-5-{[(3S)-1-(cyclopropylcarbonyl)-3-pyrrolidinyl]methyl}-2,4-dihydro-3H-1,2,4-triazol-3-one (50.5 mg, 0.100 mmol) 5-(4,4,5,5-tetramethyl-1,3,2-dioxaborolan-2-yl)-1-benzofuran (46 mg, 0.188 mmol), cesium carbonate (105 mg, 0.322 mmol), and dichloro[1,1'-bis(diphenylphosphino)ferrocene]palladium(II)-dichloromethane adduct (6.0 mg, 0.00735 mmol) were added to a microwave vial and purged with nitrogen. 1,4-Dioxane (1 mL) and water (0.5 mL) were added to the mixture, which was then heated overnight at 100° C. Analysis by LCMS indicated desired product formation and consumption of starting material. The mixture was filtered through a syringe filter and purified by reverse phase HPLC (10-90% acetonitrile/water with 0.1% TFA). The desired product fractions were collected and added to a separatory funnel containing ethyl acetate. The aqueous phase was adjusted to pH~7 and then was extracted with ethyl acetate (3×). The combined organics were washed with brine, dried over sodium sulfate, and concentrated in vacuo to afford the title product as a white solid (19 mg, 40%). MS(ES)+ m/e 465.2 [M+H]$^+$.

Example 51

5-{[(3S)-1-(cyclopropylcarbonyl)-3-pyrrolidinyl]methyl}-4-[2,6-difluoro-4-(7-quinolinyl)phenyl]-2,4-dihydro-3H-1,2,4-triazol-3-one

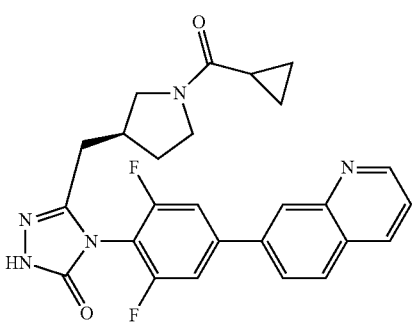 [SMILES: O=C(C1CC1)N1CC[C@@H](Cc2n[nH]c(=O)n2-c2c(F)cc(-c3ccc4cccnc4c3)cc2F)C1]

a) Following the procedure described in example 50c using 7-(4,4,5,5-tetramethyl-1,3,2-dioxaborolan-2-yl)quinoline afforded the title compound as an ivory solid (33 mg, 59%). MS(ES)+ m/e 476.0 [M+H]+.

Example 52

4'-(3-{[(3S)-1-(cyclopropylcarbonyl)-3-pyrrolidinyl]methyl}-5-oxo-1,5-dihydro-4H-1,2,4-triazol-4-yl)-3',5'-difluoro-3-methyl-4-biphenylcarbonitrile

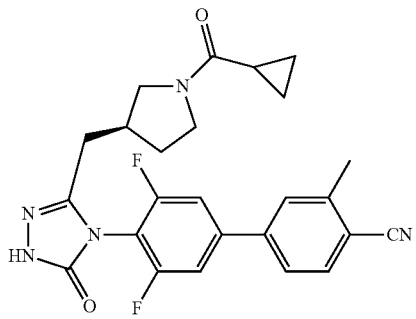 [SMILES: Cc1cc(-c2cc(F)c(-n3c(C[C@@H]4CCN(C(=O)C5CC5)C4)n[nH]c3=O)c(F)c2)ccc1C#N]

a) Following the procedure described in example 50c using 2-methyl-4-(4,4,5,5-tetramethyl-1,3,2-dioxaborolan-2-yl)benzonitrile afforded the title compound as a white solid (36 mg, 65%). MS(ES)+ m/e 464.3 [M+H]+.

Example 53

5-{[(3S)-1-(cyclopropylcarbonyl)-3-pyrrolidinyl]methyl}-4-[2,6-difluoro-4-(1H-indol-6-yl)phenyl]-2,4-dihydro-3H-1,2,4-triazol-3-one

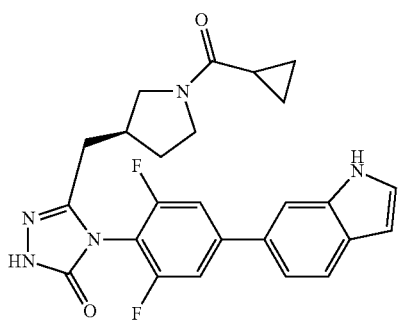 [SMILES: O=C(C1CC1)N1CC[C@@H](Cc2n[nH]c(=O)n2-c2c(F)cc(-c3ccc4cc[nH]c4c3)cc2F)C1]

a) Following the procedure described in example 50c using 6-(4,4,5,5-tetramethyl-1,3,2-dioxaborolan-2-yl)-1H-indole afforded the title compound as a white solid (14 mg, 26%). MS(ES)+ m/e 464.3 [M+H]+.

Example 54

5-{[(3S)-1-(cyclopropylcarbonyl)-3-pyrrolidinyl]methyl}-4-[3,5-difluoro-4'-(methyloxy)-4-biphenylyl]-2,4-dihydro-3H-1,2,4-triazol-3-one

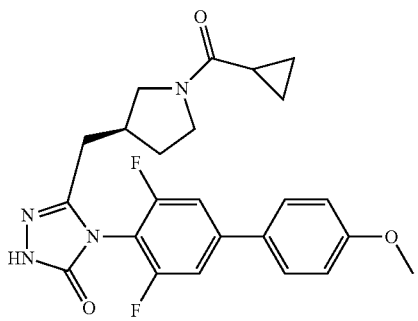 [SMILES: COc1ccc(-c2cc(F)c(-n3c(C[C@@H]4CCN(C(=O)C5CC5)C4)n[nH]c3=O)c(F)c2)cc1]

a) Following the procedure described in example 50c using 4,4,5,5-tetramethyl-2-[4-(methyloxy)phenyl]-1,3,2-dioxaborolane afforded the title compound as an ivory solid (30 mg, 57%). MS(ES)+ m/e 455.0 [M+H]+.

Example 55

4-(4'-chloro-2',3,5-trifluoro-4-biphenylyl)-5-{[(3S)-1-(cyclopropylcarbonyl)-3-pyrrolidinyl]methyl}-2,4-dihydro-3H-1,2,4-triazol-3-one

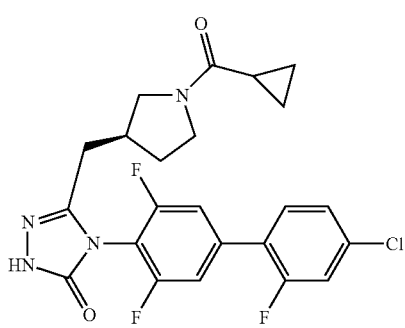 [SMILES: O=C(C1CC1)N1CC[C@@H](Cc2n[nH]c(=O)n2-c2c(F)cc(-c3ccc(Cl)cc3F)cc2F)C1]

a) Following the procedure described in example 50c using 2-(4-chloro-2-fluorophenyl)-4,4,5,5-tetramethyl-1,3,2-dioxaborolane afforded the title compound as an ivory solid (10 mg, 18%). MS(ES)+ m/e 477.0, 478.9 [M+H]+.

Example 56

4-(4'-chloro-3,5-difluoro-4-biphenylyl)-5-{[(3S)-1-(cyclopropylcarbonyl)-3-pyrrolidinyl]methyl}-2,4-dihydro-3H-1,2,4-triazol-3-one

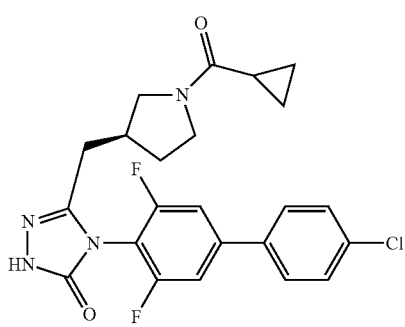 [SMILES: O=C(C1CC1)N1CC[C@@H](Cc2n[nH]c(=O)n2-c2c(F)cc(-c3ccc(Cl)cc3)cc2F)C1]

a) Following the procedure described in example 50c using 2-(4-chlorophenyl)-4,4,5,5-tetramethyl-1,3,2-dioxaborolane afforded the title compound as an ivory solid (23 mg, 42%). MS(ES)+ m/e 459.2, 461.2 [M+H]+.

Example 57

4-[4-(1-benzofuran-5-yl)-3-(methyloxy)phenyl]-5-{[(3S)-1-(cyclopropylcarbonyl)-3-pyrrolidinyl]methyl}-2,4-dihydro-3H-1,2,4-triazol-3-one

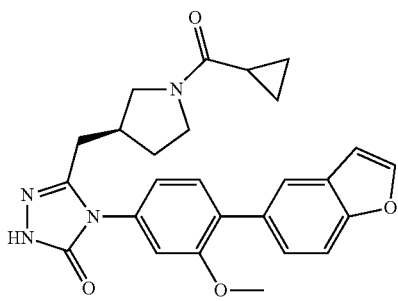 [SMILES: COc1cc(-n2c(C[C@@H]3CCN(C(=O)C4CC4)C3)n[nH]c2=O)ccc1-c1ccc2occc2c1]

a) N-[4-bromo-3-(methyloxy)phenyl]-2-{[(3S)-1-(cyclopropylcarbonyl)-3-pyrrolidinyl]acetyl}hydrazinecarboxamide To a round bottom flask was added triphosgene (0.514 g, 1.732 mmol) and dichloromethane (30 mL) under nitrogen, and the solution was cooled to −78° C. In a separate vial, 3-methoxy 4-bromoaniline (1 g, 4.95 mmol) was dissolved in dichloromethane (20 mL) and Hunig's base (1.753 mL, 9.90 mmol) was added. This solution was slowly added to the cooled solution and then the reaction was allowed to warm to room temperature. Analysis by LCMS indicated desired intermediate formation. The reaction was cooled again to −78° C. and 2-[(3S)-1-(cyclopropylcarbonyl)-3-pyrrolidinyl]acetohydrazide (0.575 g, 2.72 mmol) in dichloromethane (5 mL) was added slowly. The reaction was allowed to warm to room temperature and analysis by LCMS indicated desired product formation. The reaction was poured into a reparatory funnel and partitioned with saturated aq sodium bicarbonate. The aqueous layer was extracted with dichloromethane (3×) and the combined organic layers were dried over sodium sulfate, filtered, and concentrated in vacuo to an oil. The residue was purified by silica gel chromatography (0-40% isopropanol/ethyl acetate). The desired product fractions were combined and concentrated in vacuo to afford the title product as a tan solid (500 mg, 42%). MS(ES)+ m/e 439.0, 441.1 M+H]+.

b) 4-[4-bromo-3-(methyloxy)phenyl]-5-{[(3S)-1-(cyclopropylcarbonyl)-3-pyrrolidinyl]methyl}-2,4-dihydro-3H-1,2,4-triazol-3-one N-[4-bromo-3-(methyloxy)phenyl]-2-{[(3S)-1-(cyclopropylcarbonyl)-3-pyrrolidinyl]acetyl}hydrazinecarboxamide (500 mg, 0.911 mmol) and potassium carbonate (445 mg, 3.22 mmol) were added to a round-bottom flask and suspended in water (50 mL). The mixture was refluxed overnight at 115° C. Analysis by LCMS indicated formation of desired product (and other major by-products). A white solid (that was not desired product) had collected at the bottom of the flask and was filtered off. The pH of the filtrate was adjusted to ~6 with 1N aq HCl and was partitioned with ethyl acetate. The aqueous layer was extracted with ethyl acetate (3×) and the combined organic layers were dried over sodium sulfate, filtered, and concentrated in vacuo to an oil. The residue was purified by silica gel chromatography (0-100% ethyl acetate/hexanes, then 0-30% isopropanol/ethyl acetate). The desired fractions were combined and concentrated in vacuo to afford the title product as an off-white solid (151 mg, 38%). MS(ES)+ m/e 421.0, 422.9 M+H]+.

c) 4-[4-(1-benzofuran-5-yl)-3-(methyloxy)phenyl]-5-{[(3S)-1-(cyclopropylcarbonyl)-3-pyrrolidinyl]methyl}-2,4-dihydro-3H-1,2,4-triazol-3-one To a microwave vial were added 4-[4-bromo-3-(methyloxy)phenyl]-5-{[(3S)-1-(cyclopropylcarbonyl)-3-pyrrolidinyl]methyl}-2,4-dihydro-3H-1,2,4-triazol-3-one (35 mg, 0.083 mmol) 5-(4,4,5,5-tetramethyl-1,3,2-dioxaborolan-2-yl)-1-benzofuran (30.4 mg, 0.125 mmol), cesium carbonate (95 mg, 0.291 mmol), and dichloro[1,1'-bis(diphenylphosphino)ferrocene]palladium(II)-dichloromethane adduct (6.0 mg, 0.00735 mmol) and the mixture was purged with nitrogen. 1,4-Dioxane (1 mL) and water (0.5 mL) were added to the mixture which was heated overnight at 100° C. Analysis by LCMS indicated desired product formation and consumption of starting material. The mixture was filtered through a syringe filter and purified by reverse phase HPLC (10-90% acetonitrile/water with 0.1% TFA). The desired fractions were collected and added to a separatory funnel containing ethyl acetate. The aqueous phase was adjusted to pH~6 with 1N aq HCl. The aqueous phase was extracted with ethyl acetate (3×) and the combined organics were washed with brine, dried over sodium sulfate, and concentrated in vacuo to afford the title product as a white solid (21 mg, 55%). MS(ES)+ m/e 459.3 M+H]+.

Example 58

4-[4-(1-benzofuran-5-yl)-2-(trifluoromethyl)phenyl]-5-{[(3S)-1-(cyclopropylcarbonyl)-3-pyrrolidinyl]methyl}-2,4-dihydro-3H-1,2,4-triazol-3-one

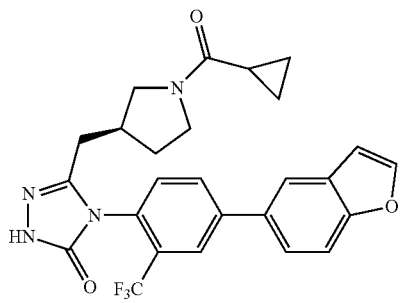 [SMILES: O=C(C1CC1)N1CC[C@@H](Cc2n[nH]c(=O)n2-c2ccc(-c3ccc4occc4c3)cc2C(F)(F)F)C1]

a) N-[4-bromo-2-(trifluoromethyl)phenyl]-2-{[(3S)-1-(cyclopropylcarbonyl)-3-pyrrolidinyl]acetyl}hydrazinecarboxamide To a round-bottom flask was added 4-bromo-1-isocyanato-2-(trifluoromethyl)benzene (0.4 mL, 2.55 mmol) and dichloromethane (10 mL) under nitrogen. The mixture was cooled to −78° C. and a solution of 2-[(3S)-1-(cyclopropylcarbonyl)-3-pyrrolidinyl]acetohydrazide (520 mg, 2.461 mmol) in dichloromethane (15 mL) was then added to the cooled solution and immediately allowed to warm to room temperature. After 1 h, analysis by LCMS indicated desired product formation. The resulting precipitate was collected and dried under vacuum filtration to yield the title product as a white solid (130 mg, 88%). MS(ES)+ m/e 476.9, 478.9 M+H]+.

b) 4-[4-bromo-2-(trifluoromethyl)phenyl]-5-{[(3S)-1-(cyclopropylcarbonyl)-3-pyrrolidinyl]methyl}-2,4-dihydro-3H-1,2,4-triazol-3-one To a round bottom flask were added N-[4-bromo-2-(trifluoromethyl)phenyl]-2-{[(3S)-1-(cyclopropylcarbonyl)-3-pyrrolidinyl]acetyl}hydrazinecarboxamide (1025 mg, 2.148 mmol) and potassium carbonate (1203 mg, 8.70 mmol). The mixture was suspended in water (100 mL) and refluxed for 16 h at 115° C. Analysis by LCMS indicated consumption of starting material and formation of desired product and by-products related to the starting material. The solution was neutralized to pH=7 with 1N aq HCl and diluted with 150 mL of ethyl acetate. The aqueous phase was extracted with ethyl acetate (3×) and the combined organic layers were washed with brine, dried over sodium sulfate, and concentrated in vacuo. This material was purified by silica gel chromatography (0-20% isopropanol/ethyl acetate), to afford the title product (177 mg, 18%). MS(ES)+ m/e 459.2, 461.2 M+H]+.

c) 4-[4-(1-benzofuran-5-yl)-2-(trifluoromethyl)phenyl]-5-{[(3S)-1-(cyclopropylcarbonyl)-3-pyrrolidinyl]methyl}-2,4-dihydro-3H-1,2,4-triazol-3-one To a microwave vial were added 4-[4-bromo-2-(trifluoromethyl)phenyl]-5-{[(3S)-1-(cyclopropylcarbonyl)-3-pyrrolidinyl]methyl}-2,4-dihydro-3H-1,2,4-triazol-3-one (55 mg, 0.072 mmol), 4-[4-bromo-2-(trifluoromethyl)phenyl]-5-{[(3S)-1-(cyclopropylcarbonyl)-3-pyrrolidinyl]methyl}-2,4-dihydro-3H-1,2,4-triazol-3-one (55 mg, 0.072 mmol), cesium carbonate (82 mg, 0.251 mmol), and dichloro[1,1'-bis(diphenylphosphino)ferrocene]palladium(II)-dichloromethane adduct (6.0 mg, 0.00735 mmol) and the mixture was purged with nitrogen. 1,4-Dioxane (1 mL) and water (0.5 mL) were added to the mixture which was heated overnight at 100° C. Analysis by LCMS indicated desired product formation and consumption of starting material. The mixture was filtered through a syringe filter and purified by reverse phase HPLC (10-90% acetonitrile/water with 0.1% TFA). The desired fractions were collected and added to a reparatory funnel containing ethyl acetate. The aqueous phase was adjusted to pH~6 with 1N aq HCl. The aqueous phase was extracted with ethyl acetate (3×), and the combined organics were washed with brine, dried over sodium sulfate, and concentrated in vacuo to afford the title product as a tan solid (15 mg, 41%). MS(ES)+ m/e 497.2 [M+H]+.

Example 59

4-[4-(1-benzofuran-5-yl)-2-hydroxyphenyl]-5-{[(3S)-1-(cyclopropylcarbonyl)-3-pyrrolidinyl]methyl}-2,4-dihydro-3H-1,2,4-triazol-3-one

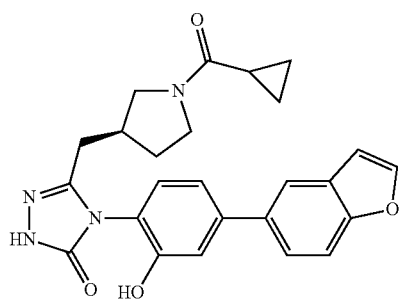 [SMILES: O=C(C1CC1)N1CC[C@@H](Cc2n[nH]c(=O)n2-c2ccc(-c3ccc4occc4c3)cc2O)C1]

a) 4-(4-bromo-2-hydroxyphenyl)-5-{[(3S)-1-(cyclopropylcarbonyl)-3-pyrrolidinyl]methyl}-2,4-dihydro-3H-1,2,4-triazol-3-one To a microwave vial was added 4-[4-bromo-2-(methyloxy)phenyl]-5-{[(3S)-1-(cyclopropylcarbonyl)-3-pyrrolidinyl]methyl}-2,4-dihydro-3H-1,2,4-triazol-3-one (132 mg, 0.313 mmol) and the solid was purged with nitrogen. Dichloromethane (1.5 mL) was added to the solid and was cooled to 0° C. Boron tribromide (2.037 mL, 2.037 mmol, 1M in dichloromethane) was added to the cooled solution and allowed to warm to room temperature. Analysis by LCMS indicated the presence of desired product and starting material. The solution was re-cooled to 0° C. and slowly treated with another portion of boron tribromide (2.037 mL, 2.037 mmol, 1M in dichloromethane). Analysis by LCMS indicated the consumption of starting material and presence of desired product. The solution was concentrated, dissolved in 2 mL dimethylsulfoxide, and purified by reverse phase HPLC (10-90% acetonitrile/water with 0.1% TFA). The desired fractions were collected and added to a separatory funnel containing ethyl acetate. The aqueous phase was adjusted to pH~6 with 1N aq HCl. The aqueous phase was extracted with ethyl acetate (3×), and the combined organics were washed with brine, dried over sodium sulfate, and concentrated in vacuo to afford the title product as a white solid (95 mg, 75%). MS(ES)+ m/e 407.1, 409.0 M+H]+.

b) 4-[4-(1-benzofuran-5-yl)-2-hydroxyphenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-2-hydroxyphenyl)-5-{[(3S)-1-(cyclopropylcarbonyl)-3-pyrrolidinyl]methyl}-2,4-dihydro-3H-1,2,4-triazol-3-one (45 mg, 0.110 mmol), 5-(4,4,5,5-tetramethyl-1,3,2-dioxaborolan-2-yl)-1-benzofuran (45 mg, 0.184 mmol), cesium carbonate (130 mg, 0.399 mmol), and dichloro[1,1'-bis(diphenylphosphino)ferrocene]palladium(II)-dichloromethane adduct (6.0 mg, 0.00735 mmol), and the mixture was purged with nitrogen. 1,4-Dioxane (1 mL) and water (0.5 mL) were added to the mixture which was heated overnight at 100° C. Analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3×), and the combined organics were washed with brine, dried over $Na_2SO_4$, and concentrated in vacuo to afford the title product as a white solid (18 mg, 37%). MS(ES)+ m/e 445.3 M+H]+.

Example 60

4-[4-(1-benzofuran-5-yl)-2,5-difluorophenyl]-5-{[(3S)-1-(cyclopropylcarbonyl)-3-pyrrolidinyl]methyl}-2,4-dihydro-3H-1,2,4-triazol-3-one

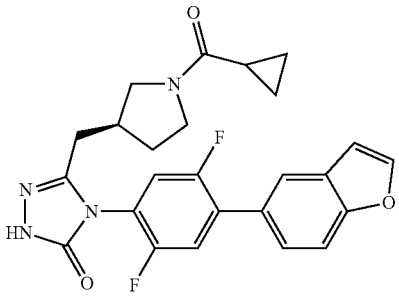 [SMILES: O=C(C1CC1)N1CC[C@@H](Cc2n[nH]c(=O)n2-c2cc(F)c(-c3ccc4occc4c3)cc2F)C1]

a) N-(4-bromo-2,5-difluorophenyl)-2-{[(3S)-1-(cyclopropylcarbonyl)-3-pyrrolidinyl]acetyl}hydrazinecarboxamide To a round bottom flask, 4-bromo-2,5-difluoroaniline (2 g, 9.62 mmol) and triphosgene (0.999 g, 3.37 mmol) were added under nitrogen and the mixture was cooled to −78° C. Dichloromethane (40 mL) was added followed by the slow addition of Hunig's base (3.36 mL, 19.23 mmol). The reaction was allowed to room temperature. Analysis by LCMS indicated desired intermediate formation. The solution was re-cooled to −78° C. and 2-[(3S)-1-(cyclopropylcarbonyl)-3-pyrrolidinyl]acetohydrazide (1.219 g, 5.77 mmol) in dichloromethane (10 mL) was added. The solution was allowed to warm to room temperature, and analysis by LCMS indicated desired product formation. After 2 h of stirring at room temperature the desired product began to precipitate out of solution and was collected by filtration and dried via vacuum filtration to afford the title product as a white solid (1340 mg, 62%). MS(ES)+ m/e 445.1, 446.9 M+H]+.

b) 4-(4-bromo-2,5-difluorophenyl)-5-{[(3S)-1-(cyclopropylcarbonyl)-3-pyrrolidinyl]methyl}-2,4-dihydro-3H-1,2,4-triazol-3-one To a round bottom flask were added N-(4-bromo-2,5-difluorophenyl)-2-{[(3S)-1-(cyclopropylcarbonyl)-3-pyrrolidinyl]acetyl}hydrazinecarboxamide (1.80 g, 4.04 mmol) and potassium carbonate (1.955 g, 14.15 mmol) and water (200 mL). The resulting suspension was refluxed for 16 h at 115° C. The pH of the solution was lowered to ~6 with 1N aq HCl and then partitioned with 150 mL of ethyl acetate. The aqueous phase was extracted with ethyl acetate (3×) and the combined organic layer was washed with brine, dried over Na$_2$SO$_4$ and concentrated in vacuo. The residue was purified by silica gel chromatography (0-100% ethyl acetate/hexanes, then 0-25% isopropanol/ethyl acetate), and the desired fractions were combined and concentrated in vacuo to afford the title product as an off-white solid (400 mg, 31%). MS(ES)+ m/e 426.9, 428.8 M+H]+.

c) 4-[4-(1-benzofuran-5-yl)-2,5-difluorophenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-2,5-difluorophenyl)-5-{[(3S)-1-(cyclopropylcarbonyl)-3-pyrrolidinyl]methyl}-2,4-dihydro-3H-1,2,4-triazol-3-one (50 mg, 0.117 mmol), 5-(4,4,5,5-tetramethyl-1,3,2-dioxaborolan-2-yl)-1-benzofuran (42.8 mg, 0.176 mmol), cesium carbonate (114 mg, 0.351 mmol), and dichloro[1,1'-bis(diphenylphosphino)ferrocene]palladium(II)-dichloromethane adduct (6.0 mg, 0.00735 mmol). The mixture was purged with nitrogen followed by the addition of 1,4-dioxane (1 mL) and water (0.5 mL). The suspension was heated overnight at 100° C. and analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3×), and the combined organics were washed with brine, dried over Na$_2$SO$_4$ and concentrated in vacuo to afford the title product as a white solid (25 mg, 46%). MS(ES)+ m/e 465.2 M+H]+.

Example 61

5-{[(3S)-1-(cyclopropylcarbonyl)-3-pyrrolidinyl]methyl}-4-[2,5-difluoro-4-(7-quinolinyl)phenyl]-2,4-dihydro-3H-1,2,4-triazol-3-one

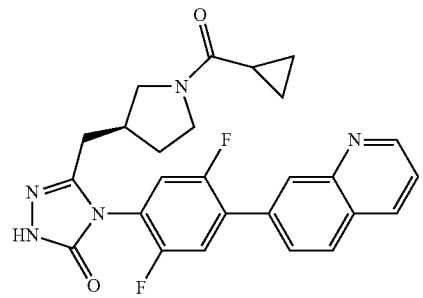 [SMILES: O=C(C1CC1)N1CC[C@@H](Cc2n[nH]c(=O)n2-c2cc(F)c(-c3ccc4cccnc4c3)cc2F)C1]

a) Following the procedure described in example 60c using 7-(4,4,5,5-tetramethyl-1,3,2-dioxaborolan-2-yl)quinoline afforded the title compound as an ivory solid (39 mg, 70%). MS(ES)+ m/e 476.0 [M+H]+.

Example 62

4'-(3-{[(3S)-1-(cyclopropylcarbonyl)-3-pyrrolidinyl]methyl}-5-oxo-1,5-dihydro-4H-1,2,4-triazol-4-yl)-2',5'-difluoro-3-methyl-4-biphenylcarbonitrile

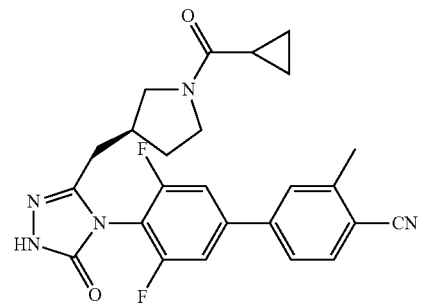 [SMILES: Cc1cc(-c2cc(F)c(-n3c(C[C@@H]4CCN(C(=O)C5CC5)C4)n[nH]c3=O)c(F)c2)ccc1C#N]

a) Following the procedure described in example 60c using 2-methyl-4-(4,4,5,5-tetramethyl-1,3,2-dioxaborolan-2-yl)

benzonitrile afforded the title compound as an ivory solid (40 mg, 81%). MS(ES)+ m/e 464.3 [M+H]+.

Example 63

5-{[(3S)-1-(cyclopropylcarbonyl)-3-pyrrolidinyl]methyl}-4-[2,5-difluoro-4-(1H-indol-6-yl)phenyl]-2,4-dihydro-3H-1,2,4-triazol-3-one

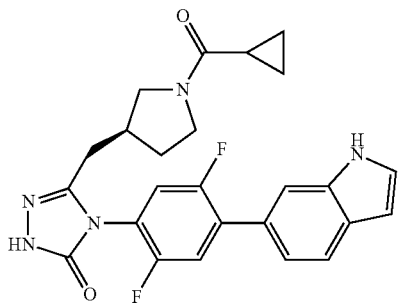 [SMILES: O=C(C1CC1)N1CC[C@@H](Cc2n[nH]c(=O)n2-c2cc(F)c(-c3ccc4cc[nH]c4c3)cc2F)C1]

a) Following the procedure described in example 60c using 6-(4,4,5,5-tetramethyl-1,3,2-dioxaborolan-2-yl)-1H-indole afforded the title compound as an ivory solid (14 mg, 26%). MS(ES)+ m/e 464.3 [M+H]+.

Example 64

4-[4-(1-benzofuran-5-yl)-2,3-difluorophenyl]-5-{[(3S)-1-(cyclopropylcarbonyl)-3-pyrrolidinyl]methyl}-2,4-dihydro-3H-1,2,4-triazol-3-one

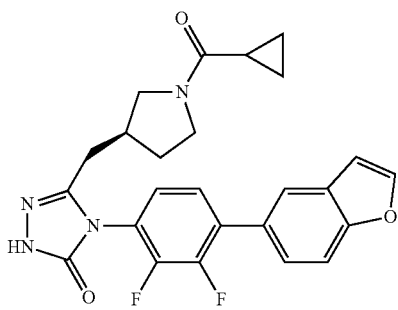 [SMILES: O=C(C1CC1)N1CC[C@@H](Cc2n[nH]c(=O)n2-c2ccc(-c3ccc4occc4c3)c(F)c2F)C1]

a) N-(4-bromo-2,3-difluorophenyl)-2-{[(3S)-1-(cyclopropylcarbonyl)-3-pyrrolidinyl]acetyl}hydrazinecarboxamide To a round bottom flask, 4-bromo-2,3-difluoroaniline (2 g, 9.62 mmol) and triphosgene (0.999 g, 3.37 mmol) were added under nitrogen and cooled to −78° C. Dichloromethane (40 mL) was added followed by the slow addition of Hunig's base (3.36 mL, 19.23 mmol). The reaction was allowed to warm to room temperature and analysis by LCMS indicated desired intermediate formation. The solution was re-cooled to −78° C. and 2-[(3S)-1-(cyclopropylcarbonyl)-3-pyrrolidinyl]acetohydrazide (1.051 g, 4.97 mmol) in dichloromethane (10 mL) was added. The solution was allowed to warm to room temperature, and analysis by LCMS indicated desired product formation. After 2 h of stirring at room temperature and blowing nitrogen gently over the solution, the desired product began to precipitate and was collected by filtration and dried via vacuum filtration to afford the title product (1400 mg, 63%). MS(ES)+ m/e 445.1, 447.1 M+H]+.

b) 4-(4-bromo-2,3-difluorophenyl)-5-{[(3S)-1-(cyclopropylcarbonyl)-3-pyrrolidinyl]methyl}-2,4-dihydro-3H-1,2,4-triazol-3-one To a round bottom flask were added N-(4-bromo-2,5-difluorophenyl)-2-{[(3S)-1-(cyclopropylcarbonyl)-3-pyrrolidinyl]acetyl}hydrazinecarboxamide (1.40 g, 3.14 mmol) and potassium carbonate (1.800 g, 13.02 mmol) and water (100 mL). The resulting suspension was refluxed for 16 h at 110° C. The pH of the solution was lowered to ~6 with 1N aq HCl and partitioned with 150 mL of ethyl acetate. The aqueous phase was extracted with ethyl acetate (3×) and the combined organic layer was washed with brine, dried over Na₂SO₄ and concentrated in vacuo. The residue was purified by silica gel chromatography (0-100% ethyl acetate/hexanes, then 0-25% isopropanol/ethyl acetate), and the desired fractions were combined and concentrated in vacuo to afford the title product as a white solid (380 mg, 27%). MS(ES)+ m/e 426.9, 428.6 M+H]+.

c) 4-[4-(1-benzofuran-5-yl)-2,3-difluorophenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-2,3-difluorophenyl)-5-{[(3S)-1-(cyclopropylcarbonyl)-3-pyrrolidinyl]methyl}-2,4-dihydro-3H-1,2,4-triazol-3-one (50 mg, 0.117 mmol), 5-(4,4,5,5-tetramethyl-1,3,2-dioxaborolan-2-yl)-1-benzofuran (42.8 mg, 0.176 mmol), cesium carbonate (114 mg, 0.351 mmol), and dichloro[1,1'-bis(diphenylphosphino)ferrocene]palladium(II)-dichloromethane adduct (6.0 mg, 0.00735 mmol). The mixture was purged with nitrogen, followed by the addition of 1,4-dioxane (1 mL) and water (0.5 mL). The resulting suspension was heated overnight at 100° C., at which point analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3×), and the combined organics were washed with brine, dried over Na₂SO₄ and concentrated in vacuo to afford the title product as a white solid (37 mg, 68%). MS(ES)+ m/e 465.1 M+H]+.

Example 65

5-{[(3S)-1-(cyclopropylcarbonyl)-3-pyrrolidinyl]methyl}-4-[2,3-difluoro-4-(7-quinolinyl)phenyl]-2,4-dihydro-3H-1,2,4-triazol-3-one

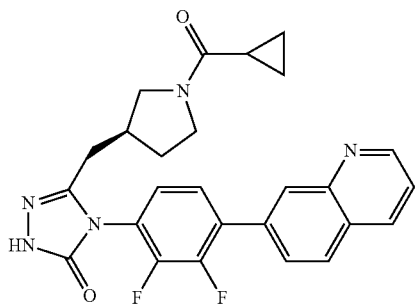 [SMILES: O=C(C1CC1)N1CC[C@@H](Cc2n[nH]c(=O)n2-c2ccc(-c3ccc4cccnc4c3)c(F)c2F)C1]

a) Following the procedure described in example 64c using 7-(4,4,5,5-tetramethyl-1,3,2-dioxaborolan-2-yl)quinoline afforded the title compound as an ivory solid (22 mg, 40%). MS(ES)+ m/e 476.0 [M+H]+.

Example 66

5-{[1-(cyclopropylcarbonyl)-3-azetidinyl]methyl}-4-[4-(1H-indazol-6-yl)phenyl]-2,4-dihydro-3H-1,2,4-triazol-3-one

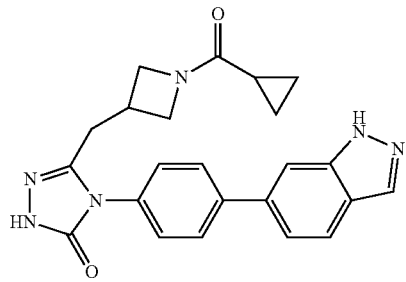 [SMILES: O=C(C1CC1)N1CC(Cc2n[nH]c(=O)n2-c2ccc(-c3ccc4cn[nH]c4c3)cc2)C1]

a) 1,1-dimethylethyl 3-[2-(ethyloxy)-2-oxoethyl]-1-azetidinecarboxylate

In an oven-dried 250 mL round bottom flask under nitrogen, a mixture of (1-{[(1,1-dimethylethyl)oxy]carbonyl}-3-azetidinyl)acetic acid (10 g, 46.5 mmol) in diethyl ether (100 mL) was treated with N-(3-dimethylaminopropyl)-N'-ethylcarbodiimide hydrochloride (9.80 g, 51.1 mmol), 4-(dimethylamino)pyridine (0.568 g, 4.65 mmol), and ethanol (5.97 mL, 102 mmol) at room temperature and the white mixture was stirred over the weekend. The white reaction mixture became a colorless solution with gummy material at the bottom of the flask after 1 h. The reaction mixture was diluted with ether (300 mL) and washed with 1M aq NaHSO4 solution (150 mL) and saturated aq NaHCO3 solution (150 mL). The organic phase was isolated, dried over MgSO4, and concentrated in vacuo to give the title compound (10.55 g, 93%) as a clear colorless liquid. MS(ES)+ m/e 244.4 [M+H]+.

b) ethyl[1-(cyclopropylcarbonyl)-3-azetidinyl]acetate

In a round bottom flask, a solution of 1,1-dimethylethyl 3-[2-(ethyloxy)-2-oxoethyl]-1-azetidinecarboxylate (10.55 g, 43.3 mmol) in 4M HCl in dioxane (50 mL, 200 mmol) was stirred at room temperature for 1 h. Analysis by LCMS showed that the reaction was complete; conversion was observed to the des-BOC intermediate [M+H]+=144.0 (by ELS, no UV214 detection) and an unknown [M+H]+=179.9. The reaction was concentrated in vacuo. A solution of this intermediate (as the HCl salt) in dichloromethane (50 mL) was treated with N,N-diisopropylethylamine (15.14 mL, 87 mmol) and stirred for 2 min at room temperature. The pale yellow solution was treated with cyclopropanecarbonyl chloride (4.33 mL, 47.7 mmol) by syringe at room temperature and then stirred for 1 h. The reaction was diluted with water (200 mL), the layers were separated and the aqueous layer was extracted with dichloromethane (100 mL). The organic layers were combined, dried over MgSO4, and concentrated in vacuo to give the title compound as an orange liquid (10.54 g, 65% pure, 75% yield). This product could also be prepared by using 10% TFA in dichloromethane. 1H NMR in DMSO-d6 showed ~2:1 desired product:by-product. MS(ES)+ m/e 211.9 [M+H]+.

c) 2-[1-(cyclopropylcarbonyl)-3-azetidinyl]acetohydrazide

In a round bottom flask equipped with reflux condenser under nitrogen, a solution of ethyl[1-(cyclopropylcarbonyl)-3-azetidinyl]acetate (0.433 g, 2.097 mmol) and hydrazine monohydrate (1.3 mL, 41.9 mmol) in ethanol (10 mL) was stirred at 80° C. for 16.5 h. The reaction was cooled to room temperature and concentrated in vacuo. The residue was then concentrated down from methanol and then toluene. The residue was dissolved in dichloromethane, filtered through sodium sulfate, and concentrated in vacuo to a colorless oil. The oil still looked wet and was too heavy, so it was dissolved again in dichloromethane and filtered through sodium sulfate, rinsing with additional dichloromethane. The combined organics were concentrated in vacuo and then concentrated under high vacuum pressure to yield the crude title product as a yellow oil (0.316 g, 86% pure, 66% yield). MS(ES)+ m/e 198.1 [M+H]+, 395.1 [2M+H]+.

d) N-(4-bromophenyl)-2-{[1-(cyclopropylcarbonyl)-3-azetidinyl]acetyl}hydrazinecarboxamide In a round bottom flask, a solution of 2-[1-(cyclopropylcarbonyl)-3-azetidinyl]acetohydrazide (0.316 g, 1.602 mmol) in dichloromethane (10 mL) was treated with 4-bromophenylisocyanate (0.317 g, 1.602 mmol) and the reaction mixture was stirred at room temperature for 1 h (white precipitate formed). The white solid was filtered, rinsing with cold dichloromethane (4×), and dried under air suction to give the title compound (0.455 g, 87% pure, 62% yield). MS(ES)+ m/e 394.9, 396.6 [M+H]+.

e) 4-(4-bromophenyl)-5-{[1-(cyclopropylcarbonyl)-3-azetidinyl]methyl}-2,4-dihydro-3H-1,2,4-triazol-3-one In a round bottom flask equipped with reflux condenser, a mixture of N-(4-bromophenyl)-2-{[1-(cyclopropylcarbonyl)-3-azetidinyl]acetyl}hydrazinecarboxamide (4.71 g, 5.48 mmol) and potassium carbonate (3.79 g, 27.4 mmol) in water (400 mL) was stirred at reflux (oil bath temp=130° C.) for 14 h. The reaction was cooled to room temperature. The reaction mixture was concentrated in vacuo and then taken up into ethyl acetate (250 mL) and water (100 mL). The pH of the mixture was adjusted to ~5-5.5 (pH paper) using 1N aq HCl solution and then the layers were separated. The aqueous layer was extracted with ethyl acetate (2×150 mL). The organic layers were combined, dried over MgSO4, and concentrated in vacuo. Purification of the residue by silica gel chromatography (0-10% methanol/ethyl acetate) followed by drying in a vacuum oven (70° C.) overnight provided the title compound as a white solid (0.93 g, 38.7%). MS(ES)+ m/e 377.0, 379.0 [M+H]+.

f) 5-{[1-(cyclopropylcarbonyl)-3-azetidinyl]methyl}-4-[4-(1H-indazol-6-yl)phenyl]-2,4-dihydro-3H-1,2,4-triazol-3-one In a microwave vial purged with nitrogen, a mixture of 4-(4-bromophenyl)-5-{[1-(cyclopropylcarbonyl)-3-azetidinyl]methyl}-2,4-dihydro-3H-1,2,4-triazol-3-one (70 mg, 0.186 mmol), 1,1'-bis(diphenylphosphino)ferrocene-palladium(II)dichloride dichloromethane complex (8 mg, 9.80 µmol), and 5-(4,4,5,5-tetramethyl-1,3,2-dioxaborolan-2-yl)-1H-indazole (50 mg, 0.205 mmol)) in 1,4-dioxane (2 mL) and 2M aq potassium carbonate (0.7 mL, 1.400 mmol) was stirred at 100° C. in an oil bath for 16 h. The reaction was cooled to room temperature and diluted with ethyl acetate (10 mL). The layers were separated and the aqueous layer was adjusted to pH~6-6.5 using 1N aq HCl. The aqueous layer was extracted with ethyl acetate (2×30 mL). The organic layers were combined, dried over MgSO$_4$, and concentrated in vacuo. Purification of the residue by reverse phase HPLC (10-90% acetonitrile/water+0.1% NH$_4$OH) provided the title compound as a white solid (20 mg, 26%). MS(ES)+ m/e 415.2 [M+H]$^+$.

Example 67

5-{[1-(cyclopropylcarbonyl)-3-azetidinyl]methyl}-4-[4-(1H-indol-6-yl)phenyl]-2,4-dihydro-3H-1,2,4-triazol-3-one

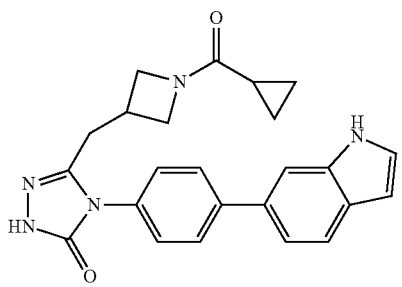 [SMILES: O=C(C1CC1)N1CC(Cc2n[nH]c(=O)n2-c2ccc(-c3ccc4cc[nH]c4c3)cc2)C1]

a) Following the procedure described in example 66f using 1H-indol-6-ylboronic acid and purification by flash chromatography (0-5% methanol/ethyl acetate) afforded the title compound as an ivory solid (68%). MS(ES)+ m/e 414.1 [M+H]$^+$.

Example 68

5-{[1-(cyclopropylcarbonyl)-3-azetidinyl]methyl}-4-[4-(6-quinolinyl)phenyl]-2,4-dihydro-3H-1,2,4-triazol-3-one

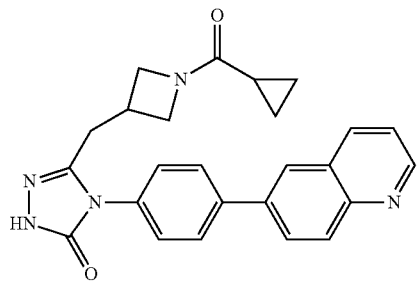

a) Following the procedure described in example 66f using 6-(4,4,5,5-tetramethyl-1,3,2-dioxaborolan-2-yl)quinoline and purification by flash chromatography (0-5% methanol/ethyl acetate) afforded the title compound as an ivory solid (55%). MS(ES)+ m/e 426.1 [M+H]$^+$.

Example 69

5-{[1-(cyclopropylcarbonyl)-3-azetidinyl]methyl}-4-[4'-(methyloxy)-4-biphenylyl]-2,4-dihydro-3H-1,2,4-triazol-3-one

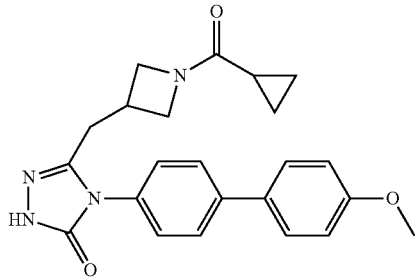 [SMILES: COc1ccc(-c2ccc(-n3c(CC4CN(C(=O)C5CC5)C4)n[nH]c3=O)cc2)cc1]

a) Following the procedure described in example 66f using [4-(methyloxy)phenyl]boronic acid and purification by flash chromatography (0-5% methanol/ethyl acetate) afforded the title compound as an orange solid (67%). MS(ES)+ m/e 405.3 [M+H]$^+$.

Example 70

5-{[1-(cyclopropylcarbonyl)-3-azetidinyl]methyl}-4-[4'-(dimethylamino)-4-biphenylyl]-2,4-dihydro-3H-1,2,4-triazol-3-one

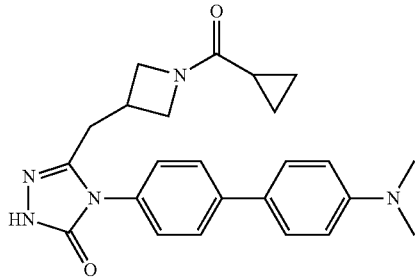 [SMILES: CN(C)c1ccc(-c2ccc(-n3c(CC4CN(C(=O)C5CC5)C4)n[nH]c3=O)cc2)cc1]

a) Following the procedure described in example 66f using [4-(dimethylamino)phenyl]boronic acid and purification by flash chromatography (0-5% methanol/ethyl acetate) and then reverse phase HPLC (10-70% acetonitrile/water with 0.1% NH$_4$OH) afforded the title compound as a white solid (38%). MS(ES)+ m/e 418.2 [M+H]$^+$.

Example 71

4-[4-(1-benzofuran-5-yl)phenyl]-5-{[1-(cyclopropylcarbonyl)-3-azetidinyl]methyl}-2,4-dihydro-3H-1,2,4-triazol-3-one

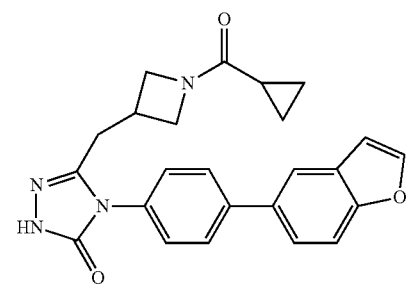 [SMILES: O=C(C1CC1)N1CC(Cc2n[nH]c(=O)n2-c2ccc(-c3ccc4occc4c3)cc2)C1]

a) In a microwave vial purged with nitrogen, a mixture of 4-(4-bromophenyl)-5-{[1-(cyclopropylcarbonyl)-3-azetidinyl]methyl}-2,4-dihydro-3H-1,2,4-triazol-3-one (83 mg, 0.220 mmol), 1,1'-bis(diphenylphosphino)ferrocene-palladium(II)dichloride dichloromethane complex (9 mg, 11 μmol), and 5-(4,4,5,5-tetramethyl-1,3,2-dioxaborolan-2-yl)-1-benzofuran (59 mg, 0.242 mmol) in 1,4-dioxane (2 mL) and 2M aq potassium carbonate (0.5 mL, 1.00 mmol) was stirred at 100° C. in an oil bath for 22 h. Additional 5-(4,4,5,5-tetramethyl-1,3,2-dioxaborolan-2-yl)-1-benzofuran (59 mg, 0.242 mmol) and 1,1'-bis(diphenylphosphino)ferrocene-palladium(II)dichloride dichloromethane complex (9 mg, 11 μmol) were added and the reaction mixture was heated at 100° C. in an oil bath for 20 h. The reaction was cooled to room temperature, poured into water (50 mL), and adjusted to pH~4.5 with 1N aq HCl. The aqueous layer was extracted with ethyl acetate (3×50 mL). The combined organic layers were dried over sodium sulfate, filtered, and concentrated in vacuo. Purification of the residue by flash chromatography (ethyl acetate, then 0-10% methanol/ethyl acetate) followed by a second purification by reverse phase HPLC (20-70% acetonitrile/water+0.1% NH$_4$OH) provided the title compound as an ivory solid (37 mg, 38%). MS(ES)+ m/e 415.2 [M+H]$^+$.

Example 72

5-{[1-(cyclopropylcarbonyl)-3-azetidinyl]methyl}-4-[2-fluoro-4-(1H-indol-6-yl)phenyl]-2,4-dihydro-3H-1,2,4-triazol-3-one

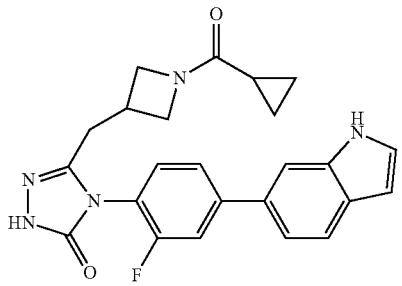 [SMILES: O=C(C1CC1)N1CC(Cc2n[nH]c(=O)n2-c2ccc(-c3ccc4cc[nH]c4c3)cc2F)C1]

a) N-(4-bromo-2-fluorophenyl)-2-{[1-(cyclopropylcarbonyl)-3-azetidinyl]acetyl}hydrazinecarboxamide Following the procedure described in example 66d using 4-bromo-2-fluorophenylisocyanate afforded the title compound as a white solid (45% pure, 38% yield). MS(ES)+ m/e 413.1, 415.0 [M+H]$^+$.

b) 4-(4-bromo-2-fluorophenyl)-5-{[1-(cyclopropylcarbonyl)-3-azetidinyl]methyl}-2,4-dihydro-3H-1,2,4-triazol-3-one Following the procedure described in example 66e using N-(4-bromo-2-fluorophenyl)-2-{[1-(cyclopropylcarbonyl)-3-azetidinyl]acetyl}hydrazinecarboxamide as well as a second purification via flash chromatography (0-5% methanol/ethyl acetate) afforded the title compound as a white solid (9%). MS(ES)+ m/e 394.9, 396.8 [M+H]$^+$.

c) 5-{[1-(cyclopropylcarbonyl)-3-azetidinyl]methyl}-4-[2-fluoro-4-(1H-indol-6-yl)phenyl]-2,4-dihydro-3H-1,2,4-triazol-3-one In a microwave vial purged with nitrogen, a mixture of 4-(4-bromo-2-fluorophenyl)-5-{[1-(cyclopropylcarbonyl)-3-azetidinyl]methyl}-2,4-dihydro-3H-1,2,4-triazol-3-one (64 mg, 0.162 mmol), 1,1'-bis(diphenylphosphino)ferrocene-palladium(II)dichloride dichloromethane complex (15 mg, 0.018 mmol), and 1H-indol-6-ylboronic acid (30 mg, 0.186 mmol) in 1,4-dioxane (1.5 mL) and 2M aq potassium carbonate (0.5 mL, 1.000 mmol) were stirred at 100° C. in an oil bath for 16 h. The reaction was cooled to room temperature, diluted with ethyl acetate (10 mL), and then the layers were separated. The aqueous layer was neutralized using 1N aq HCl and then extracted with ethyl acetate (2×20 mL). The organic layers were combined, dried over MgSO$_4$, and concentrated in vacuo. Purification of the residue by silica gel chromatography (0-5% methanol/ethyl acetate) provided the title compound as an impure solid. Subsequent purification of this solid by reverse phase HPLC (10-70% acetonitrile/water+0.1% NH$_4$OH) followed by dessication in a vacuum oven over the weekend provided the title compound as a white solid (16 mg, 23%). MS(ES)+ m/z 432.2 [M+H]$^+$.

Example 73

4'-(3-{[1-(cyclopropylcarbonyl)-3-azetidinyl]methyl}-5-oxo-1,5-dihydro-4H-1,2,4-triazol-4-yl)-3'-fluoro-4-biphenylcarbonitrile

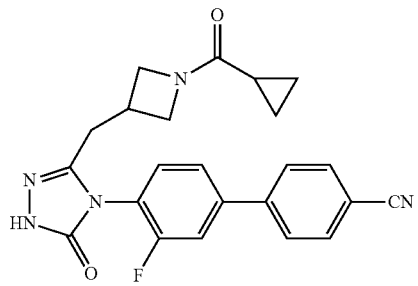 [SMILES: N#Cc1ccc(-c2ccc(-n3c(CC4CN(C(=O)C5CC5)C4)n[nH]c3=O)c(F)c2)cc1]

a) Following the procedure described in example 72c using (4-cyanophenyl)boronic acid and purification by successive triturations in dichloromethane/diethyl ether, dichloromethane, and hot ethanol afforded the title compound as a white solid (72%). MS(ES)+ m/e 418.2 [M+H]$^+$.

Example 74

5-{[(3S)-1-(cyclopropylcarbonyl)-3-pyrrolidinyl]methyl}-4-[3'-(phenylcarbonyl)-4-biphenylyl]-2,4-dihydro-3H-1,2,4-triazol-3-one

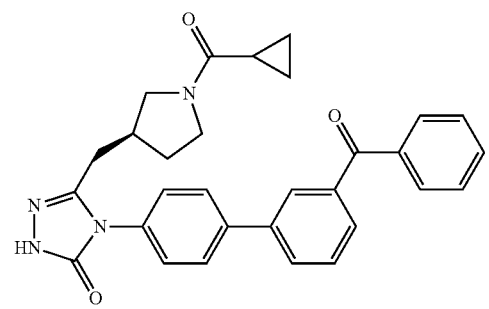 [SMILES: O=C(c1ccccc1)c1cccc(-c2ccc(-n3c(C[C@@H]4CCN(C(=O)C5CC5)C4)n[nH]c3=O)cc2)c1]

a) In a sealed tube, a mixture of 5-{[(3S)-1-(cyclopropylcarbonyl)-3-pyrrolidinyl]methyl}-4-[4-(4,4,5,5-tetramethyl-1,3,2-dioxaborolan-2-yl)phenyl]-2,4-dihydro-3H-1,2,4-triazol-3-one (179 mg, 0.265 mmol), 3-bromobenzophenone (66 mg, 0.253 mmol), and 1,1'-bis(diphenylphosphino)ferrocene-palladium(II)dichloride dichloromethane complex (10 mg, 0.012 mmol) in 2M aq potassium carbonate (0.5 mL, 1.00 mmol) and 1,4-dioxane (1.5 mL) was stirred at 100° C. for 1 h. The reaction was cooled to room temperature and the reaction mixture was diluted with ethyl acetate (10 mL). The layers were separated and the aqueous layer was acidified to pH~5 using 1N aq HCl. The aqueous layer was then extracted with ethyl acetate (20 mL). The organic layers were combined, dried over MgSO₄, and concentrated in vacuo. Purification of the residue by silica gel chromatography (0-3% methanol/ethyl acetate) provided the title compound as an ivory solid (68 mg, 55%) after drying in the vacuum oven (70° C.) for 4 days. MS(ES)+ m/e 493.2 [M+H]⁺.

Example 75

5-{[(3S)-1-(cyclopropylcarbonyl)-3-pyrrolidinyl]methyl}-4-[3-fluoro-3'-(phenylcarbonyl)-4-biphenylyl]-2,4-dihydro-3H-1,2,4-triazol-3-one

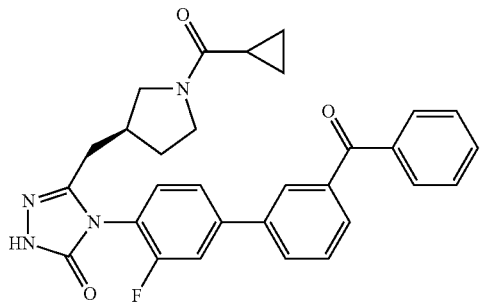 [SMILES: O=C(c1ccccc1)c1cccc(-c2ccc(-n3c(C[C@@H]4CCN(C(=O)C5CC5)C4)n[nH]c3=O)c(F)c2)c1]

a) In a sealed microwave vial under nitrogen, a mixture of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (124 mg, 0.303 mmol), bis(pinacolato)diboron (81 mg, 0.318 mmol), potassium acetate (89 mg, 0.909 mmol) and 1,1'-bis(diphenylphosphino)ferrocene-palladium(II)dichloride dichloromethane complex (12.37 mg, 0.015 mmol) in 1,4-dioxane (2.5 mL) was stirred at 100° C. in an oil bath for 1 h. The reaction was cooled to room temperature. Analysis by LCMS showed complete conversion to the boronic ester intermediate (boronic ester cleavage to acid also observed on LCMS due to water/TFA conditions). 3-Bromobenzophenone (79 mg, 0.303 mmol) and 2M aq potassium carbonate (0.45 mL, 0.909 mmol) were added to the reaction mixture. The resultant reaction mixture was stirred at 100° C. in an oil bath for 1 h. The reaction was cooled to room temperature. The reaction mixture was then transferred to a separatory funnel and the layers were separated. The aqueous layer was adjusted to pH~5 using 1N aq HCl and then extracted with ethyl acetate (2×50 mL). The organic layers were combined, dried over MgSO₄, and concentrated in vacuo. Purification of the residue by silica gel chromatography (0-5% methanol/ethyl acetate) provided the desired product as a white solid, which was dried in a vacuum oven (70° C.) overnight. The solid was further purified by reverse phase HPLC (10-80% acetonitrile/water+0.1% NH₄OH). The desired product was dissolved in acetonitrile (2 mL) and water (10 mL), frozen, and lyophilized over the weekend. The solid was further dried in a vacuum oven (70° C.) overnight to give the title compound as a white solid (72 mg, 46%). MS(ES)+ m/e 511.1 [M+H]⁺.

Example 76

4-[2-chloro-4-(1H-indol-5-yl)phenyl]-5-{[(3S)-1-(cyclopropylcarbonyl)-3-pyrrolidinyl]methyl}-2,4-dihydro-3H-1,2,4-triazol-3-one

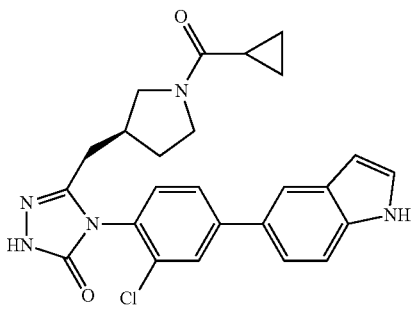 [SMILES: O=C(C1CC1)N1CC[C@@H](Cc2n[nH]c(=O)n2-c2ccc(-c3ccc4[nH]ccc4c3)cc2Cl)C1]

a) N-(4-bromo-2-chlorophenyl)-2-{[(3S)-1-(cyclopropylcarbonyl)-3-pyrrolidinyl]acetyl}hydrazinecarboxamide To a solution of 2-[(3S)-1-(cyclopropylcarbonyl)-3-pyrrolidinyl]acetohydrazide (700 mg, 3.31 mmol) in dry dichloromethane (15 mL) was added 4-bromo-2-chloro-1-isocyanatobenzene (770 mg, 3.31 mmol). The reaction was stirred overnight, diluted with hexane (15 mL), and the precipitate collected and washed with hexane to provide the title compound (1.3 g, 2.93 mmol, 88% yield) as a white solid. ¹H NMR (400 MHz, DMSO-d₆) δ ppm 9.85 (br. s, 1H), 8.82 (br. s, 1H), 8.50-8.23 (m, 1H), 8.05 (dd, J=5.3, 8.8 Hz, 1H), 7.72 (d, J=1.8 Hz, 1H), 7.49 (d, J=8.8 Hz, 1H), 3.81 (dd, J=7.6, 9.9 Hz, 0.5H), 3.77-3.39 (m, 2H), 3.31-3.13 (m, 1H), 2.94 (d, J=19.5 Hz, 0.5H), 2.64-2.54 (m, 0.5H), 2.47-2.39 (m, 0.5H), 2.28 (dd, J=7.3, 16.7 Hz, 2H), 2.17-1.88 (m, 1H), 1.80-1.47 (m, 2H), 0.81-0.61 (m, 4H).

b) 4-(4-bromo-2-chlorophenyl)-5-{[(3S)-1-(cyclopropylcarbonyl)-3-pyrrolidinyl]methyl}-2,4-dihydro-3H-1,2,4-triazol-3-one To a suspension of N-(4-bromo-2-chlorophenyl)-2-{[(3S)-1-(cyclopropylcarbonyl)-3-pyrrolidinyl]acetyl}hydrazinecarboxamide (1.3 g, 2.93 mmol) in water (60 mL) was added K₂CO₃ (2.025 g, 14.65 mmol). The reaction flask was equipped with a reflux condenser and heated to reflux (bath=120° C.) with stirring. After 5 h (analysis by LCMS indicated no starting material remained), the reaction mixture was cooled to room temperature and filtered to collect a small amount of white precipitate (this was determined to contain very little product and was discarded). The aqueous filtrate was adjusted to pH~5.5 with 1N aq HCl and extracted with ethyl acetate (2×). The combined organics were dried over Na₂SO₄, filtered, and evaporated to provide the title product (570 mg, 1.339 mmol, 46% yield) as a foam. The product was determined to be 75% pure by LCMS (UV214) and was carried on in the next step without further purification. ¹H NMR (400 MHz, CDCl₃) δ ppm 7.80 (dt, J=2.3, 5.7

Hz, 1H), 7.68-7.52 (m, 1H), 7.28-7.22 (m, 1H), 4.01-3.35 (m, 2H), 3.34-2.99 (m, 1H), 2.74-2.08 (m, 3H), 1.82-1.66 (m, 1H), 1.59-1.51 (m, 1H), 1.12-0.91 (m, 1H), 0.83-0.69 (m, 1H).

c) 4-[2-chloro-4-(1H-indol-5-yl)phenyl]-5-{[(3S)-1-(cyclopropylcarbonyl)-3-pyrrolidinyl]methyl}-2,4-dihydro-3H-1,2,4-triazol-3-one A mixture of 4-(4-bromo-2-chlorophenyl)-5-{[(3S)-1-(cyclopropylcarbonyl)-3-pyrrolidinyl]methyl}-2,4-dihydro-3H-1,2,4-triazol-3-one (140 mg, 0.329 mmol), 5-(4,4,5,5-tetramethyl-1,3,2-dioxaborolan-2-yl)-1H-indole (80 mg, 0.329 mmol), potassium carbonate (182 mg, 1.315 mmol), and tetrakis(triphenylphosphine)palladium(0) (19.0 mg, 0.016 mmol) in 1,4-dioxane (5 mL) and water (2 mL) was heated at 120° C. for 3.5 hr. The reaction mixture was cooled and loaded onto a silica gel pre-column and purified by flash chromatography (dichloromethane to 6% methanol in dichloromethane) to afford the title product (73 mg, 0.158 mmol, 48% yield). $^1$H NMR (400 MHz, CDCl$_3$) δ ppm 8.96-8.78 (m, 1H), 8.37 (br. s, 1H), 7.92-7.82 (m, 2H), 7.76-7.64 (m, 1H), 7.56-7.47 (m, 1H), 7.47-7.39 (m, 2H), 7.36-7.30 (m, 1H), 6.76-6.61 (m, 1H), 4.04-3.02 (m, 4H), 2.80-2.39 (m, 3H), 2.34-2.03 (m, 1H), 1.84-1.60 (m, 1H), 1.07-0.94 (m, 2H), 0.76 (dd, J=3.3, 7.8 Hz, 2H).

Example 77

4-[2-chloro-4-(1H-indazol-5-yl)phenyl]-5-{[(3S)-1-(cyclopropylcarbonyl)-3-pyrrolidinyl]methyl}-2,4-dihydro-3H-1,2,4-triazol-3-one

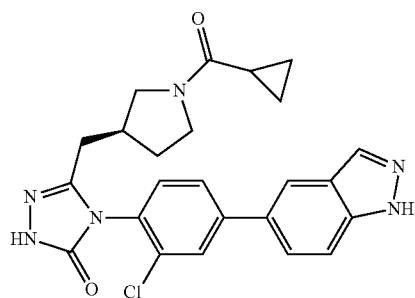

a) Following the procedure described in example 76c using 1H-indazol-5-ylboronic acid afforded the title compound as a solid (27 mg, 0.058 mmol, 18% yield). $^1$H NMR (400 MHz, CDCl$_3$) δ ppm 10.45 (br. s, 1H), 9.28-9.11 (m, 1H), 8.18 (d, J=4.3 Hz, 1H), 7.98 (d, J=4.3 Hz, 1H), 7.88-7.79 (m, 1H), 7.74-7.52 (m, 3H), 7.50-7.40 (m, 1H), 3.96 (dt, J=6.6, 9.9 Hz, 0.5H), 3.86-3.71 (m, 1H), 3.71-3.58 (m, 1H), 3.48-3.38 (m, 0.5H), 3.38-3.02 (m, 1H), 2.83-2.38 (m, 3H), 2.33-2.00 (m, 1H), 1.92-1.62 (m, 1H), 1.34-1.26 (m, 1H), 1.09-0.94 (m, 2H), 0.77 (dd, J=3.0, 7.8 Hz, 2H).

Example 78

4-[4-(1-benzofuran-5-yl)-2-chlorophenyl]-5-{[(3S)-1-(cyclopropylcarbonyl)-3-pyrrolidinyl]methyl}-2,4-dihydro-3H-1,2,4-triazol-3-one

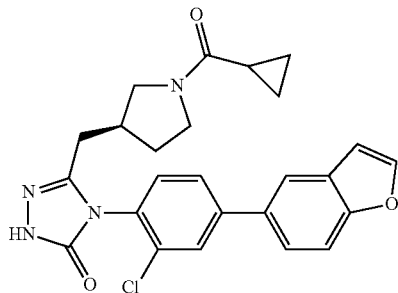

a) Following the procedure described in example 76c using 5-(4,4,5,5-tetramethyl-1,3,2-dioxaborolan-2-yl)-1-benzofuran afforded the title compound as a solid (77 mg, 0.166 mmol, 51% yield). $^1$H NMR (400 MHz, CDCl$_3$) δ ppm 9.40 (br. d, 1H), 7.97-7.79 (m, 2H), 7.79-7.60 (m, 3H), 7.58-7.50 (m, 1H), 7.50-7.40 (m, 1H), 6.87 (s, 1H), 4.10-3.24 (m, 4H), 3.24-3.05 (m, 0.5H), 2.83-2.36 (m, 3H), 2.35-2.04 (m, 1H), 1.86-1.71 (m, 0.5H), 1.60-1.51 (m, 1H), 1.08-0.92 (m, 2H), 0.86-0.69 (m, 2H).

Example 79

4-[2-chloro-4-(1H-indol-6-yl)phenyl]-5-{[(3S)-1-(cyclopropylcarbonyl)-3-pyrrolidinyl]methyl}-2,4-dihydro-3H-1,2,4-triazol-3-one

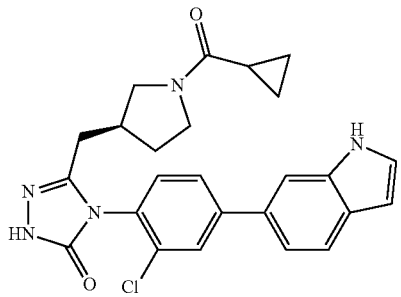 [SMILES: O=C(C1CC1)N1CC[C@@H](Cc2n[nH]c(=O)n2-c2ccc(-c3ccc4cc[nH]c4c3)cc2Cl)C1]

a) Following the procedure described in example 76c using 1H-indol-6-ylboronic acid afforded the title compound as a solid (52 mg, 0.113 mmol, 34% yield). $^1$H NMR (400 MHz, CDCl$_3$) δ ppm 9.32-9.13 (m, 1H), 8.49 (d, J=7.6 Hz, 1H), 7.86 (dt, J=2.1, 7.3 Hz, 1H), 7.75 (dd, J=3.9, 8.2 Hz, 1H), 7.73-7.64 (m, 1H), 7.62 (d, J=5.8 Hz, 1H), 7.47-7.30 (m, 3H), 6.74-6.53 (m, 1H), 3.96 (dt, J=7.3, 10.0 Hz, 0.5H), 3.84-3.70 (m, 1H), 3.70-3.57 (m, 1H), 3.47-3.27 (m, 0.5H), 3.11 (ddd, J=4.7, 7.3, 12.0 Hz, 0.5H), 2.79-2.39 (m, 3H), 2.32-2.03 (m, 1H), 1.84-1.69 (m, 0.5H), 1.66-1.54 (m, 1H), 1.08-0.93 (m, 2H), 0.83-0.69 (m, 2H).

Example 80

5-{[(3S)-1-(cyclopropylcarbonyl)-3-pyrrolidinyl]methyl}-4-[4'-fluoro-3-(methyloxy)-4-biphenylyl]-2,4-dihydro-3H-1,2,4-triazol-3-one

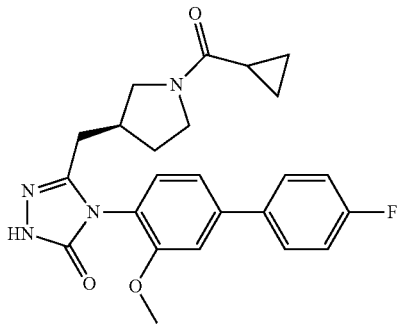 [SMILES: COc1cc(-c2ccc(F)cc2)ccc1-n1c(C[C@@H]2CCN(C(=O)C3CC3)C2)n[nH]c1=O]

a) N-[4-bromo-2-(methyloxy)phenyl]-2-{[(3S)-1-(cyclopropylcarbonyl)-3-pyrrolidinyl]acetyl}hydrazinecarboxamide Following the procedure described in example 76a using 4-bromo-1-isocyanato-2-(methyloxy)benzene afforded the title compound as a solid (1.48 g, 3.37 mmol, 97% yield). MS(ES)+ m/e 440.0 [M+H]$^+$.

b) 4-[4-bromo-2-(methyloxy)phenyl]-5-{[(3S)-1-(cyclopropylcarbonyl)-3-pyrrolidinyl]methyl}-2,4-dihydro-3H-1,2,4-triazol-3-one Following the procedure described in example 76b using N-[4-bromo-2-(methyloxy)phenyl]-2-{[(3S)-1-(cyclopropylcarbonyl)-3-pyrrolidinyl]acetyl}hydrazinecarboxamide and purification of the residue by flash chromatography (0-5% methanol/dichloromethane) afforded the title compound as a foam (587 mg, 1.393 mmol, 41% yield). MS(ES)+ m/e 422.0 [M+H]$^+$.

c) 5-{[(3S)-1-(cyclopropylcarbonyl)-3-pyrrolidinyl]methyl}-4-[4'-fluoro-3-(methyloxy)-4-biphenylyl]-2,4-dihydro-3H-1,2,4-triazol-3-one Following the procedure described in Example 76c using 4-[4-bromo-2-(methyloxy)phenyl]-5-{[(3S)-1-(cyclopropylcarbonyl)-3-pyrrolidinyl]methyl}-2,4-dihydro-3H-1,2,4-triazol-3-one and (4-fluorophenyl)boronic acid gave the title compound as a solid (60 mg, 0.137 mmol, 72% yield). $^1$H NMR (400 MHz, CDCl$_3$) δ ppm 9.27-9.05 (m, 1H), 7.58 (dd, J=5.3, 7.3 Hz, 2H), 7.34 (ddd, J=2.3, 4.0, 7.8 Hz, 1H), 7.28-7.11 (m, 3H), 4.02-3.87 (m, 3H), 3.80-3.67 (m, 1H), 3.62 (ddd, J=4.2, 8.0, 11.9 Hz, 1H), 3.49-2.96 (m, 1H), 2.77-2.36 (m, 2H), 2.32-1.99 (m, 1H), 1.88-1.67 (m, 1H), 1.59-1.50 (m, 1H), 1.09-0.92 (m, 2H), 0.84-0.67 (m, 2H).

Example 81

5-{[(3S)-1-(cyclopropylcarbonyl)-3-pyrrolidinyl]methyl}-4-[4-(1H-indol-5-yl)-2-(methyloxy)phenyl]-2,4-dihydro-3H-1,2,4-triazol-3-one

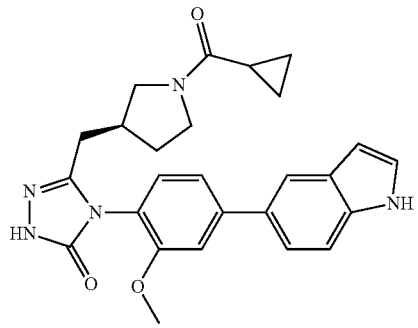 [SMILES: COc1cc(-c2ccc3[nH]ccc3c2)ccc1-n1c(C[C@@H]2CCN(C(=O)C3CC3)C2)n[nH]c1=O]

a) Following the procedure described in Example 80c using 5-(4,4,5,5-tetramethyl-1,3,2-dioxaborolan-2-yl)-1H-indole gave the title compound as a solid (65 mg, 0.142 mmol, 75% yield). $^1$H NMR (400 MHz, CDCl$_3$) δ ppm 9.32-9.09 (m, 1H), 8.43 (br. s., 1H), 7.88 (s, 1H), 7.53-7.40 (m, 2H), 7.39-7.29 (m, 3H), 6.65 (d, J=2.3 Hz, 1H), 4.01-3.87 (m, 3H), 3.82-3.69 (m, 1H), 3.69-3.53 (m, 1H), 3.48-3.01 (m, 1H), 2.76-2.36 (m, 2H), 2.27-2.01 (m, 1H), 1.83-1.67 (m, 1H), 1.61-1.51 (m, 1H), 1.08-0.91 (m, 2H), 0.83-0.68 (m, 2H).

Example 82

4-[4-(1-benzofuran-5-yl)-2-(methyloxy)phenyl]-5-{[(3S)-1-(cyclopropylcarbonyl)-3-pyrrolidinyl]methyl}-2,4-dihydro-3H-1,2,4-triazol-3-one

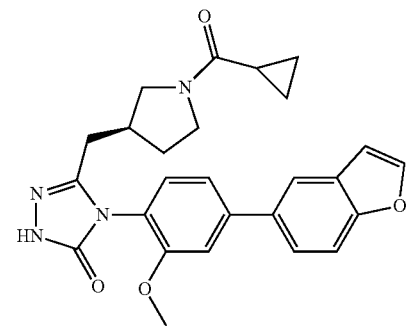 [SMILES: COc1cc(-c2ccc3occc3c2)ccc1-n1c(C[C@@H]2CCN(C(=O)C3CC3)C2)n[nH]c1=O]

a) Following the procedure described in Example 80c using 5-(4,4,5,5-tetramethyl-1,3,2-dioxaborolan-2-yl)-1-benzofuran gave the title compound as a solid (65 mg, 0.142 mmol, 75% yield). MS(ES)+ m/e 431.0 [M+H]$^+$. $^1$H NMR (400 MHz, CDCl$_3$) δ ppm 9.00-8.78 (m, 1H), 7.82 (s, 1H), 7.75-7.69 (m, 1H), 7.66-7.58 (m, 1H), 7.58-7.43 (m, 1H), 7.40-7.31 (m, 1H), 6.87 (dt, J=1.1, 2.1 Hz, 1H), 3.99-3.88 (m, 5H), 3.81-3.69 (m, 1H), 3.69-3.53 (m, 1H), 3.48-3.22 (m, 1H), 3.14-2.63 (m, 1H), 2.63-2.39 (m, 3H), 2.32-1.99 (m, 1H), 1.85-1.62 (m, 1H), 1.06-0.95 (m, 2H), 0.81-0.71 (m, 2H).

Example 83

5-{[(3S)-1-(cyclopropylcarbonyl)-3-pyrrolidinyl]methyl}-4-[4-(1H-indol-6-yl)-2-(methyloxy)phenyl]-2,4-dihydro-3H-1,2,4-triazol-3-one

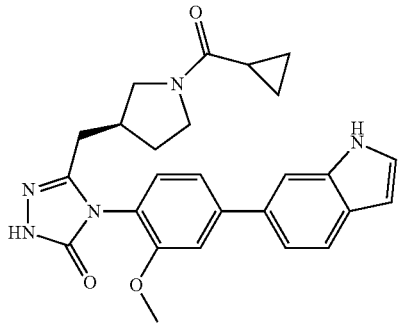 [SMILES: COc1cc(-c2ccc3cc[nH]c3c2)ccc1-n1c(C[C@@H]2CCN(C(=O)C3CC3)C2)n[nH]c1=O]

a) Following the procedure described in Example 80c using 1H-indol-6-ylboronic acid gave the title compound as a solid (68 mg, 0.149 mmol, 78% yield). $^1$H NMR (400 MHz, CDCl$_3$) δ ppm 9.57-9.30 (m, 1H), 8.54 (br. s., 1H), 7.74 (dd, J=3.2, 8.2 Hz, 1H), 7.61 (d, J=3.3 Hz, 1H), 7.43-7.30 (m, 3H), 6.62 (q, J=3.0 Hz, 1H), 4.01-3.35 (m, 5H), 3.35-3.00 (m, 1H), 2.77-2.35 (m, 2H), 2.32-2.00 (m, 1H), 1.83-1.68 (m, 1H), 1.61-1.49 (m, 1H), 1.08-0.94 (m, 2H), 0.82-0.69 (m, 2H).

Example 84

4'-(3-{[(3S)-1-(cyclopropylcarbonyl)-3-pyrrolidinyl]methyl}-5-oxo-1,5-dihydro-4H-1,2,4-triazol-4-yl)-3'-(methyloxy)-4-biphenylcarbonitrile

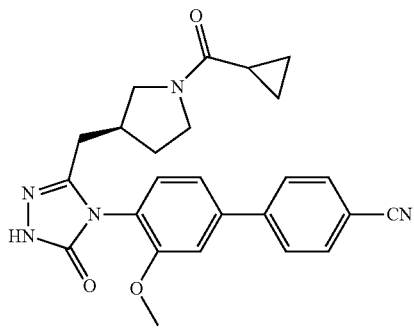 [SMILES: COc1cc(-c2ccc(C#N)cc2)ccc1-n1c(C[C@@H]2CCN(C(=O)C3CC3)C2)n[nH]c1=O]

a) Following the procedure described in Example 80c using 4-(4,4,5,5-tetramethyl-1,3,2-dioxaborolan-2-yl)benzonitrile and performing a second purification with reverse phase HPLC (10-90% acetonitrile/water with 0.1% TFA) gave the title compound as a solid (20 mg, 0.045 mmol, 24% yield). $^1$H NMR (400 MHz, CDCl$_3$) δ ppm 9.07 (d, 1H), 7.84-7.75 (m, 2H), 7.75-7.67 (m, 2H), 7.40 (ddd, J=2.1, 5.2, 7.8 Hz, 1H), 7.35-7.29 (m, 1H), 7.25-7.18 (m, 1H), 3.94 (s, 3H), 3.80-3.68 (m, 1H), 3.68-3.54 (m, 1H), 3.50-3.22 (m, 1H), 3.12-2.63 (m, 1H), 2.63-2.38 (m, 2H), 2.32-2.18 (m, 1H), 2.16-2.02 (m, 1H), 1.85-1.52 (m, 2H), 1.08-0.94 (m, 2H), 0.78 (dd, J=3.5, 7.8 Hz, 2H).

Example 85

5-{[(3S)-1-(cyclopropylcarbonyl)-3-pyrrolidinyl]methyl}-4-[4-(7-fluoro-1-benzofuran-5-yl)phenyl]-2,4-dihydro-3H-1,2,4-triazol-3-one

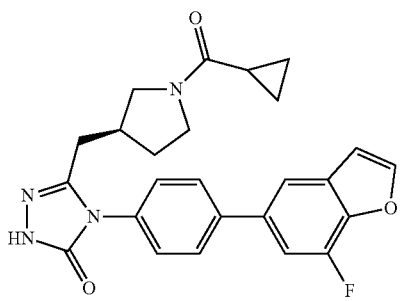 [SMILES: O=C(C1CC1)N1CC[C@@H](Cc2n[nH]c(=O)n2-c2ccc(-c3cc(F)c4occc4c3)cc2)C1]

a) [(4-bromo-2-fluoro-6-formylphenyl)oxy]acetic Acid

A solution of 5-bromo-3-fluoro-2-hydroxybenzaldehyde (4.57 mmol) in acetonitrile (30 mL) was treated with potassium carbonate (12.66 mmol). The reaction mixture was stirred for 30 min and was then treated with methyl bromoacetate (5.48 mmol). The resulting mixture was stirred at room temperature overnight. Analysis by LCMS indicated the formation of the desired intermediate ester, and the reaction mixture was concentrated to dryness in vacuo. The crude material was dissolved in a 3:1 methanol:water mixture (20 mL) and was heated to 50° C. with stirring for 2 h. The reaction was then cooled to room temperature and was acidified to pH~3 using 1N aq HCl. The methanol was removed in vacuo and the resulting aqueous suspension was diluted with water (100 mL) and was extracted with ethyl acetate. The combined organic layers were washed with saturated aqueous sodium bicarbonate, dried over magnesium sulfate, filtered, and concentrated in vacuo to give the crude title product. The beige solid was used without further purification (1.05 g, 83% yield). MS(ES)+ m/e 276.9, 278.9 [M+H]$^+$.

b) 5-bromo-7-fluoro-1-benzofuran-2-carboxylic Acid

A solution of [(4-bromo-2-fluoro-6-formylphenyl)oxy]acetic acid (3.79 mmol) in acetic anhydride (10 mL) was treated with sodium acetate (11.37 mmol). The resulting solution was heated to reflux and stirred overnight. The brown reaction solution was allowed to cool to room temperature, and was diluted with toluene (10 mL). The solution was then treated with 1N aq NaOH (20 mL) and was stirred at room temperature for 30 min. The solution was then further diluted with water (50 mL) and was extracted using hexanes. The aqueous phase was then acidified to pH~1 using 1N aq HCl, and was extracted with ethyl acetate. The ethyl acetate layers were combined, washed with saturated aqueous sodium bicarbonate, dried over magnesium sulfate, filtered, and concentrated in vacuo to provide the title compound (0.47 g, 48% yield) which was used without further purification. MS(ES)+ m/e 258.5, 260.7 [M+H]$^+$. $^1$H NMR (400 MHz, DMSO-d$_6$) δ ppm 7.88 (d, J=1.77 Hz, 1H) 7.75 (dd, J=10.36, 1.77 Hz, 1H) 7.69 (d, J=2.53 Hz, 1H).

c) 5-bromo-7-fluoro-1-benzofuran

A solution of 5-bromo-7-fluoro-1-benzofuran-2-carboxylic acid (1.274 mmol) in quinoline (2 mL) was treated with copper dust (0.236 mmol). The reaction was purged with nitrogen, sealed and irradiated in a microwave reactor at 230° C. for 60 min. The solution was diluted with ethyl acetate and was filtered through Celite. The filtrate was concentrated in vacuo, and the residue was purified by flash chromatography (hexanes) to provide the title compound as a clear oil (280 mg, 100% yield). $^1$H NMR (400 MHz, DMSO-d$_6$) δ ppm 8.17 (d, J=2.02 Hz, 1H) 7.77 (d, J=1.77 Hz, 1H) 7.55 (dd, J=10.48, 1.64 Hz, 1H) 7.07 (dd, J=3.16, 2.15 Hz, 1H).

d) 5-{[(3S)-1-(cyclopropylcarbonyl)-3-pyrrolidinyl]methyl}-4-[4-(7-fluoro-1-benzofuran-5-yl)phenyl]-2,4-dihydro-3H-1,2,4-triazol-3-one A solution of 5-{[(3S)-1-(cyclopropylcarbonyl)-3-pyrrolidinyl]methyl}-4-[4-(4,4,5,5-tetramethyl-1,3,2-dioxaborolan-2-yl)phenyl]-2,4-dihydro-3H-1,2,4-triazol-3-one (0.297 mmol) in dioxane (1.5 mL) was treated with 5-bromo-7-fluoro-1-benzofuran (0.297 mmol), dichloro[1,1'-bis(diphenylphosphino)ferrocene]palladium(II)-dichloromethane adduct (17 mg), and 2M aq potassium carbonate (0.89 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, filtered, and concentrated in vacuo. The crude residue was purified by reverse phase HPLC (20-50% acetonitrile/water+0.1% NH$_4$OH) to afford the title compound as a beige solid (47%). MS(ES)+ m/e 447.1 [M+H]$^+$.

Example 86

4-[4-(2,1,3-benzoxadiazol-5-yl)phenyl]-5-{[(3S)-1-(cyclopropylcarbonyl)-3-pyrrolidinyl]methyl}-2,4-dihydro-3H-1,2,4-triazol-3-one

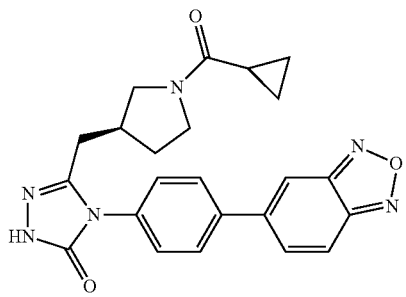 [SMILES: O=C(C1CC1)N1CC[C@@H](Cc2n[nH]c(=O)n2-c2ccc(-c3ccc4nonc4c3)cc2)C1]

a) Following the procedure described in Example 85d with 5-bromo-2,1,3-benzoxadiazole provided the title compound as a beige solid (40%). MS(ES)+ m/e 431.2 [M+H]$^+$.

Example 87

5-{[(3S)-1-(cyclopropylcarbonyl)-3-pyrrolidinyl]methyl}-4-[2-fluoro-4-(1H-indazol-5-yl)phenyl]-2,4-dihydro-3H-1,2,4-triazol-3-one

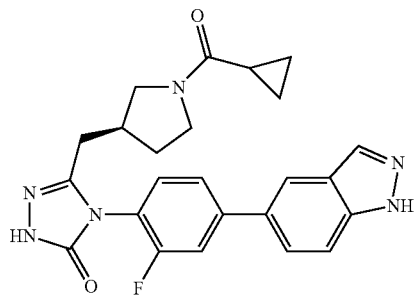 [SMILES: O=C(C1CC1)N1CC[C@@H](Cc2n[nH]c(=O)n2-c2ccc(-c3ccc4[nH]ncc4c3)cc2F)C1]

a) A solution of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol) in dioxane (1.5 mL) was treated with 5-(4,4,5,5-tetramethyl-1,3,2-dioxaborolan-2-yl)-1H-indazole (0.269 mmol), dichloro[1,1'-bis(diphenylphosphino)ferrocene]palladium(II)-dichloromethane adduct (10 mg), and 2M aq potassium carbonate (0.733 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, filtered, and concentrated in vacuo. The crude residue was purified by reverse phase HPLC (10-50% acetonitrile/water+0.1% NH$_4$OH) to afford the title compound as a beige solid (32%). MS(ES)+ m/e 447.2 [M+H]$^+$.

Example 88

5-{[(3S)-1-(cyclopropylcarbonyl)-3-pyrrolidinyl]methyl}-4-[2-fluoro-4-(6-quinolinyl)phenyl]-2,4-dihydro-3H-1,2,4-triazol-3-one

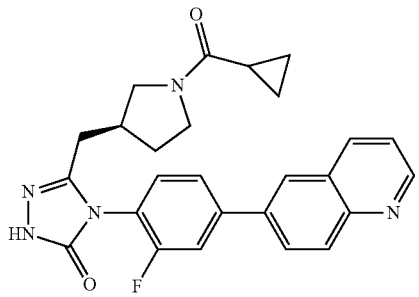 [SMILES: O=C(C1CC1)N1CC[C@@H](Cc2n[nH]c(=O)n2-c2ccc(-c3ccc4ncccc4c3)cc2F)C1]

a) Following the procedure described in Example 87a with 6-(4,4,5,5-tetramethyl-1,3,2-dioxaborolan-2-yl)quinoline provided the title compound as a white solid (57%). MS(ES)+ m/e 458.2 [M+H]+.

Example 89

5-[4-(3-{[(3S)-1-(cyclopropylcarbonyl)-3-pyrrolidinyl]methyl}-5-oxo-1,5-dihydro-4H-1,2,4-triazol-4-yl)phenyl]-1,3-dihydro-2H-indol-2-one

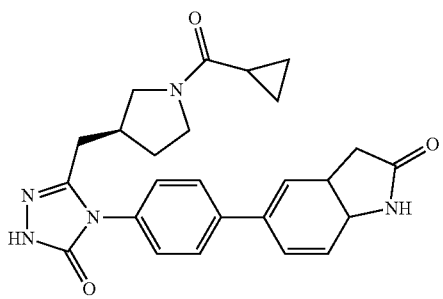 [SMILES: O=C1CC2C=C(c3ccc(-n4c(C[C@@H]5CCN(C(=O)C6CC6)C5)n[nH]c4=O)cc3)C=CC2N1]

a) Following the procedure described in Example 85d with 5-bromo-1,3-dihydro-2H-indol-2-one provided the title compound as an ivory solid (29%). Reverse phase HPLC (10-40% acetonitrile/water+0.1% NH4OH) was utilized in purifying this compound. MS(ES)+ m/e 444.2 [M+H]+.

Example 90

5-{[(3S)-1-(cyclopropylcarbonyl)-3-pyrrolidinyl]methyl}-4-[4-(1H-indazol-6-yl)phenyl]-2,4-dihydro-3H-1,2,4-triazol-3-one

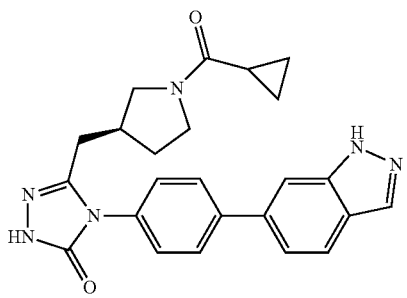 [SMILES: O=C(C1CC1)N1CC[C@@H](Cc2n[nH]c(=O)n2-c2ccc(-c3ccc4cn[nH]c4c3)cc2)C1]

a) Following the procedure described in Example 85d with 6-bromo-1H-indazole provided the title compound as an ivory solid (40%). Reverse phase HPLC (10-40% acetonitrile/water+0.1% NH4OH) was utilized in purifying this compound. MS(ES)+ m/e 429.0 [M+H]+.

Example 91

7-[4-(3-{[(3S)-1-(cyclopropylcarbonyl)-3-pyrrolidinyl]methyl}-5-oxo-1,5-dihydro-4H-1,2,4-triazol-4-yl)phenyl]-1(2H)-isoquinolinone

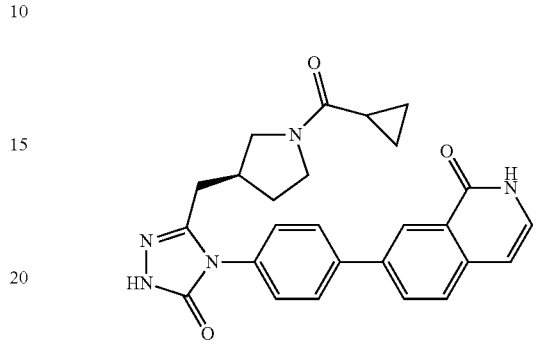

a) Following the procedure described in Example 85d with 7-bromo-1(2H)-isoquinolinone provided the title compound as an ivory solid (37%). Reverse phase HPLC (10-40% acetonitrile/water+0.1% NH4OH) was utilized in purifying this compound. MS(ES)+ m/e 456.1 [M+H]+.

Example 92

5-{[(3S)-1-(cyclopropylcarbonyl)-3-pyrrolidinyl]methyl}-4-[4-(2,3-dihydro-1-benzofuran-5-yl)-2-fluorophenyl]-2,4-dihydro-3H-1,2,4-triazol-3-one

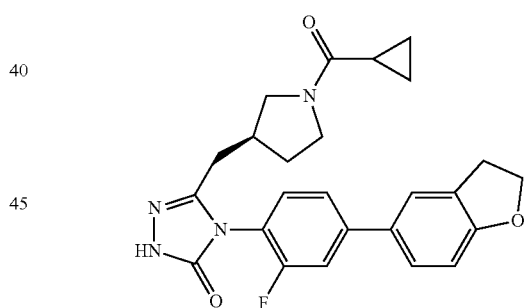

a) 5-{[(3S)-1-(cyclopropylcarbonyl)-3-pyrrolidinyl]methyl}-4-[2-fluoro-4-(4,4,5,5-tetramethyl-1,3,2-dioxaborolan-2-yl)phenyl]-2,4-dihydro-3H-1,2,4-triazol-3-one A solution of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.733 mmol) in dioxane (3 mL) was treated with bis(pinocolato)diboron (0.733 mmol), dichloro[1,1'-bis(diphenylphosphino)ferrocene]palladium(II)-dichloromethane adduct (30 mg) and potassium acetate (1.466 mmol). The reaction mixture was purged with nitrogen, sealed, and stirred at 100° C. overnight. The reaction mixture was then cooled to room temperature, diluted with ethyl acetate (30 mL), and was filtered through Celite. The filtrate was concentrated to dryness in vacuo to afford the crude title compound as a brown solid (quantitative), which was used as is. MS(ES)+ m/e 457.3 [M+H]+ (boronic ester almost completely hydrolyzes to free acid with MS(ES)+ m/e 375.0 [M+H]+).

b) 5-{[(3S)-1-(cyclopropylcarbonyl)-3-pyrrolidinyl]methyl}-4-[4-(2,3-dihydro-1-benzofuran-5-yl)-2-fluorophenyl]-2,4-dihydro-3H-1,2,4-triazol-3-one A solution of 5-{[(3S)-1-(cyclopropylcarbonyl)-3-pyrrolidinyl]methyl}-4-[2-fluoro-4-(4,4,5,5-tetramethyl-1,3,2-dioxaborolan-2-yl)phenyl]-2,4-dihydro-3H-1,2,4-triazol-3-one (0.351 mmol) in dioxane (1.5 mL) was treated with 5-bromo-2,3-dihydro-1-benzofuran (0.319 mmol), dichloro[1,1'-bis(diphenylphosphino)ferrocene]palladium(II)-dichloromethane adduct (18 mg), and 2M aq potassium carbonate (0.956 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, filtered, and concentrated in vacuo. The crude residue was purified by reverse phase HPLC (20-50% acetonitrile/water+0.1% NH4OH) to afford the title compound (29%). MS(ES)+ m/e 449.0 [M+H]+.

Example 93

5-{[(3S)-1-(cyclopropylcarbonyl)-3-pyrrolidinyl]methyl}-4-[4-(2,3-dihydro-1H-indol-5-yl)-2-fluorophenyl]-2,4-dihydro-3H-1,2,4-triazol-3-one

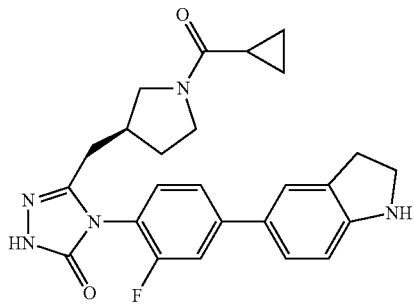 [SMILES: O=C(C1CC1)N1CC[C@@H](Cc2n[nH]c(=O)n2-c2ccc(-c3ccc4c(c3)CCN4)cc2F)C1]

a) Following the procedure described in Example 92b with 5-bromo-2,3-dihydro-1H-indole and adjusting the pH of the aqueous layer during the work-up to ~7 provided the title compound as an ivory solid (13%). MS(ES)+ m/e 448.1 [M+H]+.

Example 94

4-[4-(1,3-benzothiazol-5-yl)phenyl]-5-{[(3S)-1-(cyclopropylcarbonyl)-3-pyrrolidinyl]methyl}-2,4-dihydro-3H-1,2,4-triazol-3-one

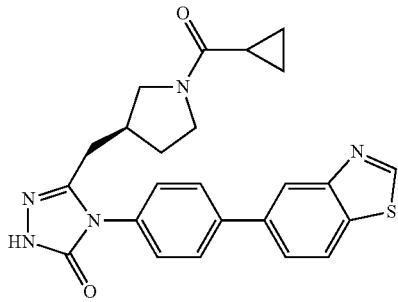 [SMILES: O=C(C1CC1)N1CC[C@@H](Cc2n[nH]c(=O)n2-c2ccc(-c3ccc4scnc4c3)cc2)C1]

a) Following the procedure described in Example 85d (except that the reaction mixture was stirred over the weekend) with 5-bromo-1,3-benzothiazole provided the title compound as an ivory solid (41%). MS(ES)+ m/e 446.2 [M+H]+.

Example 95

5-{[(3S)-1-(cyclopropylcarbonyl)-3-pyrrolidinyl]methyl}-4-{4'-[(dimethylamino)methyl]-4-biphenylyl}-2,4-dihydro-3H-1,2,4-triazol-3-one

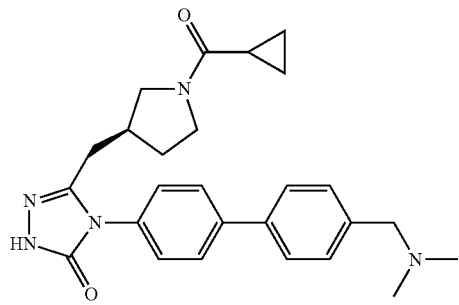 [SMILES: CN(C)Cc1ccc(-c2ccc(-n3c(C[C@@H]4CCN(C(=O)C5CC5)C4)n[nH]c3=O)cc2)cc1]

a) A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in dioxane (1.5 mL) was treated with the HCl salt of N,N-dimethyl-1-[4-(4,4,5,5-tetramethyl-1,3,2-dioxaborolan-2-yl)phenyl]methanamine (0.281 mmol), dichloro[1,1'-bis(diphenylphosphino)ferrocene]palladium(II)-dichloromethane adduct (10 mg), and 2M aq potassium carbonate (0.767 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, treated with Si-Thiol (Silicycle, 20 mg), filtered, and concentrated in vacuo. The crude residue was purified by reverse phase HPLC (20-50% acetonitrile/water+0.1% NH4OH) to afford the title compound as a beige amorphous solid (28%). MS(ES)+ m/e 446.3 [M+H]+.

Example 96

5-{[(3S)-1-(cyclopropylcarbonyl)-3-pyrrolidinyl]methyl}-4-(3'-fluoro-4-biphenylyl)-2,4-dihydro-3H-1,2,4-triazol-3-one

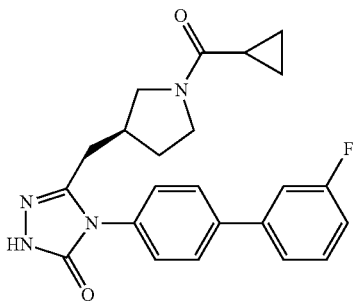 [SMILES: O=C(C1CC1)N1CC[C@@H](Cc2n[nH]c(=O)n2-c2ccc(-c3cccc(F)c3)cc2)C1]

a) Following the procedure described in Example 95a with (3-fluorophenyl)boronic acid provided the title compound as a beige amorphous solid (59%). MS(ES)+ m/e 407.4 [M+H]+.

Example 97

5-{[(3S)-1-(cyclopropylcarbonyl)-3-pyrrolidinyl]methyl}-4-[3'-(methyloxy)-4-biphenylyl]-2,4-dihydro-3H-1,2,4-triazol-3-one

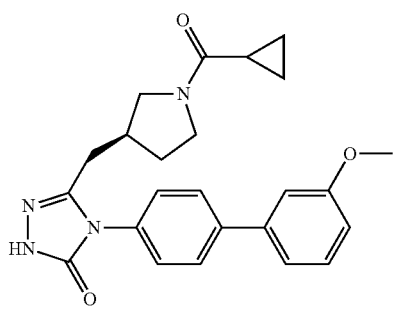 [SMILES: COc1cccc(-c2ccc(-n3c(C[C@@H]4CCN(C(=O)C5CC5)C4)n[nH]c3=O)cc2)c1]

a) Following the procedure described in Example 95a (except no Si-Thiol treatment) with [3-(methyloxy)phenyl]boronic acid gave an incomplete reaction after overnight. More dichloro[1,1'-bis(diphenylphosphino)ferrocene]palladium(II)-dichloromethane adduct (10 mg) was added and the reaction was irradiated in a microwave (Biotage Initiator) at 150° C. for 10 min, providing the title compound as a beige amorphous solid (56%). MS(ES)+ m/e 419.2 [M+H]+.

Example 98

5-{[(3S)-1-(cyclopropylcarbonyl)-3-pyrrolidinyl]methyl}-4-[3'-(dimethylamino)-4-biphenylyl]-2,4-dihydro-3H-1,2,4-triazol-3-one

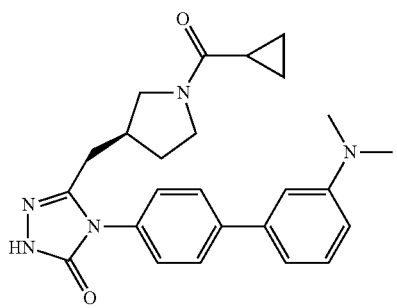 [SMILES: CN(C)c1cccc(-c2ccc(-n3c(C[C@@H]4CCN(C(=O)C5CC5)C4)n[nH]c3=O)cc2)c1]

a) Following the procedure described in Example 95a with [3-(dimethylamino)phenyl]boronic acid and no Si-Thiol treatment provided the title compound as a beige amorphous solid (59%). MS(ES)+ m/e 432.2 [M+H]+.

Example 99

5-{[(3S)-1-(cyclopropylcarbonyl)-3-pyrrolidinyl]methyl}-4-[4'-(hydroxymethyl)-4-biphenylyl]-2,4-dihydro-3H-1,2,4-triazol-3-one

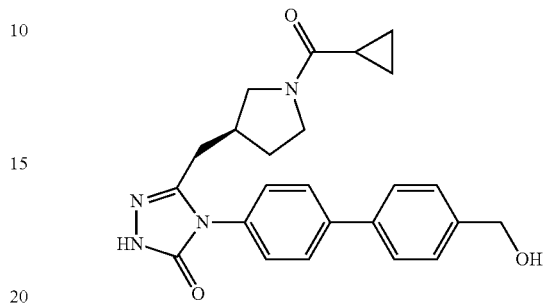

a) Following the procedure described in Example 95a with [4-(hydroxymethyl)phenyl]boronic acid and no Si-Thiol treatment provided the title compound as a beige amorphous solid (68%). MS(ES)+ m/e 419.2 [M+H]+.

Example 100

5-{[(3S)-1-(cyclopropylcarbonyl)-3-pyrrolidinyl]methyl}-4-[3'-(hydroxymethyl)-4-biphenylyl]-2,4-dihydro-3H-1,2,4-triazol-3-one

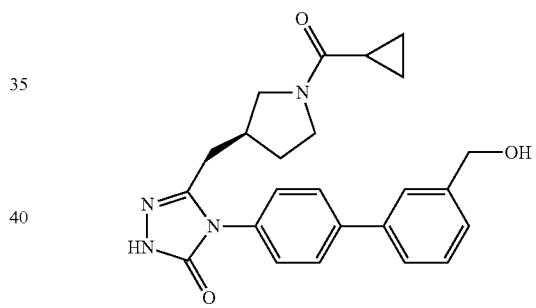

a) Following the procedure described in Example 95a with [[3-(hydroxymethyl)phenyl]boronic acid (1.0 eq) and no Si-Thiol treatment provided the title compound as an ivory amorphous solid (59%). MS(ES)+ m/e 419.2 [M+H]+.

Example 101

4-[4-(1,3-benzoxazol-5-yl)phenyl]-5-{[(3S)-1-(cyclopropylcarbonyl)-3-pyrrolidinyl]methyl}-2,4-dihydro-3H-1,2,4-triazol-3-one

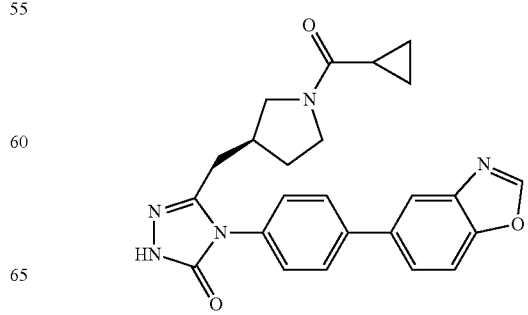

a) Following the procedure described in Example 85d (but added treatment with Si-Thiol (Silicycle, 20 mg) prior to filtration) with 5-bromo-1,3-benzoxazole for 14 h and a second purification by flash chromatography (0-10% methanol/dichloromethane) provided the title compound as an amorphous white solid (28%). MS(ES)+ m/e 430.1 [M+H]+.

Example 102

5-{[(3S)-1-(cyclopropylcarbonyl)-3-pyrrolidinyl]methyl}-4-[4'-(1H-pyrazol-1-yl)-4-biphenylyl]-2,4-dihydro-3H-1,2,4-triazol-3-one

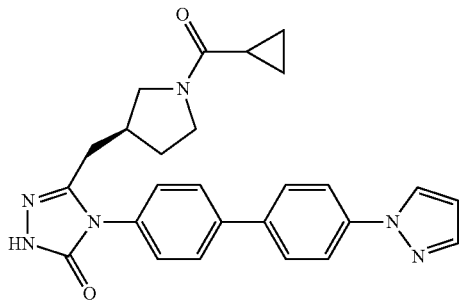 [SMILES: O=C(C1CC1)N1CC[C@@H](Cc2n[nH]c(=O)n2-c2ccc(-c3ccc(-n4cccn4)cc3)cc2)C1]

a) Following the procedure described in Example 95a with [4-(1H-pyrazol-1-yl)phenyl]boronic acid provided the title compound as a pink amorphous solid (53%). MS(ES)+ m/e 455.0 [M+H]+.

Example 103

5-{[(3S)-1-(cyclopropylcarbonyl)-3-pyrrolidinyl]methyl}-4-[3'-(1H-pyrazol-5-yl)-4-biphenylyl]-2,4-dihydro-3H-1,2,4-triazol-3-one

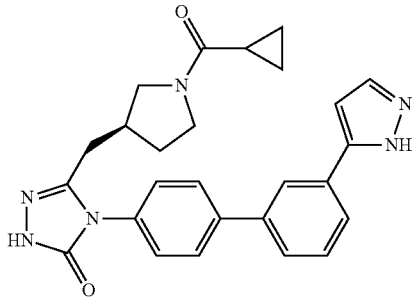 [SMILES: O=C(C1CC1)N1CC[C@@H](Cc2n[nH]c(=O)n2-c2ccc(-c3cccc(-c4ccn[nH]4)c3)cc2)C1]

a) Following the procedure described in Example 95a with [3-(1H-pyrazol-5-yl)phenyl]boronic acid provided the title compound as an ivory amorphous solid (33%). MS(ES)+ m/e 455.0 [M+H]+.

Example 104

4-[4-(1,3-benzothiazol-5-yl)-2-fluorophenyl]-5-{[(3S)-1-(cyclopropylcarbonyl)-3-pyrrolidinyl]methyl}-2,4-dihydro-3H-1,2,4-triazol-3-one

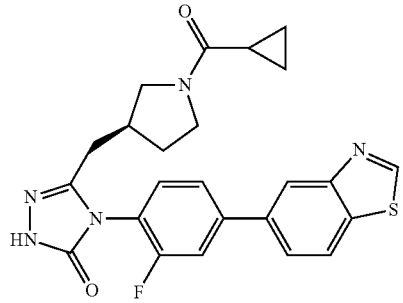 [SMILES: O=C(C1CC1)N1CC[C@@H](Cc2n[nH]c(=O)n2-c2ccc(-c3ccc4scnc4c3)cc2F)C1]

a) A solution of 5-{[(3S)-1-(cyclopropylcarbonyl)-3-pyrrolidinyl]methyl}-4-[2-fluoro-4-(4,4,5,5-tetramethyl-1,3,2-dioxaborolan-2-yl)phenyl]-2,4-dihydro-3H-1,2,4-triazol-3-one (0.230 mmol) in dioxane (1.5 mL) was treated with 5-bromo-1,3-benzothiazole (0.230 mmol), dichloro[1,1'-bis(diphenylphosphino)ferrocene]palladium(II)-dichloromethane adduct (9 mg), and 2M aq potassium carbonate (0.690 mmol). The reaction mixture was purged with nitrogen, sealed, and stirred at 100° C. overnight. The reaction mixture was cooled to room temperature and was diluted with water (50 mL). The aqueous layer was acidified to pH~4 using 1N aq HCl and was extracted with dichloromethane. The organic layer was dried over magnesium sulfate, treated with Si-Thiol (Silicycle, 20 mg), filtered, and concentrated in vacuo. Silica gel chromatography (0-8% methanol/dichloromethane) and reverse phase HPLC (20-50% acetonitrile w/0.1% TFA/water w/0.1% TFA) were utilized in purifying this compound. The product fractions from the HPLC were combined, adjusted to pH~5 with the addition of saturated aq sodium bicarbonate, and extracted with dichloromethane. The organic layer was dried over magnesium sulfate, filtered, and concentrated in vacuo, providing the title compound as an amorphous off-white solid (39%). MS(ES)+ m/e 464.3 [M+H]+.

Example 105

5-{[(3S)-1-(cyclopropylcarbonyl)-3-pyrrolidinyl]methyl}-4-[4-(2-naphthalenyl)phenyl]-2,4-dihydro-3H-1,2,4-triazol-3-one

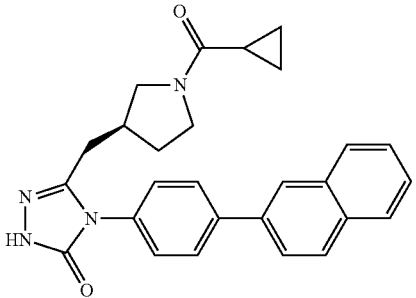 [SMILES: O=C(C1CC1)N1CC[C@@H](Cc2n[nH]c(=O)n2-c2ccc(-c3ccc4ccccc4c3)cc2)C1]

a) Following the procedure described in Example 95a with 2-naphthalenylboronic acid provided the title compound as a pink amorphous solid (56%). Reverse phase HPLC (25-55% acetonitrile w/0.1% TFA/water w/0.1% TFA) was utilized in purifying this compound. The product fractions from the HPLC were combined, adjusted to pH~5 with the addition of saturated aq sodium bicarbonate, and extracted with dichloromethane. The organic layer was dried over magnesium sulfate, filtered, and concentrated in vacuo. MS(ES)+ m/e 439.2 [M+H]+.

Example 106

5-{[(3S)-1-(cyclopropylcarbonyl)-3-pyrrolidinyl]methyl}-4-[3'-(1H-pyrazol-1-yl)-4-biphenylyl]-2,4-dihydro-3H-1,2,4-triazol-3-one

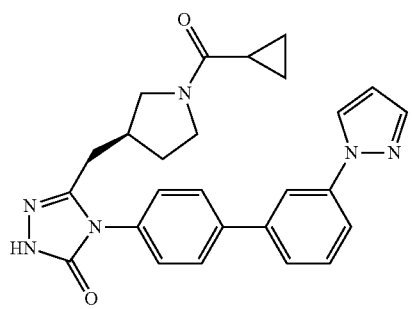 [SMILES: O=C(C1CC1)N1CC[C@@H](Cc2n[nH]c(=O)n2-c2ccc(-c3cccc(-n4cccn4)c3)cc2)C1]

a) Following the procedure described in Example 95a with 1-[3-(4,4,5,5-tetramethyl-1,3,2-dioxaborolan-2-yl)phenyl]-1H-pyrazole (1.0 eq) provided the title compound as an ivory amorphous solid (53%). Reverse phase HPLC (25-55% acetonitrile w/0.1% TFA/water w/0.1% TFA) was utilized in purifying this compound. The product fractions from the HPLC were combined, adjusted to pH~5 with the addition of saturated aq sodium bicarbonate, and extracted with dichloromethane. The organic layer was dried over magnesium sulfate, filtered, and concentrated in vacuo. MS(ES)+ m/e 455.1 [M+H]+.

Example 107

5-{[(3S)-1-(cyclopropylcarbonyl)-3-pyrrolidinyl]methyl}-4-[4'-(1H-pyrazol-5-yl)-4-biphenylyl]-2,4-dihydro-3H-1,2,4-triazol-3-one

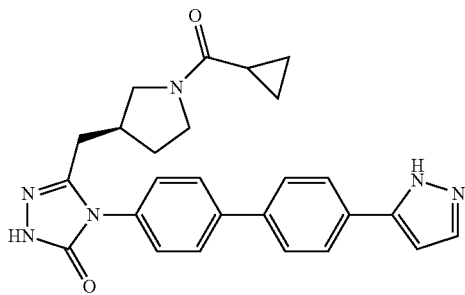 [SMILES: O=C(C1CC1)N1CC[C@@H](Cc2n[nH]c(=O)n2-c2ccc(-c3ccc(-c4ccn[nH]4)cc3)cc2)C1]

a) Following the procedure described in Example 95a with [4-(1H-pyrazol-5-yl)phenyl]boronic acid provided the title compound as an ivory amorphous solid (8%). Reverse phase HPLC (25-55% acetonitrile/water+0.1% NH4OH) was utilized in purifying this compound. MS(ES)+ m/e 455.1 [M+H]+.

Example 108

4-[4-(1,3-benzothiazol-6-yl)phenyl]-5-{[(3S)-1-(cyclopropylcarbonyl)-3-pyrrolidinyl]methyl}-2,4-dihydro-3H-1,2,4-triazol-3-one

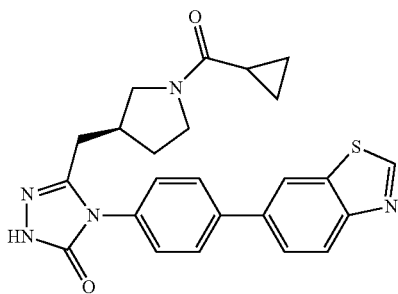 [SMILES: O=C(C1CC1)N1CC[C@@H](Cc2n[nH]c(=O)n2-c2ccc(-c3ccc4ncsc4c3)cc2)C1]

a) Following the procedure described in Example 101a with 6-bromo-1,3-benzothiazole provided the title compound as an off-white amorphous solid (54%). Reverse phase HPLC (15-40% acetonitrile/water+0.1% NH4OH) was utilized in purifying this compound. MS(ES)+ m/e 446.3 [M+H]+.

Example 109

5-{[(3S)-1-(cyclopropylcarbonyl)-3-pyrrolidinyl]methyl}-4-{3'-[(dimethylamino)methyl]-4-biphenylyl}-2,4-dihydro-3H-1,2,4-triazol-3-one

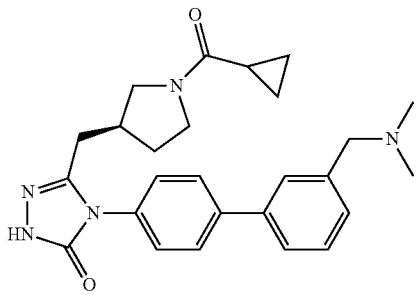 [SMILES: CN(C)Cc1cccc(-c2ccc(-n3c(C[C@@H]4CCN(C(=O)C5CC5)C4)n[nH]c3=O)cc2)c1]

a) Following the procedure described in Example 95a (except crude reaction mixture was diluted with brine (50 mL) and then extracted with tetrahydrofuran rather than dichloromethane, and no Si-Thiol treatment was utilized) with the HCl salt of N,N-dimethyl-1-[3-(4,4,5,5-tetramethyl-1,3,2-dioxaborolan-2-yl)phenyl]methanamine provided the title compound as a white amorphous solid (4%). Reverse phase HPLC (20-50% acetonitrile w/0.1% TFA/water w/0.1% TFA) was initially utilized in purifying this compound, followed by reverse phase HPLC (20% acetonitrile/aq. ammonium formate (pH~4)). The fractions were combined and adjusted to pH~9 using NH4OH and the solution was extracted with dichloromethane. The resulting organic phase was dried over magnesium sulfate, filtered, and concentrated in vacuo. MS(ES)+ m/e 446.4 [M+H]+.

Example 110

5-{[(3S)-1-(cyclopropylcarbonyl)-3-pyrrolidinyl]methyl}-4-(3,4'-difluoro-4-biphenylyl)-2,4-dihydro-3H-1,2,4-triazol-3-one

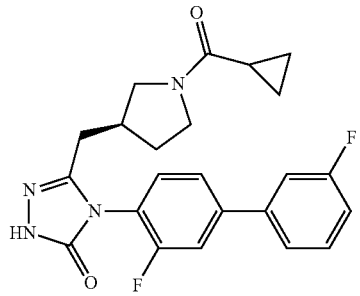 [SMILES: O=C(C1CC1)N1CC[C@@H](Cc2n[nH]c(=O)n2-c2ccc(-c3cccc(F)c3)cc2F)C1]

a) A solution of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol) in dioxane (1.5 mL) was treated with (4-fluorophenyl)boronic acid (0.269 mmol), dichloro[1,1'-bis(diphenylphosphino)ferrocene]palladium (II)-dichloromethane adduct (10 mg), and 2M aq potassium carbonate (0.733 mmol). The reaction mixture was purged with nitrogen, sealed, and irradiated in a microwave (Biotage Initiator) at 150° C. for 10 min. The reaction mixture was cooled to room temperature and was diluted with water (50 mL). The aqueous layer was acidified to pH~4 using 1N aq HCl and was extracted with dichloromethane. The organic layer was dried over magnesium sulfate, treated with Si-Thiol (Silicycle, 20 mg), filtered, and concentrated in vacuo. The crude residue was purified by reverse phase HPLC (20-50% acetonitrile/water+0.1% NH₄OH) to afford the title compound as an off-white solid (61%). MS(ES)+ m/e 425.0 [M+H]+.

Example 111

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarbonitrile

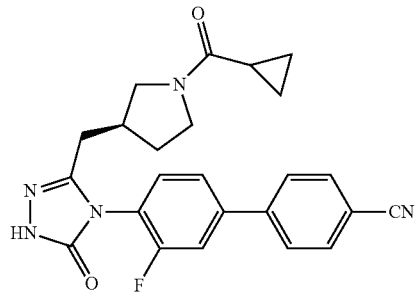 [SMILES: N#Cc1ccc(-c2ccc(-n3c(C[C@@H]4CCN(C(=O)C5CC5)C4)n[nH]c3=O)c(F)c2)cc1]

a) Following the procedure described in Example 110a with (4-cyanophenyl)boronic acid provided the title compound as a white amorphous solid (55%). MS(ES)+ m/e 432.1 [M+H]+.

Example 112

5-{[(3S)-1-(cyclopropylcarbonyl)-3-pyrrolidinyl]methyl}-4-[4'-(dimethylamino)-3-fluoro-4-biphenylyl]-2,4-dihydro-3H-1,2,4-triazol-3-one

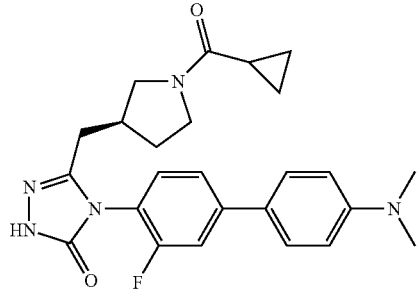 [SMILES: CN(C)c1ccc(-c2ccc(-n3c(C[C@@H]4CCN(C(=O)C5CC5)C4)n[nH]c3=O)c(F)c2)cc1]

a) Following the procedure described in Example 110a with [4-(dimethylamino)phenyl]boronic acid provided the title compound as a white amorphous solid (50%). MS(ES)+ m/e 450.1 [M+H]+.

Example 113

4'-(3-{[(3S)-1-(cyclopropylcarbonyl)-3-pyrrolidinyl]methyl}-5-oxo-1,5-dihydro-4H-1,2,4-triazol-4-yl)-3,3'-difluoro-4-biphenylcarbonitrile

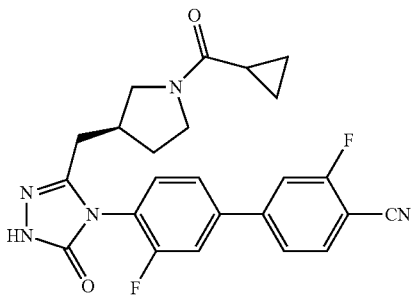 [SMILES: N#Cc1ccc(-c2ccc(-n3c(C[C@@H]4CCN(C(=O)C5CC5)C4)n[nH]c3=O)c(F)c2)cc1F]

a) Following the procedure described in Example 110a with (4-cyano-3-fluorophenyl)boronic acid provided the title compound as a white amorphous solid (59%). MS(ES)+ m/e 450.1 [M+H]+.

Example 114

5-{[(3S)-1-(cyclopropylcarbonyl)-3-pyrrolidinyl]methyl}-4-[3-fluoro-4'-(1H-pyrazol-1-yl)-4-biphenylyl]-2,4-dihydro-3H-1,2,4-triazol-3-one

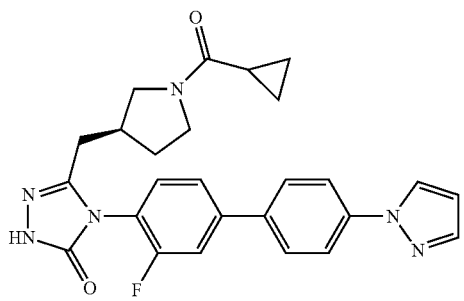 [SMILES: O=C(C1CC1)N1CC[C@@H](Cc2n[nH]c(=O)n2-c2ccc(-c3ccc(-n4cccn4)cc3)cc2F)C1]

a) Following the procedure described in Example 110a (irradiating in the microwave for 15 min) with [4-(1H-pyrazol-1-yl)phenyl]boronic acid provided the title compound as an off-white amorphous solid (48%). MS(ES)+ m/e 473.3 [M+H]+.

Example 115

5-{[(3S)-1-(cyclopropylcarbonyl)-3-pyrrolidinyl]methyl}-4-[2-fluoro-4-(5-quinolinyl)phenyl]-2,4-dihydro-3H-1,2,4-triazol-3-one

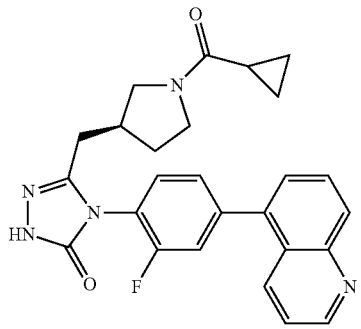 [SMILES: O=C(C1CC1)N1CC[C@@H](Cc2n[nH]c(=O)n2-c2ccc(-c3cccc4ncccc34)cc2F)C1]

a) Following the procedure described in Example 114a with 5-quinolinylboronic acid provided the title compound as an off-white amorphous solid (59%). MS(ES)+ m/e 458.3 [M+H]+.

Example 116

5-{[(3S)-1-(cyclopropylcarbonyl)-3-pyrrolidinyl]methyl}-4-[3-fluoro-4'-(methyloxy)-4-biphenylyl]-2,4-dihydro-3H-1,2,4-triazol-3-one

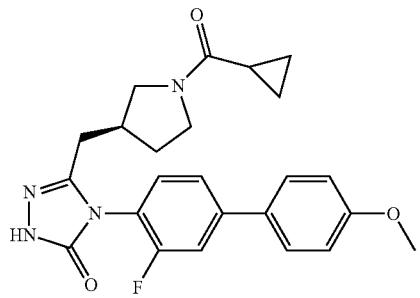 [SMILES: COc1ccc(-c2ccc(-n3c(C[C@@H]4CCN(C(=O)C5CC5)C4)n[nH]c3=O)c(F)c2)cc1]

a) Following the procedure described in Example 114a with [4-(methyloxy)phenyl]boronic acid provided the title compound as an off-white amorphous solid (62%). MS(ES)+ m/e 437.3 [M+H]+.

Example 117

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-methyl-4-biphenylcarbonitrile

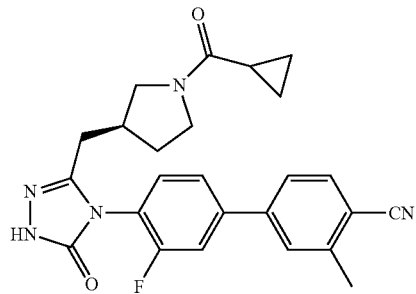 [SMILES: Cc1cc(-c2ccc(-n3c(C[C@@H]4CCN(C(=O)C5CC5)C4)n[nH]c3=O)c(F)c2)ccc1C#N]

a) A solution of 5-{[(3S)-1-(cyclopropylcarbonyl)-3-pyrrolidinyl]methyl}-4-[2-fluoro-4-(4,4,5,5-tetramethyl-1,3,2-dioxaborolan-2-yl)phenyl]-2,4-dihydro-3H-1,2,4-triazol-3-one (0.245 mmol) in dioxane (1.5 mL) was treated with 4-bromo-2-methylbenzonitrile (0.245 mmol), dichloro[1,1'-bis(diphenylphosphino)ferrocene]palladium(II)-dichloromethane adduct (10 mg), and 2M aq potassium carbonate (0.736 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH~4 using 1N aq HCl and was extracted with dichloromethane. The organic layer was dried over magnesium sulfate, treated with Si-Thiol (Silicycle, 20 mg), filtered, and concentrated in vacuo. The crude residue was purified by reverse phase HPLC (20-50% acetonitrile/water+0.1% NH4OH) to afford the title compound as an amorphous off-white solid (57%). MS(ES)+ m/e 446.2 [M+H]+.

Example 118

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-(methyloxy)-4-biphenylcarbonitrile

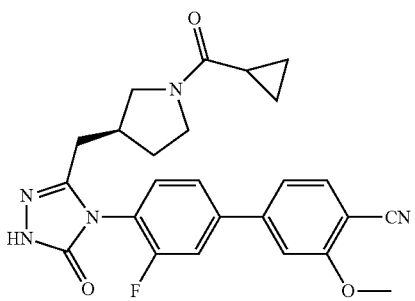 [SMILES: COc1cc(-c2ccc(-n3c(C[C@@H]4CCN(C(=O)C5CC5)C4)n[nH]c3=O)c(F)c2)ccc1C#N]

a) Following the procedure described in Example 117a with 4-bromo-2-(methyloxy)benzonitrile provided the title compound as an off-white amorphous solid (26%). MS(ES)+ m/e 462.3 [M+H]+.

Example 119

5-{[(3S)-1-(cyclopropylcarbonyl)-3-pyrrolidinyl]methyl}-4-[2-fluoro-4-(6-quinoxalinyl)phenyl]-2,4-dihydro-3H-1,2,4-triazol-3-one

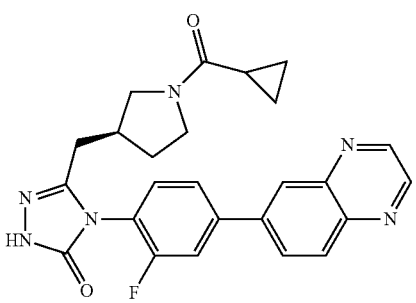

a) Following the procedure described in Example 117a with 6-bromoquinoxaline provided the title compound as an off-white amorphous solid (33%). MS(ES)+ m/e 459.2 [M+H]+.

Example 120

5-{[(3S)-1-(cyclopropylcarbonyl)-3-pyrrolidinyl]methyl}-4-[4-(1-methyl-1H-indol-6-yl)phenyl]-2,4-dihydro-3H-1,2,4-triazol-3-one

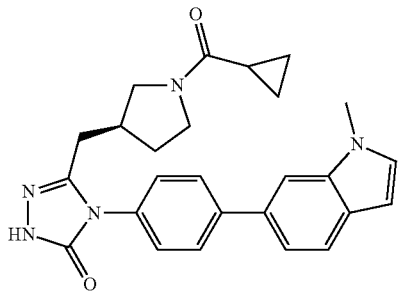 [SMILES: Cn1ccc2ccc(-c3ccc(-n4c(C[C@@H]5CCN(C(=O)C6CC6)C5)n[nH]c4=O)cc3)cc21]

a) 6-bromo-1-methyl-1H-indole

A solution of 6-bromo-1H-indole (1.530 mmol) in dimethyl sulfoxide (10 mL) was treated with potassium carbonate (4.59 mmol) and was stirred at room temperature for 30 min. The solution was then treated with methyl iodide (1.683 mmol) and was stirred at room temperature overnight. The solution was diluted with water (100 mL) and was extracted with ethyl acetate. The combined organic phases were washed with water and brine, dried over magnesium sulfate, filtered and concentrated in vacuo. The crude residue was purified by silica gel chromatography (hexanes) to provide the title compound as a yellow oil (62%). $^1$H NMR (400 MHz, DMSO-$d_6$) δ ppm 7.70 (s, 1H) 7.50 (d, J=8.34 Hz, 1H) 7.35 (d, J=3.03 Hz, 1H) 7.14 (dd, J=8.34, 1.77 Hz, 1H) 6.44 (d, J=3.03 Hz, 1H) 3.78 (s, 3H).

b) 5-{[(3S)-1-(cyclopropylcarbonyl)-3-pyrrolidinyl]methyl}-4-[4-(1-methyl-1H-indol-6-yl)phenyl]-2,4-dihydro-3H-1,2,4-triazol-3-one Following the procedure described in Example 101a with 6-bromo-1-methyl-1H-indole provided the title compound as an off-white amorphous solid (30%). Reverse phase HPLC (20-50% acetonitrile/water+0.1% NH$_4$OH), silica gel chromatography (0-8% methanol/dichloromethane), and reverse phase HPLC (10-90% acetonitrile/water+0.1% NH$_4$OH) were utilized in purifying this compound. MS(ES)+ m/e 442.2 [M+H]$^+$.

Example 121

5-{[(3S)-1-(cyclopropylcarbonyl)-3-pyrrolidinyl]methyl}-4-[2-fluoro-4-(6-quinazolinyl)phenyl]-2,4-dihydro-3H-1,2,4-triazol-3-one

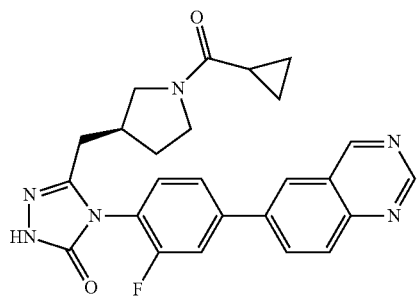

a) Following the procedure described in Example 117a with 6-bromoquinazoline provided the title compound as a white amorphous solid (18%). Reverse phase HPLC (10-40% acetonitrile/water+0.1% NH$_4$OH) as well as trituration of the resulting solid with hexanes were utilized in purifying this compound. MS(ES)+ m/e 459.2 [M+H]$^+$.

Example 122

5-{[(3S)-1-(cyclopropylcarbonyl)-3-pyrrolidinyl]methyl}-4-[2-fluoro-4-(2-methyl-6-quinolinyl)phenyl]-2,4-dihydro-3H-1,2,4-triazol-3-one

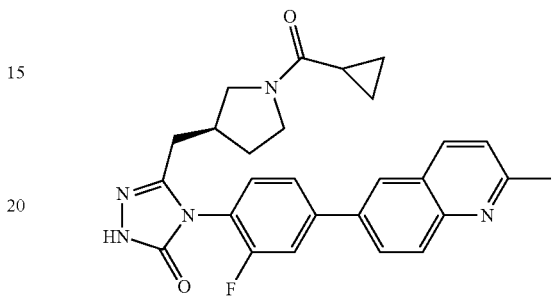

a) Following the procedure described in Example 117a with 6-bromo-2-methylquinoline provided the title compound as an ivory amorphous solid (25%). MS(ES)+ m/e 472.2 [M+H]$^+$.

Example 123

5-{[(3S)-1-(cyclopropylcarbonyl)-3-pyrrolidinyl]methyl}-4-[4-(1-naphthalenyl)phenyl]-2,4-dihydro-3H-1,2,4-triazol-3-one

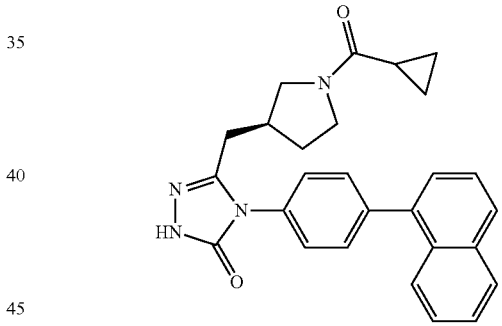

a) A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in dioxane (1.5 mL) was treated with 1-naphthalenylboronic acid (0.281 mmol), dichloro[1,1'-bis(diphenylphosphino)ferrocene]palladium(II)-dichloromethane adduct (10 mg), and 2M aq potassium carbonate (0.767 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH~4 using 1N aq HCl and was extracted with dichloromethane. The organic layer was treated with Si-Thiol (Silicycle, 20 mg), dried over magnesium sulfate, filtered, and concentrated in vacuo. The crude residue was purified by reverse phase HPLC (30-60% acetonitrile w/0.1% TFA/water w/0.1% TFA). The product fractions from the HPLC were combined, adjusted to pH~5 with the addition of saturated aq sodium bicarbonate, and extracted with dichloromethane. The organic layer was dried over magnesium sulfate, filtered, and concentrated in vacuo to afford the title compound as an amorphous white solid (56%). MS(ES)+ m/e 439.2 [M+H]$^+$.

Example 124

5-{[(3S)-1-(cyclopropylcarbonyl)-3-pyrrolidinyl]methyl}-4-[2-fluoro-4-(7-quinolinyl)phenyl]-2,4-dihydro-3H-1,2,4-triazol-3-one

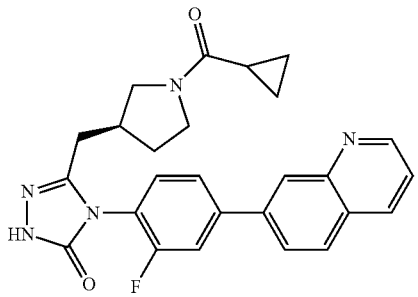

a) Following the procedure described in Example 117a with 7-bromoquinoline provided the title compound as a tan amorphous solid (55%). MS(ES)+ m/e 458.1 [M+H]+.

Example 125

5-{[(3S)-1-(cyclopropylcarbonyl)-3-pyrrolidinyl]methyl}-4-(1,1':4',1''-terphenyl-4-yl)-2,4-dihydro-3H-1,2,4-triazol-3-one

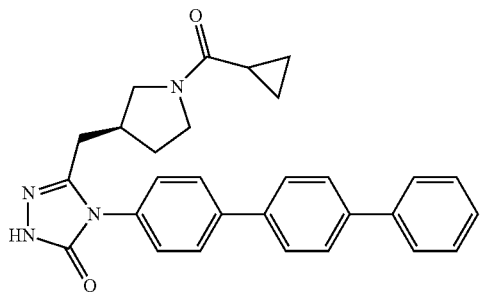 [SMILES: O=C(C1CC1)N1CC[C@@H](Cc2n[nH]c(=O)n2-c2ccc(-c3ccc(-c4ccccc4)cc3)cc2)C1]

a) Following the procedure described in Example 123a with 4-biphenylylboronic acid provided the title compound as a tan amorphous solid (37%). MS(ES)+ m/e 465.3 [M+H]+.

Example 126

5-{[(3S)-1-(cyclopropylcarbonyl)-3-pyrrolidinyl]methyl}-4-[4-(3-quinolinyl)phenyl]-2,4-dihydro-3H-1,2,4-triazol-3-one

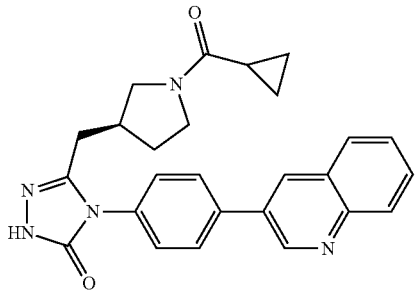 [SMILES: O=C(C1CC1)N1CC[C@@H](Cc2n[nH]c(=O)n2-c2ccc(-c3cnc4ccccc4c3)cc2)C1]

a) Following the procedure described in Example 123a with 3-quinolinylboronic acid (1.0 eq) provided the title compound as an ivory amorphous solid (29%). Reverse phase HPLC (20-50% acetonitrile/water+0.1% NH4OH) as well as reverse phase HPLC (10-35% acetonitrile w/0.1% TFA/water w/0.1% TFA) were utilized in purifying this compound. MS(ES)+ m/e 440.1 [M+H]+.

Example 127

5-{[(3S)-1-(cyclopropylcarbonyl)-3-pyrrolidinyl]methyl}-4-[3,3'-difluoro-4'-(1H-pyrazol-1-yl)-4-biphenylyl]-2,4-dihydro-3H-1,2,4-triazol-3-one

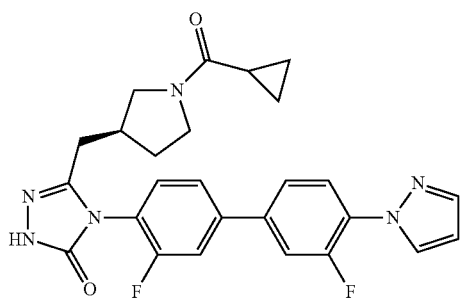 [SMILES: O=C(C1CC1)N1CC[C@@H](Cc2n[nH]c(=O)n2-c2ccc(-c3ccc(-n4cccn4)c(F)c3)cc2F)C1]

a) Following the procedure described in Example 114a with 1-[2-fluoro-4-(4,4,5,5-tetramethyl-1,3,2-dioxaborolan-2-yl)phenyl]-1H-pyrazole provided the title compound as an ivory amorphous solid (47%). Reverse phase HPLC (25-55% acetonitrile w/0.1% TFA/water w/0.1% TFA) was utilized in purifying this compound. MS(ES)+ m/e 465.3 [M+H]+.

Example 128

4'-(3-{[(3S)-1-(cyclopropylcarbonyl)-3-pyrrolidinyl]methyl}-5-oxo-1,5-dihydro-4H-1,2,4-triazol-4-yl)-2,3'-difluoro-4-biphenylcarbonitrile

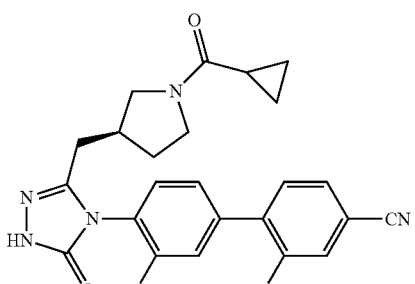

a) Following the procedure described in Example 117a with 4-bromo-3-fluorobenzonitrile provided the title compound as an ivory amorphous solid (39%). Reverse phase HPLC (25-55% acetonitrile w/0.1% TFA/water w/0.1% TFA) and silica gel chromatography (0-8% methanol/dichloromethane) were utilized in purifying this compound. MS(ES)+ m/e 450.1 [M+H]+.

Example 129

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-2-methyl-4-biphenylcarbonitrile

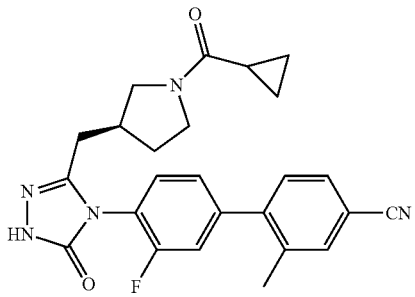 [SMILES: Cc1cc(C#N)ccc1-c1ccc(-n2c(C[C@@H]3CCN(C(=O)C4CC4)C3)n[nH]c2=O)c(F)c1]

a) Following the procedure described in Example 114a with (4-cyano-2-methylphenyl)boronic acid provided the title compound (66%). MS(ES)+ m/e 446.3 [M+H]+.

Example 130

3-chloro-4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarbonitrile

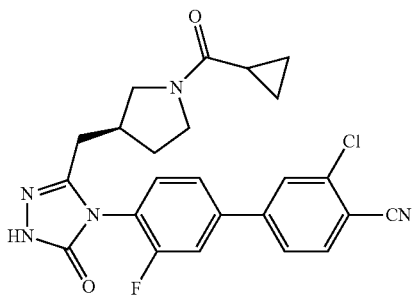 [SMILES: N#Cc1ccc(-c2ccc(-n3c(C[C@@H]4CCN(C(=O)C5CC5)C4)n[nH]c3=O)c(F)c2)cc1Cl]

a) Following the procedure described in Example 117a with 4-bromo-2-chlorobenzonitrile provided the title compound as a white amorphous solid (48%). Reverse phase HPLC (20-50% acetonitrile w/0.1% TFA/water w/0.1% TFA) was utilized in purifying this compound. MS(ES)+ m/e 466.1 [M+H]+.

Example 131

5-{[(3S)-1-(cyclopropylcarbonyl)-3-pyrrolidinyl]methyl}-4-[4-(6-hydroxy-2-naphthalenyl)phenyl]-2,4-dihydro-3H-1,2,4-triazol-3-one

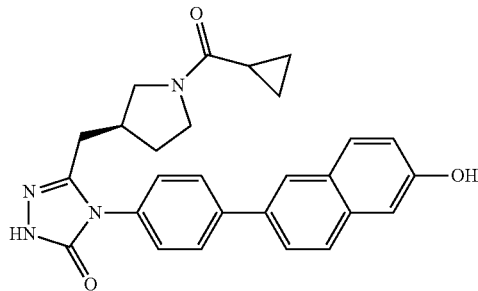 [SMILES: O=C(C1CC1)N1CC[C@@H](Cc2n[nH]c(=O)n2-c2ccc(-c3ccc4cc(O)ccc4c3)cc2)C1]

a) A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in dioxane (1.5 mL) was treated with (6-hydroxy-2-naphthalenyl)boronic acid (0.281 mmol), dichloro[1,1'-bis(diphenylphosphino)ferrocene]palladium (II)-dichloromethane adduct (10 mg), and 2M aq potassium carbonate (0.767 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH~4 using 1N aq HCl and was extracted with dichloromethane. The aqueous phase was then diluted with brine (50 mL) and extracted with tetrahydrofuran, which was subsequently combined with the dichloromethane organic phase. The resulting organic phase was treated with Si-Thiol (Silicycle, 20 mg), dried over magnesium sulfate, filtered, and concentrated in vacuo. The crude residue was purified by reverse phase HPLC (20-50% acetonitrile w/0.1% TFA/water w/0.1% TFA). The product fractions from the HPLC were combined, adjusted to pH~5 with the addition of saturated aq sodium bicarbonate, further diluted with brine, and extracted with tetrahydrofuran. The organic layer was dried over magnesium sulfate, filtered, and concentrated in vacuo. The resulting product was purified by reverse phase HPLC (10-40% acetonitrile/water+0.1% NH$_4$OH) to afford the title compound as an amorphous white solid (23%). MS(ES)+ m/e 455.0 [M+H]+.

Example 132

5-{[(3S)-1-(cyclopropylcarbonyl)-3-pyrrolidinyl]methyl}-4-[2-fluoro-4-(6-isoquinolinyl)phenyl]-2,4-dihydro-3H-1,2,4-triazol-3-one

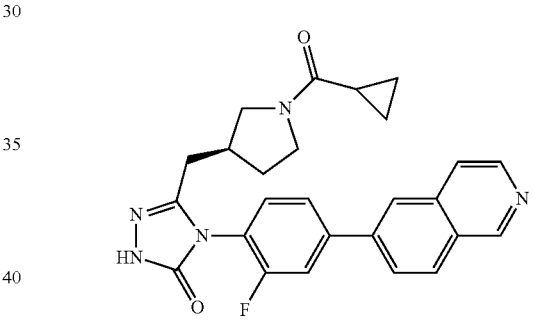

a) Following the procedure described in Example 117a with 6-bromoisoquinoline provided the title compound as an ivory amorphous solid (47%). MS(ES)+ m/e 458.2 [M+H]+.

Example 133

5-{[(3S)-1-(cyclopropylcarbonyl)-3-pyrrolidinyl]methyl}-4-[2-fluoro-4-(7-isoquinolinyl)phenyl]-2,4-dihydro-3H-1,2,4-triazol-3-one

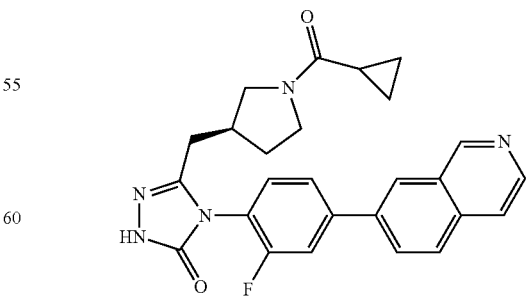

a) Following the procedure described in Example 117a with 7-bromoisoquinoline provided the title compound as a white amorphous solid (47%). MS(ES)+ m/e 458.2 [M+H]+.

Example 134

5-{[(3S)-1-(cyclopropylcarbonyl)-3-pyrrolidinyl]methyl}-4-[4-(2,3-dihydro-1H-inden-5-yl)phenyl]-2,4-dihydro-3H-1,2,4-triazol-3-one

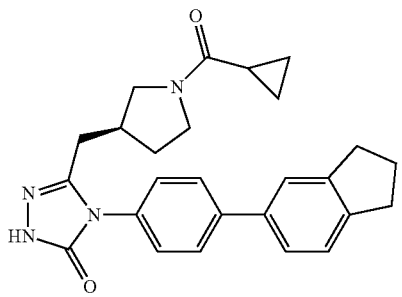 [SMILES: O=C(C1CC1)N1CC[C@@H](Cc2n[nH]c(=O)n2-c2ccc(-c3ccc4c(c3)CCC4)cc2)C1]

a) 5-bromo-2,3-dihydro-1H-indene

A solution of 5-bromo-2,3-dihydro-1H-inden-1-one (4.74 mmol) in HF-pyridine (5 mL) in a 100 mL Nalgene round bottomed flask was cooled to 0° C. and treated with triethylsilane (11.85 mmol) over a period of 5 min. The reaction solution was allowed to warm to room temperature and was stirred for 3 h. Analysis by LCMS indicated only partial conversion of the starting material, so the reaction contents were cooled to 0° C. and treated with more triethylsilane (11.85 mmol). The reaction solution was allowed to warm to room temperature and was stirred for 2 days. The reaction was quenched with 50 mL of ice water and after one hour was further diluted with an additional 50 mL of water. The mixture was extracted with dichloromethane. The resulting organic layer was dried over magnesium sulfate, filtered, and concentrated in vacuo. The resulting residue was purified by silica gel chromatography (hexanes) to afford the title compound as a clear oil (65%). $^1$H NMR (400 MHz, CDCl$_3$) δ ppm 7.35 (s, 1H) 7.23 (d, J=2.02 Hz, 1H) 7.08 (d, J=8.08 Hz, 1H) 2.79-2.96 (m, 4H) 2.05-2.11 (m, 2H).

b) 5-{[(3S)-1-(cyclopropylcarbonyl)-3-pyrrolidinyl]methyl}-4-[4-(2,3-dihydro-1H-inden-5-yl)phenyl]-2,4-dihydro-3H-1,2,4-triazol-3-one A solution of 5-{[(3S)-1-(cyclopropylcarbonyl)-3-pyrrolidinyl]methyl}-4-[4-(4,4,5,5-tetramethyl-1,3,2-dioxaborolan-2-yl)phenyl]-2,4-dihydro-3H-1,2,4-triazol-3-one (0.252 mmol) in dioxane (1.5 mL) was treated with 5-bromo-2,3-dihydro-1H-indene (0.252 mmol), dichloro[1,1'-bis(diphenylphosphino)ferrocene]palladium(II)-dichloromethane adduct (10 mg), and 2M aq potassium carbonate (0.756 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH ~4 using 1N aq HCl and was extracted with dichloromethane. The resulting organic phase was treated with Si-Thiol (Silicycle, 20 mg), dried over magnesium sulfate, filtered, and concentrated in vacuo. The crude residue was purified by reverse phase HPLC (35-65% acetonitrile w/0.1% TFA/water w/0.1% TFA). The product fractions from the HPLC were combined, adjusted to pH~5 with the addition of saturated aq sodium bicarbonate, and extracted with dichloromethane. The organic layer was dried over magnesium sulfate, filtered, and concentrated in vacuo to afford the title compound as an amorphous off-white solid (39%). MS(ES)+ m/e 429.1 [M+H]$^+$.

Example 135

5-{[(3S)-1-(cyclopropylcarbonyl)-3-pyrrolidinyl]methyl}-4-[2-fluoro-4-(2-methyl-7-quinolinyl)phenyl]-2,4-dihydro-3H-1,2,4-triazol-3-one

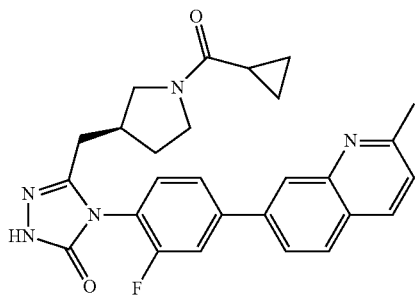 [SMILES: Cc1ccc2ccc(-c3ccc(-n4c(C[C@@H]5CCN(C(=O)C6CC6)C5)n[nH]c4=O)c(F)c3)cc2n1]

a) Following the procedure described in Example 117a with 7-bromo-2-methylquinoline provided the title compound as an ivory amorphous solid (55%). MS(ES)+ m/e 472.2 [M+H]$^+$.

Example 136

5-{[(3S)-1-(cyclopropylcarbonyl)-3-pyrrolidinyl]methyl}-4-[4'-(dimethylamino)-3-fluoro-3'-methyl-4-biphenylyl]-2,4-dihydro-3H-1,2,4-triazol-3-one

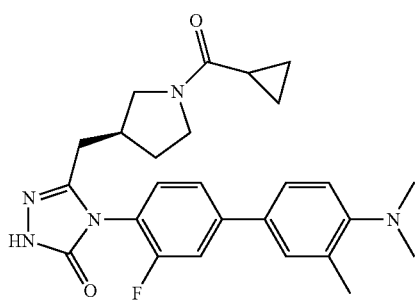 [SMILES: Cc1cc(-c2ccc(-n3c(C[C@@H]4CCN(C(=O)C5CC5)C4)n[nH]c3=O)c(F)c2)ccc1N(C)C]

a) Following the procedure described in Example 114a with [4-(dimethylamino)-3-methylphenyl]boronic acid (1.0 eq) provided the title compound as an ivory amorphous solid (60%). Reverse phase HPLC (20-50% acetonitrile w/0.1%

TFA/water w/0.1% TFA) was utilized in purifying this compound. MS(ES)+ m/e 464.3 [M+H]+.

Example 137

5-{[(3S)-1-(cyclopropylcarbonyl)-3-pyrrolidinyl]methyl}-4-[2-fluoro-4-(1-methyl-2,3-dihydro-1H-indol-5-yl)phenyl]-2,4-dihydro-3H-1,2,4-triazol-3-one

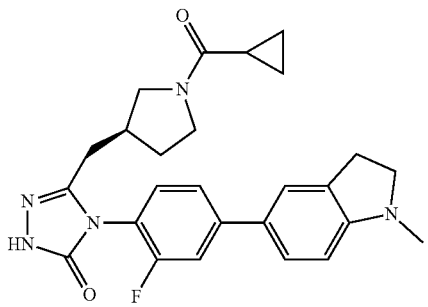 [SMILES: CN1CCc2cc(-c3ccc(-n4c(C[C@@H]5CCN(C(=O)C6CC6)C5)n[nH]c4=O)c(F)c3)ccc21]

a) Following the procedure described in Example 114a with 1-methyl-5-(4,4,5,5-tetramethyl-1,3,2-dioxaborolan-2-yl)-2,3-dihydro-1H-indole provided the title compound as a white amorphous solid (24%). Reverse phase HPLC (20-50% acetonitrile/water+0.1% NH₄OH), silica gel chromatography (0-8% methanol/dichloromethane), reverse phase HPLC (20-50% acetonitrile w/0.1% TFA/water w/0.1% TFA), and chiral HPLC (30% methanol/acetonitrile) were all utilized in purifying this compound. MS(ES)+ m/e 462.4 [M+H]+.

Example 138

5-{[(3S)-1-(cyclopropylcarbonyl)-3-pyrrolidinyl]methyl}-4-[2-fluoro-4-(3-quinolinyl)phenyl]-2,4-dihydro-3H-1,2,4-triazol-3-one

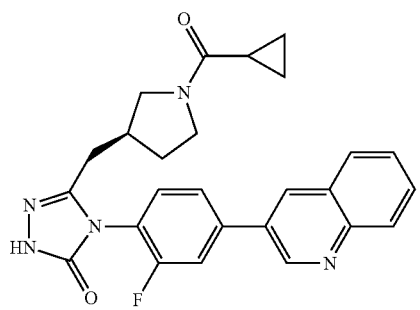 [SMILES: O=C(C1CC1)N1CC[C@@H](Cc2n[nH]c(=O)n2-c2ccc(-c3cnc4ccccc4c3)cc2F)C1]

a) Following the procedure described in Example 114a with 3-quinolinylboronic acid provided the title compound as an ivory amorphous solid (57%). Reverse phase HPLC (10-40% acetonitrile w/0.1% TFA/water w/0.1% TFA) was utilized in purifying this compound. MS(ES)+ m/e 458.0 [M+H]+.

Example 139

5-{[(3S)-1-(cyclopropylcarbonyl)-3-pyrrolidinyl]methyl}-4-(3',4'-dichloro-3-fluoro-4-biphenylyl)-2,4-dihydro-3H-1,2,4-triazol-3-one

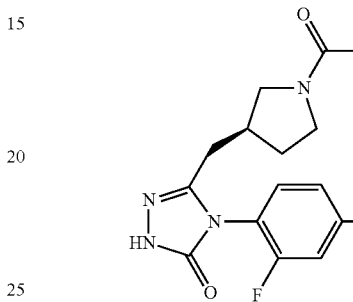

a) Following the procedure described in Example 114a with (3,4-dichlorophenyl)boronic acid provided the title compound as an ivory amorphous solid (38%). Reverse phase HPLC (35-65% acetonitrile w/0.1% TFA/water w/0.1% TFA) was utilized in purifying this compound. MS(ES)+ m/e 475.0 [M+H]+.

Example 140

5-{[(3S)-1-(cyclopropylcarbonyl)-3-pyrrolidinyl]methyl}-4-[4'-(dimethylamino)-3-fluoro-2'-methyl-4-biphenylyl]-2,4-dihydro-3H-1,2,4-triazol-3-one

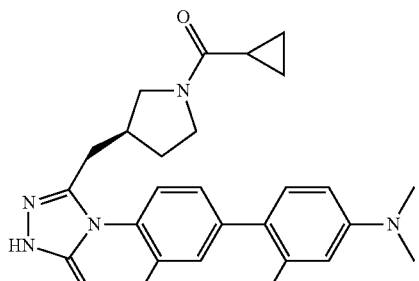

a) Following the procedure described in Example 117a with (4-bromo-3-methylphenyl)dimethylamine provided the title compound as an ivory amorphous solid (22%). Reverse phase HPLC (20-50% acetonitrile w/0.1% TFA/water w/0.1% TFA) and reverse phase HPLC (30-60% acetonitrile/ water+0.1% NH₄OH) were utilized in purifying this compound. MS(ES)+ m/e 464.3 [M+H]⁺.

Example 141

4-(4'-chloro-3,3'-difluoro-4-biphenylyl)-5-{[(3S)-1-(cyclopropylcarbonyl)-3-pyrrolidinyl]methyl}-2,4-dihydro-3H-1,2,4-triazol-3-one

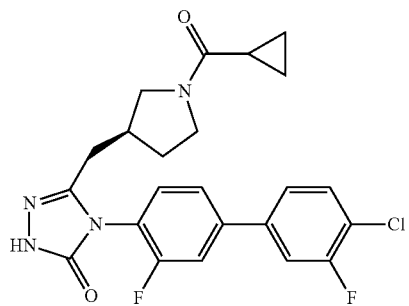

a) Following the procedure described in Example 114a with (4-chloro-3-fluorophenyl)boronic acid provided the title compound as an ivory amorphous solid (18%). Reverse phase HPLC (35-65% acetonitrile w/0.1% TFA/water w/0.1% TFA) and reverse phase HPLC (10-40% acetonitrile/water+0.1% NH₄OH) were utilized in purifying this compound. MS(ES)+ m/e 459.2 [M+H]⁺.

Example 142

4-(4'-chloro-3-fluoro-3'-methyl-4-biphenylyl)-5-{[(3S)-1-(cyclopropylcarbonyl)-3-pyrrolidinyl]methyl}-2,4-dihydro-3H-1,2,4-triazol-3-one

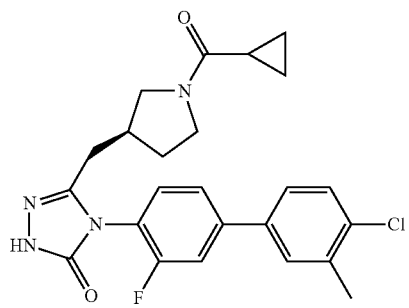 [SMILES: Cc1cc(-c2ccc(-n3c(C[C@@H]4CCN(C(=O)C5CC5)C4)n[nH]c3=O)c(F)c2)ccc1Cl]

a) Following the procedure described in Example 114a with (4-chloro-3-methylphenyl)boronic acid provided the title compound as an ivory amorphous solid (43%). Reverse phase HPLC (35-65% acetonitrile w/0.1% TFA/water w/0.1% TFA) was utilized in purifying this compound. MS(ES)+ m/e 455.0 [M+H]⁺.

Example 143

4-[4'-chloro-3-fluoro-3'-(methyloxy)-4-biphenylyl]-5-{[(3S)-1-(cyclopropylcarbonyl)-3-pyrrolidinyl]methyl}-2,4-dihydro-3H-1,2,4-triazol-3-one

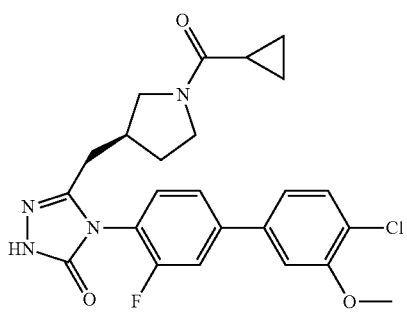 [SMILES: COc1cc(-c2ccc(-n3c(C[C@@H]4CCN(C(=O)C5CC5)C4)n[nH]c3=O)c(F)c2)ccc1Cl]

a) Following the procedure described in Example 114a with [4-chloro-3-(methyloxy)phenyl]boronic acid provided the title compound as an ivory amorphous solid (45%). Reverse phase HPLC (35-65% acetonitrile w/0.1% TFA/water w/0.1% TFA) was utilized in purifying this compound. MS(ES)+ m/e 471.2 [M+H]⁺.

Example 144

5-{[(3S)-1-(cyclopropylcarbonyl)-3-pyrrolidinyl]methyl}-4-(2',4'-dichloro-3-fluoro-4-biphenylyl)-2,4-dihydro-3H-1,2,4-triazol-3-one

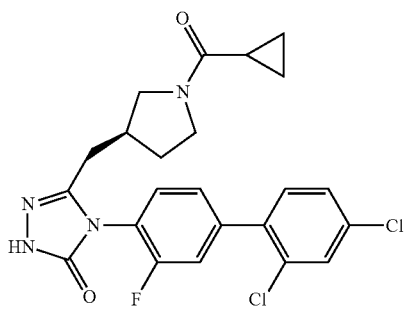 [SMILES: O=C(C1CC1)N1CC[C@@H](Cc2n[nH]c(=O)n2-c2ccc(-c3ccc(Cl)cc3Cl)cc2F)C1]

a) Following the procedure described in Example 114a with (2,4-dichlorophenyl)boronic acid provided the title compound as an ivory amorphous solid (43%). Reverse phase HPLC (35-65% acetonitrile w/0.1% TFA/water w/0.1% TFA) was utilized in purifying this compound. MS(ES)+ m/e 475.0 [M+H]+.

Example 145

4-(4'-chloro-2',3-difluoro-4-biphenylyl)-5-{[(3S)-1-(cyclopropylcarbonyl)-3-pyrrolidinyl]methyl}-2,4-dihydro-3H-1,2,4-triazol-3-one

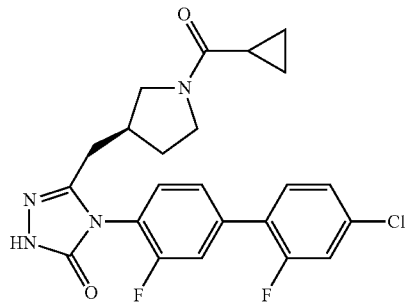

a) Following the procedure described in Example 114a with (4-chloro-2-fluorophenyl)boronic acid provided the title compound as an ivory amorphous solid (40%). Reverse phase HPLC (35-65% acetonitrile w/0.1% TFA/water w/0.1% TFA) was utilized in purifying this compound. MS(ES)+ m/e 459.2 [M+H]+.

Example 146

4-(4'-chloro-3-fluoro-2'-methyl-4-biphenylyl)-5-{[(3S)-1-(cyclopropylcarbonyl)-3-pyrrolidinyl]methyl}-2,4-dihydro-3H-1,2,4-triazol-3-one

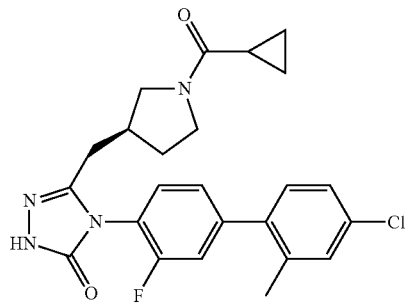 [SMILES: Cc1cc(Cl)ccc1-c1ccc(-n2c(C[C@@H]3CCN(C(=O)C4CC4)C3)n[nH]c2=O)c(F)c1]

a) Following the procedure described in Example 114a with (4-chloro-2-methylphenyl)boronic acid provided the title compound as an ivory amorphous solid (43%). Reverse phase HPLC (35-65% acetonitrile w/0.1% TFA/water w/0.1% TFA) was utilized in purifying this compound. MS(ES)+ m/e 455.0 [M+H]+.

Example 147

5-{[(3S)-1-(cyclopropylcarbonyl)-3-pyrrolidinyl]methyl}-4-[2-fluoro-4-(7-quinazolinyl)phenyl]-2,4-dihydro-3H-1,2,4-triazol-3-one

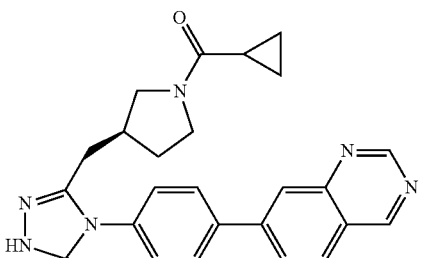

a) Following the procedure described in Example 117a with 7-bromoquinazoline provided the title compound as a white amorphous solid (21%). Reverse phase HPLC (20-50% acetonitrile w/0.1% TFA/water w/0.1% TFA) and reverse phase HPLC (10-40% acetonitrile/water+0.1% NH4OH) were utilized in purifying this compound. MS(ES)+ m/e 459.3 [M+H]+.

Example 148

4-(4'-chloro-3-fluoro-4-biphenylyl)-5-{[(3S)-1-(cyclopropylcarbonyl)-3-pyrrolidinyl]methyl}-2,4-dihydro-3H-1,2,4-triazol-3-one

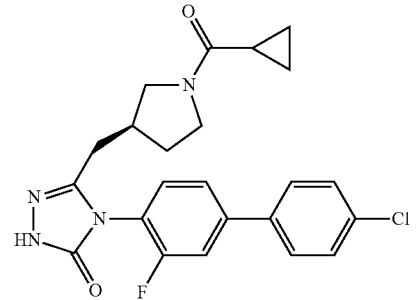 [SMILES: O=C(C1CC1)N1CC[C@@H](Cc2n[nH]c(=O)n2-c2ccc(-c3ccc(Cl)cc3)cc2F)C1]

a) Following the procedure described in Example 114a with (4-chlorophenyl)boronic acid (1.0 eq) provided the title compound as a tan amorphous solid (30%). Reverse phase HPLC (35-65% acetonitrile w/0.1% TFA/water w/0.1% TFA) was utilized in purifying this compound. MS(ES)+ m/e 441.1 [M+H]+.

Example 149

5-{[(3S)-1-(cyclopropylcarbonyl)-3-pyrrolidinyl]methyl}-4-[4-(2,3-dihydro-1H-inden-5-yl)-2-fluorophenyl]-2,4-dihydro-3H-1,2,4-triazol-3-one

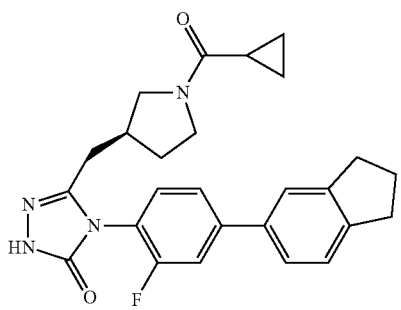 [SMILES: O=C(C1CC1)N1CC[C@@H](Cc2n[nH]c(=O)n2-c2ccc(-c3ccc4c(c3)CCC4)cc2F)C1]

a) Following the procedure described in Example 117a with 5-bromo-2,3-dihydro-1H-indene (1.1 eq) provided the title compound as an ivory amorphous solid (32%). Reverse phase HPLC (35-65% acetonitrile w/0.1% TFA/water w/0.1% TFA) and reverse phase HPLC (35-65% acetonitrile/water+0.1% NH₄OH) were utilized in purifying this compound. MS(ES)+ m/e 447.2 [M+H]+.

Example 150

5-{[(3S)-1-(cyclopropylcarbonyl)-3-pyrrolidinyl]methyl}-4-[2-fluoro-4-(1-oxo-2,3-dihydro-1H-inden-5-yl)phenyl]-2,4-dihydro-3H-1,2,4-triazol-3-one

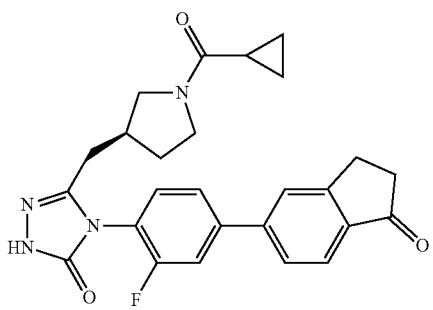 [SMILES: O=C1CCc2cc(-c3ccc(-n4c(C[C@@H]5CCN(C(=O)C6CC6)C5)n[nH]c4=O)c(F)c3)ccc21]

a) Following the procedure described in Example 117a with 5-bromo-2,3-dihydro-1H-inden-1-one provided the title compound as an ivory amorphous solid (39%). Reverse phase HPLC (10-90% acetonitrile w/0.1% TFA/water w/0.1% TFA) was utilized in purifying this compound. MS(ES)+ m/e 461.3 [M+H]+.

Example 151

5-{[(3S)-1-(cyclopropylcarbonyl)-3-pyrrolidinyl]methyl}-4-[4'-(4-morpholinyl)-4-biphenylyl]-2,4-dihydro-3H-1,2,4-triazol-3-one

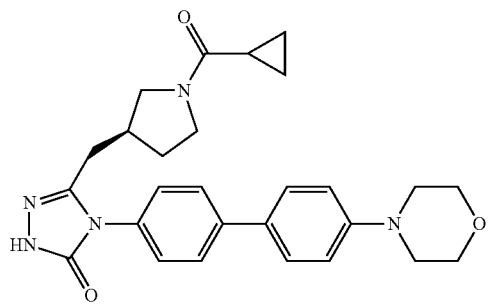 [SMILES: O=C(C1CC1)N1CC[C@@H](Cc2n[nH]c(=O)n2-c2ccc(-c3ccc(N4CCOCC4)cc3)cc2)C1]

a) Following the procedure described in Example 123a with [4-(4-morpholinyl)phenyl]boronic acid provided the title compound as an ivory amorphous solid (71%). Reverse phase HPLC (25-55% acetonitrile/water+0.1% NH₄OH) was utilized in purifying this compound. MS(ES)+ m/e 474.2 [M+H]+.

Example 152

5-{[(3S)-1-(cyclopropylcarbonyl)-3-pyrrolidinyl]methyl}-4-[4'-(1H-pyrrol-1-yl)-4-biphenylyl]-2,4-dihydro-3H-1,2,4-triazol-3-one

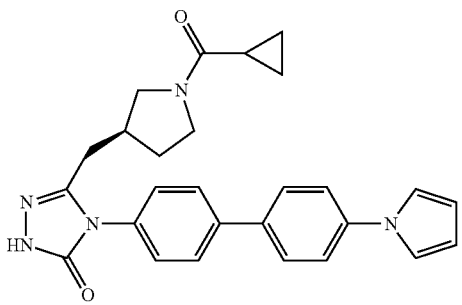 [SMILES: O=C(C1CC1)N1CC[C@@H](Cc2n[nH]c(=O)n2-c2ccc(-c3ccc(-n4cccc4)cc3)cc2)C1]

a) A solution of 5-{[(3S)-1-(cyclopropylcarbonyl)-3-pyrrolidinyl]methyl}-4-[4-(4,4,5,5-tetramethyl-1,3,2-dioxaborolan-2-yl)phenyl]-2,4-dihydro-3H-1,2,4-triazol-3-one (0.252 mmol) in dioxane (1.5 mL) was treated with 1-(4-bromophenyl)-1H-pyrrole (0.252 mmol), dichloro[1,1'-bis(diphenylphosphino)ferrocene]palladium(II)-dichloromethane adduct (10 mg), and 2M aq potassium carbonate (0.756 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH~4 using 1N aq HCl and was extracted with dichloromethane. The resulting organic phase was treated with Si-Thiol (Silicycle, 20 mg), dried over magnesium sulfate, filtered, and concentrated in vacuo. The crude residue was purified by reverse phase HPLC (35-65% acetonitrile/water+0.1% NH₄OH). The resulting product was purified by silica gel chromatography (0-8% methanol/dichloromethane) to afford the title compound as an amorphous white solid (42%). MS(ES)+ m/e 454.1 [M+H]⁺.

Example 153

5-{[(3S)-1-(cyclopropylcarbonyl)-3-pyrrolidinyl]methyl}-4-[4'-(1-pyrrolidinyl)-4-biphenylyl]-2,4-dihydro-3H-1,2,4-triazol-3-one

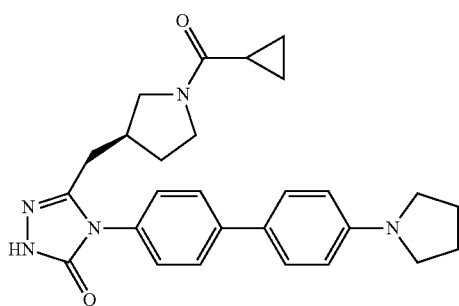 [SMILES: O=C(C1CC1)N1CC[C@@H](Cc2n[nH]c(=O)n2-c2ccc(-c3ccc(N4CCCC4)cc3)cc2)C1]

a) Following the procedure described in Example 123a with 1-[4-(4,4,5,5-tetramethyl-1,3,2-dioxaborolan-2-yl)phenyl]pyrrolidine provided the title compound as a white amorphous solid (41%). Reverse phase HPLC (30-60% acetonitrile/water+0.1% NH₄OH) was utilized in purifying this compound. MS(ES)+ m/e 458.2 [M+H]⁺.

Example 154

5-{[(3S)-1-(cyclopropylcarbonyl)-3-pyrrolidinyl]methyl}-4-[4-(7-quinolinyl)phenyl]-2,4-dihydro-3H-1,2,4-triazol-3-one

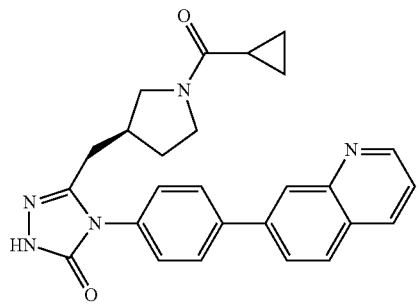 [SMILES: O=C(C1CC1)N1CC[C@@H](Cc2n[nH]c(=O)n2-c2ccc(-c3ccc4cccnc4c3)cc2)C1]

a) Following the procedure described in Example 152a with 7-bromoquinoline provided the title compound as a white amorphous solid (63%). Reverse phase HPLC (10-40% acetonitrile w/0.1% TFA/water w/0.1% TFA) was utilized in purifying this compound. MS(ES)+ m/e 440.1 [M+H]⁺.

Example 155

5-{[(3S)-1-(cyclopropylcarbonyl)-3-pyrrolidinyl]methyl}-4-(2',3,4'-trifluoro-4-biphenylyl)-2,4-dihydro-3H-1,2,4-triazol-3-one

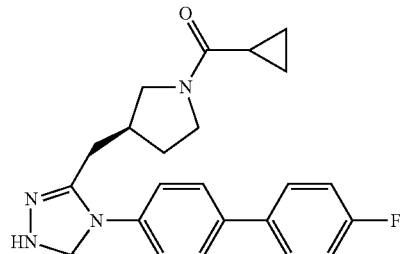

a) Following the procedure described in Example 114a with (2,4-difluorophenyl)boronic acid provided the title compound as a white amorphous solid (54%). Reverse phase HPLC (25-55% acetonitrile w/0.1% TFA/water w/0.1% TFA) was utilized in purifying this compound. MS(ES)+ m/e 443.1 [M+H]⁺.

Example 156

5-{[(3S)-1-(cyclopropylcarbonyl)-3-pyrrolidinyl]methyl}-4-[2',3-difluoro-4'-(methyloxy)-4-biphenylyl]-2,4-dihydro-3H-1,2,4-triazol-3-one

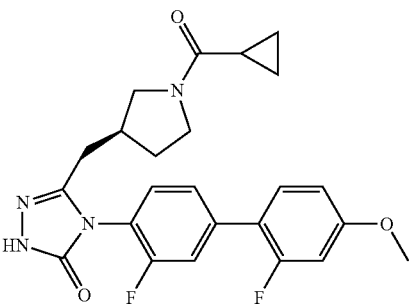 [SMILES: COc1ccc(-c2ccc(-n3c(C[C@@H]4CCN(C(=O)C5CC5)C4)n[nH]c3=O)c(F)c2)c(F)c1]

a) Following the procedure described in Example 114a with [2-fluoro-4-(methyloxy)phenyl]boronic acid provided the title compound as a white amorphous solid (57%).

Reverse phase HPLC (25-55% acetonitrile w/0.1% TFA/water w/0.1% TFA) was utilized in purifying this compound. MS(ES)+ m/e 455.0 [M+H]+.

Example 157

5-{[(3S)-1-(cyclopropylcarbonyl)-3-pyrrolidinyl]methyl}-4-[2-fluoro-4-(4-quinolinyl)phenyl]-2,4-dihydro-3H-1,2,4-triazol-3-one

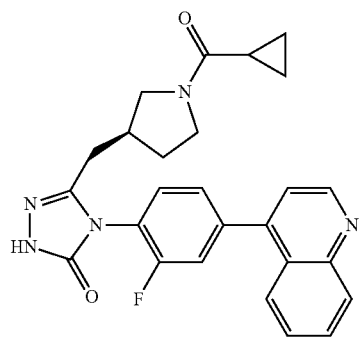 [SMILES: O=C(C1CC1)N1CC[C@@H](Cc2n[nH]c(=O)n2-c2ccc(-c3ccnc4ccccc34)cc2F)C1]

a) Following the procedure described in Example 114a with 4-quinolinylboronic acid provided the title compound as a white amorphous solid (37%). Reverse phase HPLC (5-25% acetonitrile w/0.1% TFA/water w/0.1% TFA) was utilized in purifying this compound. MS(ES)+ m/e 458.2 [M+H]+.

Example 158

N-[4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylyl]acetamide

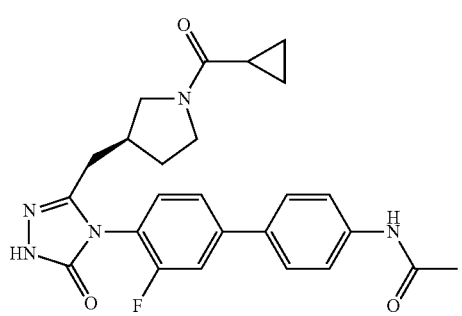 [SMILES: CC(=O)Nc1ccc(-c2ccc(-n3c(C[C@@H]4CCN(C(=O)C5CC5)C4)n[nH]c3=O)c(F)c2)cc1]

a) Following the procedure described in Example 114a with [4-(acetylamino)phenyl]boronic acid provided the title compound as a white amorphous solid (60%). Reverse phase HPLC (10-40% acetonitrile w/0.1% TFA/water w/0.1% TFA) was utilized in purifying this compound. MS(ES)+ m/e 464.3 [M+H]+.

Example 159

4-[4-(1-benzofuran-5-yl)phenyl]-5-{[(3R)-1-(cyclopropylcarbonyl)-3-pyrrolidinyl]methyl}-2,4-dihydro-3H-1,2,4-triazol-3-one

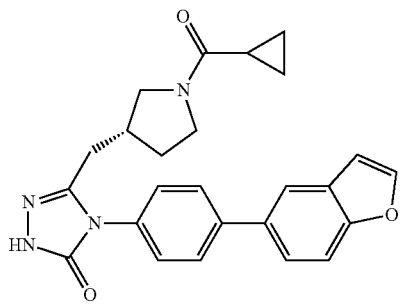 [SMILES: O=C(C1CC1)N1CC[C@H](Cc2n[nH]c(=O)n2-c2ccc(-c3ccc4occc4c3)cc2)C1]

a) 1,1-dimethylethyl (3R)-3-[2-(ethyloxy)-2-oxoethyl]-1-pyrrolidinecarboxylate

In an oven-dried 250 mL round bottom flask under nitrogen, ((3R)-1-{[(1,1-dimethylethyl)oxy]carbonyl}-3-pyrrolidinyl)acetic acid (2.181 mmol) dissolved in diethyl ether (5 mL) was treated with 1-ethyl-3-(3-dimethylaminopropyl)carbodiimide hydrochloride (2.4 mmol), 4-(dimethylamino)pyridine (0.218 mmol), and ethanol (4.8 mmol) at room temperature and the mixture was stirred overnight. The resulting white gummy precipitate was diluted with ether (100 mL) and washed with 1M aq sodium hydrogen sulfate solution (100 mL), saturated aq sodium bicarbonate solution (100 mL), and brine (100 mL). The organic phase was isolated, dried over magnesium sulfate, and concentrated in vacuo to give the title compound as a clear oil (95%). MS(ES)+ m/e 258.1 [M+H]+, 280.0 [M+Na]+.

b) ethyl [(3R)-1-(cyclopropylcarbonyl)-3-pyrrolidinyl]acetate

In a round bottom flask, a solution of 1,1-dimethylethyl (3R)-3-[2-(ethyloxy)-2-oxoethyl]-1-pyrrolidinecarboxylate (2.08 mmol) in 4M HCl in dioxane (10 mL, 40 mmol) was stirred at room temperature for 1 h. Analysis of an aliquot by LCMS confirmed complete removal of the BOC group from the starting material. The reaction was concentrated in vacuo to give a pale yellow liquid, which was dissolved in diethyl ether and concentrated to dryness in vacuo to yield a white solid. A solution of this intermediate as the HCl salt in dichloromethane (100 mL) was treated with N,N-diisopropylethylamine (4.16 mmol) and stirred for 5 min at room temperature. The yellow solution was treated with cyclopropanecarbonyl chloride (2.287 mmol) dropwise by syringe. The solution was allowed to warm to room temperature and stirred for 1 h. The reaction was diluted with dichloromethane (100 mL) and was washed with water, dried over magnesium sulfate, and concentrated in vacuo to give the title compound as a yellow oil (quantitative). MS(ES)+ m/e 226.1 [M+H]+.

c) 2-[(3R)-1-(cyclopropylcarbonyl)-3-pyrrolidinyl]acetohydrazide

In a round bottom flask equipped with reflux condenser, a yellow solution of ethyl [(3R)-1-(cyclopropylcarbonyl)-3-pyrrolidinyl]acetate (2.095 mmol) in ethanol (5 mL) was treated with hydrazine monohydrate (41.9 mmol). The resultant yellow solution was stirred at 80° C. (reflux) overnight. The reaction was cooled to room temperature and concentrated in vacuo. Ethanol (10 mL) was added and the reaction was concentrated to give a clear oil. The oil was dissolved in dichloromethane (white solution observed), dried over magnesium sulfate, filtered, and concentrated in vacuo to give the title compound as a clear oil (quantitative). MS(ES)+ m/e 212.1 [M+H]+, 423.2 [2M+H]+.

d) N-(4-bromophenyl)-2-{[(3R)-1-(cyclopropylcarbonyl)-3-pyrrolidinyl]acetyl}hydrazinecarboxamide In a round bottom flask under nitrogen, a solution of 2-[(3R)-1-(cyclopropylcarbonyl)-3-pyrrolidinyl]acetohydrazide (2.16 mmol) in dichloromethane (5 mL) was cooled to 0° C. and 1-bromo-4-isocyanatobenzene (2.16 mmol) was added. Once the isocyanate dissolved, the cooling bath was removed and the reaction was allowed to warm to room temperature and was stirred for 3 h. The reaction was filtered to collect the white precipitate, washed with 10 mL cold dichloromethane, air dried for 1 h and then dried in a vacuum oven (60° C.) overnight to provide the title compound (88% yield). MS(ES)+ m/e 409.1, 411.1 [M+H]+.

e) 4-(4-bromophenyl)-5-{[(3R)-1-(cyclopropylcarbonyl)-3-pyrrolidinyl]methyl}-2,4-dihydro-3H-1,2,4-triazol-3-one In a round bottom flask equipped with reflux condenser, N-(4-bromophenyl)-2-{[(3R)-1-(cyclopropylcarbonyl)-3-pyrrolidinyl]acetyl}hydrazinecarboxamide (1.896 mmol) in water (75 mL) was treated with potassium carbonate (9.48 mmol). The resulting slurry was stirred at reflux overnight (15 h). The heating was turned off and the reaction was allowed to cool to room temperature. The pH was adjusted to ~4 using 6N aq HCl. The aqueous solution was concentrated in vacuo to ~50 mL, which was then extracted with ethyl acetate. The combined organic phases were washed with brine, dried over sodium sulfate, filtered and concentrated in vacuo. The crude product was purified by flash chromatography (0-10% methanol/dichloromethane). The fractions were concentrated in vacuo to provide the title compound as an off-white amorphous solid (65%). MS(ES)+ m/e 391.1, 393.2 [M+H]+.

f) 4-[4-(1-benzofuran-5-yl)phenyl]-5-{[(3R)-1-(cyclopropylcarbonyl)-3-pyrrolidinyl]methyl}-2,4-dihydro-3H-1,2,4-triazol-3-one A solution of 4-(4-bromophenyl)-5-{[(3R)-1-(cyclopropylcarbonyl)-3-pyrrolidinyl]methyl}-2,4-dihydro-3H-1,2,4-triazol-3-one (0.256 mmol) in dioxane (1.5 mL) was treated with 5-(4,4,5,5-tetramethyl-1,3,2-dioxaborolan-2-yl)-1-benzofuran (0.281 mmol), dichloro[1,1'-bis(diphenylphosphino)ferrocene]palladium(II)-dichloromethane adduct (10 mg), and 2M aq potassium carbonate (0.767 mmol). The reaction mixture was purged with nitrogen, sealed, and irradiated in a microwave (Biotage Initiator) at 150° C. for 15 min. The reaction mixture was cooled to room temperature and was diluted with water (50 mL). The aqueous layer was acidified to pH ~4 using 1N aq HCl and was extracted with dichloromethane. The resulting organic phase was treated with Si-Thiol (Silicycle, 20 mg), dried over magnesium sulfate, filtered, and concentrated in vacuo. The crude residue was purified by reverse phase HPLC (20-50% acetonitrile/water+0.1% NH$_4$OH) to afford the title compound as an amorphous white solid (35%). MS(ES)+ m/e 429.0 [M+H]+.

Example 160

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-4-biphenylcarboxylic Acid

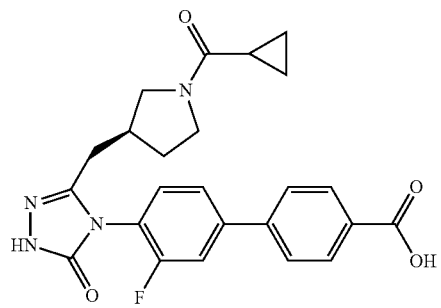 [SMILES: O=C(O)c1ccc(-c2ccc(-n3c(C[C@@H]4CCN(C(=O)C5CC5)C4)n[nH]c3=O)c(F)c2)cc1]

a) A microwave vial was charged with 4(4-bromo-2-fluorophenyl)-5-{[(3S)-1-(cyclopropylcarbonyl)-3-pyrrolidinyl]methyl}-2,4-dihydro-3H-1,2,4-triazol-3-one (0.29 mmol), 4-(dihydroxyboranyl)benzoic acid (0.32 mmol), PdCl$_2$(dppf) (0.015 mmol), a solution of K$_2$CO$_3$ (0.73 mmol) in water (1 mL), and 1,4-dioxane (3 mL). The vial was purged with nitrogen, sealed and irradiated in a microwave reactor for 30 min at 130° C. (pressure ~3-4 bar). Analysis of the crude reaction by LCMS indicated ~80% conversion to desired product. Re-subjection of the reaction to the microwave at 130° C. for 30 min did not progress the reaction any further as judged by LCMS. The reaction mixture was concentrated under reduced pressure and the residue was dissolved in DMSO (3 mL), filtered through a syringe filter, and purified by reverse phase HPLC (10-90% acetonitrile/water+0.1% TFA). The appropriate product fractions were concentrated to remove a majority of the acetonitrile, leaving an aqueous suspension of product which was collected by filtration and dried to constant weight to provide the title product (38 mg, 0.084 mmol, 29% yield) as an off-white solid. MS(ES)+ m/e 451.0 [M+H]+.

Example 161

4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-biphenylcarboxylic Acid

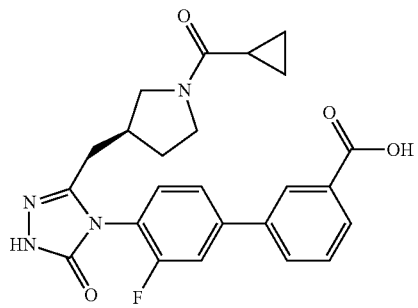 [SMILES: O=C(O)c1cccc(-c2ccc(-n3c(C[C@@H]4CCN(C(=O)C5CC5)C4)n[nH]c3=O)c(F)c2)c1]

a) A microwave vial was charged with 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.29 mmol), 3-(dihydroxyboranyl)benzoic acid (0.29 mmol), PdCl₂(dppf) (0.015 mmol), a solution of K₂CO₃ (0.733 mmol) in water (1 mL), and 1,4-dioxane (3 mL). The vial was purged with nitrogen, sealed, and irradiated in a microwave reactor for 30 min at 130° C. (pressure ~3-4 bar). Analysis of the crude reaction by LCMS indicated ~80% conversion to desired product. The reaction mixture was concentrated under reduced pressure and the residue was dissolved in DMSO (3 mL), filtered through a syringe filter, and purified by reverse phase HPLC (10-90% acetonitrile/water+0.1% TFA). The appropriate product fractions were concentrated to remove a majority of the acetonitrile (product did not crash out). The mixture was adjusted to pH~12 with 1N aq NaOH and partitioned with ethyl acetate. The aqueous layer was separated and adjusted to pH~2 with 1N aq HCl, causing a gummy precipitate to form which was collected by filtration and dried to constant weight to provide the title product (39 mg, 0.087 mmol, 30% yield) as a tan solid. MS(ES)+ m/e 451.0 [M+H]⁺.

Example 162

5-{[1-(cyclopropylcarbonyl)-3-azetidinyl]methyl}-4-[4-(7-quinolinyl)phenyl]-2,4-dihydro-3H-1,2,4-triazol-3-one

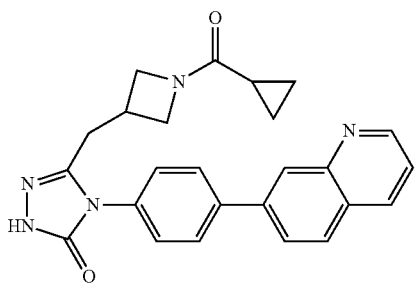 [SMILES: O=C(C1CC1)N1CC(Cc2n[nH]c(=O)n2-c2ccc(-c3ccc4cccnc4c3)cc2)C1]

a) Following the procedure described in Example 66f with 7-(4,4,5,5-tetramethyl-1,3,2-dioxaborolan-2-yl)quinoline afforded the title compound as a white solid (61%). MS(ES)+ m/e 426.0 [M+H]⁺.

Example 163

5-{[1-(cyclopropylcarbonyl)-3-azetidinyl]methyl}-4-[2-fluoro-4-(7-quinolinyl)phenyl]-2,4-dihydro-3H-1,2,4-triazol-3-one

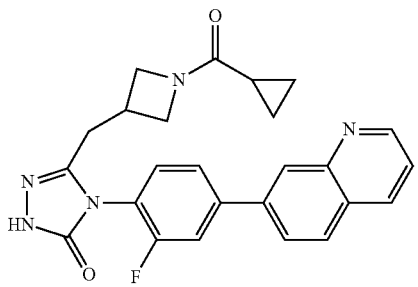 [SMILES: O=C(C1CC1)N1CC(Cc2n[nH]c(=O)n2-c2ccc(-c3ccc4cccnc4c3)cc2F)C1]

a) Following the procedure described in Example 72c with 7-quinoline boronic acid and purification by reverse phase HPLC (10-73% acetonitrile/water with 0.1% NH₄OH) afforded the title compound as a tan solid (49%). MS(ES)+ m/e 444.2 [M+H]⁺.

Example 164

4-[2-fluoro-4-(7-quinolinyl)phenyl]-5-[(1-propanoyl-3-azetidinyl)methyl]-2,4-dihydro-3H-1,2,4-triazol-3-one

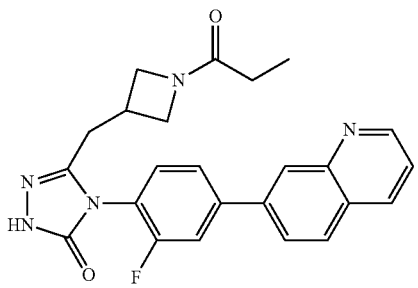 [SMILES: CCC(=O)N1CC(Cc2n[nH]c(=O)n2-c2ccc(-c3ccc4cccnc4c3)cc2F)C1]

a) 1,1-dimethylethyl 3-(2-hydrazino-2-oxoethyl)-1-azetidinecarboxylate

Following the procedure described in Example 66c with 1,1-dimethylethyl 3-[2-(ethyloxy)-2-oxoethyl]-1-azetidinecarboxylate provided the title compound as a colourless oil (87% pure, 92% yield). MS(ES)+ m/e 230.3 [M+H]⁺, 459.3 [2M+H]⁺.

b) 1,1-dimethylethyl 3-[2-(2-{[(4-bromo-2-fluorophenyl)amino]carbonyl}hydrazino)-2-oxoethyl]-1-azetidinecarboxylate In a round bottom flask under nitrogen, a solution of 1,1-dimethylethyl 3-(2-hydrazino-2-oxoethyl)-1-azetidinecarboxylate (15.18 mmol) in dichloromethane (20 mL) at 0° C. was treated with 4-bromo-2-fluorophenylisocyanate (15.18 mmol). The cooling bath was removed and the clear yellow solution was stirred at room temperature for 1 h. The reaction mixture was concentrated in vacuo to afford the crude title compound as a white foamy solid. This material was used directly without further purification. MS(ES)+ m/e 445.2, 447.2 [M+H]⁺.

c) 4-(4-bromo-2-fluorophenyl)-2-propanoyl-5-[(1-propanoyl-3-azetidinyl)methyl]-2,4-dihydro-3H-1,2,4-triazol-3-one In a 250 mL round bottom flask equipped with reflux condenser and stir bar, a mixture of 1,1-dimethylethyl 3-[2-(2-{[(4-bromo-2-fluorophenyl)amino]carbonyl}hydrazino)-2-oxoethyl]-1-azetidinecarboxylate (15.18 mmol) and potassium carbonate (76 mmol) in 1-propanol (20 mL) and water (100 mL) was stirred at reflux (oil bath, 130° C.) for 27 h. The reaction mixture was cooled to room temperature, concentrated in vacuo, and diluted with water (50 mL) and ethyl acetate (50 mL). The layers were separated and the aqueous layer was acidified to pH~5 using 1N aq HCl and extracted with ethyl acetate (2×100 mL). The organic layers were combined, dried over magnesium sulphate, and concentrated in vacuo. Purification of the residue by silica gel chromatography (0-10% methanol/ethyl acetate) provided 1.5 g of material containing both starting material and BOC-protected product. To this flask was added water (50 mL) and potassium carbonate (14.47 mmol). The reaction was stirred at reflux (oil bath, 130° C.) for 16 h. The reaction was cooled to room temperature and concentrated in vacuo to give the unprotected cyclized product. To this was added 1N aq sodium hydroxide (50 mL) followed by di-tert-butyl dicarbonate (15.18 mmol) and the reaction was stirred overnight. The reaction was cooled to room temperature, concentrated in vacuo and diluted with ethyl acetate (50 mL) and water (10 mL). The layers were separated and the aqueous layer was acidified to pH 5 using 1N aq HCl. The aqueous layer was extracted with ethyl acetate (2×100 mL). The organic layers were combined, dried over magnesium sulphate and concentrated in vacuo. Purification of the residue by silica gel chromatography (0-5% methanol/ethyl acetate) did not provide any desired products. The aqueous layer was concentrated in vacuo and treated with dichloromethane (50 mL) and N,N-diisopropylethylamine (28.6 mmol). The reaction mixture was stirred for 5 min at room temperature and then propionyl chloride (15.18 mmol) was added by syringe. The reaction was stirred for 1 h at room temperature. Analysis by LCMS showed that the reaction was complete for 4-(4-bromo-2-fluorophenyl)-5-[(1-propanoyl-3-azetidinyl)methyl]-2,4-dihydro-3H-1,2,4-triazol-3-one [M+H]+=383.0, 384.7. The reaction was quenched with water (20 mL) and the layers were separated. The aqueous layer was acidified to pH 5 using 1N HCl solution and extracted with ethyl acetate (2×50 mL). The organic layers were combined, dried over magnesium sulphate, and concentrated in vacuo. Purification of the residue by silica gel chromatography (0-5% methanol/ethyl acetate) provided the title compound as an off-white solid (277 mg, 3% yield). MS(ES)+ m/e 439.2, 441.1 [M+H]+.

d) 4-[2-fluoro-4-(7-quinolinyl)phenyl]-5-[(1-propanoyl-3-azetidinyl)methyl]-2,4-dihydro-3H-1,2,4-triazol-3-one In a microwave vial purged with nitrogen, a mixture of 4-(4-bromo-2-fluorophenyl)-2-propanoyl-5-[(1-propanoyl-3-azetidinyl)methyl]-2,4-dihydro-3H-1,2,4-triazol-3-one (0.37 mmol), 1,1'-bis(diphenylphosphino)ferrocene-palladium(II)dichloride dichloromethane complex (0.02 mmol) and 7-quinoline boronic acid (0.39 mmol) in 1,4-dioxane (2 mL) and 2M aq potassium carbonate (2 mL) was stirred at 100° C. in an oil bath for 1 h. The reaction was cooled to room temperature and the layers were separated. The aqueous layer was acidified to pH~5.5 using 1N HCl solution and extracted with ethyl acetate (50 mL). The organic layers were combined, dried over magnesium sulphate, and concentrated in vacuo to give a tan solid. Trituration in dichloromethane followed by treatment with hot ethanol (5 mL), which was allowed to cool to room temperature, and then filtration afforded the desired product as a white solid, 93% pure. Subsequent purification of the filtrate and white solid by reverse phase HPLC (20-60% acetonitrile/water with 0.1% NH4OH) provided the title compound as a white solid (119 mg, 74%). MS(ES)+ m/e 432.1 [M+H]+.

Example 165

5-[(1-propanoyl-3-azetidinyl)methyl]-4-[4-(7-quinolinyl)phenyl]-2,4-dihydro-3H-1,2,4-triazol-3-one

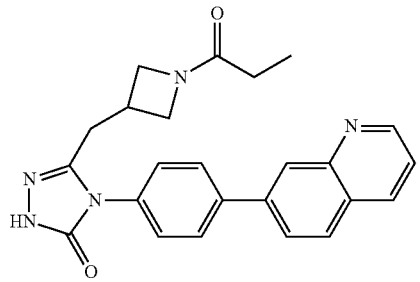 [SMILES: CCC(=O)N1CC(Cc2n[nH]c(=O)n2-c2ccc(-c3ccc4cccnc4c3)cc2)C1]

a) 1,1-dimethylethyl 3-[2-(2-{[(4-bromophenyl)amino]carbonyl}hydrazino)-2-oxoethyl]-1-azetidinecarboxylate Following the procedure described in Example 164b with 4-bromophenylisocyanate afforded the crude title compound as a white foamy solid. MS(ES)+ m/e 426.9, 428.8 [M+H]+.

b) 4-(4-bromophenyl)-5-[(1-propanoyl-3-azetidinyl)methyl]-2,4-dihydro-3H-1,2,4-triazol-3-one In a round bottom flask equipped with reflux condenser, a mixture of 1,1-dimethylethyl 3-[2-(2-{[(4-bromophenyl)amino]carbonyl}hydrazino)-2-oxoethyl]-1-azetidinecarboxylate (5.69 mmol) and potassium carbonate (28.5 mmol) in water (110 mL) was stirred at reflux (oil bath, 130° C.) for 16 h. The reaction mixture was cooled to room temperature and concentrated in vacuo partially and then lyophilized overnight to give a white solid. The solid was treated with dichloromethane (20 mL) followed by N,N-diisopropylethylamine (11.45 mmol) and the mixture was stirred at room temperature for 10 min. The reaction mixture was cooled to 0° C. and propionyl chloride (5.76 mmol) was added. The reaction was allowed to warm to room temperature and the reaction was stirred at room temperature for 2 h. The reaction was quenched with water (100 mL) and 1N HCl solution (10 mL), stirred for 10 min, and then acidified to pH~5 using 1N aq HCl. The layers were separated and the aqueous layer was extracted with ethyl acetate (2×50 mL). The organic layers were combined, dried over magnesium sulphate, and concentrated in vacuo. Purification of the residue by silica gel chromatography (0-7% methanol/ethyl acetate) afforded 4-(4-bromophenyl)-2-propanoyl-5-[(1-propanoyl-3-azetidinyl)methyl]-2,4-dihydro-3H-1,2,4-triazol-3-one as a pale yellow solid (660 mg) and the title compound as an ivory solid (341 mg, 60% pure, 10% yield). MS(ES)+ m/e 365.0, 366.8 [M+H]+.

c) 5-[(1-propanoyl-3-azetidinyl)methyl]-4-[4-(7-quinolinyl)phenyl]-2,4-dihydro-3H-1,2,4-triazol-3-one Following the procedure described in Example 164d with 4-(4-bromophenyl)-5-[(1-propanoyl-3-azetidinyl)methyl]-2,4-dihydro-3H-1,2,4-triazol-3-one afforded the title compound as a white solid (55%). MS(ES)+ m/e 414.1 [M+H]+.

Example 166

3-({4-[2-fluoro-4-(7-quinolinyl)phenyl]-5-oxo-4,5-dihydro-1H-1,2,4-triazol-3-yl}methyl)-N,N-dimethyl-1-azetidinecarboxamide

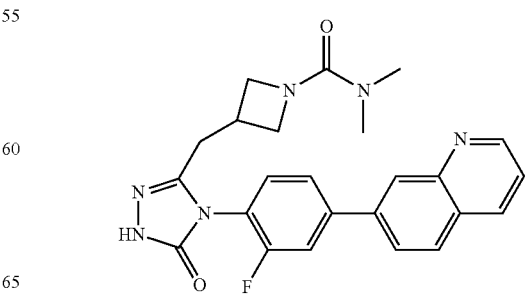

a) 5-(3-azetidinylmethyl)-4-[2-fluoro-4-(7-quinolinyl)phenyl]-2,4-dihydro-3H-1,2,4-triazol-3-one In a round bottom flask equipped with reflux condenser, a mixture of N-(4-bromo-2-fluorophenyl)-2-{[1-(cyclopropylcarbonyl)-3-azetidinyl]acetyl}hydrazine carboxamide (4.77 mmol) and potassium carbonate (23.84 mmol) in 1-propanol (10 mL) and water (100 mL) was stirred at vigorous reflux (oil bath, 130° C.) for 22 h. The pale yellow solution was cooled to room temperature and concentrated in vacuo. Water (12 mL) was added to the flask followed by 7-(4,4,5,5-tetramethyl-1,3,2-dioxaborolan-2-yl)quinoline (5.24 mmol), 1,1'-bis(diphenylphosphino)ferrocene-palladium(II)dichloride dichloromethane complex (0.24 mmol) and 1,4-dioxane (30 mL). The flask containing the reaction mixture was equipped with stir bar and reflux condenser, and the reaction was stirred at 100° C. for 5 h. The reaction mixture was cooled to room temperature, diluted with ethyl acetate (100 mL) and water (50 mL), and the layers were separated. The aqueous layer was adjusted to pH~5 using 1N HCl solution and extracted with ethyl acetate (2×100 mL). The organic layers were combined, dried over magnesium sulphate, and concentrated in vacuo. The aqueous layer was lyophilized to give a solid, which was taken up into methanol (25 mL), dichloromethane (25 mL) and ethyl acetate (25 mL) and filtered to remove the salts. The mother liquor was concentrated in vacuo. Methanol (5 mL) was added and a precipitate formed. The precipitate was filtered off and the mother liquor was concentrated in vacuo to provide the title compound as an oil (815 mg, 67% pure, 31% yield). MS(ES)+ m/e 376.0 [M+H]+.

b) 3-({4-[2-fluoro-4-(7-quinolinyl)phenyl]-5-oxo-4,5-dihydro-1H-1,2,4-triazol-3-yl}methyl)-N,N-dimethyl-1-azetidinecarboxamide In a round bottom flask under nitrogen at room temperature, a mixture of 5-(3-azetidinylmethyl)-4-[2-fluoro-4-(7-quinolinyl)phenyl]-2,4-dihydro-3H-1,2,4-triazol-3-one (0.38 mmol) in dichloromethane (2 mL) was treated with N,N-diisopropylethylamine (0.77 mmol) by syringe and stirred for 2 min. The starting material did not dissolve. N-methyl-2-pyrrolidone (2 mL) was added to the mixture and some material dissolved. The mixture was heated with a heat gun to accelerate dissolution and was then left to cool to room temperature. Dimethylcarbamoyl chloride (0.38 mmol) was then added dropwise by syringe to the reaction, which was stirred for 1 h. The reaction mixture was concentrated to remove the dichloromethane. The resultant solution was directly purified by reverse phase HPLC (10-70% acetonitrile/water with 0.1% NH4OH) and subsequently purified by silica gel chromatography (0-3% methanol/ethyl acetate) to provide the title compound as a white solid (31 mg, 18%). MS(ES)+ m/e 447.2 [M+H]+.

Example 167

4-[2-fluoro-4-(7-quinolinyl)phenyl]-5-({1-[(1-methylcyclopropyl)carbonyl]-3-azetidinyl}methyl)-2,4-dihydro-3H-1,2,4-triazol-3-one

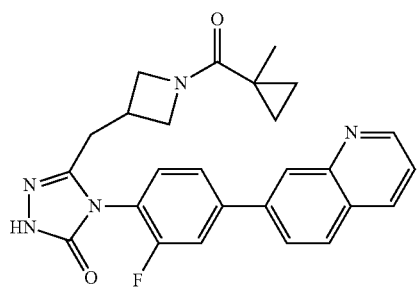 [SMILES: CC1(C(=O)N2CC(Cc3n[nH]c(=O)n3-c3ccc(-c4ccc5cccnc5c4)cc3F)C2)CC1]

a) In a round bottom flask under nitrogen, a solution of 5-(3-azetidinylmethyl)-4-[2-fluoro-4-(7-quinolinyl)phenyl]-2,4-dihydro-3H-1,2,4-triazol-3-one (1.07 mmol) in N,N-dimethylformamide (5 mL) was treated with 1-methylcyclopropanecarboxylic acid (1.285 mmol), N-[3-(dimethylamino)propyl]-N'-ethylcarbodiimide hydrochloride (2.14 mmol), N,N-diisopropylethylamine (3.21 mmol) and then 1H-1,2,3-benzotriazol-1-ol (2.14 mmol). The reaction mixture was stirred at room temperature for 1.5 h and then concentrated in vacuo. Purification of the residue by reverse phase HPLC (10-70% acetonitrile/water with 0.1% NH4OH) and subsequent silica gel chromatography (0-3% methanol/ethyl acetate) followed by trituration in ethanol provided the title compound as a white solid (45 mg, 9.2%). MS(ES)+ m/e 458.2 [M+H]+.

Example 168

4-[5-chloro-2-fluoro-4-(7-quinolinyl)phenyl]-5-{[(3S)-1-(cyclopropylcarbonyl)-3-pyrrolidinyl]methyl}-2,4-dihydro-3H-1,2,4-triazol-3-one

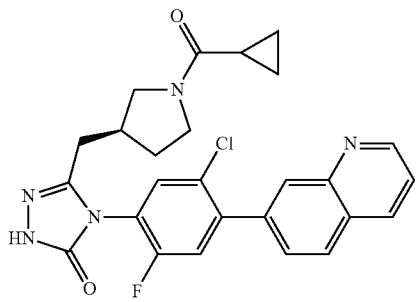 [SMILES: O=C(C1CC1)N1CC[C@@H](Cc2n[nH]c(=O)n2-c2cc(Cl)c(-c3ccc4cccnc4c3)cc2F)C1]

a) N-(4-bromo-5-chloro-2-fluorophenyl)-2-{[(3S)-1-(cyclopropylcarbonyl)-3-pyrrolidinyl]acetyl}hydrazinecarboxamide To a round bottom flask was added triphosgene (2.66 mmol) and dichloromethane (20 mL) under nitrogen, and the solution was cooled to −78° C. In a separate vial, 4-bromo-5-chloro-2-fluoroaniline (6.83 mmol) was dissolved in dichloromethane (20 mL) and Hunig's base (17.1 mmol) was added. This solution was slowly added to the cooled solution and then the reaction was allowed to warm to room temperature. After 10 min, analysis by LCMS indicated desired intermediate formation. The reaction was cooled again to −78° C. and 2-[(3S)-1-(cyclopropylcarbonyl)-3-pyrrolidinyl]acetohydrazide (3.98 mmol) in dichloromethane (5 mL) was added slowly. The reaction was allowed to warm to room temperature and stirred for 30 min. Analysis by LCMS indicated desired product formation. The reaction was poured into a separatory funnel and partitioned with saturated aq sodium bicarbonate. The aqueous layer was extracted with dichloromethane (3×) and the combined organic layers were dried over Na2SO4, filtered, and concentrated to an oil. The residue was purified by silica gel chromatography (0-15% isopropanol/ethyl acetate). The desired fractions were combined and concentrated to afford the title product as an oil (1.12 g, 60%). MS(ES)+ m/e 461.1, 463.0 [M+H]+.

b) 4-(4-bromo-5-chloro-2-fluorophenyl)-5-{[(3S)-1-(cyclopropylcarbonyl)-3-pyrrolidinyl]methyl}-2,4-dihydro-3H-1,2,4-triazol-3-one N-(4-bromo-5-chloro-2-fluorophenyl)-2-{[(3S)-1-(cyclopropylcarbonyl)-3-pyrrolidinyl]acetyl}hydrazinecarboxamide (2.426 mmol) and K$_2$CO$_3$ (8.49 mmol) were added to a round-bottom flask and suspended in water (105 mL). The mixture was heated at reflux (115° C.) for 21 h. Analysis by LCMS indicated formation of desired product (and other major by-products). The reaction was cooled to room temperature and the pH was adjusted to ~6 with 1N aq HCl and poured into a separatory funnel containing ethyl acetate. The aqueous layer was extracted with ethyl acetate (3×) and the combined organic layers were dried over Na$_2$SO$_4$, filtered, and concentrated to an oil. The residue was purified by silica gel chromatography (0-30% isopropanol/ethyl acetate). The desired fractions were combined and concentrated to afford the title product as an off-white solid (401 mg, 38%). MS(ES)+ m/e 443.0, 445.0 [M+H]$^+$.

c) 4-[5-chloro-2-fluoro-4-(7-quinolinyl)phenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-5-chloro-2-fluorophenyl)-5-{[(3S)-1-(cyclopropylcarbonyl)-3-pyrrolidinyl]methyl}-2,4-dihydro-3H-1,2,4-triazol-3-one (0.124 mmol), 7-(4,4,5,5-tetramethyl-1,3,2-dioxaborolan-2-yl)quinoline (0.16 mmol), cesium carbonate (0.37 mmol), and dichloro[1,1'-bis(diphenylphosphino)ferrocene]palladium(II)-dichloromethane adduct (0.0062 mmol). The mixture was purged with nitrogen and suspended in 1,4-dioxane (1 mL) and water (0.5 mL). The mixture was heated for 15 h at 100° C. Analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3×), and the combined organics were washed with brine, dried over Na$_2$SO$_4$, and concentrated to afford the title product as an off-white solid (20 mg, 33%). MS(ES)+ m/e 492.2, 494.0 [M+H]$^+$.

Example 169

4-[4-(1-benzofuran-5-yl)-5-chloro-2-fluorophenyl]-5-{[(3S)-1-(cyclopropylcarbonyl)-3-pyrrolidinyl]methyl}-2,4-dihydro-3H-1,2,4-triazol-3-one

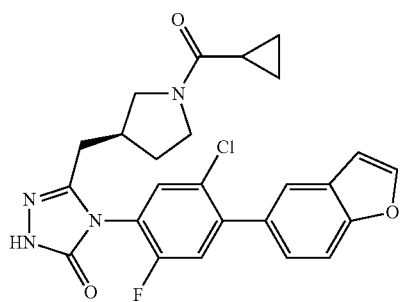 [SMILES: O=C(C1CC1)N1CC[C@@H](Cc2n[nH]c(=O)n2-c2cc(Cl)c(-c3ccc4occc4c3)cc2F)C1]

a) Following the procedure described in Example 168c with 5-(4,4,5,5-tetramethyl-1,3,2-dioxaborolan-2-yl)-1-benzofuran afforded the title compound as an off-white solid (17 mg, 29%). MS(ES)+ m/e 481.0, 482.9 [M+H]$^+$.

Example 170

5-{[(3S)-1-(cyclopropylcarbonyl)-3-pyrrolidinyl]methyl}-4-[2-fluoro-5-methyl-4-(7-quinolinyl)phenyl]-2,4-dihydro-3H-1,2,4-triazol-3-one

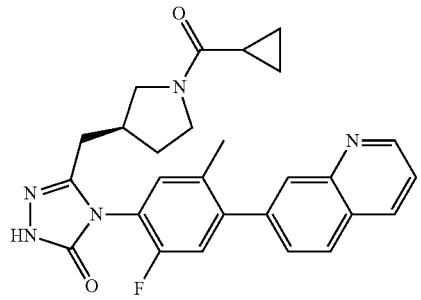 [SMILES: Cc1cc(-n2c(C[C@@H]3CCN(C(=O)C4CC4)C3)n[nH]c2=O)c(F)cc1-c1ccc2cccnc2c1]

a) N-(4-bromo-2-fluoro-5-methylphenyl)-2-{[(3S)-1-(cyclopropylcarbonyl)-3-pyrrolidinyl]acetyl}hydrazinecarboxamide To a round bottom flask was added triphosgene (2.57 mmol) and dichloromethane (20 mL) under nitrogen, and the solution was cooled to −78° C. In a separate vial, 4-bromo-2-fluoro-5-methylaniline (7.35 mmol) was dissolved in dichloromethane (20 mL) and Hunig's base (18.4 mmol) was added. This solution was slowly added to the cooled solution and then the reaction was allowed to warm to room temperature. After 10 min, analysis by LCMS indicated desired intermediate formation. The reaction was cooled again to −78° C. and 2-[(3S)-1-(cyclopropylcarbonyl)-3-pyrrolidinyl]acetohydrazide (4.41 mmol) in dichloromethane (5 mL) was added slowly. The reaction was allowed to warm to room temperature and stirred for 20 min. Analysis by LCMS indicated desired product formation. The reaction was poured into a separatory funnel and partitioned with saturated aq sodium bicarbonate. The aqueous layer was extracted with dichloromethane (3×) and the combined organic layers were dried over Na$_2$SO$_4$, filtered, and concentrated to an oil. The residue was purified by silica gel chromatography (0-15% isopropanol/ethyl acetate). The desired fractions were combined and concentrated to afford the title product as an oil (1.9 g, 59%). MS(ES)+ m/e 441.0, 442.9 [M+H]$^+$.

b) 4-(4-bromo-5-chloro-2-fluorophenyl)-5-{[(3S)-1-(cyclopropylcarbonyl)-3-pyrrolidinyl]methyl}-2,4-dihydro-3H-1,2,4-triazol-3-one N-(4-bromo-2-fluoro-5-methylphenyl)-2-{[(3S)-1-(cyclopropylcarbonyl)-3-pyrrolidinyl]acetyl}hydrazinecarboxamide (4.31 mmol) and K$_2$CO$_3$ (14.5 mmol) were added to a round-bottom flask and suspended in water (180 mL). The mixture was heated at reflux (115° C.) for 15 h. Analysis by LCMS indicated formation of desired product (and other major by-products). The reaction was cooled to room temperature and the pH was adjusted to ~6 with 1N and 6N aq HCl, and then poured into a separatory funnel containing ethyl acetate. The aqueous layer was extracted with ethyl acetate (3×) and the combined organic layers were dried over Na₂SO₄, filtered, and concentrated to an oil. The residue was purified by silica gel chromatography (0-20% isopropanol/ethyl acetate). The desired fractions were combined and concentrated to afford the title product as an off-white solid (915 mg, 50%). MS(ES)+ m/e 422.9, 424.7 [M+H]⁺.

c) 5-{[(3S)-1-(cyclopropylcarbonyl)-3-pyrrolidinyl]methyl}-4-[2-fluoro-5-methyl-4-(7-quinolinyl)phenyl]-2,4-dihydro-3H-1,2,4-triazol-3-one To a microwave vial were added 4-(4-bromo-2-fluoro-5-methylphenyl)-5-{[(3S)-1-(cyclopropylcarbonyl)-3-pyrrolidinyl]methyl}-2,4-dihydro-3H-1,2,4-triazol-3-one (0.160 mmol), 7-(4,4,5,5-tetramethyl-1,3,2-dioxaborolan-2-yl)quinoline (0.20 mmol), cesium carbonate (0.39 mmol), and dichloro[1,1'-bis(diphenylphosphino)ferrocene]palladium (II)-dichloromethane adduct (0.0062 mmol). The mixture was purged with nitrogen and suspended in 1,4-dioxane (1 mL) and water (0.5 mL). The mixture was heated for 15 h at 100° C. Analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3x), and the combined organics were washed with brine, dried over Na₂SO₄, and concentrated to afford the title product as a white solid (52 mg, 84%). MS(ES)+ m/e 472.2 [M+H]⁺.

Example 171

4-[4-(1-benzofuran-5-yl)-2-fluoro-5-methylphenyl]-5-{[(3S)-1-(cyclopropylcarbonyl)-3-pyrrolidinyl]methyl}-2,4-dihydro-3H-1,2,4-triazol-3-one

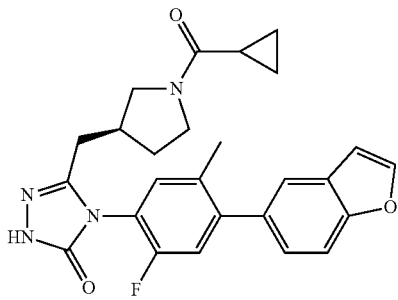 [SMILES: Cc1cc(-n2c(C[C@@H]3CCN(C(=O)C4CC4)C3)n[nH]c2=O)c(F)cc1-c1ccc2occc2c1]

a) Following the procedure described in Example 170c with 5-(4,4,5,5-tetramethyl-1,3,2-dioxaborolan-2-yl)-1-benzofuran afforded the title compound as an off-white solid (28 mg, 46%). MS(ES)+ m/e 461.3 [M+H]⁺.

Example 172

4-[4-(1-benzofuran-5-yl)-2-chloro-6-fluorophenyl]-5-{[(3S)-1-(cyclopropylcarbonyl)-3-pyrrolidinyl]methyl}-2,4-dihydro-3H-1,2,4-triazol-3-one

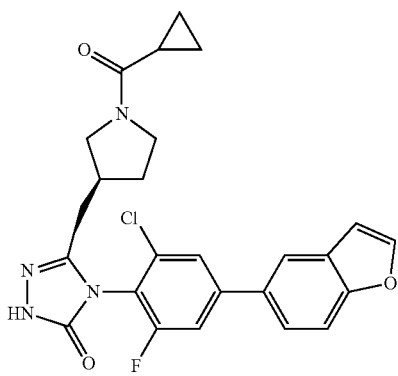 [SMILES: O=C(C1CC1)N1CC[C@@H](Cc2n[nH]c(=O)n2-c2c(F)cc(-c3ccc4occc4c3)cc2Cl)C1]

a) N-(4-bromo-2-chloro-6-fluorophenyl)-2-{[(3S)-1-(cyclopropylcarbonyl)-3-pyrrolidinyl]acetyl}hydrazinecarboxamide To a round bottom flask was added triphosgene (2.63 mmol) and dichloromethane (20 mL) under nitrogen, and the solution was cooled to −78° C. In a separate vial, 4-bromo-2-chloro-6-fluoroaniline (6.46 mmol) was dissolved in dichloromethane (20 mL) and Hunig's base (17.2 mmol) was added. This solution was slowly added to the cooled solution and then the reaction was allowed to warm to room temperature. After 5 h, analysis by LCMS indicated desired intermediate formation. The reaction was cooled again to −78° C. and 2-[(3S)-1-(cyclopropylcarbonyl)-3-pyrrolidinyl]acetohydrazide (4.31 mmol) in dichloromethane (5 mL) was added slowly. The reaction was allowed to warm to room temperature and stirred for 70 h. Analysis by LCMS indicated desired product formation. The mixture was concentrated and suspended in water (130 mL). Potassium carbonate (9.85 mmol) was added and the mixture was heated at reflux (110° C.) for 18 h. Analysis by LCMS indicated a small amount of desired product (and other major by-products). The reaction was cooled to room temperature and the pH was adjusted to ~6 with 1N and 6N aq HCl, and then poured into a separatory funnel containing ethyl acetate. The aqueous layer was extracted with ethyl acetate (3x) and the combined organic layers were dried over Na₂SO₄, filtered, and concentrated to an oil. The residue was purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3x), and the combined organics were washed with brine, dried over Na₂SO₄, and concentrated to afford the title product as an off-white solid (12 mg, 1% over two steps). MS(ES)+ m/e 443.0, 445.0 [M+H]⁺.

b) 4-[4-(1-benzofuran-5-yl)-2-chloro-6-fluorophenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-2-chloro-6-fluorophenyl)-5-{[(3S)-1-(cyclopropylcarbonyl)-3-pyrrolidinyl]methyl}-2,4-dihydro-3H-1,2,4-triazol-3-one (0.027 mmol), 5-(4,4,5,5-tetramethyl-1,3,2-dioxaborolan-2-yl)-1-benzofuran (0.04 mmol), cesium carbonate (0.08 mmol), and dichloro[1,1'-bis(diphenylphosphino)ferrocene]palladium (II)-dichloromethane adduct (0.0012 mmol). The mixture was purged with nitrogen and suspended in 1,4-dioxane (0.3 mL) and water (0.15 mL). The mixture was heated for 15 h at 100° C. Analysis by LCMS indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3x), and the combined organics were washed with brine, dried over Na₂SO₄, and concentrated to afford the title product as an off-white solid and nearly equal mixture of atropisomeric diastereomers (7.0 mg, 54%). MS(ES)+ m/e 481.0 [M+H]⁺.

Example 173

4-[4-(1-benzofuran-5-yl)-3-hydroxyphenyl]-5-{[(3S)-1-(cyclopropylcarbonyl)-3-pyrrolidinyl]methyl}-2,4-dihydro-3H-1,2,4-triazol-3-one

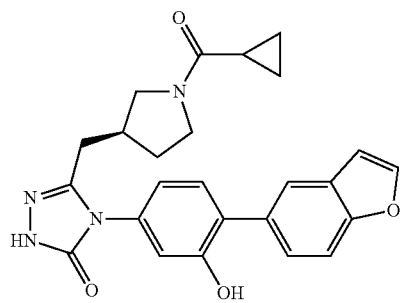 [SMILES: O=C(C1CC1)N1CC[C@@H](Cc2n[nH]c(=O)n2-c2ccc(-c3ccc4occc4c3)c(O)c2)C1]

a) 4-(4-bromo-3-hydroxyphenyl)-5-{[(3S)-1-(cyclopropylcarbonyl)-3-pyrrolidinyl]methyl}-2,4-dihydro-3H-1,2,4-triazol-3-one To a round bottom flask, 4-[4-bromo-3-(methyloxy)phenyl]-5-{[(3S)-1-(cyclopropylcarbonyl)-3-pyrrolidinyl]methyl}-2,4-dihydro-3H-1,2,4-triazol-3-one (0.349 mmol) was dissolved in dichloromethane (3.5 mL) and cooled to 0° C. Boron tribromide (2.443 mmol) was added to the solution slowly, which was then allowed to warm to room temperature. The reaction was stirred for 1 h, and analysis by LCMS indicated complete conversion to desired product. The reaction was poured into a reparatory funnel and partitioned with saturated aq sodium bicarbonate. The aqueous layer was extracted with dichloromethane (3x) and the combined organic layers were dried over $Na_2SO_4$, filtered, and concentrated to afford the title product as a tan solid (110 mg, 77%). MS(ES)+ m/e 407.1, 408.9 [M+H]+.

b) 4-[4-(1-benzofuran-5-yl)-3-hydroxyphenyl]-5-{[(3S)-1-(cyclopropylcarbonyl)-3-pyrrolidinyl]methyl}-2,4-dihydro-3H-1,2,4-triazol-3-one To a microwave vial were added 4-(4-bromo-3-hydroxyphenyl)-5-{[(3S)-1-(cyclopropylcarbonyl)-3-pyrrolidinyl]methyl}-2,4-dihydro-3H-1,2,4-triazol-3-one (0.172 mmol), 5-(4,4,5,5-tetramethyl-1,3,2-dioxaborolan-2-yl)-1-benzofuran (0.26 mmol), $Cs_2CO_3$ (0.52 mmol), and dichloro[1,1'-bis(diphenylphosphino)ferrocene]palladium(II)-dichloromethane adduct (0.00735 mmol). The mixture was purged with nitrogen followed by the addition of 1,4-dioxane (1 mL) and water (0.5 mL). The suspension was heated for 16 h at 100° C., at which point LCMS analysis indicated desired product formation and consumption of starting material. The mixture was filtered through a syringe filter and purified by reverse phase HPLC (10-90% acetonitrile/water+0.1% TFA). The desired fractions were collected and added to a separatory funnel containing ethyl acetate. The aqueous phase was adjusted to pH~6 with 1N aq HCl. The aqueous phase was extracted with ethyl acetate (3x), and the combined organics were washed with brine, dried over $Na_2SO_4$, filtered, and concentrated to afford the title product as a white solid (20 mg, 26%). MS(ES)+ m/e 445.2 [M+H]+.

Example 174

6-[4-(3-{[(3S)-1-(cyclopropylcarbonyl)-3-pyrrolidinyl]methyl}-5-oxo-1,5-dihydro-4H-1,2,4-triazol-4-yl)-3-fluorophenyl]-4(1H)-quinazolinone

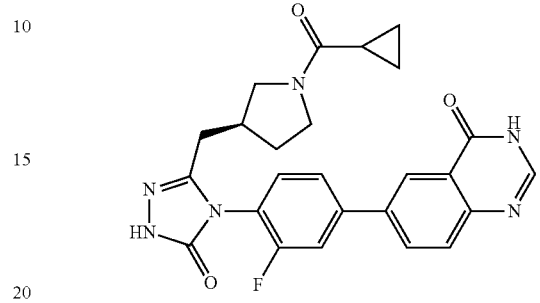

a) A solution of 5-{[(3S)-1-(cyclopropylcarbonyl)-3-pyrrolidinyl]methyl}-4-[2-fluoro-4-(4,4,5,5-tetramethyl-1,3,2-dioxaborolan-2-yl)phenyl]-2,4-dihydro-3H-1,2,4-triazol-3-one (0.238 mmol) in 1,4-dioxane (1.5 mL) was treated with 6-bromo-4(1H)-quinazolinone (0.238 mmol), dichloro[1,1'-bis(diphenylphosphino)ferrocene]palladium (II)-dichloromethane adduct (10 mg) and 2M aq potassium carbonate (0.715 mmol). The reaction mixture was purged with nitrogen, sealed, and irradiated in a microwave at 150° C. for 15 min. The reaction mixture was cooled to room temperature and was diluted with water (50 mL). The aqueous layer was acidified to pH~4 using 1N aq HCl and was extracted with dichloromethane. The organic layer was dried over sodium sulfate, treated with Si-Thiol (Silicycle, 20 mg), filtered, and concentrated in vacuo. The crude residue was purified by reverse phase HPLC (10-40% acetonitrile w/0.1% TFA/water w/0.1% TFA). The product fractions from the HPLC were combined, adjusted to pH~5 with the addition of saturated aq sodium bicarbonate, and extracted with dichloromethane. The organic layer was dried over magnesium sulfate, filtered, and concentrated in vacuo. The resulting product was then purified by flash chromatography (0-10% methanol/dichloromethane). The resulting product was suspended in water (0.5 mL) and was lyophilized to afford the title compound as an amorphous white solid (11%). MS(ES)+ m/e 475.1 [M+H]+.

Example 175

7-[4-(3-{[(3S)-1-(cyclopropylcarbonyl)-3-pyrrolidinyl]methyl}-5-oxo-1,5-dihydro-4H-1,2,4-triazol-4-yl)-3-fluorophenyl]-4(1H)-quinazolinone

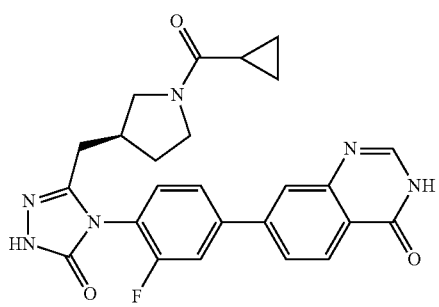 [SMILES: O=C(C1CC1)N1CC[C@@H](Cc2n[nH]c(=O)n2-c2ccc(-c3ccc4c(=O)[nH]cnc4c3)cc2F)C1]

a) Following the procedure described in Example 174a with 7-chloro-4(1H)-quinazolinone afforded the title compound as an amorphous white solid (15%). MS(ES)+ m/e 475.1 [M+H]+.

Example 176

4-(4'-acetyl-3-fluoro-4-biphenylyl)-5-{[(3S)-1-(cyclopropylcarbonyl)-3-pyrrolidinyl]methyl}-2,4-dihydro-3H-1,2,4-triazol-3-one

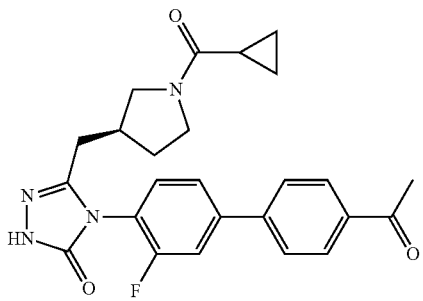 [SMILES: CC(=O)c1ccc(-c2ccc(-n3c(C[C@@H]4CCN(C(=O)C5CC5)C4)n[nH]c3=O)c(F)c2)cc1]

a) A solution of 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol) in 1,4-dioxane (1.5 mL) was treated with (4-acetylphenyl)boronic acid (0.244 mmol), dichloro[1,1'-bis(diphenylphosphino)ferrocene]palladium (II)-dichloromethane adduct (10 mg) and 2M aq potassium carbonate (0.733 mmol). The reaction mixture was purged with nitrogen, sealed, and irradiated in a microwave at 150° C. for 15 min. The reaction mixture was cooled to room temperature and was diluted with water (50 mL). The aqueous layer was acidified to pH~4 using 1N aq HCl and was extracted with dichloromethane. The organic layer was dried over sodium sulfate, treated with Si-Thiol (Silicycle, 20 mg), filtered, and concentrated in vacuo. The crude residue was purified by reverse phase HPLC (20-50% acetonitrile w/0.1% TFA/water w/0.1% TFA). The product fractions from the HPLC were combined, adjusted to pH~5 with the addition of saturated aq sodium bicarbonate, and extracted with dichloromethane. The organic layer was dried over magnesium sulfate, filtered, and concentrated in vacuo to afford the title compound as an amorphous white solid (54%). MS(ES)+ m/e 449.1 [M+H]+.

Example 177

N-[4'-(3-{[(3S)-1-(cyclopropylcarbonyl)-3-pyrrolidinyl]methyl}-5-oxo-1,5-dihydro-4H-1,2,4-triazol-4-yl)-3'-fluoro-3-biphenylyl]acetamide

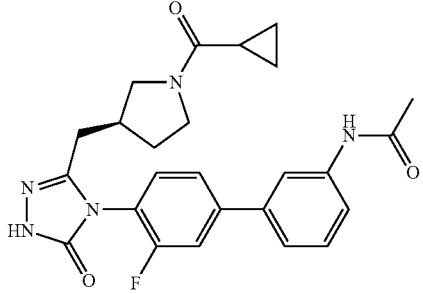 [SMILES: CC(=O)Nc1cccc(-c2ccc(-n3c(C[C@@H]4CCN(C(=O)C5CC5)C4)n[nH]c3=O)c(F)c2)c1]

a) Following the procedure described in Example 176a with [3-(acetylamino)phenyl]boronic acid (1.1 eq) afforded the title compound as an amorphous white solid (54%). Reverse phase HPLC (10-40% acetonitrile w/0.1% TFA/water w/0.1% TFA) was utilized in purifying this compound. The product fractions from the HPLC were combined, adjusted to pH~5 with the addition of saturated aq sodium bicarbonate, and extracted with dichloromethane. The organic layer was dried over sodium sulfate, filtered, and concentrated in vacuo. MS(ES)+ m/e 464.3 [M+H]+.

Example 178

5-{[(3S)-1-(cyclopropylcarbonyl)-3-pyrrolidinyl]methyl}-4-[3-fluoro-4'-(1-pyrrolidinyl)-4-biphenylyl]-2,4-dihydro-3H-1,2,4-triazol-3-one

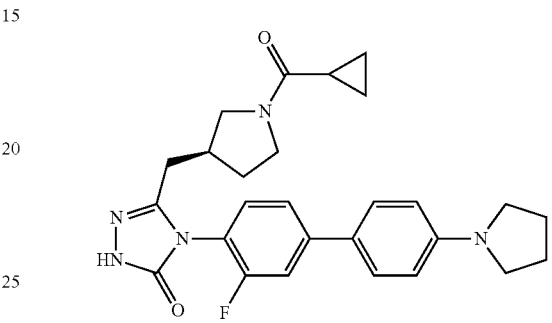

a) Following the procedure described in Example 176a with 1-[4-(4,4,5,5-tetramethyl-1,3,2-dioxaborolan-2-yl)phenyl]pyrrolidine (1.1 eq) afforded the title compound as an amorphous white solid (60%). Reverse phase HPLC (35-65% acetonitrile/water w/0.1% NH4OH) was utilized in purifying this compound. MS(ES)+ m/e 476.0 [M+H]+.

Example 179

5-{[(3S)-1-(cyclopropylcarbonyl)-3-pyrrolidinyl]methyl}-4-[4'-(2-methyl-1,3-thiazol-4-yl)-4-biphenylyl]-2,4-dihydro-3H-1,2,4-triazol-3-one

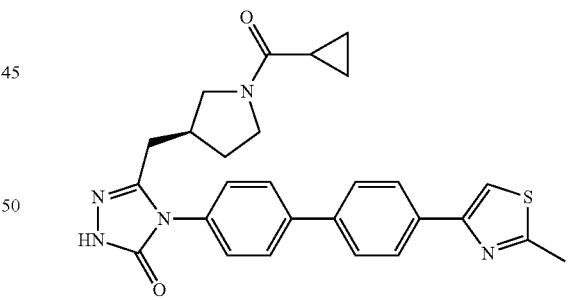

a) A solution of 4-(4-bromophenyl)-5-{[(3S)-1-(cyclopropylcarbonyl)-3-pyrrolidinyl]methyl}-2,4-dihydro-3H-1,2,4-triazol-3-one (0.256 mmol) in 1,4-dioxane (1.5 mL) was treated with 2-methyl-4-[4-(4,4,5,5-tetramethyl-1,3,2-dioxaborolan-2-yl)phenyl]-1,3-thiazole (0.281 mmol), dichloro[1,1'-bis(diphenylphosphino) ferrocene]palladium (II)-dichloromethane adduct (10 mg) and 2M aq potassium carbonate (0.767 mmol). The reaction mixture was purged with nitrogen, sealed, and irradiated in a microwave at 150° C. for 15 min. The reaction mixture was cooled to room temperature and was diluted with water (50 mL). The aqueous layer was acidified to pH~4 using 1N aq HCl and was extracted with dichloromethane. The organic layer was dried over sodium sulfate, treated with Si-Thiol (Silicycle, 20 mg), filtered, and concentrated in vacuo. The crude residue was purified by reverse phase HPLC (25-55% acetonitrile w/0.1% TFA/water w/0.1% TFA). The product fractions from the HPLC were combined, adjusted to pH~5 with the addition of saturated aq sodium bicarbonate, and extracted with dichloromethane. The organic layer was dried over magnesium sulfate, filtered, and concentrated in vacuo. The resulting product was then purified by flash chromatography (3-10% methanol/dichloromethane) to afford the title compound as an amorphous white solid (40%). MS(ES)+ m/e 486.2 [M+H]+.

Example 180

5-{[(3S)-1-(cyclopropylcarbonyl)-3-pyrrolidinyl]methyl}-4-[4'-(5-methyl-1,3,4-oxadiazol-2-yl)-4-biphenylyl]-2,4-dihydro-3H-1,2,4-triazol-3-one

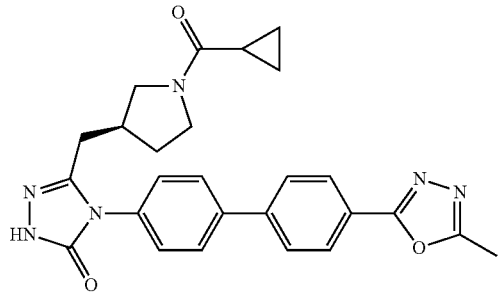 [SMILES: Cc1nnc(-c2ccc(-c3ccc(-n4c(C[C@@H]5CCN(C(=O)C6CC6)C5)n[nH]c4=O)cc3)cc2)o1]

a) Following the procedure described in Example 179a with [4-(5-methyl-1,3,4-oxadiazol-2-yl)phenyl]boronic acid afforded the title compound as an amorphous white solid (60%). Reverse phase HPLC (10-40% acetonitrile w/0.1% TFA/water w/0.1% TFA) was utilized in purifying this compound. The product fractions from the HPLC were combined, adjusted to pH~5 with the addition of saturated aq sodium bicarbonate, and extracted with dichloromethane. The organic layer was dried over sodium sulfate, filtered, and concentrated in vacuo. MS(ES)+ m/e 471.1 [M+H]+.

Example 181

5-{[(3S)-1-(cyclopropylcarbonyl)-3-pyrrolidinyl]methyl}-4-[2-fluoro-4-(3-oxo-2,3-dihydro-1H-inden-5-yl)phenyl]-2,4-dihydro-3H-1,2,4-triazol-3-one

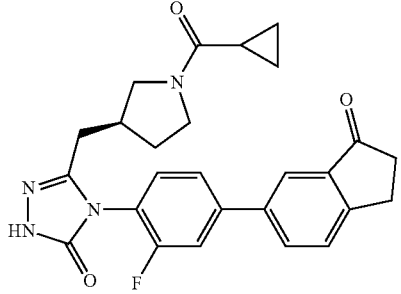 [SMILES: O=C1CCc2ccc(-c3ccc(-n4c(C[C@@H]5CCN(C(=O)C6CC6)C5)n[nH]c4=O)c(F)c3)cc21]

a) Following the procedure described in Example 174a with 6-bromo-2,3-dihydro-1H-inden-1-one afforded the title compound as an amorphous ivory solid (21%). Reverse phase HPLC (15-45% acetonitrile w/0.1% TFA/water w/0.1% TFA) was utilized in purifying this compound. The product fractions from the HPLC were combined, adjusted to pH~5 with the addition of saturated aq sodium bicarbonate, and extracted with dichloromethane. The organic layer was dried over sodium sulfate, filtered, and concentrated in vacuo. MS(ES)+ m/e 461.2 [M+H]+.

Example 182

5-{[(3S)-1-(cyclopropylcarbonyl)-3-pyrrolidinyl]methyl}-4-[4-(2,3-dihydro-1H-indol-6-yl)-2-fluorophenyl]-2,4-dihydro-3H-1,2,4-triazol-3-one

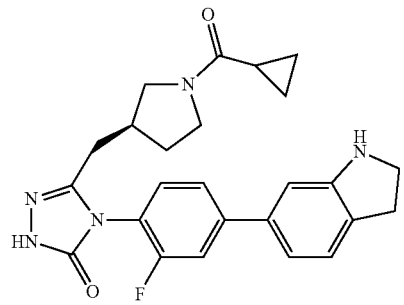 [SMILES: O=C(C1CC1)N1CC[C@@H](Cc2n[nH]c(=O)n2-c2ccc(-c3ccc4c(c3)NCC4)cc2F)C1]

a) Following the procedure described in Example 174a with 6-bromo-2,3-dihydro-1H-indole afforded the title compound as an amorphous ivory solid (21%). Reverse phase HPLC (25-55% acetonitrile/water w/0.1% NH4OH) and flash chromatography (0-10% methanol/dichloromethane) were utilized in purifying this compound. MS(ES)+ m/e 448.1 [M+H]+.

Example 183

5-{[(3S)-1-(cyclopropylcarbonyl)-3-pyrrolidinyl]methyl}-4-[3-fluoro-4'-(2-oxo-1-pyrrolidinyl)-4-biphenylyl]-2,4-dihydro-3H-1,2,4-triazol-3-one

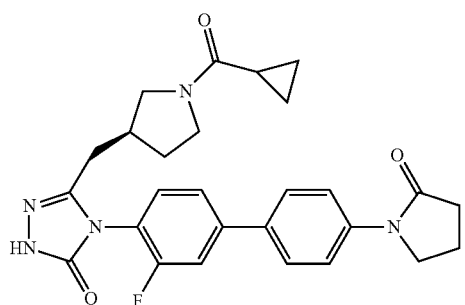 [SMILES: O=C(C1CC1)N1CC[C@@H](Cc2n[nH]c(=O)n2-c2ccc(-c3ccc(N4CCCC4=O)cc3)cc2F)C1]

a) Following the procedure described in Example 174a with 1-(4-bromophenyl)-2-pyrrolidinone afforded the title compound as an amorphous ivory solid (13%). Reverse phase HPLC (15-45% acetonitrile w/0.1% TFA/water w/0.1% TFA), flash chromatography (0-10% methanol/dichloromethane), and reverse phase HPLC (10-40% acetonitrile/ water+0.1% NH₄OH) were utilized in purifying this compound. MS(ES)+ m/e 490.3 [M+H]⁺.

Example 184

5-{[(3S)-1-(cyclopropylcarbonyl)-3-pyrrolidinyl]methyl}-4-[2-fluoro-4-(1,2,3,4-tetrahydro-7-quinolinyl)phenyl]-2,4-dihydro-3H-1,2,4-triazol-3-one

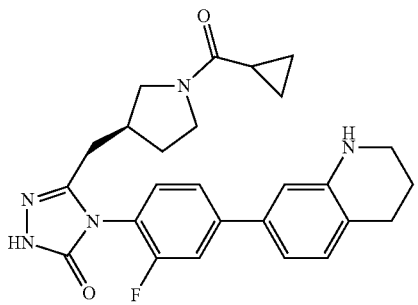 [SMILES: O=C(C1CC1)N1CC[C@@H](Cc2n[nH]c(=O)n2-c2ccc(-c3ccc4c(c3)NCCC4)cc2F)C1]

a) Following the procedure described in Example 174a (except the aqueous reaction mixture was adjusted to pH~6 upon workup) with 7-bromo-1,2,3,4-tetrahydroquinoline (HCl salt) afforded the title compound as an amorphous ivory solid (14%). Flash chromatography (0-10% methanol/dichloromethane), reverse phase HPLC (10-40% acetonitrile w/0.1% TFA/water w/0.1% TFA), and reverse phase HPLC (20-50% acetonitrile/water+0.1% NH₄OH) were utilized in purifying this compound. MS(ES)+ m/e 462.5 [M+H]⁺.

Example 185

5-{[(3S)-1-acetyl-3-pyrrolidinyl]methyl}-4-[4-(7-quinolinyl)phenyl]-2,4-dihydro-3H-1,2,4-triazol-3-one

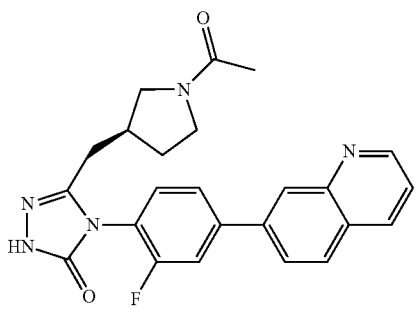 [SMILES: CCC(=O)N1CC[C@@H](Cc2n[nH]c(=O)n2-c2ccc(-c3ccc4cccnc4c3)cc2F)C1]

a) 4-(4-bromophenyl)-5-[(3S)-3-pyrrolidinylmethyl]-2,4-dihydro-3H-1,2,4-triazol-3-one Hydrochloride In a round bottom flask under nitrogen, 1,1-dimethylethyl (3S)-3-{[4-(4-bromophenyl)-5-oxo-4,5-dihydro-1H-1,2,4-triazol-3-yl]methyl}-1-pyrrolidinecarboxylate (3.54 mmol) in 4M HCl in dioxane (40 mmol) was stirred at room temperature for 2 h. The solvent was removed by concentration in vacuo to give the title compound as the HCl salt (1.25 g, 96% yield). MS(ES)+ m/e 322.9, 325.0 [M+H]⁺.

b) 5-{[(3S)-1-acetyl-3-pyrrolidinyl]methyl}-4-(4-bromophenyl)-2,4-dihydro-3H-1,2,4-triazol-3-one In 4 mL screwcap vial was placed 4-(4-bromophenyl)-5-[(3S)-3-pyrrolidinylmethyl]-2,4-dihydro-3H-1,2,4-triazol-3-one hydrochloride (0.417 mmol) and 1 mL dichloromethane. N,N-Diisopropylethylamine (1.374 mmol) was added. The vial contents were stirred for 1 min. In a separate vial, acetyl chloride (0.417 mmol) was diluted with 1 mL dichloromethane and added to the prior solution dropwise via pipette. The vial was capped and the reaction was stirred at room temperature overnight. Analysis by LCMS displayed the reaction had only progressed to 70% completion. A solution of acetyl chloride (0.050 mL) in 1 mL dichloromethane was prepared and 0.100 mL of this solution was added to the reaction. After 1 h, the reaction had progressed to 90% completion via LCMS analysis. Another 0.100 mL of the acetyl chloride solution in dichloromethane was added to the reaction. After 1 h, LCMS analysis displayed the reaction was complete. The solution was washed with saturated aq NH₄Cl. The organic layer was separated, dried over sodium sulfate, filtered, and concentrated in vacuo. Purification of the residue by silica gel chromatography (0-20% methanol:ethyl acetate) afforded the title compound (77 mg, 50% yield). MS(ES)+ m/e 365.0, 366.7 [M+H]⁺.

c) 5-{[(3S)-1-acetyl-3-pyrrolidinyl]methyl}-4-[4-(7-quinolinyl)phenyl]-2,4-dihydro-3H-1,2,4-triazol-3-one A solution of 5-{[(3S)-1-acetyl-3-pyrrolidinyl]methyl}-4-(4-bromophenyl)-2,4-dihydro-3H-1,2,4-triazol-3-one (0.211 mmol) in dioxane (2 mL) was treated with 7-(4,4,5,5-tetramethyl-1,3,2-dioxaborolan-2-yl)quinoline (0.216 mmol), dichloro[1,1'-bis(diphenylphosphino)ferrocene]palladium (II)-dichloromethane adduct (20 mg), and 2M aq potassium carbonate (1 mL). The reaction mixture was purged with nitrogen, sealed, and stirred at 110° C. for 1 h. The reaction mixture was cooled to room temperature, diluted with water, neutralized with the dropwise addition of 6N aq HCl, and extracted with ethyl acetate. The organic layer was dried over sodium sulfate, filtered, and concentrated in vacuo. Reverse phase HPLC (10-70% acetonitrile/water+0.1% NH₄OH) was utilized to purify the title compound (29 mg, 33%). MS(ES)+ m/e 413.8 [M+H]⁺.

Example 186

5-{[(3S)-1-propanoyl-3-pyrrolidinyl]methyl}-4-[4-(7-quinolinyl)phenyl]-2,4-dihydro-3H-1,2,4-triazol-3-one

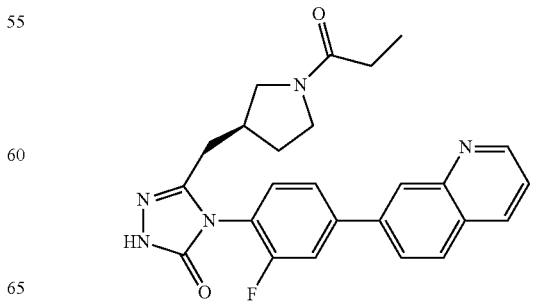

a) 4-(4-bromophenyl)-5-{[(3S)-1-propanoyl-3-pyrrolidinyl]methyl}-2,4-dihydro-3H-1,2,4-triazol-3-one In a 4 mL screwcap vial was placed 4-(4-bromophenyl)-5-[(3S)-3-pyrrolidinylmethyl]-2,4-dihydro-3H-1,2,4-triazol-3-one hydrochloride (0.278 mmol). Added to the vial were dichloromethane (2 mL) and N,N-diisopropylethylamine (0.859 mmol). The vial contents were stirred for 1 min, at which point propanoyl chloride (0.319 mmol) was added. The vial was capped and the contents were stirred at room temperature for 2 h. The reaction was quenched with saturated aq NH$_4$Cl (1 mL) and the solution was stirred vigorously for 1 min. The separation of the two layers occurred upon settling of the solution. The organic layer was removed, dried over sodium sulfate, filtered, and concentrated in vacuo. Silica gel chromatography (0-10% methanol:ethyl acetate) was utilized to purify the title compound (65 mg, 61% yield). MS(ES)+ m/e 379.1, 380.8 [M+H]$^+$.

b) 5-{[(3S)-1-propanoyl-3-pyrrolidinyl]methyl}-4-[4-(7-quinolinyl)phenyl]-2,4-dihydro-3H-1,2,4-triazol-3-one A solution of 4-(4-bromophenyl)-5-{[(3S)-1-propanoyl-3-pyrrolidinyl]methyl}-2,4-dihydro-3H-1,2,4-triazol-3-one (0.171 mmol) in dioxane (2 mL) was treated with 7-(4,4,5,5-tetramethyl-1,3,2-dioxaborolan-2-yl)quinoline (0.176 mmol), dichloro[1,1'-bis(diphenylphosphino)ferrocene]palladium(II)-dichloromethane adduct (15 mg), and 2M aq potassium carbonate (1 mL). The reaction mixture was purged with nitrogen, sealed, and stirred at 110° C. for 1 h. The reaction mixture was cooled to room temperature, diluted with water, neutralized with the dropwise addition of 6N aq HCl, and extracted with ethyl acetate. The organic layer was dried over sodium sulfate, filtered, and concentrated in vacuo. Reverse phase HPLC (10-70% acetonitrile/water+0.1% NH$_4$OH) was utilized to purify the title compound (44 mg, 59%). MS(ES)+ m/e 427.8 [M+H]$^+$.

Example 187

(3S)—N,N-dimethyl-3-({5-oxo-4-[4-(7-quinolinyl)phenyl]-4,5-dihydro-1H-1,2,4-triazol-3-yl}methyl)-1-pyrrolidinecarboxamide

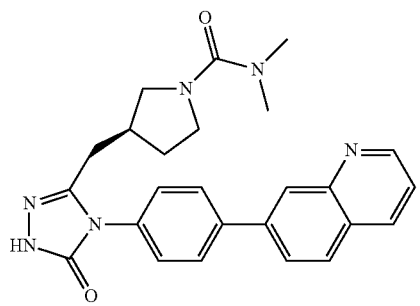 [SMILES: CN(C)C(=O)N1CC[C@@H](Cc2n[nH]c(=O)n2-c2ccc(-c3ccc4cccnc4c3)cc2)C1]

a) (3S)-3-{[4-(4-bromophenyl)-5-oxo-4,5-dihydro-1H-1,2,4-triazol-3-yl]methyl}-N,N-dimethyl-1-pyrrolidinecarboxamide Following the procedure described in Example 186a with N,N'-dimethylcarbamoyl chloride (1 eq) provided the title compound (100%). No purification was performed on this intermediate material. MS(ES)+ m/e 393.8, 395.8 [M+H]$^+$.

b) (3S)—N,N-dimethyl-3-({5-oxo-4-[4-(7-quinolinyl)phenyl]-4,5-dihydro-1H-1,2,4-triazol-3-yl}methyl)-1-pyrrolidinecarboxamide A solution of (3S)-3-{[4-(4-bromophenyl)-5-oxo-4,5-dihydro-1H-1,2,4-triazol-3-yl]methyl}-N,N-dimethyl-1-pyrrolidinecarboxamide (0.342 mmol) in dioxane (2 mL) was treated with 7-(4,4,5,5-tetramethyl-1,3,2-dioxaborolan-2-yl)quinoline (0.353 mmol), dichloro[1,1'-bis(diphenylphosphino)ferrocene]palladium(II)-dichloromethane adduct (25 mg), and 2M aq potassium carbonate (1 mL). The reaction mixture was purged with nitrogen, sealed, and stirred at 110° C. for 1 h. The reaction mixture was cooled to room temperature, diluted with water, neutralized with the dropwise addition of 6N aq HCl, and extracted with ethyl acetate. The organic layer was dried over sodium sulfate, filtered, and concentrated in vacuo. Reverse phase HPLC (10-65% acetonitrile/water+0.1% NH$_4$OH) was utilized to purify the title compound (65 mg, 42%). MS(ES)+ m/e 442.8 [M+H]$^+$.

Example 188

5-{[(3S)-1-(2-methylpropanoyl)-3-pyrrolidinyl]methyl}-4-[4-(7-quinolinyl)phenyl]-2,4-dihydro-3H-1,2,4-triazol-3-one

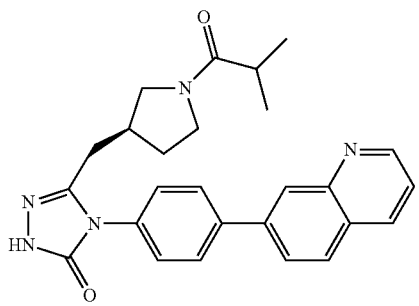

a) 4-(4-bromophenyl)-5-{[(3S)-1-(2-methylpropanoyl)-3-pyrrolidinyl]methyl}-2,4-dihydro-3H-1,2,4-triazol-3-one Following the procedure described in Example 186a with isobutyryl chloride (1.07 eq) provided the title compound (75 mg, 68%). Silica gel chromatography (0-10% methanol:ethyl acetate) was utilized in purifying this compound. MS(ES)+ m/e 393.1, 395.0 [M+H]$^+$.

b) 5-{[(3S)-1-(2-methylpropanoyl)-3-pyrrolidinyl]methyl}-4-[4-(7-quinolinyl)phenyl]-2,4-dihydro-3H-1,2,4-triazol-3-one Following the procedure described in Example 186b with 4-(4-bromophenyl)-5-{[(3S)-1-(2-methylpropanoyl)-3-pyrrolidinyl]methyl}-2,4-dihydro-3H-1,2,4-triazol-3-one provided the title compound (45 mg, 54%). Reverse phase HPLC

Example 189

5-{[(3S)-1-(2,2-dimethylpropanoyl)-3-pyrrolidinyl]methyl}-4-[4-(7-quinolinyl)phenyl]-2,4-dihydro-3H-1,2,4-triazol-3-one

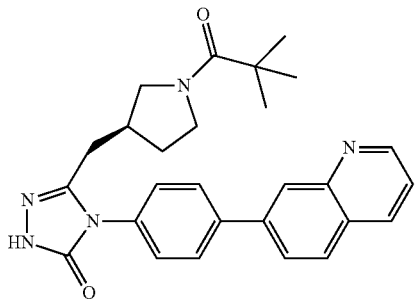 [SMILES: CC(C)(C)C(=O)N1CC[C@@H](Cc2n[nH]c(=O)n2-c2ccc(-c3ccc4cccnc4c3)cc2)C1]

a) 4-(4-bromophenyl)-5-{[(3S)-1-(2,2-dimethylpropanoyl)-3-pyrrolidinyl]methyl}-2,4-dihydro-3H-1,2,4-triazol-3-one Following the procedure described in Example 186a with trimethylacetyl chloride (1.07 eq) provided the title compound (113 mg, 59%). Silica gel chromatography (0-10% methanol:ethyl acetate) was utilized in purifying this compound. MS(ES)+ m/e 393.1, 395.0 [M+H]+.

b) 5-{[(3S)-1-(2,2-dimethylpropanoyl)-3-pyrrolidinyl]methyl}-4-[4-(7-quinolinyl)phenyl]-2,4-dihydro-3H-1,2,4-triazol-3-one A solution of 4-(4-bromophenyl)-5-{[(3S)-1-(2,2-dimethylpropanoyl)-3-pyrrolidinyl]methyl}-2,4-dihydro-3H-1,2,4-triazol-3-one (0.277 mmol) in dioxane (2 mL) was treated with 7-(4,4,5,5-tetramethyl-1,3,2-dioxaborolan-2-yl)quinoline (0.294 mmol), dichloro[1,1'-bis(diphenylphosphino)ferrocene]palladium(II)-dichloromethane adduct (20 mg), and 2M aq potassium carbonate (1 mL). The reaction mixture was purged with nitrogen, sealed, and stirred at 110° C. for 1 h. The reaction mixture was cooled to room temperature, diluted with water, neutralized with the dropwise addition of 6N aq HCl, and extracted with ethyl acetate. The organic layer was dried over sodium sulfate, filtered, and concentrated in vacuo. The residue was purified by reverse phase HPLC (10-70% acetonitrile/water+0.1% NH4OH) and then reverse phase HPLC (10-40% acetonitrile w/0.1% TFA/water w/0.1% TFA). The combined product fractions were concentrated in vacuo for 30 min to remove the acetonitrile. The aqueous solution was neutralized with the addition of saturated aqueous sodium bicarbonate and extracted with dichloromethane (2×). The combined organic layers were dried over sodium sulfate, filtered, and concentrated in vacuo to afford the title compound (49 mg, 38% yield). MS(ES)+ m/e 456.0 [M+H]+.

Example 190

5-({(3S)-1-[(1-methylcyclopropyl)carbonyl]-3-pyrrolidinyl}methyl)-4-[4-(7-quinolinyl)phenyl]-2,4-dihydro-3H-1,2,4-triazol-3-one

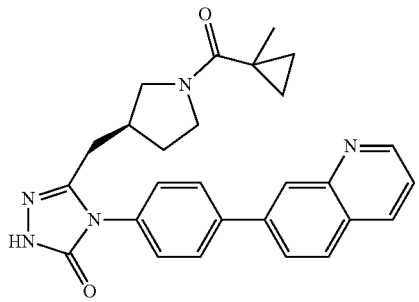 [SMILES: CC1(C(=O)N2CC[C@@H](Cc3n[nH]c(=O)n3-c3ccc(-c4ccc5cccnc5c4)cc3)C2)CC1]

a) 4-(4-bromophenyl)-5-({(3S)-1-[(1-methylcyclopropyl)carbonyl]-3-pyrrolidinyl}methyl)-2,4-dihydro-3H-1,2,4-triazol-3-one Into a 5 mL microwave vial was placed 4-(4-bromophenyl)-5-[(3S)-3-pyrrolidinylmethyl]-2,4-dihydro-3H-1,2,4-triazol-3-one hydrochloride (0.473 mmol), 1-methylcyclopropanecarboxylic acid (0.499 mmol), N-(3-dimethylaminopropyl)-N'-ethylcarbodiimide hydrochloride (1.200 mmol), 1-hydroxybenzotriazole (1.208 mmol), N,N-diisopropylethylamine (1.431 mmol), and N,N-dimethylformamide (2 mL). The vial was capped and the contents were stirred at room temperature for 4 h. Purification of the crude material by reverse phase HPLC (10-40% acetonitrile w/0.1% TFA/water w/0.1% TFA) followed by collection and concentration of the desired fractions provided the title compound (166 mg, 87%). MS(ES)+ m/e 405.0, 407.1 [M+H]+.

b) 5-({(3S)-1-[(1-methylcyclopropyl)carbonyl]-3-pyrrolidinyl}methyl)-4-[4-(7-quinolinyl)phenyl]-2,4-dihydro-3H-1,2,4-triazol-3-one Following the procedure described in Example 189b with 4-(4-bromophenyl)-5-({(3S)-1-[(1-methylcyclopropyl)carbonyl]-3-pyrrolidinyl}methyl)-2,4-dihydro-3H-1,2,4-triazol-3-one (166 mg) provided the title compound (22 mg, 11%). Two reverse phase HPLC purifications (10-60% acetonitrile/water+0.1% NH4OH followed with 5-40% acetonitrile w/0.1% TFA/water w/0.1% TFA) were utilized in purifying this compound. MS(ES)+ m/e 453.8 [M+H]+.

Example 191

(3S)-3-({4-[3-fluoro-4'-(methyloxy)-4-biphenylyl]-5-oxo-4,5-dihydro-1H-1,2,4-triazol-3-yl}methyl)-N,N-dimethyl-1-pyrrolidinecarboxamide

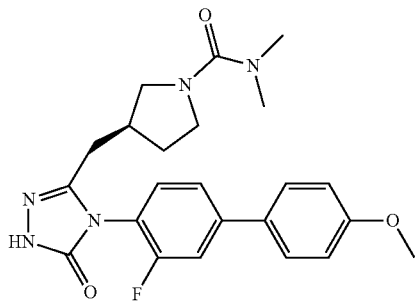 [SMILES: COc1ccc(-c2ccc(-n3c(C[C@@H]4CCN(C(=O)N(C)C)C4)n[nH]c3=O)c(F)c2)cc1]

a) 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate Into a 250 mL round bottom flask was placed 1,1-dimethylethyl (3S)-3-[2-(2-{[(4-bromo-2-fluorophenyl)amino]carbonyl}hydrazino)-2-oxoethyl]-1-pyrrolidinecarboxylate (4.35 mmol). Added to the flask was K$_2$CO$_3$ (21.71 mmol), water (100 mL), and 1-propanol (10.00 mL). The solution was stirred at reflux (140° C.) for 16 h and then cooled to room temperature and filtered to remove an undetermined solid. The filtrate was concentrated in vacuo. Added to the white solid was 1N aq NaOH (10 mL) followed by the addition of Boc$_2$O (4.35 mmol). The solution was stirred at room temperature overnight. The solution was diluted with 100 mL ethyl acetate and brought to a pH=7 with the addition of 1N aq HCl. The organic layer was separated and the aqueous layer was washed twice with ethyl acetate. The combined organic layers were dried over sodium sulfate, filtered, and concentrated in vacuo. Silica gel purification (100% dichloromethane, 0-100% ethyl acetate, and 0-10% methanol:ethyl acetate) provided the title product (790 mg, 39%). MS(ES)+ m/e 442.0, 443.0 [M+H]$^+$.

b) 4-(4-bromo-2-fluorophenyl)-5-[(3S)-3-pyrrolidinylmethyl]-2,4-dihydro-3H-1,2,4-triazol-3-one Hydrochloride Following the procedure described in Example 185a with 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate provided the title compound as the HCl salt (846 mg, 100%). MS(ES)+ m/e 340.8, 342.6 [M+H]$^+$.

c) (3S)-3-{[4-(4-bromo-2-fluorophenyl)-5-oxo-4,5-dihydro-1H-1,2,4-triazol-3-yl]methyl}-N,N-dimethyl-1-pyrrolidinecarboxamide Into a 4 mL screwcap vial was placed 4-(4-bromo-2-fluorophenyl)-5-[(3S)-3-pyrrolidinylmethyl]-2,4-dihydro-3H-1,2,4-triazol-3-one hydrochloride (0.265 mmol), polystyrene-DIEA (216 mg, 3.68 mmol/g loading, 0.794 mmol) and 2 mL dichloromethane. The contents were lightly swirled. In a separate vial, N,N-dimethylaminocarbamoyl chloride (0.265 mmol) was taken up in 1 mL dichloromethane and added to the starting material dropwise via pipette. The vial was capped and the solution was lightly agitated at room temperature overnight. The reaction had only progressed by 50% via LCMS analysis. Another equivalent of N,N-dimethylaminocarbamoyl chloride (0.265 mmol) was added to the reaction. After 8 h at room temperature, another equivalent of N,N-dimethylaminocarbamoyl chloride (0.265 mmol) was added, as well as N,N-diisopropylethylamine (0.100 mL). After 1 h, the reaction mixture became clear. The solution was filtered to remove the polystyrene-DIEA and then concentrated in vacuo. Reverse phase HPLC (10-40% acetonitrile w/0.1% TFA/water w/0.1% TFA) was utilized in purifying the title compound (60 mg, 55%). MS(ES)+ m/e 412.3, 414.1 [M+H]$^+$.

d) (3S)-3-({4-[3-fluoro-4'-(methyloxy)-4-biphenylyl]-5-oxo-4,5-dihydro-1H-1,2,4-triazol-3-yl}methyl)-N,N-dimethyl-1-pyrrolidinecarboxamide A solution of (3S)-3-{[4-(4-bromo-2-fluorophenyl)-5-oxo-4,5-dihydro-1H-1,2,4-triazol-3-yl]methyl}-N,N-dimethyl-1-pyrrolidinecarboxamide (0.146 mmol) in dioxane (2 mL) was treated with 4-methoxyphenylboronic acid (0.165 mmol), dichloro[1,1'-bis(diphenylphosphino)ferrocene]palladium(II)-dichloromethane adduct (10 mg), and 2M aq potassium carbonate (1 mL). The reaction mixture was purged with nitrogen, sealed, and stirred at 110° C. for 2 h. The solution was cooled to room temperature. The dioxane layer separated from the aqueous layer and was removed via pipette and passed through a plug of celite and sodium sulfate. The plug was washed with dioxane (4 mL). All dioxane filtrates were combined and concentrated in vacuo. Reverse phase HPLC (10-70% acetonitrile/water+0.1% NH$_4$OH) was utilized in purifying the title compound (26 mg, 39%). MS(ES)+ m/e 440.0 [M+H]+.

Example 192

4-[3-fluoro-4'-(methyloxy)-4-biphenylyl]-5-{[(3S)-1-propanoyl-3-pyrrolidinyl]methyl}-2,4-dihydro-3H-1,2,4-triazol-3-one

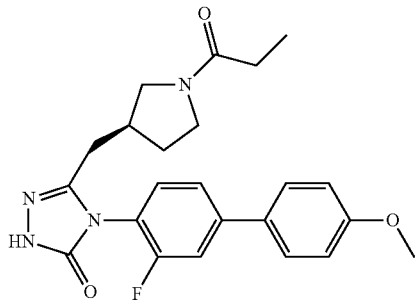 [SMILES: CCC(=O)N1CC[C@@H](Cc2n[nH]c(=O)n2-c2ccc(-c3ccc(OC)cc3)cc2F)C1]

a) 4-(4-bromo-2-fluorophenyl)-5-{[(3S)-1-propanoyl-3-pyrrolidinyl]methyl}-2,4-dihydro-3H-1,2,4-triazol-3-one Into a 4 mL screwcap vial was placed 4-(4-bromo-2-fluorophenyl)-5-[(3S)-3-pyrrolidinylmethyl]-2,4-dihydro-3H-1,2,4-triazol-3-one hydrochloride (0.318 mmol). Added to the vial in succession was dichloromethane (3 mL), N,N-diisopropylethylamine (0.916 mmol), and propanoyl chloride (0.319 mmol). The vial was capped and stirred at room temperature overnight. The solution was concentrated in vacuo and the residue was purified by reverse phase HPLC (10-40% acetonitrile w/0.1% TFA/water w/0.1% TFA). The combined product fractions were concentrated in vacuo for 1 h to remove the acetonitrile. The aqueous solution was neutralized with the addition of saturated aqueous sodium bicarbonate, and extracted twice with dichloromethane. The combined organic layers were dried over sodium sulfate, filtered, and concentrated in vacuo to afford the title compound (100 mg, 79% yield). MS(ES)+ m/e 397.0, 399.1 [M+H]$^+$.

b) 4-[3-fluoro-4'-(methyloxy)-4-biphenylyl]-5-{[(3S)-1-propanoyl-3-pyrrolidinyl]methyl}-2,4-dihydro-3H-1,2,4-triazol-3-one Following the procedure described in Example 191d with 4-(4-bromo-2-fluorophenyl)-5-{[(3S)-1-propanoyl-3-pyrrolidinyl]methyl}-2,4-dihydro-3H-1,2,4-triazol-3-one (0.252 mmol) provided the title compound (61 mg, 57%). Reverse

Example 193

5-{[(3S)-1-(2,2-dimethylpropanoyl)-3-pyrrolidinyl]methyl}-4-[3-fluoro-4'-(methyloxy)-4-biphenylyl]-2,4-dihydro-3H-1,2,4-triazol-3-one

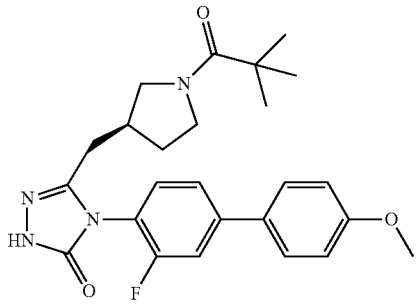 [SMILES: COc1ccc(-c2ccc(-n3c(C[C@@H]4CCN(C(=O)C(C)(C)C)C4)n[nH]c3=O)c(F)c2)cc1]

a) 1,1-dimethylethyl (3S)-3-({4-[3-fluoro-4'-(methyloxy)-4-biphenylyl]-5-oxo-4,5-dihydro-1H-1,2,4-triazol-3-yl}methyl)-1-pyrrolidinecarboxylate Following the procedure described in Example 191d with 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate (400 mg) provided the title compound (310 mg, 70%). Silica gel chromatography (0-20% methanol:ethyl acetate) was utilized in purifying this compound. MS(ES)+ m/e 469.1 [M+H]+.

b) 5-{[(3S)-1-(2,2-dimethylpropanoyl)-3-pyrrolidinyl]methyl}-4-[3-fluoro-4'-(methyloxy)-4-biphenylyl]-2,4-dihydro-3H-1,2,4-triazol-3-one Into a 8 mL screwcap vial was placed 1,1-dimethylethyl (3S)-3-({4-[3-fluoro-4'-(methyloxy)-4-biphenylyl]-5-oxo-4,5-dihydro-1H-1,2,4-triazol-3-yl}methyl)-1-pyrrolidinecarboxylate (0.162 mmol). Added to the vial was 4N HCl in dioxane (1 mL). The reaction was capped and stirred at room temperature for 2 h. The solution was concentrated in vacuo. Added to the vial were dichloromethane (1 mL) and N,N-diisopropylethylamine (0.573 mmol). In a separate vial, trimethylacetyl chloride (0.163 mmol) was taken up in 1 mL dichloromethane and was added to the starting material dropwise via pipette. The vial was capped and the reaction was stirred at room temperature for 2 h. Dichloromethane (2 mL) was added to the vial, followed by the addition of saturated aq NH4Cl. The vial was capped and lightly agitated for 1 min. The organic layer was separated, filtered through a plug of sodium sulfate, and concentrated in vacuo. Reverse phase HPLC (10-70% acetonitrile/water+0.1% NH4OH) was utilized in purifying this compound. MS(ES)+ m/e 425.2 [M+H]+.

Example 194

(3S)-3-({4-[2-fluoro-4-(7-quinolinyl)phenyl]-5-oxo-4,5-dihydro-1H-1,2,4-triazol-3-yl}methyl)-N,N-dimethyl-1-pyrrolidinecarboxamide

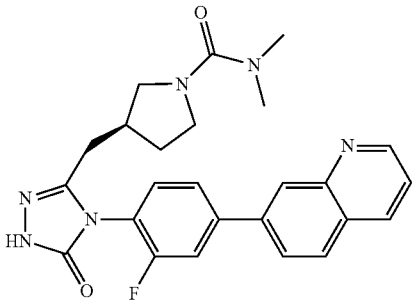 [SMILES: CN(C)C(=O)N1CC[C@@H](Cc2n[nH]c(=O)n2-c2ccc(-c3ccc4cccnc4c3)cc2F)C1]

a) 1,1-dimethylethyl (3S)-3-({4-[2-fluoro-4-(7-quinolinyl)phenyl]-5-oxo-4,5-dihydro-1H-1,2,4-triazol-3-yl}-methyl)-1-pyrrolidinecarboxylate A solution of 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate (0.770 mmol) in dioxane (6 mL) was treated with 7-(4,4,5,5-tetramethyl-1,3,2-dioxaborolan-2-yl)quinoline (0.770 mmol), dichloro[1,1'-bis(diphenylphosphino)ferrocene]palladium(II)-dichloromethane adduct (50 mg), and 2M aq potassium carbonate (3 mL). The reaction mixture was purged with nitrogen, sealed, and stirred at 110° C. for 1 h. The solution was cooled to room temperature and the dioxane layer separated from the aqueous layer. The dioxane layer was removed via pipette and was passed through a plug of celite and sodium sulfate. The plug was washed with dioxane (6 mL). All dioxane filtrates were combined and concentrated in vacuo. Silica gel chromatography (0-20% methanol:ethyl acetate) was utilized in purifying the title compound (250 mg, 65%). MS(ES)+ m/e 490.2 [M+H]+.

b) (3S)-3-({4-[2-fluoro-4-(7-quinolinyl)phenyl]-5-oxo-4,5-dihydro-1H-1,2,4-triazol-3-yl}methyl)-N,N-dimethyl-1-pyrrolidinecarboxamide Into a 8 mL screwcap vial was placed 1,1-dimethylethyl (3S)-3-({4-[2-fluoro-4-(7-quinolinyl)phenyl]-5-oxo-4,5-dihydro-1H-1,2,4-triazol-3-yl}methyl)-1-pyrrolidinecarboxylate (0.161 mmol). Added to the vial was 4N HCl in dioxane (1 mL). The reaction mixture was capped and stirred at room temperature for 2 h. The solution was concentrated in vacuo. Added to the vial were dichloromethane (1 mL) and N,N-diisopropylethylamine (0.573 mmol). In a separate vial, N,N-dimethylaminocarbamoyl chloride (0.161 mmol) was dissolved in 1 mL dichloromethane and added to the starting material dropwise via pipette. The vial was capped and the reaction was stirred at room temperature for 2 h. An extra 2 mL dichloromethane was added to the vial, followed by the addition of saturated aq NH4Cl (2 mL). The vial was capped and lightly agitated for 1 min. The organic layer was separated, filtered through a plug of sodium sulfate, and concentrated in vacuo. Reverse phase HPLC (10-65% acetonitrile/ HPLC (10-80% acetonitrile/water+0.1% NH4OH) was utilized in purifying the title compound (37 mg, 50%). MS(ES)+ m/e 453.1 [M+H]+.

water+0.1% NH₄OH) was utilized in purifying the title compound (44 mg, 59%). MS(ES)+ m/e 461.2 [M+H]⁺.

Example 195

4-[3-fluoro-4'-(methyloxy)-4-biphenylyl]-5-({(3S)-1-[(1-methylcyclopropyl)carbonyl]-3-pyrrolidinyl}methyl)-2,4-dihydro-3H-1,2,4-triazol-3-one

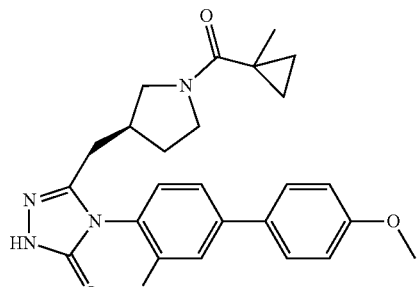

a) 4-(4-bromo-2-fluorophenyl)-5-({(3S)-1-[(1-methylcyclopropyl)carbonyl]-3-pyrrolidinyl}methyl)-2,4-dihydro-3H-1,2,4-triazol-3-one Following the procedure described in Example 190a with 4-(4-bromo-2-fluorophenyl)-5-[(3S)-3-pyrrolidinylmethyl]-2,4-dihydro-1,2,4-triazol-3-one hydrochloride (0.252 mmol) provided the title compound (40 mg, 37%). Reverse phase HPLC (15-45% acetonitrile w/0.1% TFA/water w/0.1% TFA) was utilized in purifying this compound. MS(ES)+ m/e 423.0, 425.0 [M+H]⁺.

b) 4-[3-fluoro-4'-(methyloxy)-4-biphenylyl]-5-({(3S)-1-[(1-methylcyclopropyl)carbonyl]-3-pyrrolidinyl}methyl)-2,4-dihydro-3H-1,2,4-triazol-3-one Following the procedure described in Example 191d with 4-(4-bromo-2-fluorophenyl)-5-({(3S)-1-[(1-methylcyclopropyl)carbonyl]-3-pyrrolidinyl}methyl)-2,4-dihydro-3H-1,2,4-triazol-3-one (40 mg) provided the title compound (16 mg, 37%). Reverse phase HPLC (10-75% acetonitrile/water+0.1% NH₄OH) was utilized in purifying this compound. MS(ES)+ m/e 451.1 [M+H]⁺.

Example 196

4-[2-fluoro-4-(7-quinolinyl)phenyl]-5-{[(3S)-1-propanoyl-3-pyrrolidinyl]methyl}-2,4-dihydro-3H-1,2,4-triazol-3-one

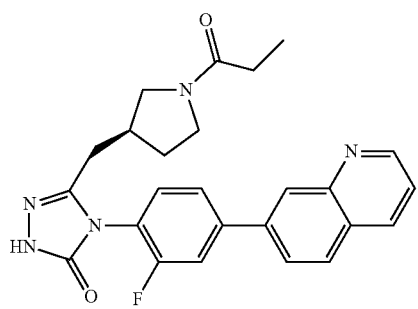 [SMILES: CCC(=O)N1CC[C@@H](Cc2n[nH]c(=O)n2-c2ccc(-c3ccc4cccnc4c3)cc2F)C1]

a) Following the procedure described in Example 194b with propanoyl chloride (163 mmol) provided the title compound (35 mg, 48%). Reverse phase HPLC (10-70% aceto-nitrile/water+0.1% NH₄OH) was utilized in purifying this compound. MS(ES)+ m/e 446.2 [M+H]⁺.

Example 197

5-{[(3S)-1-(2,2-dimethylpropanoyl)-3-pyrrolidinyl]methyl}-4-[2-fluoro-4-(7-quinolinyl)phenyl]-2,4-dihydro-3H-1,2,4-triazol-3-one

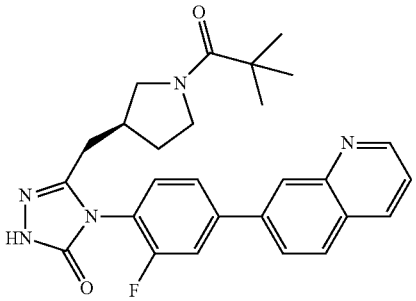 [SMILES: CC(C)(C)C(=O)N1CC[C@@H](Cc2n[nH]c(=O)n2-c2ccc(-c3ccc4cccnc4c3)cc2F)C1]

a) Following the procedure described in Example 194b trimethylacetyl chloride (187 mmol) provided the title compound (40 mg, 45%). Reverse phase HPLC (10-70% acetonitrile/water+0.1% NH₄OH) was utilized in purifying this compound. MS(ES)+ m/e 474.1 [M+H]⁺.

Example 198

4-[2-fluoro-4-(7-quinolinyl)phenyl]-5-({(3S)-1-[(1-methylcyclopropyl)carbonyl]-3-pyrrolidinyl}methyl)-2,4-dihydro-3H-1,2,4-triazol-3-one

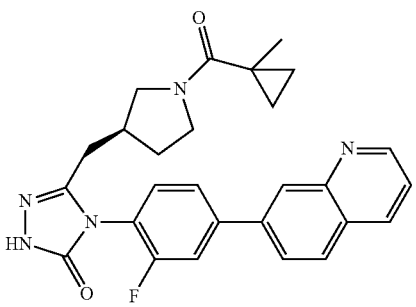 [SMILES: CC1(C(=O)N2CC[C@@H](Cc3n[nH]c(=O)n3-c3ccc(-c4ccc5cccnc5c4)cc3F)C2)CC1]

a) Into a 50 mL round bottom flask was placed 1,1-dimethylethyl (3S)-3-({4-[2-fluoro-4-(7-quinolinyl)phenyl]-5-oxo-4,5-dihydro-1H-1,2,4-triazol-3-yl}methyl)-1-pyrrolidinecarboxylate (0.082 mmol). Added was 4N HCL in dioxane (1.0 mL). The solution was stirred at room temperature for 1 h and then was concentrated in vacuo. The solid was taken up in N,N-dimethylformamide (1 mL). Added to flask was 1-methylcyclopropanecarboxylic acid (0.100 mmol), 1-hydroxybenzotriazole (0.196 mmol), N-(3-dimethylaminopropyl)-N'-ethylcarbodiimide hydrochloride (0.183 mmol), and N,N-diisopropylethylamine (0.286 mmol). The flask was capped and stirred at room temperature for 1 h. Purification of the crude material was performed by injecting the solution directly onto a reverse phase HPLC (10-40% acetonitrile w/0.1% TFA/water w/0.1% TFA). The desired fractions were combined and concentrated in vacuo. The recovered material was taken up in 1 mL dichloromethane and 1 mL acetonitrile. A 6 mL tube packed with PL-HCO3 (Stratospheres Solid Phase Extraction macroporous resin for Acid Removal, Varian Industries) was pretreated with 2 mL of dichloromethane. The product solution was added to the top of the resin via pipette and was allowed to freely pass through the column via gravity. The column was rinsed with dichloromethane (2 mL) and acetonitrile (2 mL). The recovered filtrate was concentrated in vacuo to afford the title compound (23 mg, 59%). MS(ES)+ m/e 472.2 [M+H]⁺.

Example 199

(3S)—N-ethyl-3-({4-[2-fluoro-4-(7-quinolinyl)phenyl]-5-oxo-4,5-dihydro-1H-1,2,4-triazol-3-yl}methyl)-1-pyrrolidinecarboxamide

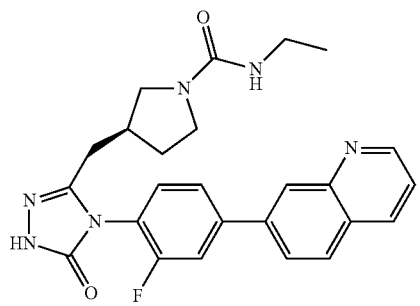 [SMILES: CCNC(=O)N1CC[C@@H](Cc2n[nH]c(=O)n2-c2ccc(-c3ccc4cccnc4c3)cc2F)C1]

a) (3S)-3-{[4-(4-bromo-2-fluorophenyl)-5-oxo-4,5-dihydro-1H-1,2,4-triazol-3-yl]methyl}-N-ethyl-1-pyrrolidinecarboxamide Into a 4 mL vial was placed 4-(4-bromo-2-fluorophenyl)-5-[(3S)-3-pyrrolidinylmethyl]-2,4-dihydro-3H-1,2,4-triazol-3-one hydrochloride (0.212 mmol) and tetrahydrofuran (2 mL). In succession was added triethylamine (0.717 mmol) and ethyl isocyanate (0.253 mmol). The vial was capped and the solution stirred at room temperature for 1 h. The solution was poured into a 10 mL solution of 1:1 dichloromethane:water. The solution was shaken and allowed to settle. The organic layer was separated, dried over sodium sulfate, filtered, and concentrated in vacuo. No further purification was performed on the title compound (74 mg, 68%). MS(ES)+ m/e 412.2, 414.1 [M+H]+.

b) (3S)—N-ethyl-3-({4-[2-fluoro-4-(7-quinolinyl)phenyl]-5-oxo-4,5-dihydro-1H-1,2,4-triazol-3-yl}methyl)-1-pyrrolidinecarboxamide A solution of (3S)-3-{[4-(4-bromo-2-fluorophenyl)-5-oxo-4,5-dihydro-1H-1,2,4-triazol-3-yl]methyl}-N-ethyl-1-pyrrolidinecarboxamide (0.179 mmol) in dioxane (2 mL) was treated with 7-(4,4,5,5-tetramethyl-1,3,2-dioxaborolan-2-yl)quinoline (0.180 mmol), dichloro[1,1'-bis(diphenylphosphino)ferrocene]palladium(II)-dichloromethane adduct (15 mg), and 2M aq potassium carbonate (1 mL). The reaction mixture was purged with nitrogen, sealed, and stirred at 110° C. for 1 h. The solution was cooled to room temperature and the dioxane layer separated from the aqueous layer. The dioxane layer was removed via pipette and was passed through a plug of celite and sodium sulfate. The plug was washed with dioxane (2 mL). All dioxane filtrates were combined and concentrated in vacuo. Reverse phase HPLC (10-70% acetonitrile/water+0.1% NH4OH) was utilized in purifying the title compound (29 mg, 35%). MS(ES)+ m/e 461.2 [M+H]+.

Example 200

5-{[(3S)-1-(4-morpholinylcarbonyl)-3-pyrrolidinyl]methyl}-4-[4-(7-quinolinyl)phenyl]-2,4-dihydro-3H-1,2,4-triazol-3-one

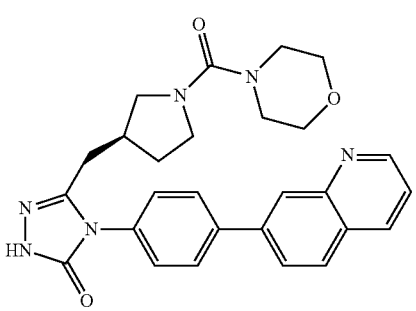 [SMILES: O=C(N1CCOCC1)N1CC[C@@H](Cc2n[nH]c(=O)n2-c2ccc(-c3ccc4cccnc4c3)cc2)C1]

a) 1,1-dimethylethyl (3S)-3-({5-oxo-4-[4-(7-quinolinyl)phenyl]-4,5-dihydro-1H-1,2,4-triazol-3-yl}methyl)-1-pyrrolidinecarboxylate A solution of 1,1-dimethylethyl (3S)-3-{[4-(4-bromophenyl)-5-oxo-4,5-dihydro-1H-1,2,4-triazol-3-yl]methyl}-1-pyrrolidinecarboxylate (1.181 mmol) in dioxane (6 mL) was treated with 7-(4,4,5,5-tetramethyl-1,3,2-dioxaborolan-2-yl)quinoline (1.215 mmol), dichloro[1,1'-bis(diphenylphosphino)ferrocene]palladium(II)-dichloromethane adduct (50 mg), and 2M aq potassium carbonate (3 mL). The reaction mixture was purged with nitrogen, sealed, and stirred at 110° C. for 1 h. The solution was cooled to room temperature and the dioxane layer separated from the aqueous layer. The dioxane layer was removed via pipette and was passed through a plug of celite and sodium sulfate. The plug was washed with dioxane (6 mL). All dioxane filtrates were combined and concentrated in vacuo. Silica gel chromatography (0-20% methanol:ethyl acetate) was utilized in purifying the title compound (386 mg, 69%). MS(ES)+ m/e 472.2 [M+H]+.

b) 5-[(3S)-3-pyrrolidinylmethyl]-4-[4-(7-quinolinyl)phenyl]-2,4-dihydro-3H-1,2,4-triazol-3-one Hydrochloride Into an 8 mL vial was placed 1,1-dimethylethyl (3S)-3-({5-oxo-4-[4-(7-quinolinyl)phenyl]-4,5-dihydro-1H-1,2,4-triazol-3-yl}methyl)-1-pyrrolidinecarboxylate (0.382 mmol). Added was 4N HCl in dioxane (2.0 mL). The vial was capped and the solution was agitated at room temperature for 1 h. The reaction was concentrated in vacuo to afford the title compound as the HCl salt (150 mg, 96%). No further purification was performed on this compound. MS(ES)+ m/e 372.2 [M+H]+.

c) 5-{[(3S)-1-(4-morpholinylcarbonyl)-3-pyrrolidinyl]methyl}-4-[4-(7-quinolinyl)phenyl]-2,4-dihydro-3H-1,2,4-triazol-3-one Into a 4 mL vial was placed 5-[(3S)-3-pyrrolidinylmethyl]-4-[4-(7-quinolinyl)phenyl]-2,4-dihydro-3H-1,2,4-triazol-3-one hydrochloride (0.147 mmol). Added in succession was dichloromethane (2 mL), N,N-diisopropylethylamine (0.458 mmol), and 4-morpholinecarbonyl chloride (0.157 mmol).

The vial was capped and the solution was stirred at room temperature for 30 min. The solution was concentrated in vacuo. Reverse phase HPLC (10-70% acetonitrile/water+ 0.1% NH₄OH) was utilized in purifying the title compound (23 mg, 31%). MS(ES)+ m/e 485.2 [M+H]⁺.

Example 201

4-[3-fluoro-4'-(methyloxy)-4-biphenylyl]-5-{[(3S)-1-(2-methylpropanoyl)-3-pyrrolidinyl]methyl}-2,4-dihydro-3H-1,2,4-triazol-3-one

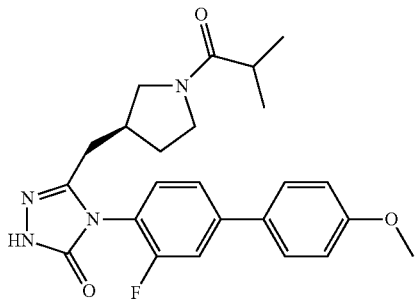 [SMILES: COc1ccc(-c2ccc(-n3c(C[C@@H]4CCN(C(=O)C(C)C)C4)n[nH]c3=O)c(F)c2)cc1]

a) Into a 50 mL round bottom flask was placed 1,1-dimethylethyl (3S)-3-({4-[3-fluoro-4'-(methyloxy)-4-biphenylyl]-5-oxo-4,5-dihydro-1H-1,2,4-triazol-3-yl}methyl)-1-pyrrolidinecarboxylate (0.342 mmol). Added to the flask was 4N HCl in dioxane (2 mL). The flask was capped and the contents were stirred at room temperature for 1 h. The solution was concentrated in vacuo. Added to the flask in succession were dichloromethane (3 mL) and N,N-diisopropylethylamine (0.200 mL). The flask was cooled to 0° C. in an ice bath. In a separate vial, isobutryl chloride (0.348 mmol) was taken up with dichloromethane (2 mL) and was added to the cold solution dropwise via pipette. The reaction was stirred for 2 h while the ice bath was allowed to warm to room temperature. The reaction was then diluted with dichloromethane (20 mL) and washed with saturated aq NH₄Cl. The organic layer was separated, dried over sodium sulfate, filtered, and concentrated in vacuo. Reverse phase HPLC (10-70% acetonitrile/water+0.1% NH₄OH) was utilized in purifying the title compound (65 mg, 43%). MS(ES)+ m/e 439.1 [M+H]⁺.

Example 202

4-[2-fluoro-4-(7-quinolinyl)phenyl]-5-{[(3S)-1-(2-methylpropanoyl)-3-pyrrolidinyl]methyl}-2,4-dihydro-3H-1,2,4-triazol-3-one

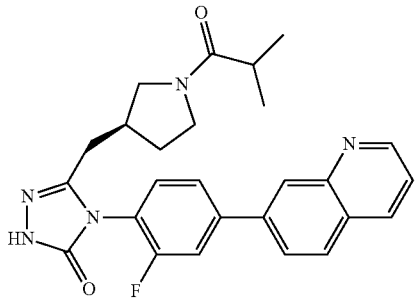 [SMILES: CC(C)C(=O)N1CC[C@@H](Cc2n[nH]c(=O)n2-c2ccc(-c3ccc4cccnc4c3)cc2F)C1]

a) Following the procedure described in Example 201a with 1,1-dimethylethyl (3S)-3-({4-[2-fluoro-4-(7-quinolinyl)phenyl]-5-oxo-4,5-dihydro-1H-1,2,4-triazol-3-yl}methyl)-1-pyrrolidinecarboxylate (0.143 mmol)) provided the title compound (18 mg, 27%). Reverse phase HPLC (10-70% acetonitrile/water+0.1% NH₄OH) was utilized in purifying this compound. MS(ES)+ m/e 460.3 [M+H]⁺.

Example 203

4-[3-fluoro-3'-(methyloxy)-4-biphenylyl]-5-{[(3S)-1-propanoyl-3-pyrrolidinyl]methyl}-2,4-dihydro-3H-1,2,4-triazol-3-one

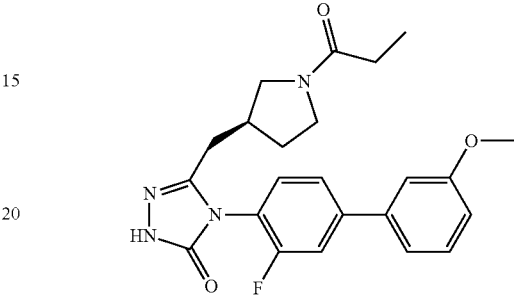

a) 1,1-dimethylethyl (3S)-3-({4-[3-fluoro-3'-(methyloxy)-4-biphenylyl]-5-oxo-4,5-dihydro-1H-1,2,4-triazol-3-yl}methyl)-1-pyrrolidinecarboxylate A solution of 1,1-dimethylethyl (3S)-3-{[4-(4-bromo-2-fluorophenyl)-5-oxo-4,5-dihydro-1H-1,2,4-triazol-3-yl]methyl}-1-pyrrolidinecarboxylate (0.499 mmol) in dioxane (3 mL) was treated with 3-methoxyphenylboronic acid pinacol ester (0.513 mmol), dichloro[1,1'-bis(diphenylphosphino)ferrocene]palladium(II)-dichloromethane adduct (30 mg), and 2M aq potassium carbonate (1.5 mL). The reaction mixture was purged with nitrogen, sealed, and stirred at 110° C. for 2 h. The solution was cooled to room temperature and the dioxane layer separated from the aqueous layer. The dioxane layer was removed via pipette and was passed through a plug of celite and sodium sulfate. The plug was washed with dioxane (10 mL). All dioxane filtrates were combined and concentrated in vacuo. Silica gel chromatography (100% ethyl acetate) was utilized in purifying the title compound (212 mg, 88%). MS(ES)+ m/e 469.3 [M+H]⁺.

b) 4-[3-fluoro-3'-(methyloxy)-4-biphenylyl]-5-{[(3S)-1-propanoyl-3-pyrrolidinyl]methyl}-2,4-dihydro-3H-1,2,4-triazol-3-one Into a 4 mL screwcap vial was placed 1,1-dimethylethyl (3S)-3-({4-[3-fluoro-3'-(methyloxy)-4-biphenylyl]-5-oxo-4,5-dihydro-1H-1,2,4-triazol-3-yl}methyl)-1-pyrrolidinecarboxylate (0.226 mmol). Added to the vial was 4N HCl in dioxane (2.0 mL). The vial was capped and the solution was stirred at room temperature for 2 h. The solution was concentrated in vacuo. Into the vial were place dichloromethane (1 mL) and N,N-diisopropylethylamine (0.14 mL). The solution was cooled in an ice bath. Into a separate vial, propanoyl chloride (0.217 mmol) was taken up in dichloromethane (1 mL) and then 0.5 ml, of this solution was added to the cold reaction. The vial was capped and stirred for 1 h, allowing the ice bath to slowly warm to room temperature. Since it was determined that the reaction was not complete, additional 0.10 mL of propanoyl chloride solution in dichloromethane was added to the reaction. After 1 h, the reaction was complete. Dichloromethane (1 mL) and saturated aq NH₄Cl were added to the reaction. The vial was lightly agitated and the liquid phases were allowed to separate. The organic layer was separated, dried over sodium sulfate, filtered, and concentrated in vacuo. Reverse phase HPLC (10-70% acetonitrile/water+0.1% NH₄OH) was utilized in purifying the title compound (21 mg, 21%). MS(ES)+ m/e 424.9 [M+H]⁺.

Example 204

5-{[(3S)-1-(cyclopropylcarbonyl)-3-pyrrolidinyl]methyl}-4-[3-fluoro-3'-(methyloxy)-4-biphenylyl]-2,4-dihydro-3H-1,2,4-triazol-3-one

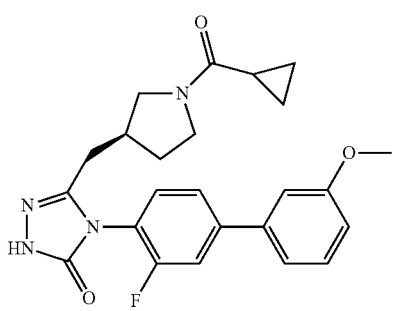 [SMILES: COc1cccc(-c2ccc(-n3c(C[C@@H]4CCN(C(=O)C5CC5)C4)n[nH]c3=O)c(F)c2)c1]

a) Following the procedure describe in 203b with cyclopropancarbonyl chloride (0.218 mmol) provided the title compound (24 mg, 24%). Reverse phase HPLC (10-70% acetonitrile/water+0.1% NH$_4$OH) was utilized in purifying this compound. MS(ES)+ m/e 437.2 [M+H]$^+$.

Example 205

5-{[(3S)-1-(cyclopropylcarbonyl)-3-pyrrolidinyl]methyl}-4-(3-fluoro-3'-hydroxy-4-biphenylyl)-2,4-dihydro-3H-1,2,4-triazol-3-one

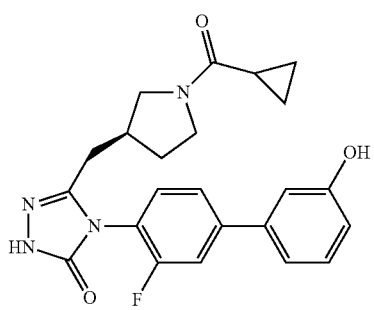 [SMILES: O=C(C1CC1)N1CC[C@@H](Cc2n[nH]c(=O)n2-c2ccc(-c3cccc(O)c3)cc2F)C1]

a) 1,1-dimethylethyl (3S)-3-{[4-(3-fluoro-3'-hydroxy-4-biphenylyl)-5-oxo-4,5-dihydro-1H-1,2,4-triazol-3-yl]methyl}-1-pyrrolidinecarboxylate Following the procedure described in Example 203a with 3-hydroxyphenyl boronic acid (0.290 mmol) provided the title compound (121 mg, 117%). Silica gel chromatography (100% ethyl acetate) was utilized in purifying this compound. Although the recovered weight exceeded the theoretical yield, no additional purification was performed. MS(ES)+ m/e 455.4 [M+H]$^+$.

b) 5-{[(3S)-1-(cyclopropylcarbonyl)-3-pyrrolidinyl]methyl}-4-(3-fluoro-3'-hydroxy-4-biphenylyl)-2,4-dihydro-3H-1,2,4-triazol-3-one Into a 4 mL screwcap vial was placed 1,1-dimethylethyl (3S)-3-{[4-(3-fluoro-3'-hydroxy-4-biphenylyl)-5-oxo-4,5-dihydro-1H-1,2,4-triazol-3-yl]methyl}-1-pyrrolidinecarboxylate (121 mg, 0.266 mmol). Added to the vial was 4N HCl in dioxane (2.0 mL). The solution was stirred at room temperature for 2 h and then was concentrated in vacuo. Added to the flask were dichloromethane (2 mL) and N,N-diisopropylethylamine (0.14 mL). The vial was cooled to 0° C. in an ice bath. In a separate vial cyclopropancarbonyl chloride (0.025 mL) was taken up in dichloromethane (1 mL). This mixture was added to the chilled reaction dropwise via pipette. The vial was capped and the reaction was stirred for 2 h while the ice bath warmed slowly to room temperature. Into the vial was added saturated aq NH$_4$Cl (0.5 mL). The solution was stirred for 5 min and then the phases settled and separated. The organic layer was removed and passed through a plug of sodium sulfate. The filtrate was concentrated in vacuo. Reverse phase HPLC (10-70% acetonitrile/water+ 0.1% NH$_4$OH) was utilized in purifying the title compound (16 mg, 14%). MS(ES)+ m/e 422.9 [M+H]$^+$.

Example 206

5-{[(3S)-1-(cyclopropylcarbonyl)-3-pyrrolidinyl]methyl}-4-(3-fluoro-4'-hydroxy-4-biphenylyl)-2,4-dihydro-3H-1,2,4-triazol-3-one

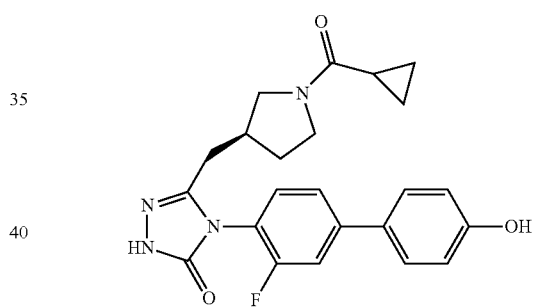

a) 1,1-dimethylethyl (3S)-3-{[4-(3-fluoro-4'-hydroxy-4-biphenylyl)-5-oxo-4,5-dihydro-1H-1,2,4-triazol-3-yl]methyl}-1-pyrrolidinecarboxylate Following the procedure described in Example 203a with 4-hydroxyphenyl boronic acid (0.508 mmol) provided the title compound. Silica gel chromatography (100% ethyl acetate) was utilized in purifying this compound (56 mg, 17%). MS(ES)+ m/e 455.2 [M+H]$^+$.

b) 5-{[(3S)-1-(cyclopropylcarbonyl)-3-pyrrolidinyl]methyl}-4-(3-fluoro-4'-hydroxy-4-biphenylyl)-2,4-dihydro-3H-1,2,4-triazol-3-one Following the procedure described in Example 205b with 1,1-dimethylethyl (3S)-3-{[4-(3-fluoro-4'-hydroxy-4-biphenylyl)-5-oxo-4,5-dihydro-1H-1,2,4-triazol-3-yl]methyl}-1-pyrrolidinecarboxylate (0.123 mmol) provided the title compound (36 mg, 31%). Reverse phase HPLC (10-70% acetonitrile/water+0.1% NH$_4$OH) was utilized in purifying this compound. MS(ES)+ m/e 423.0 [M+H]$^+$.

Example 207

5-{[(3S)-1-(cyclopropylcarbonyl)-3-pyrrolidinyl]methyl}-4-[2-fluoro-4-(6-fluoro-2-naphthalenyl)phenyl]-2,4-dihydro-3H-1,2,4-triazol-3-one

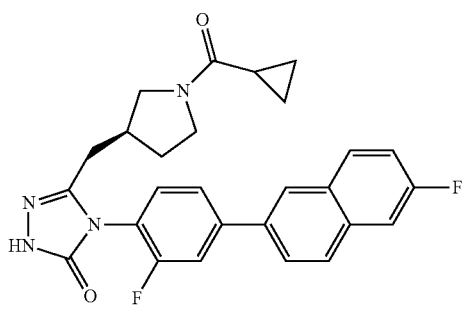 [SMILES: O=C(C1CC1)N1CC[C@@H](Cc2n[nH]c(=O)n2-c2ccc(-c3ccc4cc(F)ccc4c3)cc2F)C1]

a) Into a 5 mL microwaveable vial was placed 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol), bis(pinacolato)diboron (0.244 mmol), potassium acetate (0.977 mmol), dichloro[1,1'-bis(diphenylphosphino)ferrocene]palladium(II)-dichloromethane adduct (0.024 mmol), and 1,4-dioxane (2 mL). The vial was capped and the contents were purged with nitrogen. The solution stirred at 100° C. for 16 h. LCMS analysis displayed boronic ester intermediate present (boronic ester cleavage to acid also observed on LCMS) as well as a small amount of bromide starting material. The reaction was cooled to room temperature. Added to the vial was 2-bromo-6-fluoronaphthalene (0.244 mmol) and 2M aq potassium carbonate (1 mL). The vial was capped, purged with nitrogen, and stirred at 100° C. for 1 h. The solution was cooled to room temperature, whereby the dioxane layer separated from the aqueous layer. The dioxane layer was removed via pipette and was passed through a plug of celite and sodium sulfate. The plug was washed with dioxane (2 mL). All dioxane filtrates were combined and concentrated in vacuo. Reverse phase HPLC (30-80% acetonitrile/water+0.1% NH$_4$OH) was utilized in purifying the title compound (21 mg, 17%). MS(ES)+ m/e 475.1 [M+H]$^+$.

Example 208

5-{[(3S)-1-(cyclopropylcarbonyl)-3-pyrrolidinyl]methyl}-4-[2-fluoro-4-(8-fluoro-2-naphthalenyl)phenyl]-2,4-dihydro-3H-1,2,4-triazol-3-one

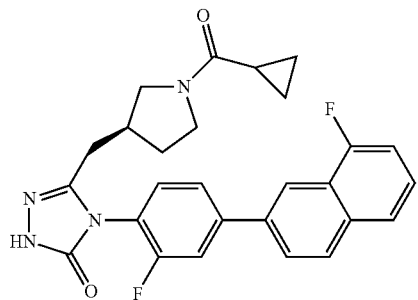 [SMILES: O=C(C1CC1)N1CC[C@@H](Cc2n[nH]c(=O)n2-c2ccc(-c3ccc4cccc(F)c4c3)cc2F)C1]

a) In a 5 mL microwaveable vial was placed 4-(4-bromo-2-fluorophenyl)-5-{[(3S)-1-(cyclopropylcarbonyl)-3-pyrrolidinyl]methyl}-2,4-dihydro-3H-1,2,4-triazol-3-one (0.244 mmol) and PdCl2(dppf)-CH2Cl2 adduct (0.024 mmol). A solution of 2-(8-fluoro-2-naphthalenyl)-4,4,5,5-tetramethyl-1,3,2-dioxaborolane (0.294 mmol; ACS Med. Chem. Lett. 2010, 1, 316-320) in 1,4-dioxane (2 mL) was added. Added last to the vial was 2M aq potassium carbonate (1.00 mL). The vial was capped, the contents were purged with nitrogen, and the solution was stirred at 100° C. for 1 h. The solution was cooled to room temperature, whereby the dioxane layer separated from the aqueous layer. The dioxane layer was removed via pipette and was passed through a plug of celite and sodium sulfate. The plug was washed with dioxane (4 mL) and the dioxane filtrates were combined and concentrated in vacuo. Reverse phase HPLC (20-80% acetonitrile/water+0.1% NH$_4$OH) was utilized in purifying the title compound (64 mg, 55%). MS(ES)+ m/e 475.1 [M+H]$^+$.

Biological Assays
FAS Assay
FAS Activity was Measured Through One of the Two Following Assays.
Assay #1:

Inhibition of FAS activity can be measured based on the detection of residual NADPH substrate after the FAS assay is quenched. This assay is run as a 10 μL endpoint assay in 384-well format, where the reaction contains 20 μM malonyl-CoA, 2 μM acetyl-CoA, 30 μM NADPH and 40 nM FAS in 50 mM sodium phosphate, pH 7.0. The assay is run by sequentially dispensing 5 μl of a malonyl-CoA solution, then enzyme solution (containing the acetyl-CoA, and NADPH) into a black, low volume assay plate (Greiner 784076) pre-dispensed with 100 nL compound solutions in DMSO. The reaction is incubated at ambient temperature for 60 minutes, then quenched with 5 μL of a developing solution composed of 90 μM resazurin, 0.3 IU/ml diaphorase in 50 mM sodium phosphate, pH 7.0. The developed reaction is read on a Molecular Devices Analyst or Acquest (or equivalent) plate reader using a 530 nm excitation wavelength filter, a 580 nm emission filter, and 561 nm dichroic filter. The test compounds are prepared in neat DMSO at a concentration of 10 mM. For inhibition curves, compounds are diluted using a three fold serial dilution and tested at 11 concentrations (e.g. 25 μM-0.42 nM). Curves are analysed using ActivityBase and XLfit, and results are expressed as pIC50 values.

Assay #2:

Inhibition of FAS can also be quantified based on the detection of the CoA products with a thio-reactive coumarin dye. This assay is run as a 10 μL endpoint assay in 384-well format, where the reaction contains 20 μM malonyl-CoA, 20 μM acetyl-CoA, 40 μM NADPH and 2 nM FAS in 50 mM sodium phosphate, pH 7.0, and 0.04% Tween-20. The assay is run by adding 5 μL enzyme solution to a black, low volume assay plate (Greiner 784076) pre-dispensed with 100 nl compound solutions in DMSO. After 30 minutes, 5 μL substrate is added, and the reaction incubated at ambient temperature for an additional 60 minutes. The reaction is then quenched with 10 μL of 6M guanidine-HCl containing 50 μM CPM (7-diethylamino-3-(4'-maleimidylphenyl)-4-methylcoumarin (CPM; thio-reactive dye), and incubated for 30 minutes. The plate is read on an Envision (PerkinElmer) or equivalent plate reader using a 380 nm excitation wavelength filter, and a 486 nm emission filter. Data fitting and compound preparations are done as described above.

Biological Data

Exemplified compounds of the present invention were tested according to the above assays and were found to be inhibitors of FAS. The IC$_{50}$ values ranged from about 1 to about 2000 nM; the IC$_{50}$ values of the preferred compounds ranged from about 1 to about 100 nM. The compounds described below were tested generally according to the assays described herein. The $IC_{50}$ for each compound was either reported in at least one experiment or the average of multiple experiments.

Example 1: 10 nM.
Example 4: 126 nM.
Example 7: 20 nM.
Example 14: 6 nM.
Example 23: 13 nM.
Example 38: 158 nM.
Example 42: 5 nM.
Example 67: 16 nM
Example 95: 200 nM
Example 116: 40 nM
Example 132: 3 nM
Example 158: 398 nM Lipogenesis Assay Cultured primary human pre-adipocytes (Zen-Bio, Cat# ASC062801) are plated at confluence (3×104 cells/well) in 96-well plates (Costar, Cat#3598) coated with 0.2% gelatin (Sigma, Cat# G-6650) in DMEM/F12 medium (InvitroGen Cat#11330-032) supplemented with 10% heat inactivated fetal bovine serum (InvitroGen, Cat#16000-044). The following day (day 1) the cell differentiation is induced by replacing the seeding medium with the differentiation medium composed of DMEM/F12 medium supplemented with 10% heat inactivated fetal bovine serum, 200 μM 3-isobutyl-1-methylxanthine (Sigma, Cat# I-5879), 20 nM dexamethasone (Sigma, Cat# D-8893), 20 nM GW1929 (Sigma, Cat# G5668) and 20 nM insulin (InvitroGen, Cat#03-0110SA). On day 7, differentiation medium is replaced by the re-feed medium made of DMEM/F12 supplemented with 10% heat inactivated serum and 20 nM insulin. The appropriate concentration of tested compounds and controls are added into this medium at that time. On day 12, the relative amount of cellular triglyceride is estimated by using a Trinder kit (Sigma, Cat# TR0100). Re-feed medium is aspirated and cells are washed with PBS (InvitroGen, Cat#14190-144) and the assay is performed according the kit manufacturer protocol. Briefly, reconstituted solutions A and B are mixed with 0.01% digitonin (Sigma, Cat# D-5628) prior to performing the assay and added onto the cells; plates are incubated at 37° C. for one hour. The absorbance is read at 540 nm. The data is first normalized using the following equation: 100*((UNK–Control 1)/(Control 2–Control 1)) where Control 1 is the Robust Mean of the 0% response control and Control 2 is the Robust Mean of the 100% response control. When multiple dilutions of compounds are tested, pXC50 are calculated from curves using the 4-parameter curve fitting with the following equation: y=(a–d)/(1+(s/c)^b)+d and with IRLS (Iterative Re-weighted Least Squares) algorithms to weight outliers (Mosteller, F. & Tukey J. W. (1977) Data Analysis and Regression, pp 353-365, Addison-Wesley).

The invention claimed is:

1. A compound of Formula (I),

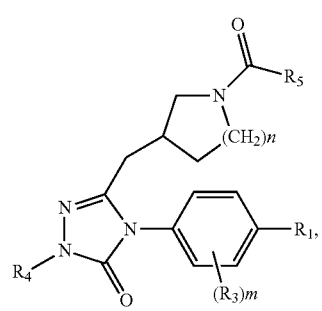

wherein, $R_1$ is a 6-membered aryl or heteroaryl ring which may be substituted or unsubstituted, in which adjacent substituents together may form an additional optionally substituted five or six membered ring which contains 0-3 heteroatoms and 0 to 2 double bonds;

each $R_3$ is independently selected from the group consisting of: halogen, C1-6alkyl, hydroxyl, and alkoxy;

$R_4$ is H or C1-6alkyl;

$R_5$ is selected from the group consisting of: C1-6alkyl, C3-7cycloalkyl, —OC1-6alkyl, $C_{4-6}$heterocycloalkyl, amino and alkylamino;

m is 0-3, n is 0-1;

or a pharmaceutically acceptable salt thereof.

2. The compound or pharmaceutically acceptable salt thereof according to claim 1, wherein the compound is represented by Formula (I)(A):

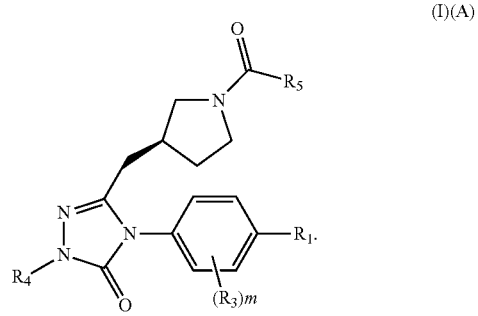

3. The compound or pharmaceutically acceptable salt thereof according to claim 1, wherein the compound is represented by Formula (I)(B)

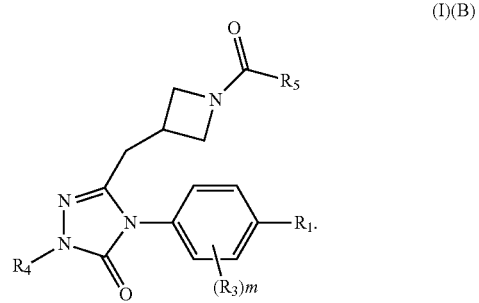

4. The compound or pharmaceutically acceptable salt thereof according to claim 1, wherein $R_1$ is a 6-membered substituted or unsubstituted aryl ring, in which adjacent substituents together may form an additional optionally substituted five or six membered ring which contains 0-3 heteroatoms and 0 to 2 double bonds.

5. The compound or pharmaceutically acceptable salt thereof according to claim 1, wherein $R_1$ is a substituted or unsubstituted 6-membered heteroaryl ring, in which adjacent substituents together may form an additional optionally substituted five or six membered ring which contains 0-3 heteroatoms and 0 to 2 double bonds.

6. The compound or pharmaceutically acceptable salt thereof according to claim 1, wherein $R_1$ is an optionally substituted bicyclic ring selected from the group consisting of: benzimidazole, indole, benzofuran, dihydrobenzofuran, dihydroindole, imidazopyridine, quinoline, azaindole, isoquinoline, isoquinolone, quinazoline, naphthalene, dihydroindene, indene, and indazole.

7. The compound or pharmaceutically acceptable salt thereof according to claim 1, wherein $R_3$ is fluoro, chloro, hydroxyl, methoxy, or methyl; and m is 0-1.

8. The compound or pharmaceutically acceptable salt thereof according to claim 1, wherein $R_5$ is cyclopropyl, ethyl, methyl or isopropyl.

9. The compound or pharmaceutically acceptable salt thereof according to claim 2, wherein:
$R_1$ is an optionally substituted bicyclic ring selected from the group consisting of: benzimidazole, indole, benzofuran, dihydrobenzofuran, dihydroindole, imidazopyridine, quinoline, azaindole, isoquinoline, isoquinolone, quinazoline, naphthalene, dihydroindene, indene, and indazole;
$R_3$ is fluoro, chloro, hydroxyl, methoxy, or methyl;
m is 0-1; and
$R_5$ is cyclopropyl, ethyl, methyl or isopropyl.

10. The compound or pharmaceutically acceptable salt thereof according to claim 9, wherein $R_1$ is an optionally substituted bicyclic ring selected from the group consisting of: quinoline, isoquinoline, isoquinolone, and quinazoline.

11. The compound or pharmaceutically acceptable salt thereof according to claim 1, wherein $R_5$ is cyclopropyl.

12. The compound or pharmaceutically acceptable salt thereof according to claim 1, wherein $R_1$ is a substituted or unsubstituted pyridine or pyrimidine, in which adjacent substituents together may form an additional optionally substituted five or six membered ring which contains 0-3 heteroatoms and 0 to 2 double bonds.

13. The compound or pharmaceutically acceptable salt thereof according to claim 1, wherein $R_4$ is H.

14. A pharmaceutical composition comprising the compound or pharmaceutically acceptable salt thereof according to claim 1 and a pharmaceutically acceptable carrier.

15. A method of treating cancer comprising administering to a human in need thereof an effective amount of the compound or pharmaceutically acceptable salt thereof according to claim 1 wherein the cancer is selected from the group consisting of: colon, kidney, lung, ovarian, and prostate.

* * * * *